(12) United States Patent
Guo et al.

(10) Patent No.: US 11,242,346 B2
(45) Date of Patent: Feb. 8, 2022

(54) MECHANISTIC TARGET OF RAPAMYCIN SIGNALING PATHWAY INHIBITORS AND THERAPEUTIC APPLICATIONS THEREOF

(71) Applicant: SUZHOU KINTOR PHARMACEUTICALS, INC., Jiangsu (CN)

(72) Inventors: Chuangxing Guo, San Diego, CA (US); Youzhi Tong, Little Neck, NY (US)

(73) Assignee: SUZHOU KINTOR PHARMACEUTICALS, INC., Suzhou (CN)

( * ) Notice: Subject to any disclaimer, the term of this patent is extended or adjusted under 35 U.S.C. 154(b) by 65 days.

(21) Appl. No.: 16/313,081

(22) PCT Filed: May 17, 2017

(86) PCT No.: PCT/CN2017/084683
§ 371 (c)(1),
(2) Date: Dec. 24, 2018

(87) PCT Pub. No.: WO2017/219800
PCT Pub. Date: Dec. 28, 2017

(65) Prior Publication Data
US 2020/0181147 A1    Jun. 11, 2020

Related U.S. Application Data

(60) Provisional application No. 62/354,754, filed on Jun. 25, 2016.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ........................... C07D 487/04; C07D 519/00
See application file for complete search history.

(56) References Cited

U.S. PATENT DOCUMENTS

| | | | | |
|---|---|---|---|---|
| 2015/0141644 A1* | 5/2015 | Yang | ...................... | A61P 43/00 544/105 |
| 2016/0115166 A1 | 4/2016 | Wu et al. | | |

FOREIGN PATENT DOCUMENTS

| | | |
|---|---|---|
| CN | 102558185 A | 7/2012 |
| CN | 102675323 A | 9/2012 |
| CN | 103450204 A | 12/2013 |

OTHER PUBLICATIONS

Dugar et al., "Synthesis and evaluation of pyrrolotriazine based molecules as PI3 kinase inhibitors," *Bioorganic and Medicinal Chemistry Letters*, 16(25):3142-3146, 2015.

PCT International Search Report and Written Opinion issued in International Application No. PCT/CN2017/084683, dated Aug. 9, 2017.

\* cited by examiner

*Primary Examiner* — Rebecca L Anderson
(74) *Attorney, Agent, or Firm* — Parker Highlander PLLC

(57) ABSTRACT

Selective mTOR inhibitors of formulas (I)-(III), processes for their preparation, pharmaceutical compositions containing them, and their use in the treatment of diseases and disorders, arising from abnormal cell growth, functions, or behaviors mediated by an mTOR kinase and/or one or more PI3K enzyme, are provided. Such diseases and disorder include cancer, immune disorders, cardiovascular disease, viral infection, inflammation, metabolism/endocrine function disorders and neurological disorders.

18 Claims, 1 Drawing Sheet

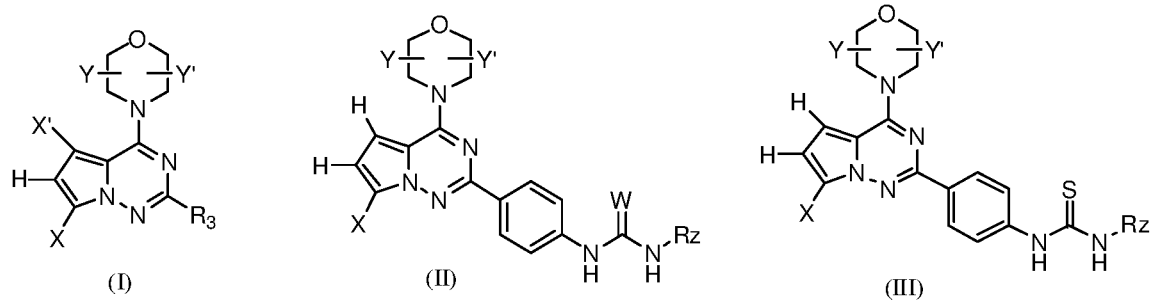

MECHANISTIC TARGET OF RAPAMYCIN SIGNALING PATHWAY INHIBITORS AND THERAPEUTIC APPLICATIONS THEREOF

CROSS REFERENCE TO RELATED APPLICATIONS

This is a U.S. National Phase application based upon PCT Application No. PCT/CN2017/084683, filed May 17, 2017 and titled "MECHANISTIC TARGET OF RAPAMYCIN SIGNALING PATHWAY INHIBITORS AND THERAPEUTIC APPLICATIONS THEREOF", which claims priority to U.S. Provisional Patent Application No. 62/354,754, filed Jun. 25, 2016, the disclosures of which are hereby incorporated by reference in their entirety.

BACKGROUND OF THE INVENTION

Phosphoinositide 3-kinases (PI3Ks) are a family of related enzymes that play a pivotal role in important cellular regulatory mechanisms. PI3Ks are capable of phosphorylating the 3'-OH position of phosphoinositide lipids (PIs) generating lipid second messengers. Their function has been linked to the regulation of numerous biological processes including cell growth, differentiation, survival, proliferation, migration. Three major groups of PI3K enzymes are known which are classified according to their physiological substrate specificity. Class III PI3K enzymes phosphorylate PI alone. In contrast, Class II PI3K enzymes phosphorylate both PI and PI 4-phosphate [PI(4)P]. Class I PI3K enzymes phosphorylate PI, PI(4)P and PI 4,5-bisphosphate [PI(4,5)P2], although only PI(4,5)P2 is believed to be the physiological cellular substrate. Phosphorylation of PI(4,5)P2 produces the lipid second messenger PI 3,4,5-triphosphate [PI(3,4,5)P3]. More distantly related members of this superfamily are Class IV kinases such as mTOR and DNA-dependent kinase that phosphorylate serine/threonine residues within protein substrates. The most studied and understood of these lipid kinases are the Class I PI3K enzymes, which are further divided into two groups: PI3K IA and PI3K IB. Class I PI3Ks are heterodimers composed of various combinations of catalytic and regulator subunit isoforms. Class IA PI3K heterodimers contain specific isoforms of the 85 kDa adaptor subunit that facilitates interaction with receptor tyrosine kinases (RTK) and either an alpha, beta or delta p110 catalytic subunit (p110α, p110β, or p110γ). Class IB PI3K heterodimers contain a p101 regulatory subunit that responds to specific GPCR-associated G-protein, βγ-subunits and a gamma p110 (p110δ) catalytic subunit.

Mammalian target of rapamycin (mTOR) is a serine/threonine kinase. It is a member of phosphatidylinositol-3 kinase (PI3K) related kinases (PIKKs) family. mTOR regulates cellular metabolism, growth, and proliferation. It effects downstream pathway and forms two complexes, mTORC1 and mTORC2. There have been reports that growth factors, cell metabolism signals such as amino acids, ATP, and oxygen levels regulate mTOR signaling. Several downstream pathways that regulate cell-cycle progression, translation, initiation, transcriptional stress responses, protein stability, and survival of cells are signaling through mTOR.

mTOR is a downstream effector of the PI3K/AKT signaling pathway, and forms two different multiprotein complexes, mTORC1 and mTORC2. These two complexes each have a separate network of protein partners, feedback loops, substrates, and regulators. mTORC1 is sensitive to rapamycin but mTORC2 is not and is generally insensitive to nutrients and energy signals. mTORC2 is activated by growth factors, phosphorylates PKCα, AKT and paxillin, and regulates the activity of the small GTPase, Rac, and Rho related to cell survival, migration and regulation of the actin cytoskeleton. The mTORC1 signaling cascade is activated by phosphorylated AKT and results in phosphorylation of S6K1, and 4EBP1, which lead to mRNA translation in oncogenic process.

Many human tumors are caused by dysregulation of mTOR signaling, such that may have higher susceptibility to inhibition of mTOR. Deregulations of multiple nodes of the mTOR pathway, like PI3K amplification/mutation, PTEN loss of function, AKT overexpression, and S6K1, 4EBP1, and eIF4E overexpression were found in many types of cancers. Therefore, mTOR is an interesting therapeutic target for treating multiple cancers, either the mTOR inhibitor as a monotherapy or in combination with inhibitors of other pathways.

mTOR is a key node in multiple networks of oncogenic signaling pathways. Upstream, PI3K/AKT signaling is deregulated through a variety of mechanisms, including overexpression or activation of growth factor receptors, mutations in PI3K and mutations/amplifications of AKT. Tumor suppressor phosphatase and tensin homologue deleted on chromosome ten (PTEN) is a negative regulator of PI3K signaling. In many tumors, the PTEN expression is down-regulated. Downstream, the mTOR effectors S6 kinase 1 (S6K1), eukaryotic initiation factor 4E-binding protein 1 (4EBP1) and eukaryotic initiation factor 4E (eIF4E) are related to cellular transformation and has been linked to poor cancer prognosis.

mTOR is a clinically validated target for treating a number of cancers such as renal cell carcinoma, endometrial cancer, and mantle cell lymphoma. To date, only the macrolide rapamycin analogues ('rapalogues') have been clinically approved as mTOR inhibitors. However, the use of rapalogues as a single agent therapy in most of the solid tumors only demonstrated modest objective response rates. The current understanding is that rapalogues only inhibit one of two functional multiprotein complexes—mTORC1 but not mTORC2, an important driver for cancer cell growth and survival. Moreover, there is a feedback loop between mTORC1 and Akt in tumor cells in which mTORC1 inhibition results in up-regulation of Akt activity and enhanced cell survival. Thus, the development of a mTORC1/mTORC2 dual inhibitor has been the focus of many drug discovery and development efforts for the next generation of mTOR inhibitors.

mTORC1/mTORC2 dual inhibitors are designed to compete with ATP in the catalytic site of mTOR. They inhibit all of the kinase-dependent functions of mTORC1 and mTORC2 and therefore, block the feedback activation of PI3K/AKT signaling, unlike rapalogs that only target mTORC1.

The close interaction of mTOR with the PI3K pathway has also led to the development of PI3K/mTOR dual inhibitors or Pan PI3K inhibitors. Despite promising preclinical efficacy results, the dual PI3K/mTOR inhibitors or Pan PI3K inhibitors are also likely to have increased toxicity hence reduced therapeutic range (maximum efficacy and scope), which makes them more difficult to combine with the agents with other mechanisms of action in clinical practice. Many of PI3K isoforms play critical roles in essential cellular regulatory mechanisms of normal cells. For example, pan PI3K inhibitor GDC-941 is a potent inhibitor of Class I PI3K isoforms—$IC_{50}$ of PI3Kα/δ: 3 nM in biochemical kinase inhibition assay with minimum activities against members of PI3K class II, III, and IV, including DNA-PK, and mTOR. Dual PI3K/mTOR inhibitor BEZ235 (Dactolisib) is a potent inhibitor of PI3Kα/γ/δ/β and mTOR (p70S6K) with IC$_{50}$'s of 4 nM/5 nM/7 nM/75 nM/6 nM in biochemical kinase inhibition assay. Despite impressive preclinical tumor inhibition efficacy, the progression of these two agents in clinical trial has been slowed down by significant side effects.

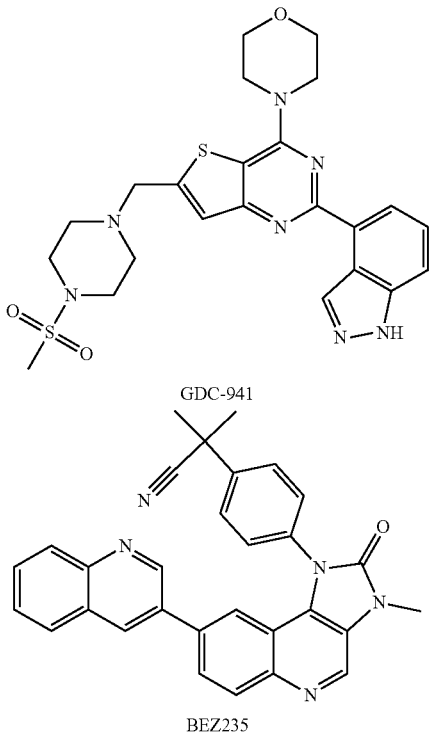

GDC-941

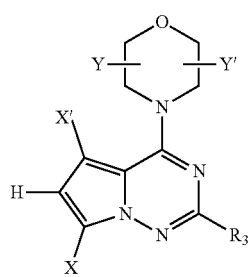

BEZ235

BRIEF SUMMARY OF THE INVENTION

The present disclosure provides selective mTOR inhibitors of formulas (I)-(III), processes for their preparation, pharmaceutical compositions containing them, and their use in the treatment of diseases and disorders, arising from abnormal cell growth, functions or behaviors mediated by an mTOR kinase and/or one or more PI3K enzyme. Such diseases and disorder include cancer, immune disorders, cardiovascular disease, viral infection, inflammation, metabolism/endocrine function disorders and neurological disorders.

An aspect of the present disclosure provides a compound of formula (I):

(I)

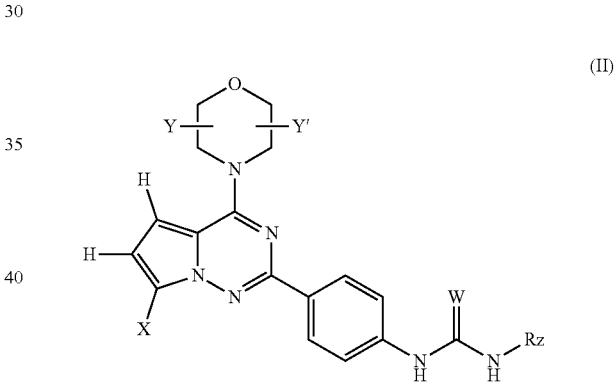

or a pharmaceutically acceptable salt, solvate or a stereoisomer or a tautomer thereof, wherein X and X' are each independently H, $C_{1-8}$ alkyl, CF3, —C(O)NR$_{11}$R$_{12}$, halogen, cyano, —S(O)R$_{13}$, —S(O)$_2$R$_{13}$, —S(O)$_2$NR$_{11}$R$_{12}$, —NR$_{13}$S(O)$_2$NR$_{11}$R$_{12}$, —OR$_{13}$, —NR$_{13}$C(O)NR$_{11}$R$_{12}$ or $C_{1-6}$ alkyl substituted with —OH, —NR$_{11}$R$_{12}$, or —OR$_{13}$; Y and Y' are each independently H, $C_{1-3}$ alkyl, oxo or cyano, or Y and Y', together with the atom to which they are attached, form a 4- to 7-membered ring including 1-4 atoms of the morpholine; R$_3$ is phenyl unsubstituted or substituted with at least one R$_{14}$, pyridine unsubstituted or substituted with one or more R$_{14}$, pyrimidine unsubstituted or substituted with one or more R$_{14}$, indole unsubstituted or substituted with one or more R$_{15}$, azaindole unsubstituted or substituted with one or more R$_{15}$, indazole unsubstituted or substituted with one or more R$_{15}$, azaindazole unsubstituted or substituted with one or more R$_{15}$; R$_{11}$ and R$_{12}$ are each independently H, alkyl, hydroxyalkyl, aryl, heteroaryl, arylalkyl or heteroarylalkyl, or R$_{11}$ and R$_{12}$, together with the nitrogen atom to which they are attached, form a 4- to 7-membered ring; R$_{13}$ is H, alkyl, aryl, heteroaryl, alkylaryl, arylalkyl, alkylheteroaryl or heteroarylalkyl; R$_{14}$ is H, alkyl, halogen, $C_{1-3}$ alkoxy, CF$_3$, amino, cyano, —NR$_{13}$C(O)NR$_{11}$R$_{12}$, —C(O)NR$_{11}$R$_{12}$, —S(O)$_2$NR$_{11}$R$_{12}$, —NR$_{13}$S(O)$_2$NR$_{11}$R$_{12}$, —NR$_{13}$C(S)NR$_{11}$R$_{12}$, —NR$_{13}$C(=N—CN)NR$_{11}$R$_{12}$, —NR$_{13}$C(=NH)NR$_{11}$R$_{12}$, or —NR$_{13}$C(=N—NO$_2$)NR$_{11}$R$_{12}$; and R$_{15}$ is H, halogen, alkyl, cyano, alkoxy, —C(O)NR$_{11}$R$_{12}$, —S(O)$_2$NR$_{11}$R$_{12}$, —NR$_{13}$S(O)$_2$NR$_{11}$R$_{12}$ or —NR$_{13}$C(O)NR$_{11}$R$_{12}$.

Another aspect of the present disclosure provides a compound of formula (II):

(II)

or a pharmaceutically acceptable salt, solvate or a stereoisomer or a tautomer thereof, wherein X is H, $C_{1-8}$ alkyl, CF3, —C(O)NR$_{11}$R$_{12}$, halogen, cyano, —S(O)R$_{13}$, —S(O)$_2$R$_{13}$, —S(O)$_2$NR$_{11}$R$_{12}$, —NR$_{13}$S(O)$_2$NR$_{11}$R$_{12}$, —OR$_{13}$, —NR$_{13}$C(O)NR$_{11}$R$_{12}$ or $C_{1-6}$ alkyl substituted with —OH, —NR$_{11}$R$_{12}$, or —OR$_{13}$; Y and Y' are each independently H, methyl, ethyl, oxo or cyano, or Y and Y', together with the atom to which they are attached, form a 4- to 7-membered ring including 1-4 atoms of the morpholine; W is O, S, N—CN, NH or N—NO$_2$; Rz is $C_{1-6}$ alkyl unsubstituted or substituted with one or more R$_{18a}$, $C_{1-6}$ cyclic alkyl unsubstituted or substituted with one or more R$_{18a}$, 5- or 6-membered heteroaryl, or phenyl unsubstituted or substituted with a 4-substitution of —C(O)NR$_{19}$R$_{20}$; R$_{18a}$ is —OH, cyano, —NR$_{11}$R$_{12}$, —OR$_{13}$, morpholine, piperazine, or heterocycle; R$_{19}$ and R$_{20}$ are each independently H, $C_{1-6}$ alkyl unsubstituted or substituted with one or more R$_{19a}$, or R$_{19}$ and R$_{20}$, together with the nitrogen atom to which they are attached, form a 3- to 8-membered monocyclic ring or a 5- to 10-membered bicyclic ring, wherein any atom in the monocyclic ring or bicyclic ring may be NR$_{21}$ or CR$_{22}$; R$_{19a}$ is —OH, —OR$_{13}$, —NR$_{11}$R$_{12}$, cyano, or morpholine; R$_{21}$ is H, methyl, $C_{1-3}$ alkyl or cyclic alkyl; $R_{22}$ is H, —OH or —$NR_{23}R_{24}$; and $R_{23}$ and $R_{24}$ are each independently H, methyl, $C_{1-3}$ alkyl or cyclic alkyl.

Still another aspect of the present disclosure provides a compound of formula (III):

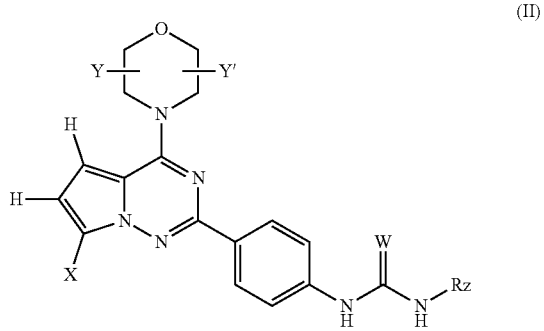

or a pharmaceutically acceptable salt, solvate or a stereoisomer or a tautomer thereof, wherein X is H, $C_{1-8}$ alkyl, CF3, —$C(O)NR_{11}R_{12}$, halogen, cyano, —$S(O)R_{13}$, —$S(O)_2R_{13}$, —$S(O)_2NR_{11}R_{12}$, —$NR_{13}S(O)_2NR_{11}R_{12}$, —$OR_{13}$, —$NR_{13}C(O)NR_{11}R_{12}$ or $C_{1-6}$ alkyl substituted with —OH, —$NR_{11}R_{12}$, or —$OR_{13}$; Y and Y' are each independently H, methyl, ethyl, oxo or cyano, or Y and Y', together with the atom to which they are attached, form a 4- to 7-membered ring including 1-4 atoms of the morpholine; W is O, S, N—CN, NH or N—$NO_2$; Rz is $C_{1-6}$ alkyl unsubstituted or substituted with one or more $R_{18a}$, $C_{1-6}$ cyclic alkyl unsubstituted or substituted with one or more $R_{18a}$, 5- or 6-membered heteroaryl, or phenyl unsubstituted or substituted with a 4-substitution of —$C(O)NR_{19}R_{20}$; $R_{18a}$ is —OH, cyano, —$NR_{11}R_{12}$, —$OR_{13}$, morpholine, piperazine, or heterocycle; $R_{19}$ and $R_{20}$ are each independently H, $C_{1-6}$ alkyl unsubstituted or substituted with one or more $R_{19a}$, or $R_{19}$ and $R_{20}$, together with the nitrogen atom to which they are attached, form a 3- to 8-membered monocyclic ring or a 5- to 10-membered bicyclic ring, wherein any atom in the monocyclic ring or bicyclic ring may be $NR_{21}$ or $CR_{22}$; $R_{19a}$ is —OH, —$OR_{13}$, —$NR_{11}R_{12}$, cyano, or morpholine; $R_{21}$ is H, methyl, $C_{1-3}$ alkyl or cyclic alkyl; $R_{22}$ is H, —OH or —$NR_{23}R_{24}$; and $R_{23}$ and $R_{24}$ are each independently H, methyl, $C_{1-3}$ alkyl or cyclic alkyl.

One aspect of the present disclosure provides a method for synthesizing compounds of formulas (I)-(III).

Still another aspect of the present disclosure provides a pharmaceutical composition comprising a compound of formulas (I)-(III) or a pharmaceutically acceptable salt thereof and a pharmaceutically acceptable carrier.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which:

FIG. 1 shows representative structures of compound disclosed in the instant disclosure.

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present invention comprises compounds of formula I, methods of using such compounds as inhibitors of mTOR kinase domain and pharmaceutical compositions containing such compounds and salts thereof.

An aspect of the present disclosure provides a compound of formula (I):

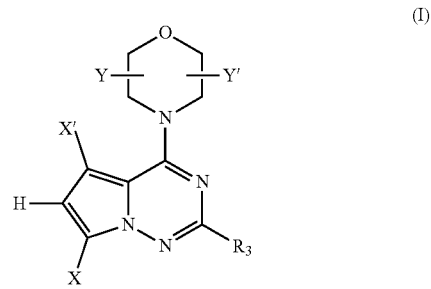

or a pharmaceutically acceptable salt, solvate or a stereoisomer or a tautomer thereof, wherein X and X' are each independently H, $C_{1-8}$ alkyl, CF3, —$C(O)NR_{11}R_{12}$, halogen, cyano, —$S(O)_2R_{13}$, —$S(O)_2R_{13}$, —$S(O)_2NR_{11}R_{12}$, —$NR_{13}S(O)_2NR_{11}R_{12}$, —$OR_{13}$, —$NR_{13}C(O)NR_{11}R_{12}$ or $C_{1-6}$ alkyl substituted with —OH, —$NR_{11}R_{12}$, or —$OR_{13}$; Y and Y' are each independently H, $C_{1-3}$ alkyl, oxo or cyano, or Y and Y', together with the atom to which they are attached, form a 4- to 7-membered ring including 1-4 atoms of the morpholine; $R_3$ is phenyl unsubstituted or substituted with at least one $R_{14}$, pyridine unsubstituted or substituted with one or more $R_{14}$, pyrimidine unsubstituted or substituted with one or more $R_{14}$, indole unsubstituted or substituted with one or more $R_{15}$, azaindole unsubstituted or substituted with one or more $R_{15}$, indazole unsubstituted or substituted with one or more $R_{15}$, azaindazole unsubstituted or substituted with one or more $R_{15}$; $R_{11}$ and $R_{12}$ are each independently H, alkyl, hydroxyalkyl, aryl, heteroaryl, arylalkyl or heteroarylalkyl, or $R_{11}$ and $R_{12}$, together with the nitrogen atom to which they are attached, form a 4- to 7-membered ring; $R_{13}$ is H, alkyl, aryl, heteroaryl, alkylaryl, arylalkyl, alkylheteroaryl or heteroarylalkyl; $R_{14}$ is H, alkyl, halogen, $C_{1-3}$ alkoxy, $CF_3$, amino, cyano, $-NR_{13}C(O)NR_{11}R_{12}$, $-C(O)NR_{11}R_{12}$, $-S(O)_2NR_{11}R_{12}$, $-NR_{13}S(O)_2NR_{11}R_{12}$, $-NR_{13}C(S)NR_{11}R_{12}$, $-NR_{13}C(=N-CN)NR_{11}R_{12}$, $-NR_{13}C(=NH)NR_{11}R_{12}$, or $-NR_{13}C(=N-NO_2)NR_{11}R_{12}$; and $R_{15}$ is H, halogen, alkyl, cyano, alkoxy, $-C(O)NR_{11}R_{12}$, $-S(O)_2NR_{11}R_{12}$, $-NR_{13}S(O)_2NR_{11}R_{12}$ or $-NR_{13}C(O)NR_{11}R_{12}$.

In some embodiments of aspects provided herein, X' is H in the compound of formula (I). In some embodiments of aspects provided herein, X is H in the compound of formula (I). In some embodiments of aspects provided herein, both X and X' are H in the compound of formula (I). In some embodiments of aspects provided herein, when X' is H in formula (I), X is t-butyl, CF3, halogen, cyano, $-S(O)R_{13}$, $-S(O)_2R_{13}$, $-S(O)_2NR_{11}R_{12}$, $-NR_{13}S(O)_2NR_{11}R_{12}$, $-OR_{13}$, $-NR_{13}C(O)NR_{11}R_{12}$ or $C_{1-6}$ alkyl substituted with $-OH$, $-NR_{11}R_{12}$, or $-OR_{13}$. In some embodiments of aspects provided herein, when both X and X' are H in formula (I), $R_3$ is pyridine or pyrimidine, which pyridine or pyrimidine is unsubstituted or substituted with one or more $-NR_{11}R_{12}$, methyl, methoxy or trifluoromethyl.

In some embodiments of aspects provided herein, when X' is H in formula (I), $R_3$ is phenyl with a 4-substitution of $-NHC(W)NHR_{18}$, wherein W is O, S, N—CN, NH or N—$NO_2$; $R_{18}$ is $C_{1-6}$ alkyl unsubstituted or substituted with one or more $R_{18a}$, $C_{1-6}$ cyclic alkyl unsubstituted or substituted with one or more $R_{18a}$, 5- or 6-membered heteroaryl, or phenyl unsubstituted or substituted with a 4-substitution of $-C(O)NR_{19}R_{20}$; $R_{18a}$ is $-OH$, cyano, $-NR_{11}R_{12}$, $-OR_{13}$, morpholine, piperazine, or heterocycle; $R_{19}$ and $R_{20}$ are each independently H, $C_{1-6}$ alkyl unsubstituted or substituted with one or more $R_{19a}$, or $R_{19}$ and $R_{20}$, together with the nitrogen atom to which they are attached, form a 3- to 8-membered monocyclic ring or a 5- to 10-membered bicyclic ring, wherein any atom in the monocyclic ring or bicyclic ring may be $NR_{21}$ or $CR_{22}$; $R_{19a}$ is $-OH$, $-OR_{13}$, $-NR_{11}R_{12}$, cyano, or morpholine; $R_{21}$ is H, methyl, $C_{1-3}$ alkyl or cyclic alkyl; $R_{22}$ is H, $-OH$ or $-NR_{23}R_{24}$; and $R_{23}$ and $R_{24}$ are each independently H, methyl, $C_{1-3}$ alkyl or cyclic alkyl.

In some embodiments of aspects provided herein, when both X and X' are H in formula (I), $R_3$ is phenyl with a 4-substitution of $-NHC(W)NHR_{18}$, wherein W is O, S, N—CN, NH or N—$NO_2$; $R_{18}$ is $C_{1-6}$ alkyl unsubstituted or substituted with one or more $R_{18a}$, $C_{1-6}$ cyclic alkyl unsubstituted or substituted with one or more $R_{18a}$, 5- or 6-membered heteroaryl, or phenyl unsubstituted or substituted with a 4-substitution of $-C(O)NR_{19}R_{20}$; $R_{18a}$ is $-OH$, cyano, $-NR_{11}R_{12}$, $-OR_{13}$, morpholine, piperazine, or heterocycle; $R_{19}$ and $R_{20}$ are each independently H, $C_{1-6}$ alkyl unsubstituted or substituted with one or more $R_{19a}$, or $R_{19}$ and $R_{20}$, together with the nitrogen atom to which they are attached, form a 3- to 8-membered monocyclic ring or a 5- to 10-membered bicyclic ring, wherein any atom in the monocyclic ring or bicyclic ring may be $NR_{21}$ or $CR_{22}$; $R_{19a}$ is $-OH$, $-OR_{13}$, $-NR_{11}R_{12}$, cyano, or morpholine; $R_{21}$ is H, methyl, $C_{1-3}$ alkyl or cyclic alkyl; $R_{22}$ is H, $-OH$ or $-NR_{23}R_{24}$; and $R_{23}$ and $R_{24}$ are each independently H, methyl, $C_{1-3}$ alkyl or cyclic alkyl.

In some embodiments of aspects provided herein, when X' is H in formula (I), $R_3$ is phenyl with a 4-substitution of $-NHC(S)NHR_{18}$, wherein W is O, S, N—CN, NH or N—$NO_2$; $R_{18}$ is $C_{1-6}$ alkyl unsubstituted or substituted with one or more $R_{18a}$, $C_{1-6}$ cyclic alkyl unsubstituted or substituted with one or more $R_{18a}$, 5- or 6-membered heteroaryl, or phenyl unsubstituted or substituted with a 4-substitution of $-C(O)NR_{19}R_{20}$; $R_{18a}$ is $-OH$, cyano, $-NR_{11}R_{12}$, $-OR_{13}$, morpholine, piperazine, or heterocycle; $R_{19}$ and $R_{20}$ are each independently H, $C_{1-6}$ alkyl unsubstituted or substituted with one or more $R_{19a}$, or $R_{19}$ and $R_{20}$, together with the nitrogen atom to which they are attached, form a 3- to 8-membered monocyclic ring or a 5- to 10-membered bicyclic ring, wherein any atom in the monocyclic ring or bicyclic ring may be $NR_{21}$ or $CR_{22}$; $R_{19a}$ is $-OH$, $-OR_{13}$, $-NR_{11}R_{12}$, cyano, or morpholine; $R_{21}$ is H, methyl, $C_{1-3}$ alkyl or cyclic alkyl; $R_{22}$ is H, $-OH$ or $-NR_{23}R_{24}$; and $R_{23}$ and $R_{24}$ are each independently H, methyl, $C_{1-3}$ alkyl or cyclic alkyl.

In some embodiments of aspects provided herein, when both X and X' are H in formula (I), $R_3$ is phenyl with a 4-substitution of $-NHC(S)NHR_{18}$, wherein W is O, S, N—CN, NH or N—$NO_2$; $R_{18}$ is $C_{1-6}$ alkyl unsubstituted or substituted with one or more $R_{18a}$, $C_{1-6}$ cyclic alkyl unsubstituted or substituted with one or more $R_{18a}$, 5- or 6-membered heteroaryl, or phenyl unsubstituted or substituted with a 4-substitution of $-C(O)NR_{19}R_{20}$; $R_{18a}$ is $-OH$, cyano, $-NR_{11}R_{12}$, $-OR_{13}$, morpholine, piperazine, or heterocycle; $R_{19}$ and $R_{20}$ are each independently H, $C_{1-6}$ alkyl unsubstituted or substituted with one or more $R_{19a}$, or $R_{19}$ and $R_{20}$, together with the nitrogen atom to which they are attached, form a 3- to 8-membered monocyclic ring or a 5- to 10-membered bicyclic ring, wherein any atom in the monocyclic ring or bicyclic ring may be $NR_{21}$ or $CR_{22}$; $R_{19a}$ is $-OH$, $-OR_{13}$, $-NR_{11}R_{12}$, cyano, or morpholine; $R_{21}$ is H, methyl, $C_{1-3}$ alkyl or cyclic alkyl; $R_{22}$ is H, $-OH$ or $-NR_{23}R_{24}$; and $R_{23}$ and $R_{24}$ are each independently H, methyl, $C_{1-3}$ alkyl or cyclic alkyl.

In some embodiments of aspects provided herein, at least one $-OH$ group in $R_3$ of the compound of formula (I) is independently converted to a corresponding phosphate ester $-OP(O)(OH)_2$. In some embodiments of aspects provided herein, at least one $-OH$ group in $R_3$ is independently converted to $-OR_{25}$, and wherein $R_{25}$ is independently an ester, ether or substituted ether. In some embodiments of aspects provided herein, at least one NH group of the $-NHC(=W)NHR_{18}$ group in $R_3$ is independently substituted with alkyl, alkylaryl, arylalkyl, alkylheteroaryl, heteroarylalkyl, or $-CH_2OR_{26}$, and wherein $R_{26}$ is independently phosphate, ester, alkyl or alkylaryl.

Another aspect of the present disclosure provides a compound of formula (II):

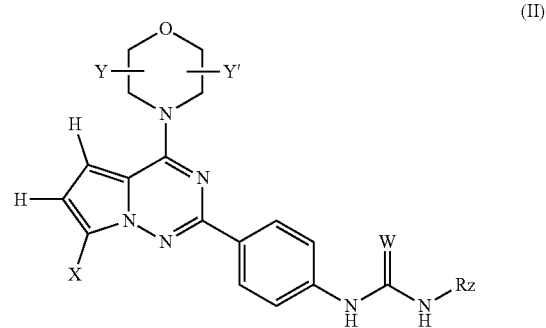

(II)

or a pharmaceutically acceptable salt, solvate or a stereoisomer or a tautomer thereof, wherein X is H, $C_{1-8}$ alkyl, CF3, $-C(O)NR_{11}R_{12}$, halogen, cyano, $-S(O)R_{13}$, $-S(O)_2R_{13}$, $-S(O)_2NR_{11}R_{12}$, $-NR_{13}S(O)_2NR_{11}R_{12}$, $-OR_{13}$, $-NR_{13}C(O)NR_{11}R_{12}$ or $C_{1-6}$ alkyl substituted with $-OH$, $-NR_{11}R_{12}$, or $-OR_{13}$; Y and Y' are each independently H, methyl, ethyl, oxo or cyano, or Y and Y', together with the atom to which they are attached, form a 4- to 7-membered ring including 1-4 atoms of the morpholine; W is O, S, N—CN, NH or N—NO$_2$; Rz is C$_{1-6}$ alkyl unsubstituted or substituted with one or more R$_{18a}$, C$_{1-6}$ cyclic alkyl unsubstituted or substituted with one or more R$_{18a}$, 5- or 6-membered heteroaryl, or phenyl unsubstituted or substituted with a 4-substitution of —C(O)NR$_{19}$R$_{20}$; R$_{18a}$ is —OH, cyano, —NR$_{11}$R$_{12}$, —OR$_{13}$, morpholine, piperazine, or heterocycle; R$_{19}$ and R$_{20}$ are each independently H, C$_{1-6}$ alkyl unsubstituted or substituted with one or more R$_{19a}$, or R$_{19}$ and R$_{20}$, together with the nitrogen atom to which they are attached, form a 3- to 8-membered monocyclic ring or a 5- to 10-membered bicyclic ring, wherein any atom in the monocyclic ring or bicyclic ring may be NR$_{21}$ or CR$_{22}$; R$_{19a}$ is —OH, —OR$_{13}$, —NR$_{11}$R$_{12}$, cyano, or morpholine; R$_{21}$ is H, methyl, C$_{1-3}$ alkyl or cyclic alkyl; R$_{22}$ is H, —OH or —NR$_{23}$R$_{24}$; and R$_{23}$ and R$_{24}$ are each independently H, methyl, C$_{1-3}$ alkyl or cyclic alkyl.

In some embodiments of aspects provided herein, X is H in the compound of formula (II). In some embodiments of aspects provided herein, R$_z$ in the compound of formula (II) is C$_{1-4}$ alkyl, C$_{1-4}$ cyclic alkyl, or C$_{1-6}$ alkyl substituted with one or more R$_{18a}$. In some embodiments of aspects provided herein, R$_z$ in the compound of formula (II) is 5- or 6-membered heteroaryl comprising pyridine, pyrimidine, pyrazine, pyridazine, imidazole, triazine, oxazole and thiazole. In some embodiments of aspects provided herein, Rz in the compound of formula (II) is phenyl unsubstituted or substituted with a 4-substitution of —C(O)NR$_{19}$R$_{20}$. In some embodiments of aspects provided herein, W in the compound of formula (II) is O or S.

In some embodiments of aspects provided herein, at least one —OH group in Rz in the compound of formula (II) is independently converted to a corresponding phosphate ester —OP(O)(OH)$_2$. In some embodiments of aspects provided herein, at least one —OH group in Rz in the compound of formula (II) is independently converted to —OR$_{25}$, and wherein R$_{25}$ is independently an ester, ether or substituted ether. In some embodiments of aspects provided herein, at least one NH group of the —NHC(=W)NHR$_z$ group in the compound of formula (II) is independently substituted with alkyl, alkylaryl, arylalkyl, alkylheteroaryl, heteroarylalkyl, or —CH$_2$OR$_{26}$, and wherein R$_{26}$ is independently phosphate, ester, alkyl or alkylaryl.

Still another aspect of the present disclosure provides a compound of formula (III):

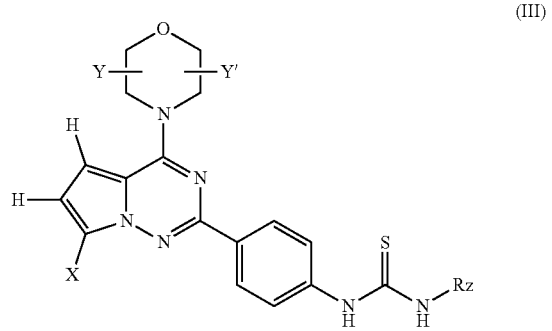

(III)

or a pharmaceutically acceptable salt, solvate or a stereoisomer or a tautomer thereof, wherein X is H, C$_{1-8}$ alkyl, CF3, —C(O)NR$_{11}$R$_{12}$, halogen, cyano, —S(O)R$_{13}$, —S(O)$_2$R$_{13}$, —S(O)$_2$NR$_{11}$R$_{12}$, —NR$_{13}$S(O)$_2$NR$_{11}$R$_{12}$, —OR$_{13}$, —NR$_{13}$C(O)NR$_{11}$R$_{12}$ or C$_{1-6}$ alkyl substituted with —OH, —NR$_{11}$R$_{12}$, or —OR$_{13}$; Y and Y' are each independently H, methyl, ethyl, oxo or cyano, or Y and Y', together with the atom to which they are attached, form a 4- to 7-membered ring including 1-4 atoms of the morpholine; Rz is C$_{1-6}$ alkyl unsubstituted or substituted with one or more R$_{18a}$, C$_{1-6}$ cyclic alkyl unsubstituted or substituted with one or more R$_{18a}$, 5- or 6-membered heteroaryl, or phenyl unsubstituted or substituted with a 4-substitution of —C(O) NR$_{19}$R$_{20}$; R$_{18a}$ is —OH, cyano, —NR$_{11}$R$_{12}$, —OR$_{13}$, morpholine, piperazine, or heterocycle; R$_{19}$ and R$_{20}$ are each independently H, C$_{1-6}$ alkyl unsubstituted or substituted with one or more R$_{19a}$, or R$_{19}$ and R$_{20}$, together with the nitrogen atom to which they are attached, form a 3- to 8-membered monocyclic ring or a 5- to 10-membered bicyclic ring, wherein any atom in the monocyclic ring or bicyclic ring may be NR$_{21}$ or CR$_{22}$; R$_{19a}$ is —OH, —OR$_{13}$, —NR$_{11}$R$_{12}$, cyano, or morpholine; R$_{21}$ is H, methyl, C$_{1-3}$ alkyl or cyclic alkyl; R$_{22}$ is H, —OH or —NR$_{23}$R$_{24}$; and R$_{23}$ and R$_{24}$ are each independently H, methyl, C$_{1-3}$ alkyl or cyclic alkyl.

In some embodiments of aspects provided herein, X is H in the compound of formula (III). In some embodiments of aspects provided herein, X is H. In some embodiments of aspects provided herein, X is t-butyl, CF$_3$, halogen, cyano, —S(O)R$_{13}$, —S(O)$_2$R$_{13}$, —S(O)$_2$NR$_{11}$R$_{12}$, —NR$_{13}$S(O)$_2$NR$_{11}$R$_{12}$, —OR$_{13}$, —NR$_{13}$C(O)NR$_{11}$R$_{12}$ or C$_{1-6}$ alkyl substituted with —OH, —NR$_{11}$R$_{12}$, or —OR$_{13}$. In some embodiments of aspects provided herein, R$_z$ is selected from C$_{1-4}$ alkyl, C$_{1-4}$ cyclic alkyl or C$_{1-6}$ alkyl substituted with one or more R$_{18a}$. In some embodiments of aspects provided herein, R$_z$ is a 5- or 6-membered heteroaryl comprising pyridine, pyrimidine, pyrazine, pyridazine, imidazole, triazine, oxazole and thiazole. In some embodiments of aspects provided herein, R$_z$ is a phenyl unsubstituted or substituted with a 4-substitution of —C(O)NR$_{19}$R$_{20}$.

In some embodiments of aspects provided herein, at least one —OH group in Rz in the compound of formula (III) is independently converted to a corresponding phosphate ester —OP(O)(OH)$_2$. In some embodiments of aspects provided herein, at least one —OH group in Rz in the compound of formula (III) is independently converted to —OR$_{25}$, and wherein R$_{25}$ is independently an ester, ether or substituted ether. In some embodiments of aspects provided herein, at least one NH group of the —NHC(S)NHR$_z$ group in the compound of formula (III) is independently substituted with alkyl, alkylaryl, arylalkyl, alkylheteroaryl, heteroarylalkyl, or —CH$_2$OR$_{26}$, and wherein R$_{26}$ is independently phosphate, ester, alkyl or alkylaryl.

In some embodiments of aspects provided herein, a compound of formulas (I)-(III), having the following chemical structures:

Example 1

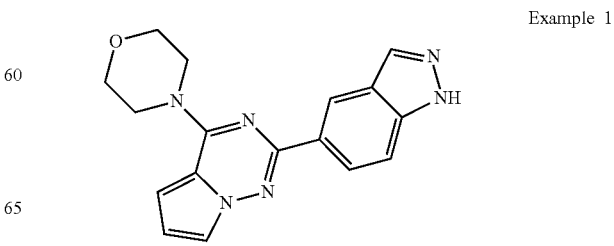

Example 2
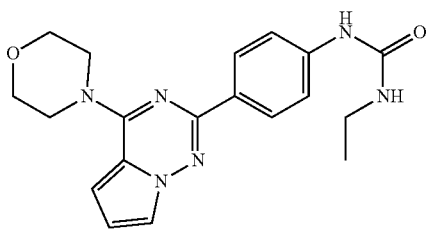
Example 3
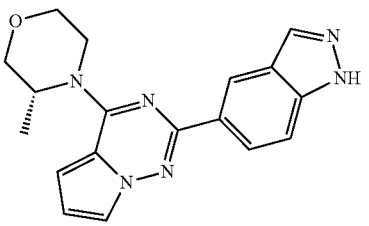
Example 4
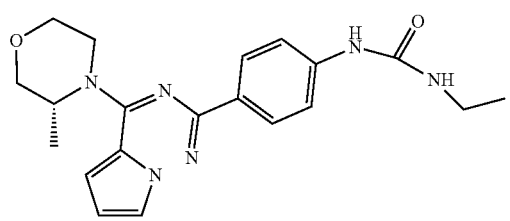
Example 5
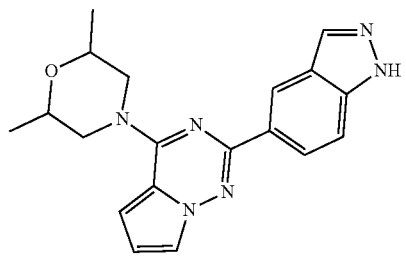
Example 6
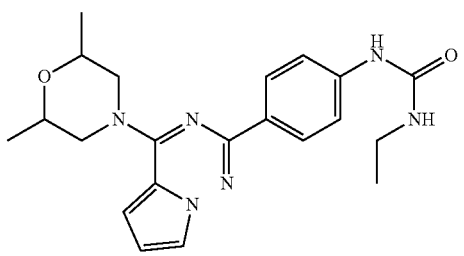
Example 7
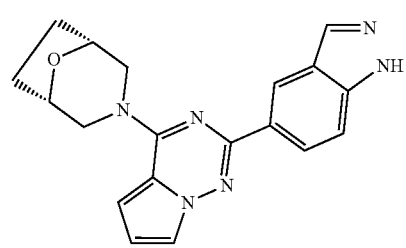
Example 8
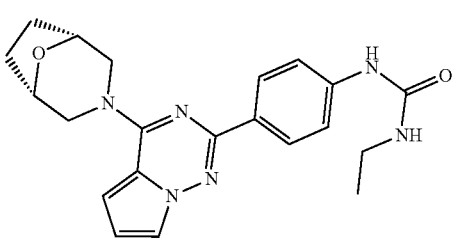
Example 9
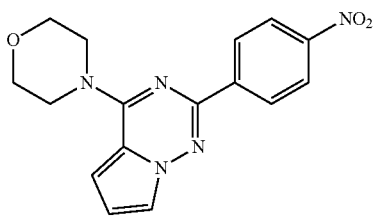
Example 10
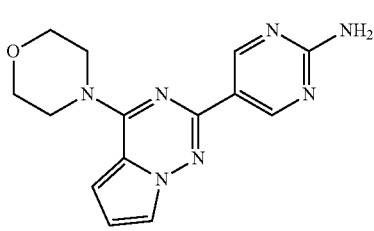
Example 11
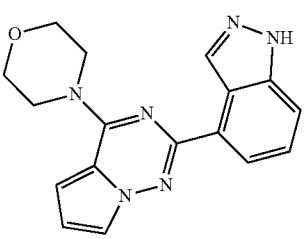
Example 12
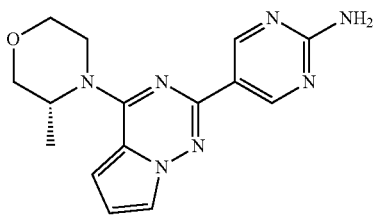
Example 13
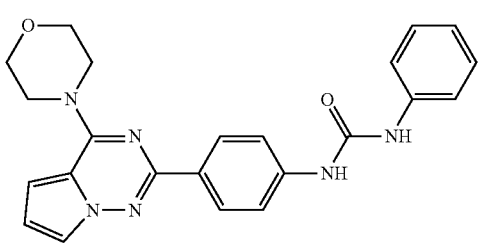

-continued

Example 14

Example 15

Example 16

Example 17

Example 18

Example 19

Example 20

Example 21

Example 22

Example 23

Example 24

Example 25

Example 26
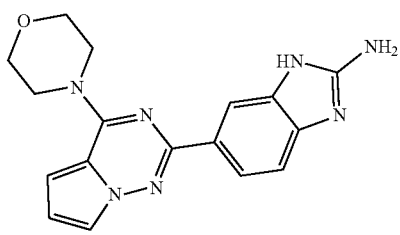
Example 27
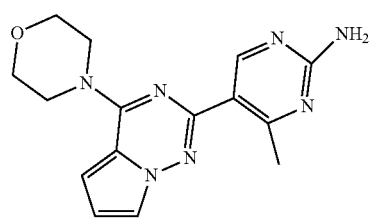
Example 28
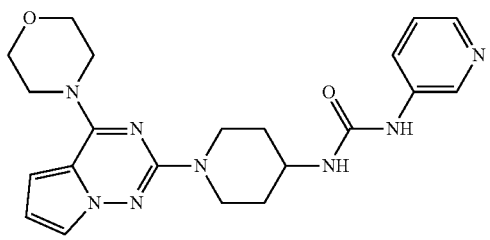
Example 29
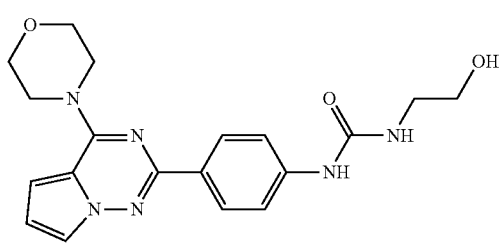
Example 30
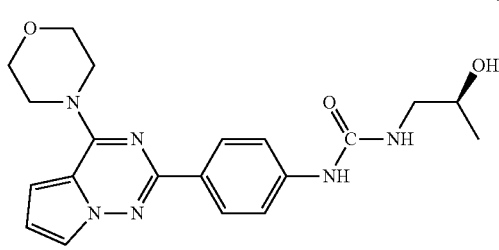
Example 31
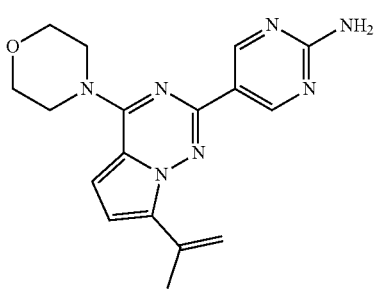
Example 32
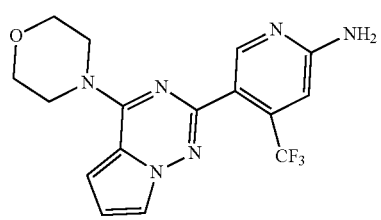
Example 33
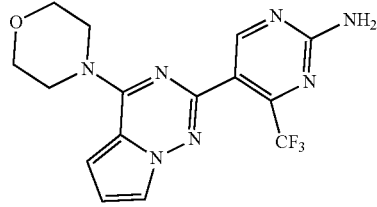
Example 34
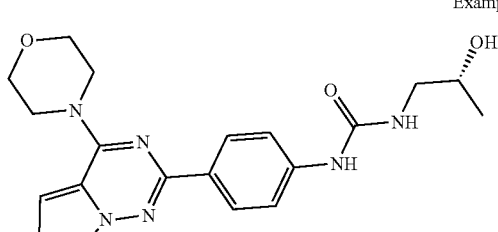
Example 35
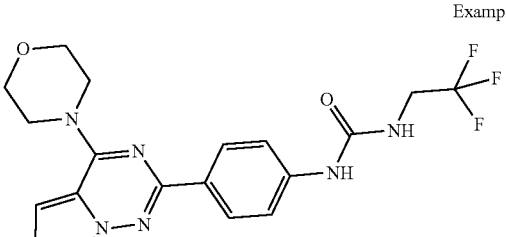
Example 36
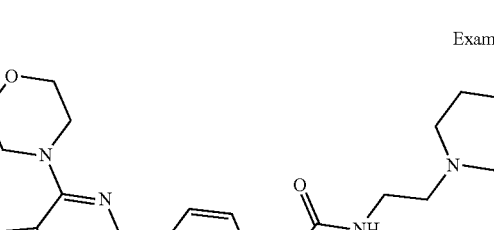
Example 37
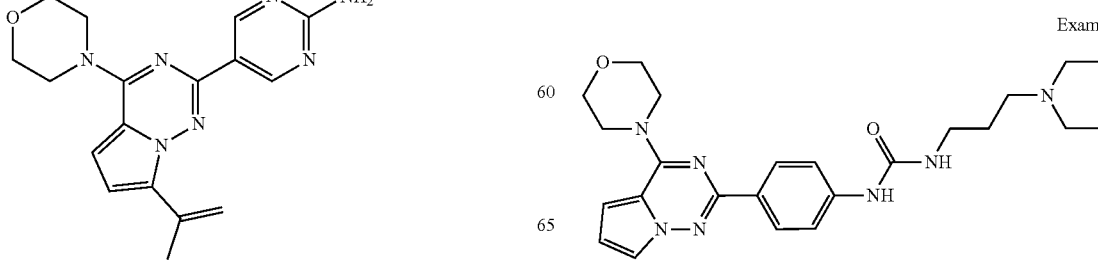

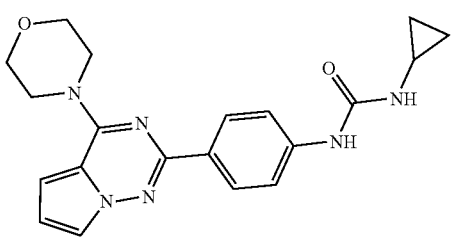
Example 38
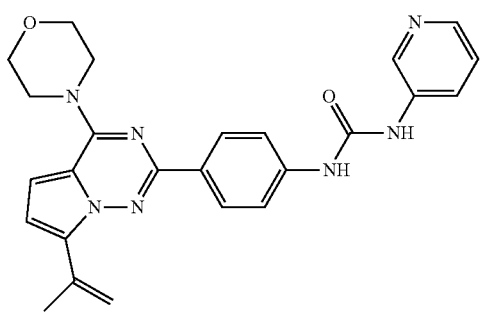
Example 39
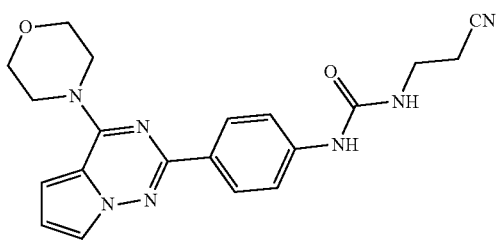
Example 40
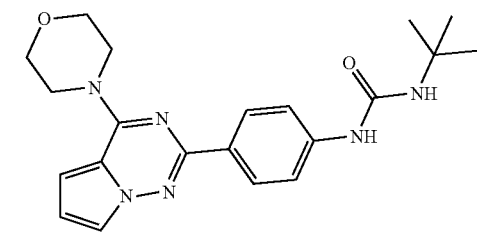
Example 41
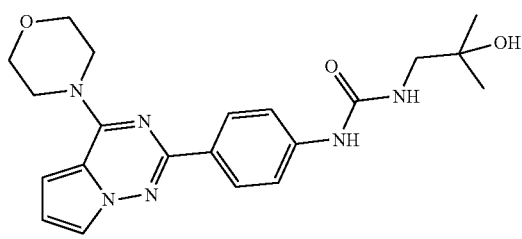
Example 42
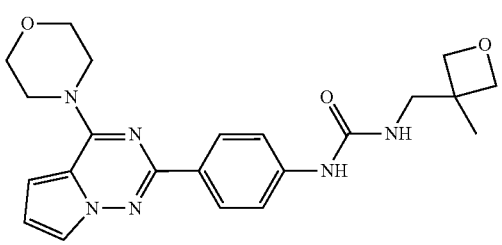
Example 43
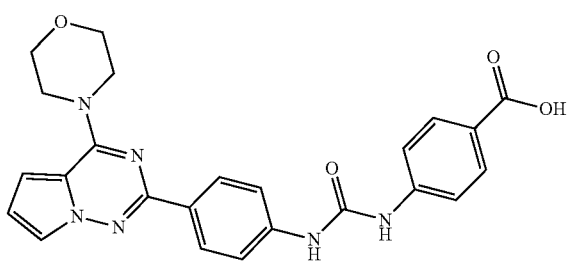
Example 44
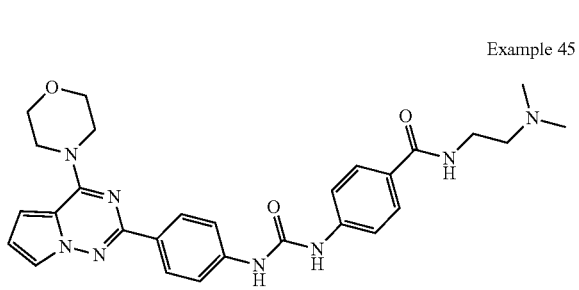
Example 45
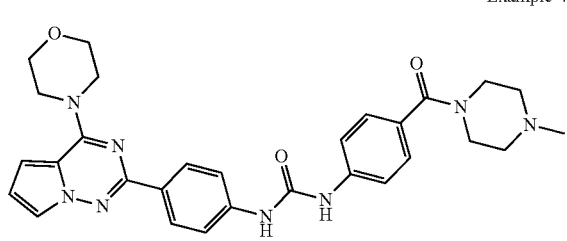
Example 46
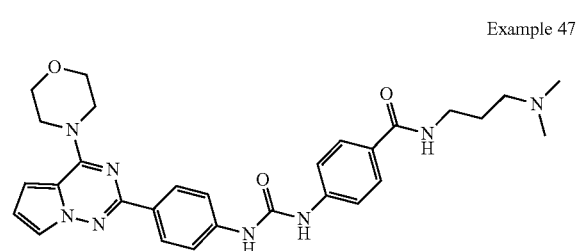
Example 47
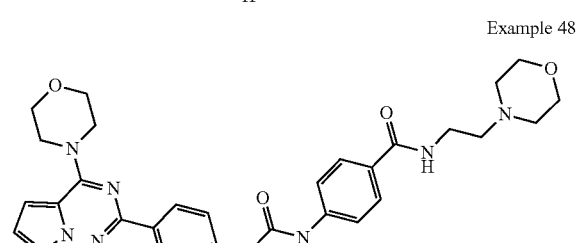
Example 48
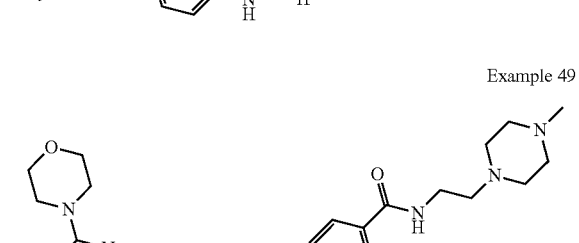
Example 49

Example 50
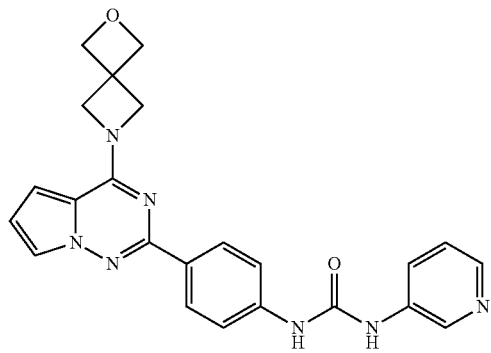
Example 55
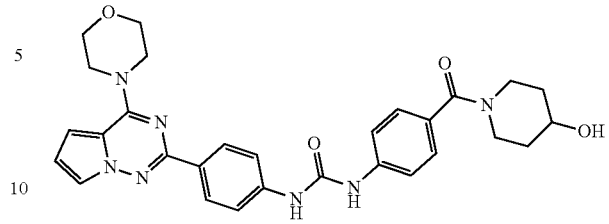
Example 51
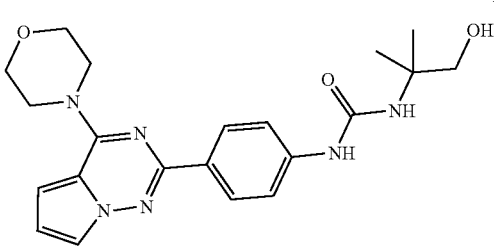
Example 56
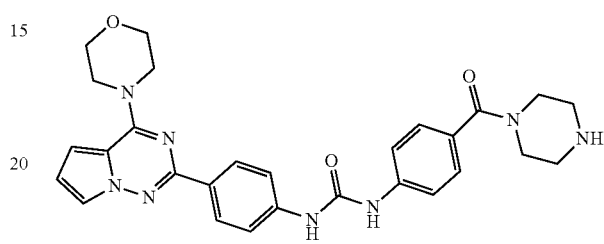
Example 52
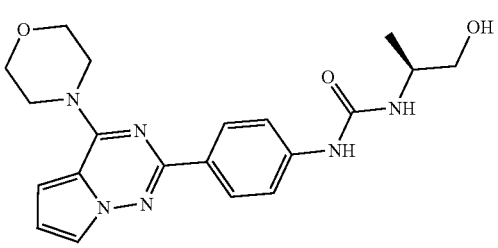
Example 57
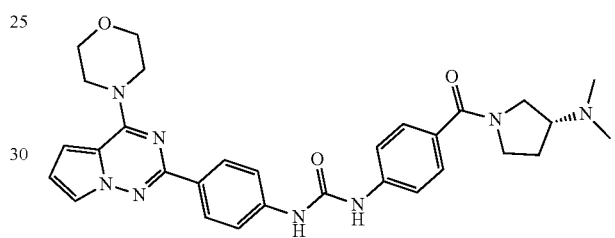
Example 53
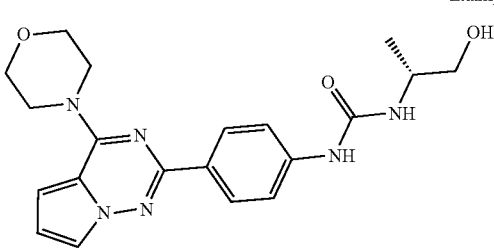
Example 58
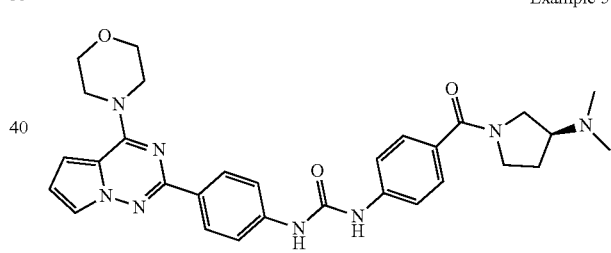
Example 54
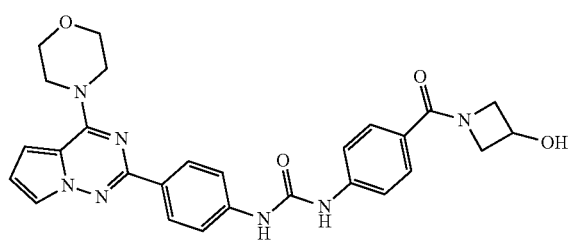
Example 59
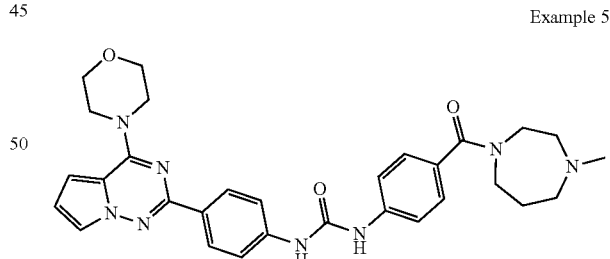
Example 60
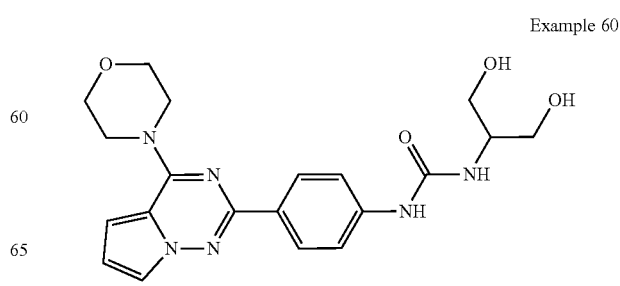

-continued
Example 61
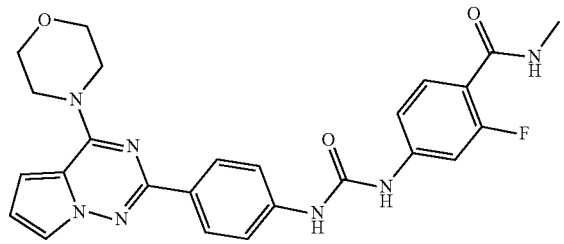
Example 62
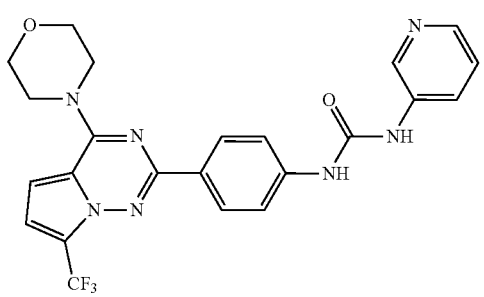
Example 63
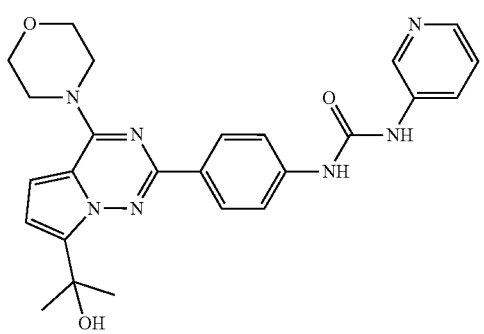
Example 64
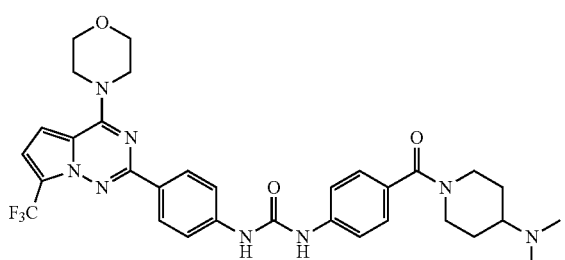
Example 65
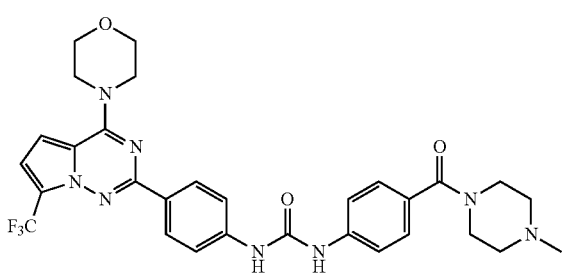
Example 66
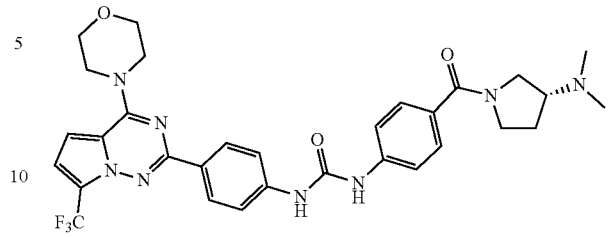
Example 67
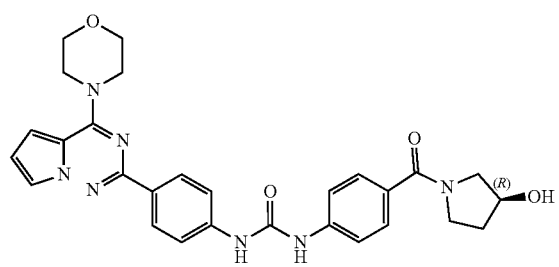
Example 68
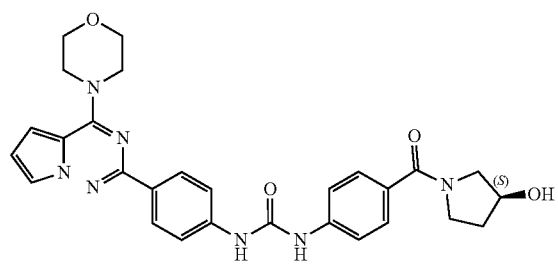
Example 69
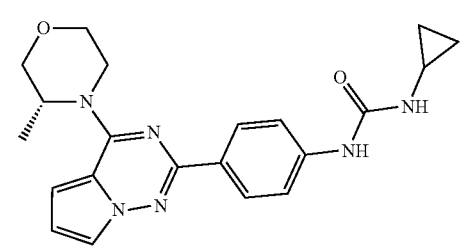
Example 70
Example 71
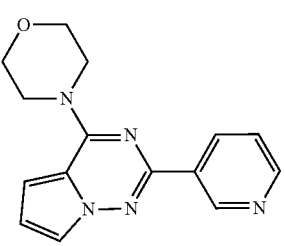

-continued
Example 72
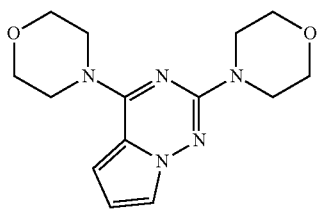
Example 73
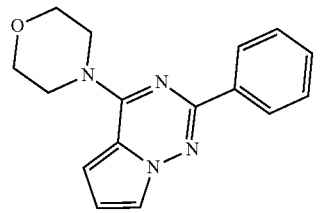
Example 74
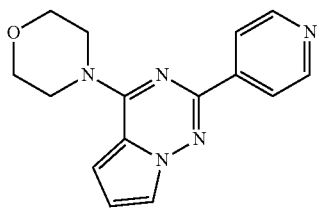
Example 75
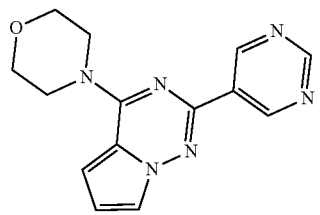
Example 76
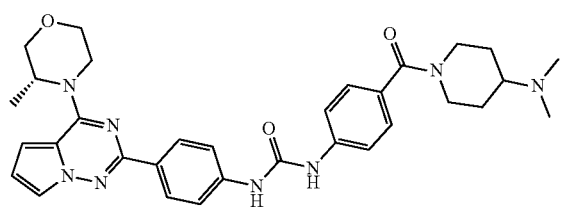
Example 77
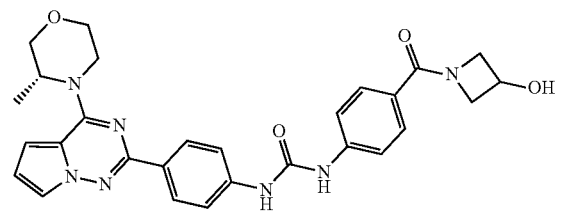
-continued
Example 78
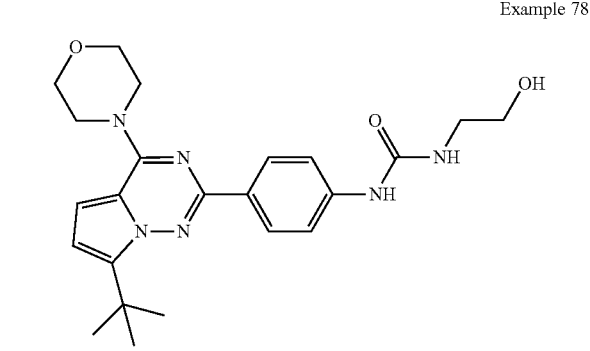
Example 79
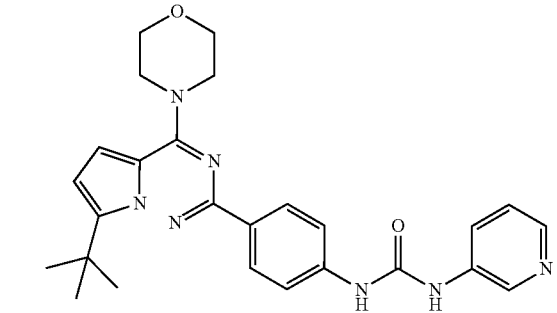
Example 80
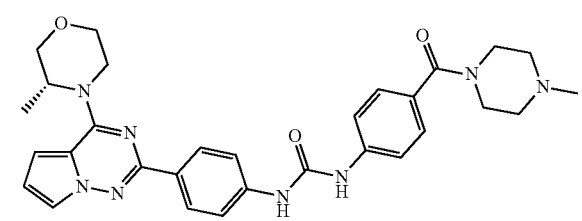
Example 81
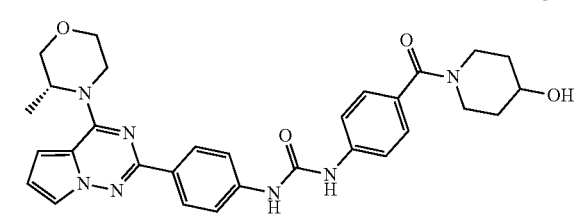
Example 82
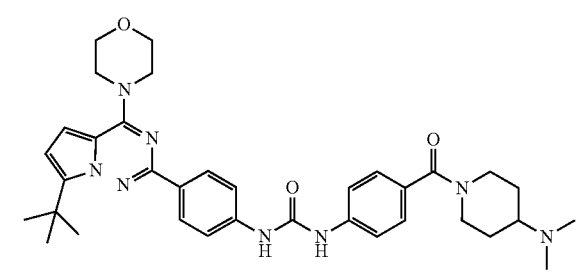

Example 83
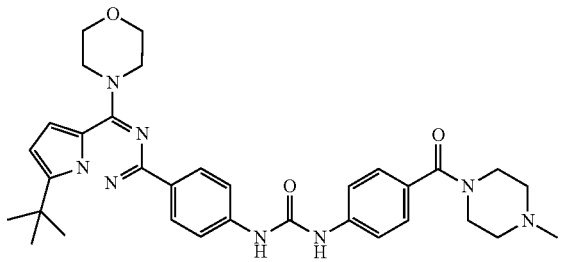
Example 84
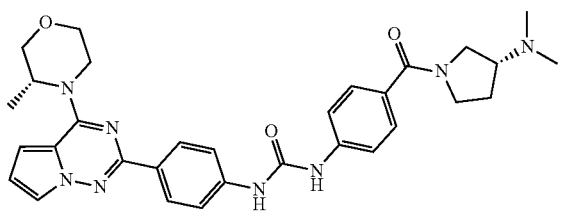
Example 85
Example 86
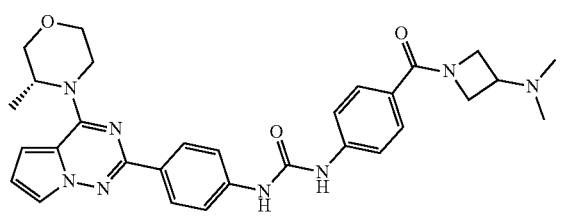
Example 87
Example 88
Example 89
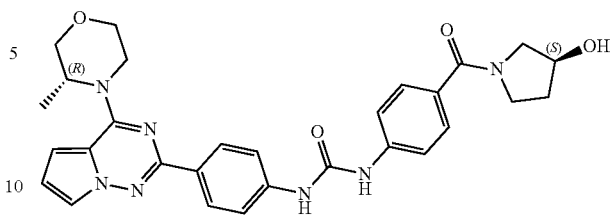
Example 90
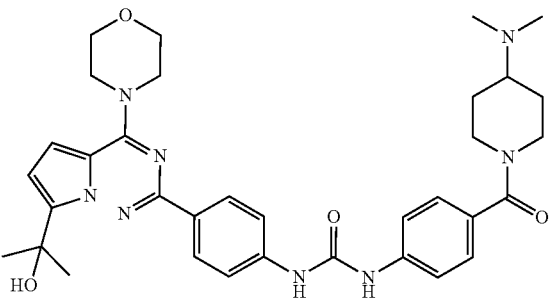
Example 91
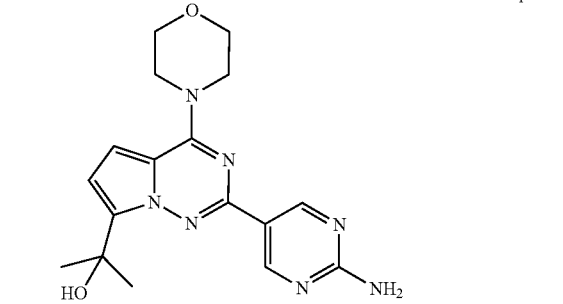
Example 92
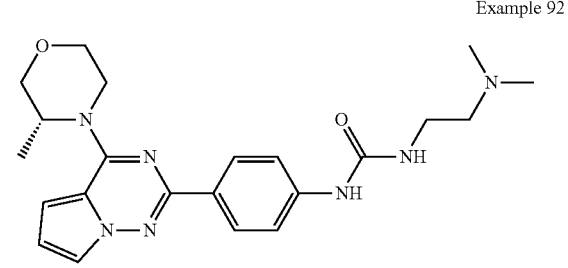
Example 93
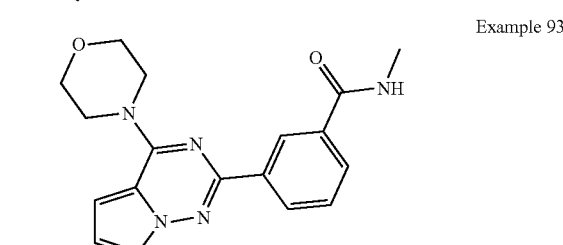
Example 94
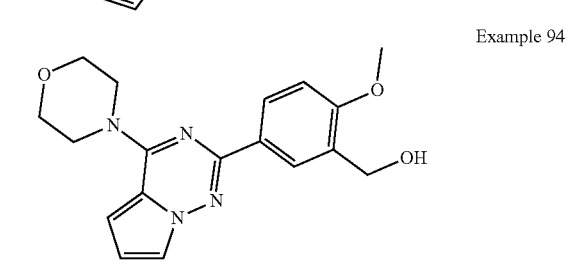

Example 95
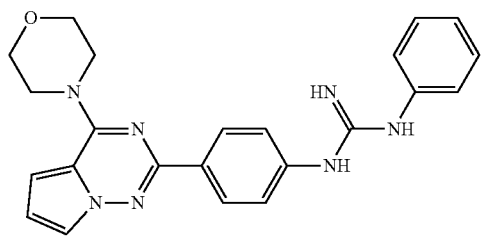
Example 96
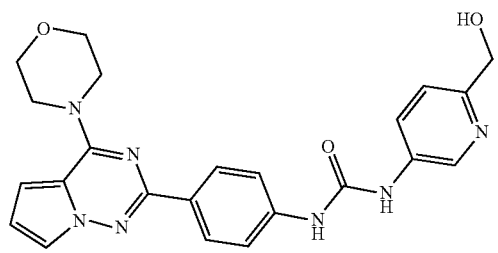
Example 97
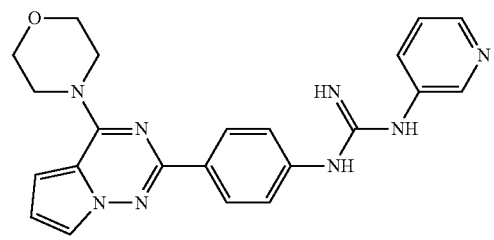
Example 98
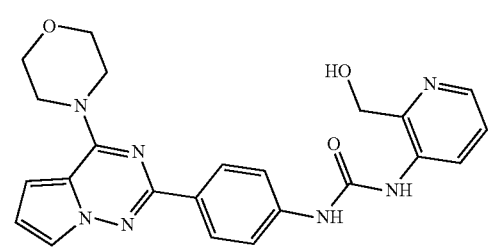
Example 99
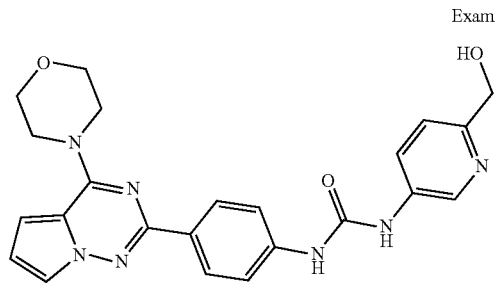
Example 100
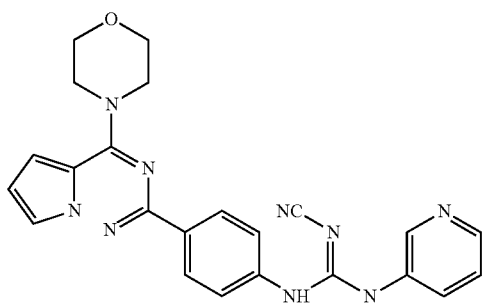
Example 101
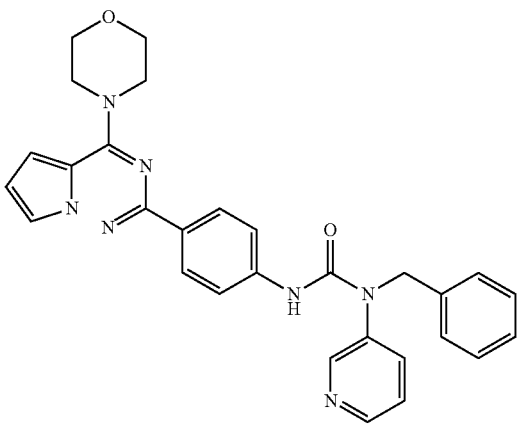
Example 102
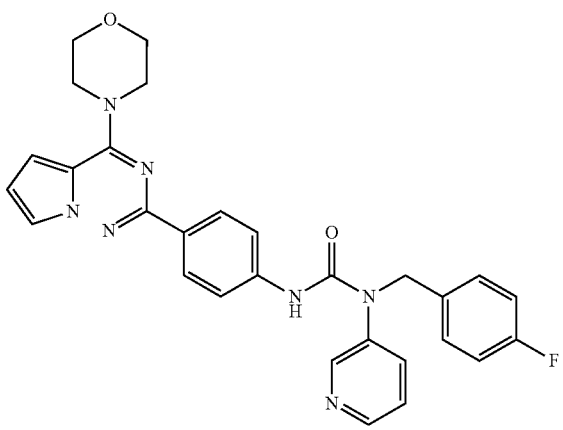
Example 103
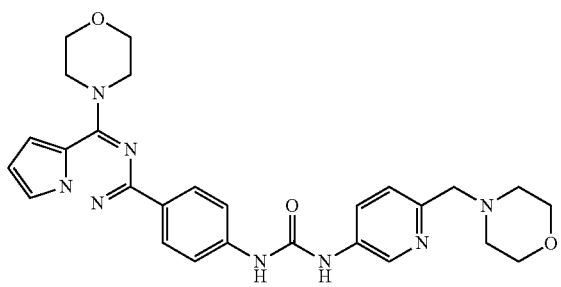

Example 104
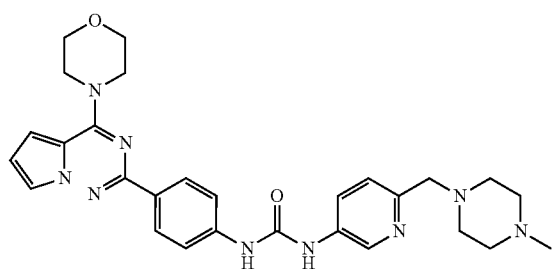
Example 105
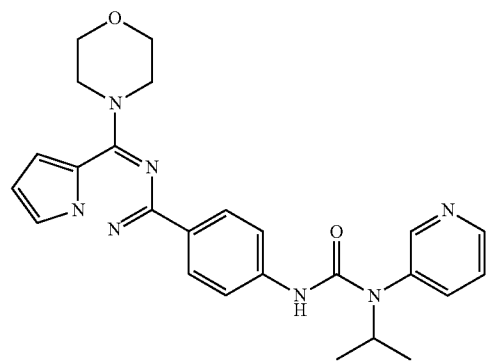
Example 106
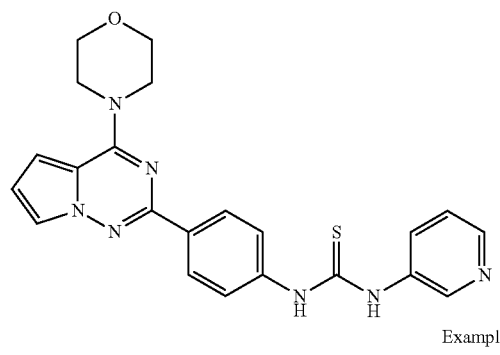
Example 107
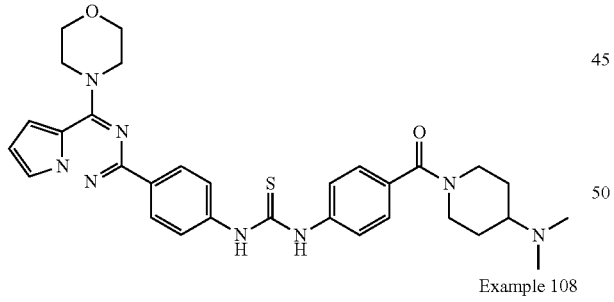
Example 108
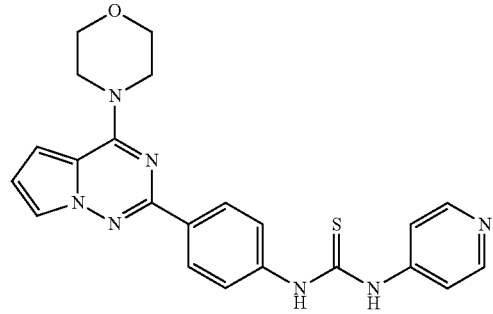
Example 109
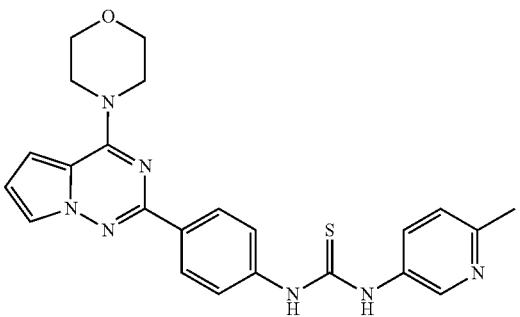
Example 110
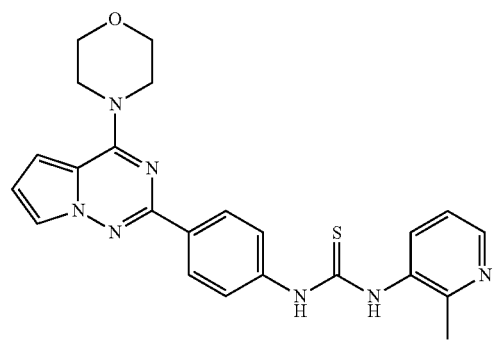
Example 111
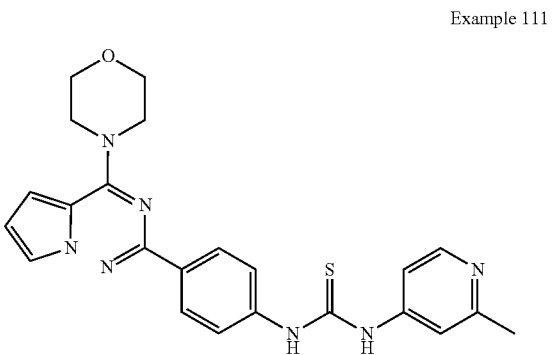
Example 112
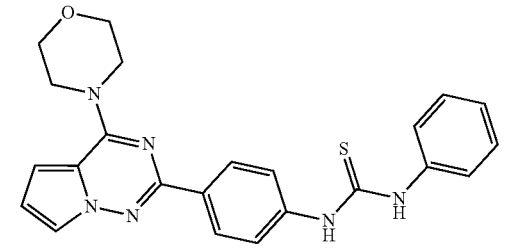
Example 113
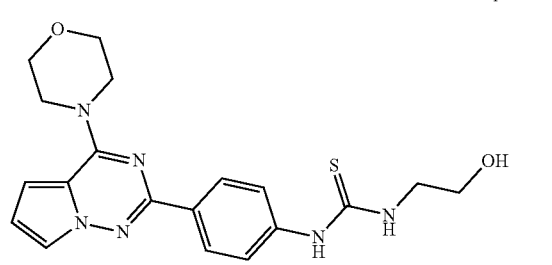

Example 114
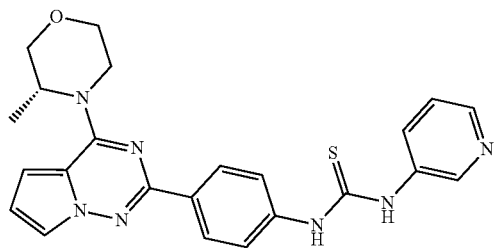
Example 115
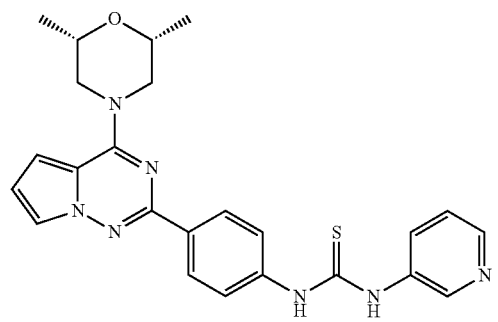
Example 116
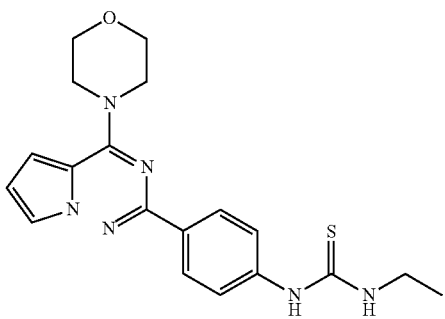
Example 117
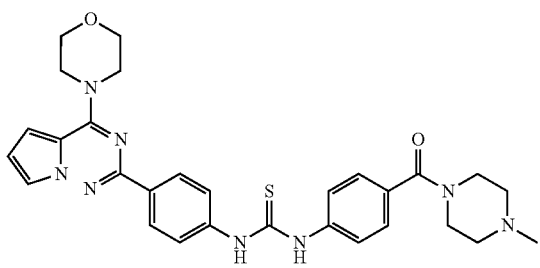
Example 118
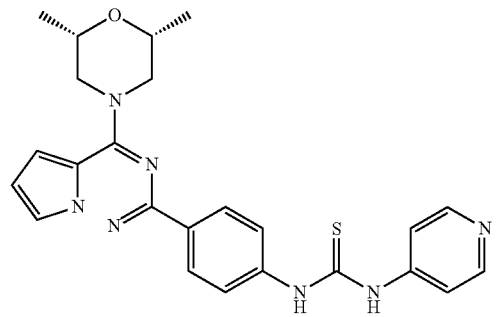
Example 119
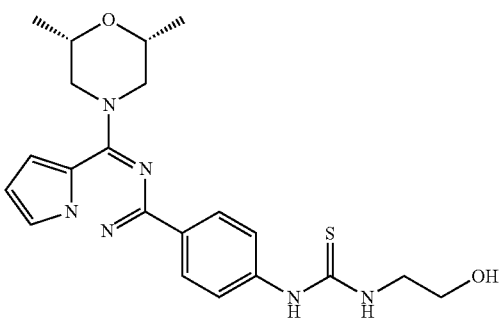
Example 120
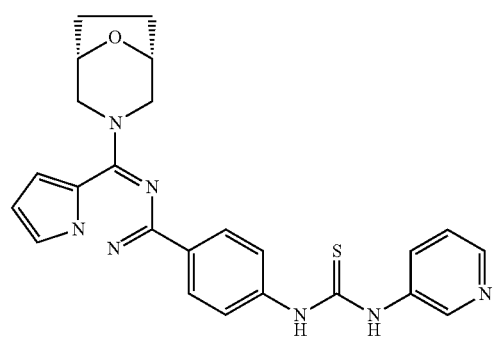
Example 121
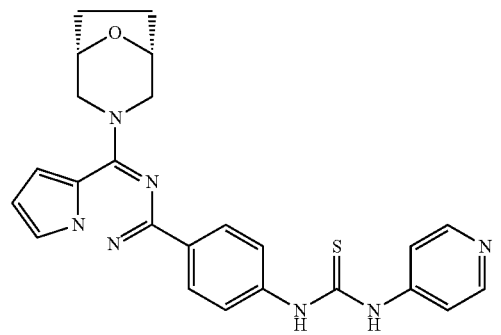
Example 122
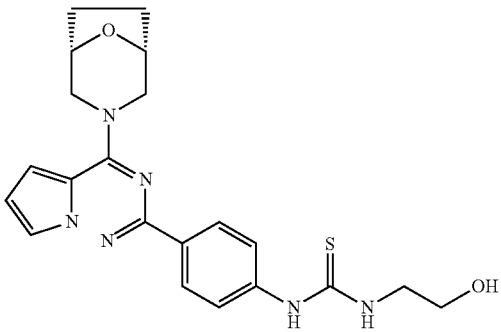

Example 123
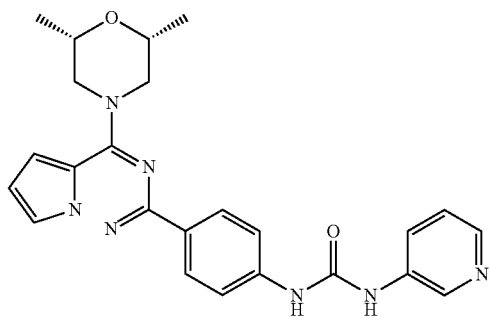
Example 124
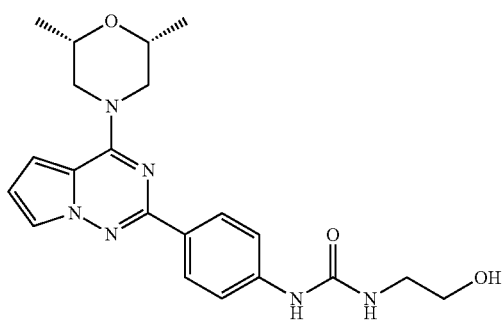
Example 125
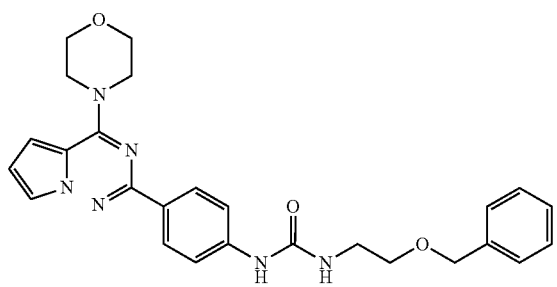
Example 126
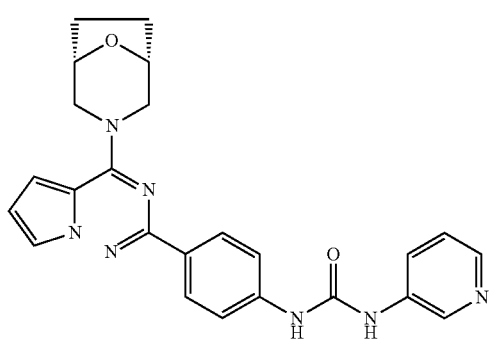
Example 127
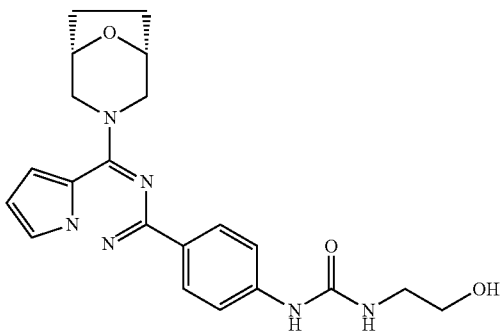
Example 128
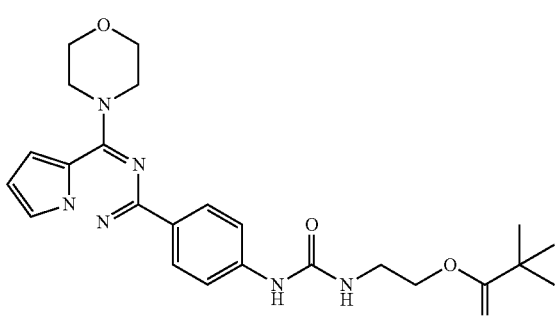
Example 129
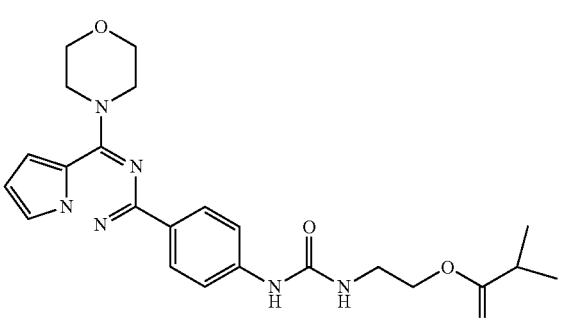
Example 130
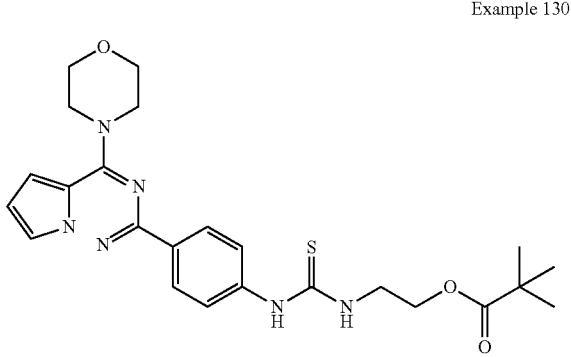

Example 131

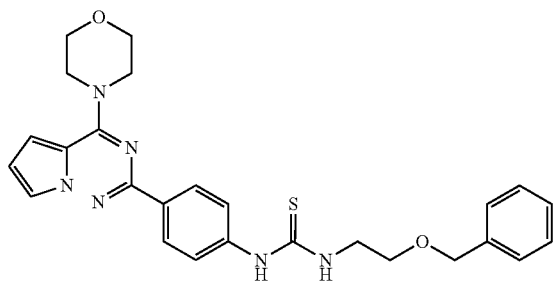

Example 132

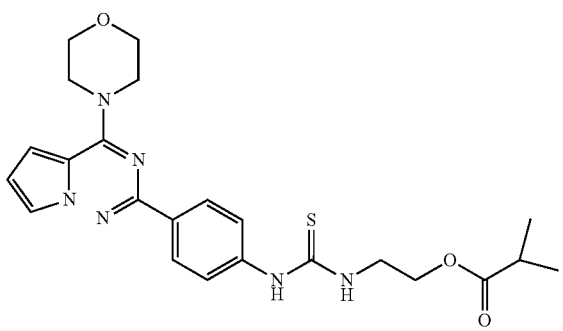

Example 133

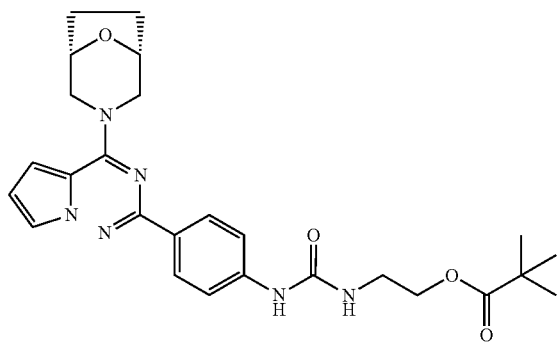

Example 134

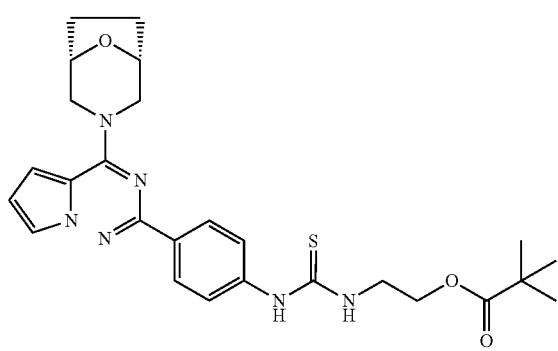

Example 135

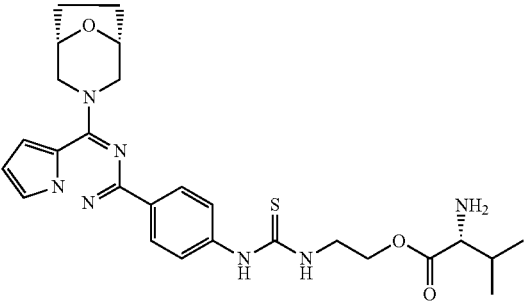

In some embodiments of aspects provided herein, at least one hydrogen of the compound is replaced with a deuterium. In some embodiments, at least one hydrogen at the bridged ring, pyrrole ring or ethylene group is replaced with a deuterium.

One aspect of the present disclosure provides a method for synthesizing compounds of formulas (I)-(III).

Still another aspect of the present disclosure provides a pharmaceutical composition comprising a compound of formulas (I)-(III) or a pharmaceutically acceptable salt thereof and a pharmaceutically acceptable carrier.

In some embodiments of aspects provided herein, a method is disclosed for treating a disease or disorder related to mTOR inhibition comprising administering a pharmaceutical composition comprising a compound of formulas (I)-(III) or a pharmaceutically acceptable salt thereof. In some embodiments of aspects provided herein, a method is disclosed for treating a disease or disorder related to mTOR inhibition comprising administering a pharmaceutical composition according to comprising a compound of formulas (I)-(III) or a pharmaceutically. In some embodiments of aspects provided herein, a method is disclosed for treating a disease or disorder related to selective mTOR inhibition. In some embodiments of aspects provided herein, a method is disclosed for related to inhibiting ATP-binding proteins including PI3K kinases. In some embodiments of aspects provided herein, the ATP-binding proteins include PI3K kinases. In some embodiments of aspects provided here, the disorder is related hyperplasia related to PI3K pathway dysregulation. In some embodiments of aspects provided here, the disorder is related hyperplasia related to mTOR pathway dysregulation. In some embodiments of aspects provided here, the disorder is related hyperplasia.

Definitions

All terms are intended to be understood as they would be understood by a person skilled in the art. Unless defined otherwise, all technical and scientific terms used herein have the same meaning as commonly understood by one of ordinary skill in the art to which the invention pertains. The following definitions supplement those in the art and are directed to the present disclosure and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a molecule" includes a plurality of such molecules, and the like.

The term "about" or "nearly" as used herein generally refers to within +/−15%, 10%, 9%, 8%, 7%, 6%, 5%, 4%, 3%, 2%, or 1% of the designated amount.

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms.

As used herein, the term "alkyl" refers to a straight or branched chain saturated aliphatic hydrocarbon. Alkyl groups include groups having from 1 to 8 carbon atoms ($C_{1-8}$ alkyl), from 1 to 6 carbon atoms ($C_{1-6}$ alkyl) and from 1 to 4 carbon atoms ($C_{1-4}$ alkyl), including, for example, methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. In some instances, a substituent of an alkyl group is specifically indicated. For example, "cyanoalkyl" refers to an alkyl group substituted with at least one cyano substituent.

"Alkenyl" refers to straight or branched chain alkene groups, which comprise at least one unsaturated carbon-carbon double bond. Alkenyl groups include $C_{2-8}$ alkenyl, $C_{2-6}$ alkenyl and $C_{2-4}$ alkenyl groups, which have from 2 to 8, 2 to 6 or 2 to 4 carbon atoms, respectively, including, for example, ethenyl, allyl or isopropenyl. "Alkynyl" refers to straight or branched chain alkyne groups, which have one or more unsaturated carbon-carbon bonds, at least one of which is a triple bond. Alkynyl groups include $C_{2-8}$ alkynyl, $C_{2-6}$ alkynyl and $C_{2-4}$ alkynyl groups, which have from 2 to 8, 2 to 6 or 2 to 4 carbon atoms, respectively.

A "cycloalkyl" is a group that comprises one or more saturated rings in which all ring members are carbon, including, for example, cyclopropyl, cyclobutyl, cyclopentyl, cyclohexyl, cycloheptyl, cyclooctyl, adamantyl. Cycloalkyl groups do not comprise an aromatic ring or a heterocyclic ring. Certain cycloalkyl groups are $C_{3-7}$ cycloalkyl, in which the cycloalkyl group contains a single ring having from 3 to 7 ring members, all of which are carbon. A "cycloalkenyl" is a group that comprises one or more unsaturated rings in which all ring members are carbon.

"Alkoxy" is meant an alkyl group as described above attached via an oxygen bridge. Alkoxy groups include $C_{1-6}$ alkoxy and $C_{1-4}$ groups, which have from 1 to 6 or from 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups.

"Alkylamino" refers to a secondary or tertiary amine that has the general structure —NH-alkyl or —N(alkyl)(alkyl), wherein each alkyl is selected independently from alkyl, cycloalkyl and (cycloalkyl)alkyl groups. Such groups include, for example, mono- and di-($C_{1-6}$ alkyl)amino groups, in which each $C_{1-6}$ alkyl may be the same or different. It will be apparent that the definition of "alkyl" as used in the term "alkylamino" differs from the definition of "alkyl" used for all other alkyl-containing groups, in the inclusion of cycloalkyl and (cycloalkyl)alkyl groups.

"Halogen" means fluorine, chlorine, bromine, and iodine. A "haloalkyl" is an alkyl group that is substituted with 1 or more independently chosen halogens (e.g., "$C_{1-6}$ haloalkyl" groups have from 1 to 6 carbon atoms and at least one halogen). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl.

A "heteroaryl" is an aromatic group in which at least one aromatic ring comprises at least one heteroatom selected from N, O and S. Heteroaryls include, for example, 5-12 membered heteroaryls. Examples included but are not limited to imidazole, furan, furazan, isothiazole, isoxazole, oxadiazole, oxazole, pyrazine, pyrazole, pyridazine, pyridine, pyrimidine, tetrazole, thiazole and thiophene.

The term "heterocyclic" refers to a ring structure containing 3-12 ring atoms, in which at least one ring atom is carbon and at least one ring atom is heteroatom selected from N, O, and S. A heterocyclic group may be aromatic or non-aromatic. Piperidine and oxetane are non-limiting examples of non-aromatic heterocycles. Thiazole and pyridine are non-limiting examples of aromatic heterocycles.

A "substituent" and "substituted," as used herein, denote that a molecular moiety is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as deuterium and carbon such as $^{13}C$. Substitution with heavier isotopes such as deuterium may afford certain therapeutic advantages resulting from greater metabolic stability; for example, increased in vivo half-life or reduced dosage requirements, and hence may be preferred in some circumstances.

Deuterium (D or $^2H$) is a non-radioactive, stable isotope of hydrogen, the natural abundance of deuterium is about 0.015%. A compound should be considered to be unnatural, if its level of deuterium has been enriched to be greater than the natural abundance level of 0.015%. In a compound of this invention, it is understood that the abundance of deuterium is substantially greater than the natural abundance of deuterium, which is 0.015%, when a particular position is designated as deuterium. A position designated as deuterium typically has a minimum isotopic enrichment factor of at least 3000 at each atom designated as deuterium in said compound. The concentration of naturally abundant stable hydrogen is small and immaterial compared to the degree of stable isotopic substitution of compounds of this invention.

The term "pharmaceutically acceptable" when used with reference to a compound of formula I is intended to refer to a form of the compound that is safe for administration to a subject. For example, a free base, a salt form, a solvate, a hydrate, a prodrug or derivative form of a compound of formula I, which has been approved for mammalian use, via oral ingestion or any other route of administration, by a governing authority or regulatory agency, such as the Food and Drug Administration (FDA) of the United States, is pharmaceutically acceptable.

Included in the compounds of formula I are the pharmaceutically acceptable salt forms of the free-base compounds. The term "pharmaceutically-acceptable salts" embraces salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

In some embodiments, the compound(s) of formula I is used to treat a subject by administering the compound(s) as a pharmaceutical composition. To this end, the compound(s), in one embodiment, is combined with one or more pharmaceutically acceptable excipients, including carriers, diluents or adjuvants, to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Regardless of the route of administration selected, the compounds of the present invention, which may be used in a suitable hydrated form, and/or the pharmaceutical compositions of the present invention, are formulated into pharmaceutically acceptable dosage forms or by other conventional methods known to those of skill in the art.

Actual dosage levels of the active ingredients in the pharmaceutical compositions of the present invention may be varied so as to obtain an effective amount of the active ingredient to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular hedgehog inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. The mode of administration can have a large effect on dosage. Higher doses may be used for localized routes of delivery.

This disclosure includes a drug which comprises the compound or a pharmaceutically acceptable salt, prodrug or solution thereof according to any one of formulas (I)-(III) as an active ingredient.

A method for treating a disease or disorder related to mTOR inhibition comprising administering a pharmaceutical composition containing any one of formulas (I)-(III) as an active ingredient.

A method for treating a disease or disorder related to selective mTOR inhibition comprising administering a pharmaceutical composition containing any one of formulas (I)-(III) as an active ingredient.

A method for treating a disease or disorder related to selective mTOR inhibition comprising orally administering a pharmaceutical composition containing any one of formulas (I)-(III) as an active ingredient.

A method for treating a disease or disorder related to inhibiting ATP-binding proteins such as PI3K kinases, comprising administering a pharmaceutical composition containing any one of formulas (I)-(III) as an active ingredient.

A method for treating a disease or disorder related to inhibiting ATP-binding proteins such as protein kinases, comprising administering a pharmaceutical composition containing any one of formulas (I)-(III) as an active ingredient.

A method of treatment using a pharmaceutical composition containing any one of formulas (I)-(III) as an active ingredient, wherein the disorder is related hyperplasia related to PI3K pathway dysregulation.

A method of treatment using a pharmaceutical composition containing any one of formulas (I)-(III) as an active ingredient, wherein the disorder is related hyperplasia related to mTOR pathway dysregulation.

A method of treatment using a pharmaceutical composition contains any one of formulas (I)-(III) as an active ingredient, wherein the disorder is related hyperplasia.

If desired, the effective daily dose of the active compound may be administered as two, three, four, five, six or more sub-doses administered separately at appropriate intervals throughout the day, optionally, in unit dosage forms. Those of skill in the art will readily appreciate that dose levels can vary as a function of the specific compound, the severity of the symptoms and the susceptibility of the subject to side effects. Dosages for a given compound disclosed herein are readily determinable by those of skill in the art by a variety of means.

Synthetic Methods

The size and scale of the synthetic methods will vary depending on the desired amount of end product. It is understood that while specific reactants and amounts are provided in the Examples, one of skill in the art knows other alternative and equally feasible sets of reactants that will also yield the same compounds. Thus, where general oxidizers, reducers, solvents of various nature (aprotic, apolar, polar, etc.) are utilized, equivalents will be known in the art and are herein contemplated for use in the present methods Many of the steps below indicate various work-ups following termination of the reaction. A work-up involves generally quenching of a reaction to terminate any remaining catalytic activity and starting reagents. This is generally followed by addition of an organic solvent and separation of the aqueous layer from the organic layer. The product is typically obtained from the organic layer and unused reactants and other spurious side products and unwanted chemicals are generally trapped in the aqueous layer and discarded. The work-up in standard organic synthetic procedures found throughout the literature is generally followed by drying the product by exposure to a drying agent to remove any excess water or aqueous byproducts remaining partially dissolved in the organic layer and concentration of the remaining organic layer. Concentration of product dissolved in solvent may be achieved by any known means, such as evaporation under pressure, evaporation under increased temperature and pressure, and the like. Such concentrating may be achieved by use of standard laboratory equipment such as rotary-evaporator distillation, and the like. This is optionally followed by one or more purification steps which may include, but is not limited to, flash column chromatography, filtration through various media and/or other preparative methods known in the art and/or crystallization/recrystallization. (See, for instance, Addison Ault, "Techniques and Experiments for Organic Chemistry," 6th Ed., University Science Books, Sausalito, Calif., 1998, Ann B. McGuire, Ed., pp. 45-59).

The compounds of formula I-III of the invention can be prepared as shown in the following reaction schemes and description thereof.

As shown in Scheme 1, 2' can be prepared from 1 and 1a via a standard basic SNAr displacement where the base can be selected (not limited to) from triethylamine, diisopropylethylamine, potassium carbonate, cesium carbonate or CsF and the solvent can be selected (not limited to) from isopropanol, toluene, ethanol, DMSO, DMA or NMP. The final compound 4' can be synthesized by coupling the chloride 2' with a boronic acid or ester 3' under Suzuki conditions. The palladium catalyst can be selected from a number of commercially available palladium catalysts such as Pd(dppb)Cl$_2$. The Ar group here can be either an aryl or a heteroaryl. The boronic acid or ester 3' can be obtained commercially, or can be prepared from an aryl bromide or aryl iodide by methods reported in the literature. Dichloride 1 can be obtained commercially, or can be prepared by methods known in the literature or by the method described in Scheme 2.

Scheme 2: Synthesis of 2,4-Dichloro-pyrrolo[2,1-f][1,2,4]triazine (1).

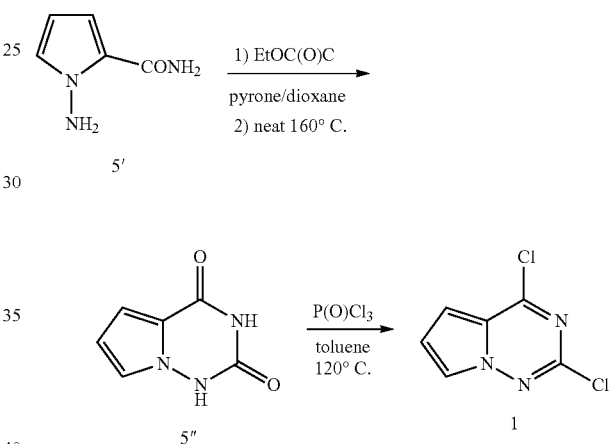

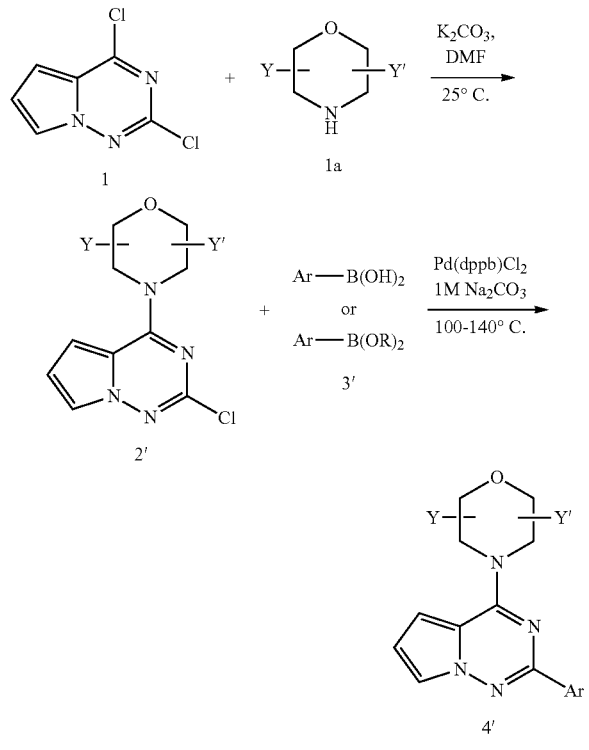

A mixture of 1-amino-1H-pyrrole-2-carboxylic acid amide 5 (1.46 g, 11.7 mmol, prepared according to J. Heterocyclic Chem. 31, 781 (1994)) and dry pyridine (1.1 mL) in 1,4-dioxane (15 mL) was added ethyl chloroformate (1.2 mL, 1.3 mmol) dropwise at 25° C. The reaction mixture was heated at reflux for 2 h, cooled down and concentrated in vacuo. The resulting residue was heated at 160° C. for 12 h. The cooled residue was triturated with methanol (2×5 mL). Filtered and dried in vacuo. Intermediate 5" was obtained as a tan solid (1.2 g, 65% yield). MS: 152 (M+H$^+$).

To a co-solvent of diisopropylethylamine (4.5 mL) and toluene (20 mL) was added intermediate 5" (1.6 g, 10.4 mmoL) and POCl$_3$ (2.94 mL). The mixture was heated at 120° C. in a sealed tube for 20 h, then poured into an ice-cooled saturated sodium bicarbonate solution (50 mL). Stirred for 15 min. Extracted with CH$_2$Cl$_2$ (3×50 mL). Combined organic layers were washed with brine (1×50 mL), dried (MgSO$_4$) and concentrated. Column chromatography purification (50-100% CH$_2$Cl$_2$ in hexanes) afforded the desired dichloride 1 as a light brown solid (1.2 g, 86% yield). $^1$H NMR (CDCl$_3$): δ 6.98 (1H, m), 7.05 (1H, m), 7.86 (1H, m); MS: 187 (M+H$^+$).

General scheme 1

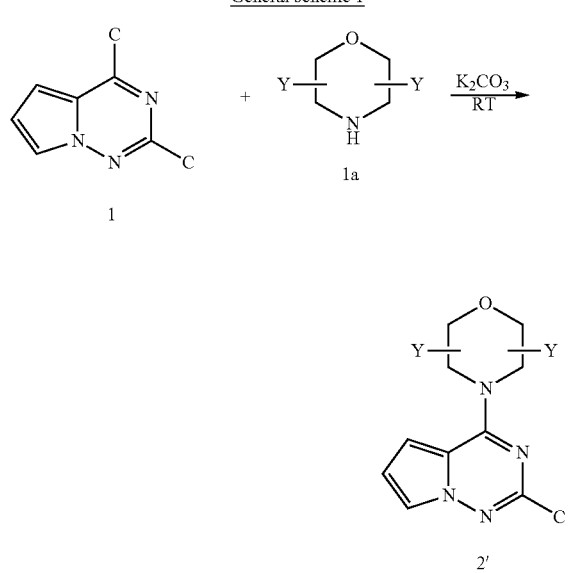

Synthesis of Compound 2

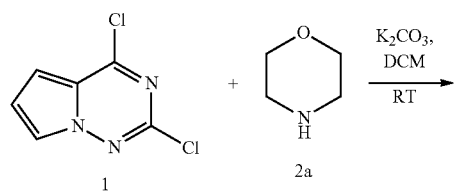

A mixture of 2,4-dichloropyrrolo[1,2-f][1,2,4]triazine (5.5 g, 29.3 mmol), morpholine (2.8 mL, 32.2 mmol) and $K_2CO_3$ (8.0 g, 58.6 mmol) in DCM (50 mL) was stirred at room temperature for 3 h. The TLC showed the starting material was completely consumed and $H_2O$ (50 mL) was added. The mixture was extracted with DCM (50 mL*2). The combined organic layers were washed with brine, dried over $Na_2SO_4$ and concentrated in vacuo to obtain 6.5 g of compound 2, yield in 93%. $^1$H NMR (CDCl$_3$, 400 MHz): δ 7.58-7.57 (m, 1H), 6.74-6.72 (m, 1H), 6.64-6.62 (m, 1H), 4.05 (t, 4H, J=4.8 Hz), 3.84 (t, 4H, J=5.2 Hz). ESI-MS (M+H)$^+$: 239.

Synthesis of Compound 3

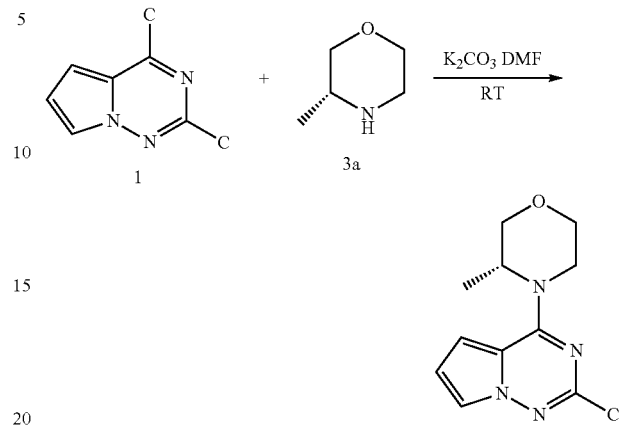

A mixture of 2,4-dichloropyrrolo[1,2-f][1,2,4]triazine (150 mg, 0.80 mmol), (R)-3-methylmorpholine hydrochloride (132 mg, 0.95 mmol) and $K_2CO_3$ (332 mg, 2.41 mmol) in DMF (5 mL) was stirred at room temperature for 3 h. The TLC showed the starting material was completely consumed and $H_2O$ (10 mL) was added to the mixture. The mixture was extracted with DCM (20 mL*2). The combined organic layers were washed with brine, dried over $Na_2SO_4$ and concentrated in vacuo to obtain 160 mg of compound 3, yield in 79.2%. $^1$H NMR (CDCl$_3$, 400 MHz): δ 7.50-7.49 (m, 1H), 6.66-6.65 (m, 1H), 6.56-6.54 (m, 1H), 4.78 (d, 1H, J=1.6 Hz), 4.52-4.49 (m, 1H), 3.97 (d, 1H, J=8 Hz), 3.76-3.67 (m, 2H), 3.59-3.47 (m, 2H), 1.42 (d, 3H, J=6.8 Hz). ESI-MS (M+H)$^+$: 253.

Synthesis of Compound 4

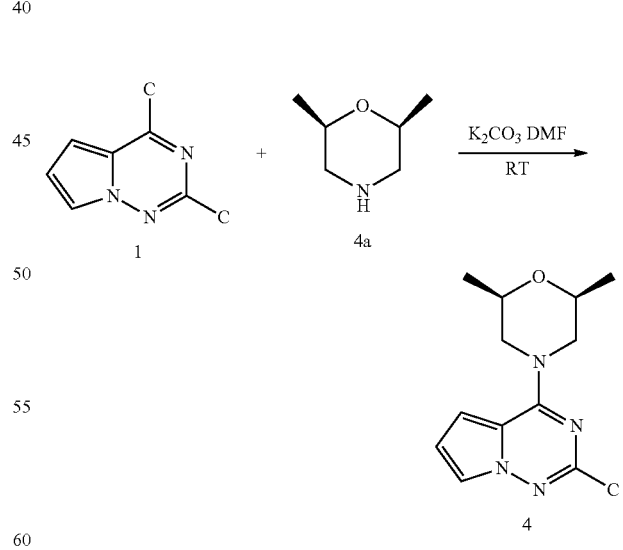

The procedure of compound 4 (140 mg, yield: 89.7%) was similar to that of compound 3.
$^1$H NMR (CDCl$_3$, 400 MHz): δ 7.60-7.59 (m, 1H), 6.77-6.76 (m, 1H), 6.67-6.65 (m, 1H), 4.69 (d, 2H, J=12.8 Hz), 3.79-3.71 (m, 2H), 2.99-2.91 (m, 2H), 1.32 (d, 6H, J=6.0 Hz).

Synthesis of Compound 5

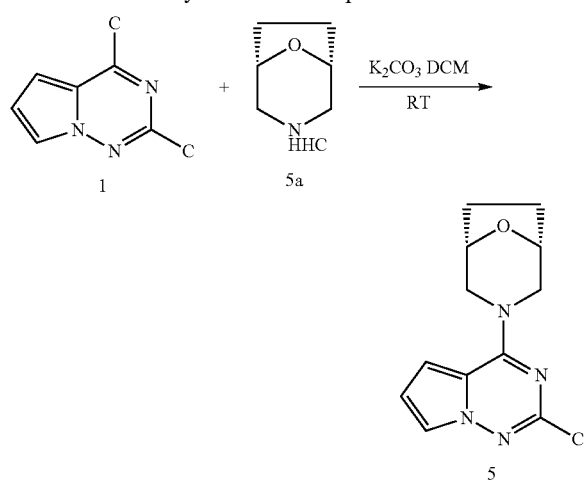

The procedure of compound 5 (140 mg, yield: 89.7%) was similar to that of compound 2. $^1$H NMR (CDCl$_3$, 400 MHz): δ 7.57 (s, 1H), 6.73-6.72 (m, 1H), 6.63-6.61 (m, 1H), 4.52-4.45 (m, 4H), 3.55-3.53 (m, 2H), 2.02-2.00 (m, 2H), 1.87-1.85 (m, 2H).

General Scheme 2

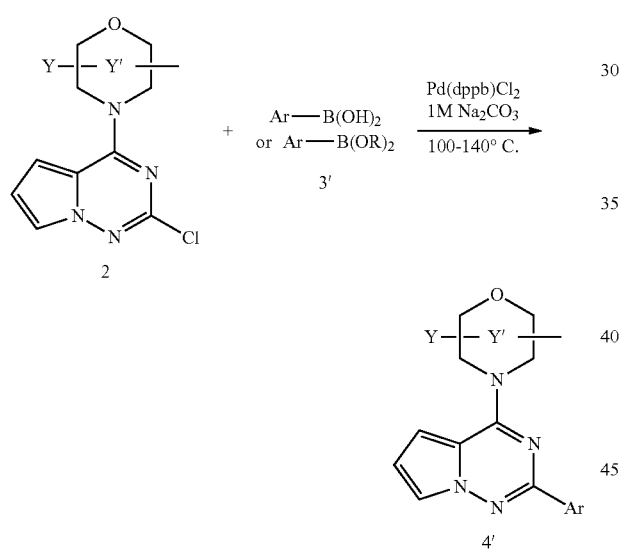

Synthesis of Example 1 (Method A)

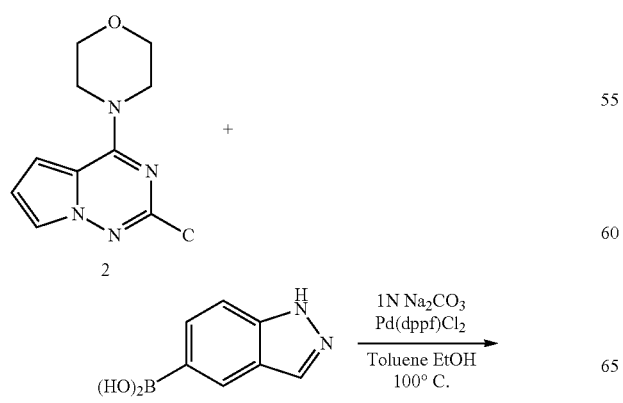

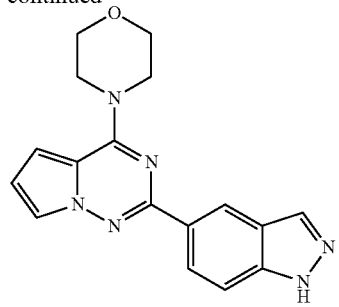

Example 1

A mixture of compound 2 (20 mg, 0.08 mmol), 1H-indazol-5-ylboronic acid (18 mg, 0.1 mmol) and Sodium bicarbonate solution (1M, 0.25 mL) in toluene (0.5 mL) and EtOH (0.15 mL) was added Pd(dppf)Cl$_2$ (3.5 mg) under N$_2$ and stirred at 120° C. for 24 h. Then the mixture was diluted with water (5 mL) and extracted with ethyl acetate (10×3 mL). The combined organic layers were washed with brine (10 mL), dried over Na$_2$SO$_4$ and concentrated in vacuo to dryness. The residue was purified by Pre-HPLC (PE:EA=1:1) to obtain 8 mg Example 1, yield in 29.8%. $^1$H NMR (CDCl$_3$, 400 MHz): δ 8.74 (s, 1H), 8.41 (d, 1H, J=8.8 Hz), 8.19 (s, 1H), 7.70 (s, 1H), 7.54 (d, 1H, J=8.8 Hz), 6.73-6.71 (m, 1H), 6.69-6.67 (m, 1H), 4.16 (t, 4H, J=4.8 Hz), 3.91 (t, 4H, J=4.8 Hz). ESI-MS (M+H)$^+$: 321.

Synthesis of Example 2 (Method A)

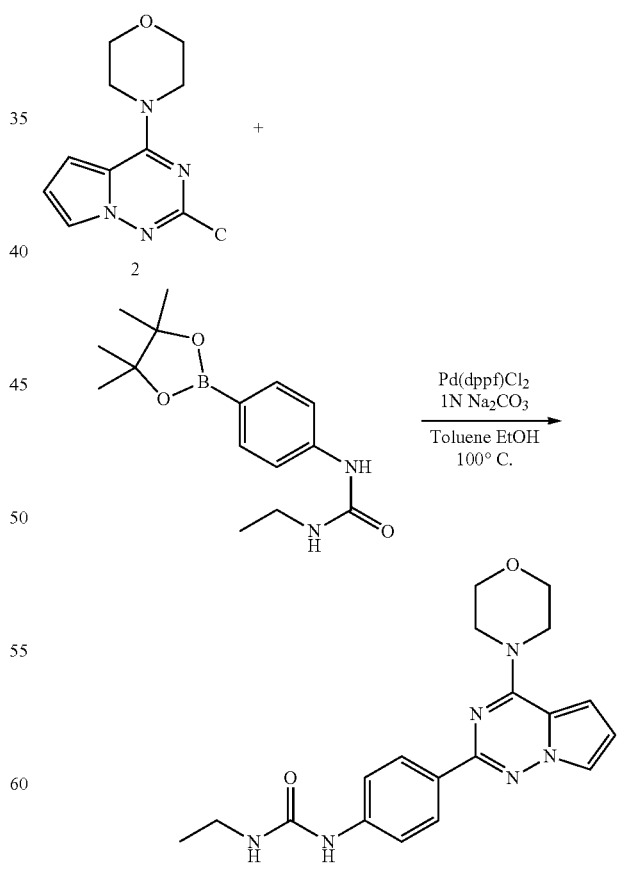

Example 2

Method A: used 20 mg of compound 2 to obtained 5 mg of Example 2, yield in 17.1%. $^1$H NMR (MeOD-d$_4$, 400

MHz): δ 8.16 (d, 2H, J=8.4 Hz), 7.68 (t, 1H, J=1.2 Hz), 7.45 (d, 2H, J=8.4 Hz), 6.92-6.90 (m, 1H), 6.71-6.69 (m, 1H), 4.14 (t, 4H, J=4.8 Hz), 3.88 (t, 4H, J=5.2 Hz), 3.27-3.23 (m, 2H), 1.82 (t, 3H, J=7.2 Hz). ESI-MS (M+H)⁺: 367.

Synthesis of Example 3 (Method A)

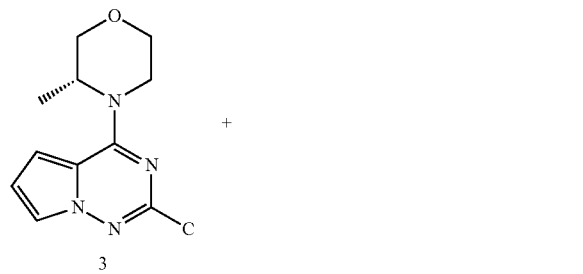

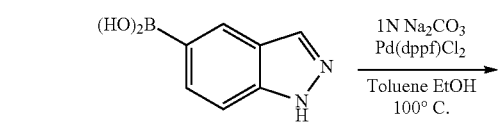

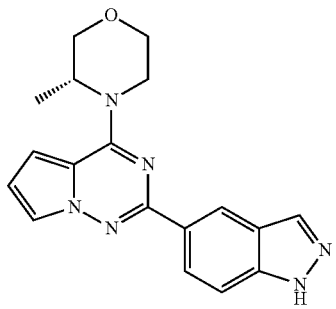

Example 3

Method A: used 20 mg of compound 3 to obtained 15 mg of Example 3, yield in 56.7%. ¹H NMR (CDCl₃, 400 MHz): δ 8.73 (s, 1H), 8.40 (d, 1H, J=8.0 Hz), 8.20 (d, 1H, J=0.8 Hz), 7.71 (s, 1H), 7.55 (d, 1H, J=8.0 Hz), 6.72 (s, 1H), 6.68 (s, 1H), 5.03 (d, 1H, J=1.6 Hz), 4.78-4.76 (m, 1H), 4.11 (d, 1H, J=8.8 Hz), 3.87 (s, 2H), 3.74-3.64 (m, 2H), 1.54 (d, 3H, J=5.6 Hz). ESI-MS (M+H)⁺: 335.

Synthesis of Example 4 (Method B)

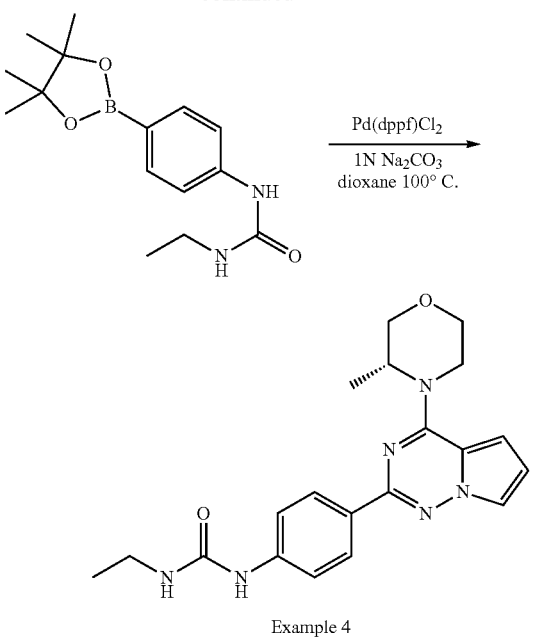

Example 4

A mixture of compound 3 (20 mg, 0.08 mmol), 1-ethyl-3-(4-(4,4,5,5-tetramethyl-1,3,2-dioxaborolan-2-yl)phenyl) urea (37 mg, 0.12 mmol) and Sodium bicarbonate solution (1N, 0.25 mL) in dioxane (0.75 mL) was added Pd(dppb)Cl₂ (3.5 mg, 0.004 mmol) under N₂ and stirred at 100° C. for 24 h. Then the mixture was diluted with water (5 mL) and extracted with ethyl acetate (3×3 mL). Combined organic layers were washed with brine (5 mL), dried over Na₂SO₄ and concentrated in vacuo to dryness. The residue was purified with silica gel column chromatography using Petroleum ether:Ethyl acetate (1:1) to obtain 13 mg Example 4, yield in 43.2%. ¹H NMR (CDCl₃, 400 MHz): δ 8.15 (d, 2H, J=6.8 Hz), 7.62 (s, 1H),), 7.40-7.39 (m, 3H),), 6.67-6.62 (m, 2H), 5.45-5.44 (m, 1H), 4.92 (d, 1H, J=0.8 Hz), 4.66-4.64 (m, 1H), 4.06-4.04 (m, 1H), 3.83-3.80 (m, 2H), 3.76-3.48 (m, 2H), 3.26 (d, 2H, J=5.6 Hz), 1.47 (d, 3H, J=6.4 Hz)), 1.12 (t, 3H, J=5.2 Hz). ESI-MS (M+H)⁺: 381.

Synthesis of Example 5 (Method A)

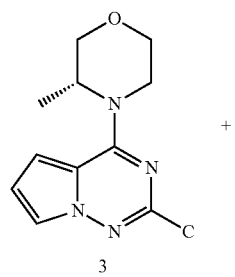

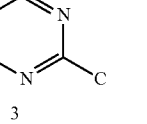

-continued

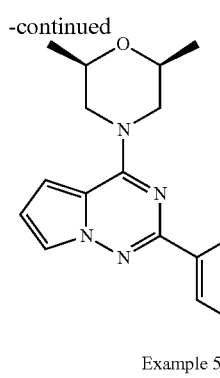

Example 5

Method A: used 20 mg of compound 4 to obtained 8 mg of Example 5, yield in 30.6%. $^1$H NMR (CDCl$_3$, 400 MHz): δ 8.66 (s, 1H), 8.33 (d, 1H, J=8.8 Hz), 8.19-8.14 (m, 1H), 7.63 (m, 1H), 7.50 (d, 1H, J=8.4 Hz), 6.67-6.62 (m, 2H), 4.77 (d, 2H, J=12.4 Hz), 3.76-3.72 (m, 2H), 2.91 (t, 2H, J=11.6 Hz), 1.28 (d, 6H, J=6.4 Hz).

Synthesis of Example 6 (Method B)

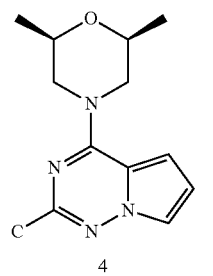

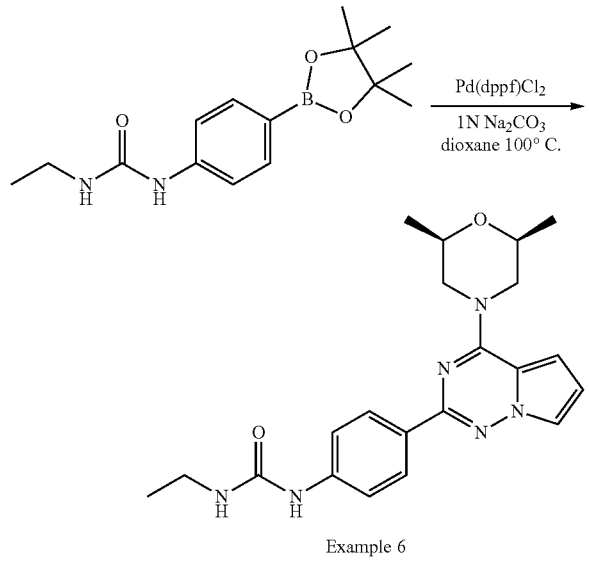

Example 6

Method B: used 20 mg of compound 4 to obtained 14 mg of Example 6, yield in 47.3%. $^1$H NMR (CDCl$_3$, 400 MHz): δ 8.12-8.11 (m, 2H), 7.64 (s, 1H), 7.38-7.37 (m, 2H), 7.08-6.97 (m, 1H), 6.72 (s, 1H), 6.64 (s, 1H), 4.74-4.71 (m, 2H), 3.79-3.78 (m, 2H), 3.30-3.29 (m, 2H), 2.96-2.93 (m, 2H), 1.29 (d, 6H, J=11.2 Hz), 1.17 (s, 3H). ESI-MS (M+H)$^+$: 395.

Synthesis of Example 7 (Method B)

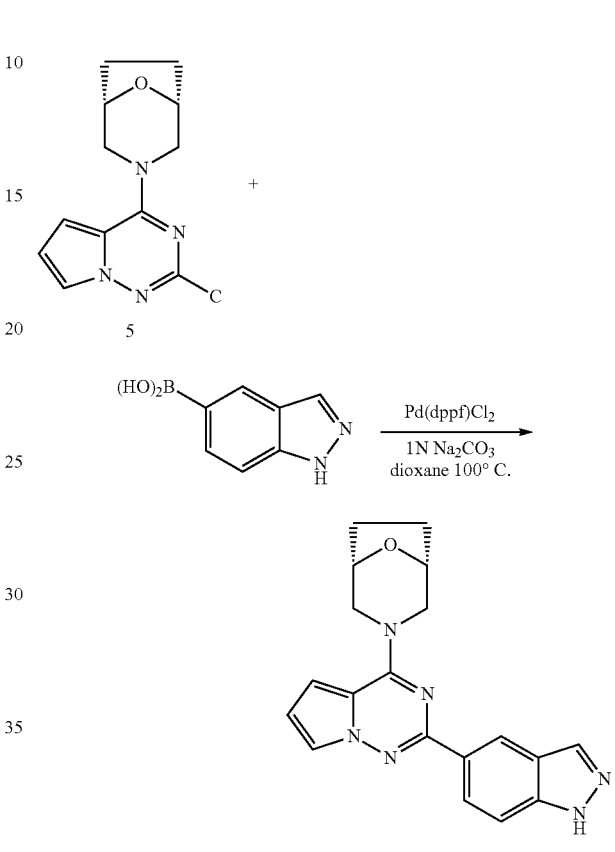

Example 7

Method B: used 20 mg of compound 5 to obtained 6 mg of Example 7, yield in 22.9%. $^1$HNMR (CDCl$_3$, 400 MHz): δ 8.75 (s, 1H), 8.43 (d, 1H, J=8.0 Hz), 8.24-8.13 (m, 1H), 7.70 (s, 1H), 7.60 (d, 1H, J=8.4 Hz), 6.73-6.66 (m, 2H), 4.67-4.58 (m, 4H), 3.62 (t, 2H, J=6.0 Hz), 3.30-3.29 (m, 2H), 2.05-1.93 (m, 2H). ESI-MS (M+H)$^+$: 347.

Synthesis of Example 8 (Method B)

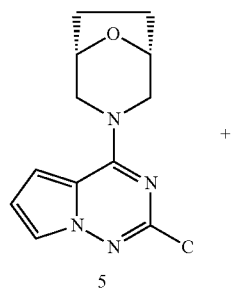

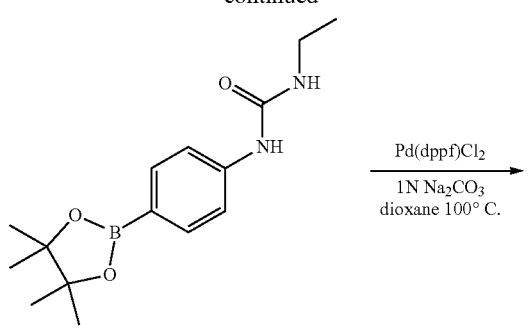

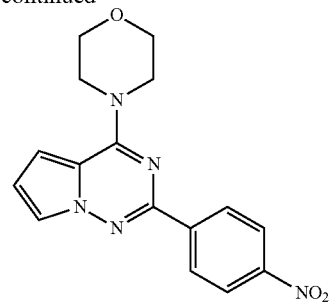

Example 9

Method A: used 20 mg of compound 2 to obtained 5 mg of Example 9, yield in 18.3%. $^1$H NMR (CDCl$_3$, 400 MHz): δ 8.46 (d, 2H, J=8.8 Hz), 8.27 (d, 2H, J=8.8 Hz), 7.72-7.71 (m, 1H), 6.77-6.72 (m, 2H), 4.15 (t, 4H, J=4.8 Hz), 3.90 (t, 4H, J=4.8 Hz). ESI-MS (M+H)$^+$: 326.

Synthesis of Example 10 (Method A)

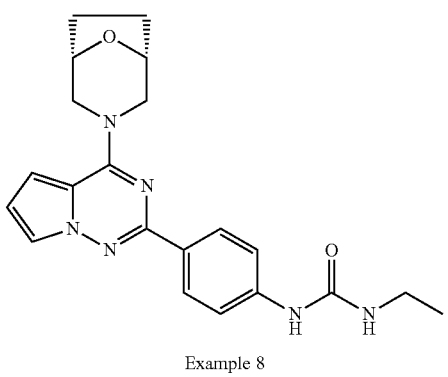

Example 8

Method B: used 20 mg of compound 5 to obtained 10 mg of Example 8, yield in 33.7%. $^1$H NMR (MeOD-d$_4$, 400 MHz): δ 8.16 (d, 2H, J=8.4 Hz), 7.57-7.55 (m, 1H), 7.46 (d, 2H, J=8.0 Hz), 6.89-6.88 (m, 1H), 6.70-6.69 (m, 1H), 4.69-4.63 (m, 2H), 4.56 (s, 1H), 4.20 (s, 1H), 3.56-3.50 (m, 2H), 3.29-3.24 (m, 2H), 2.05-2.00 (m, 2H), 1.94-1.91 (m, 2H), 1.19 (t, 3H, J=7.2 Hz). ESI-MS (M+H)$^+$: 393.

Synthesis of Example 9 (Method A)

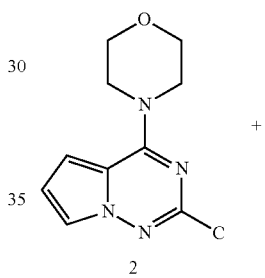

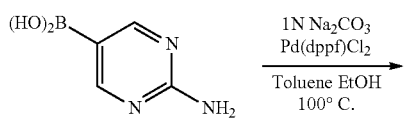

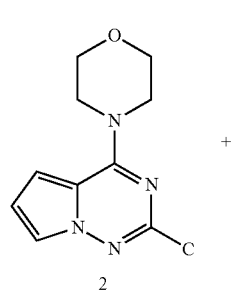

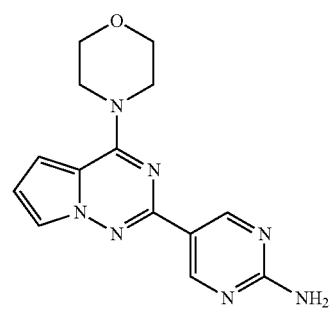

Example 10

Method A: used 20 mg of compound 2 to obtained 5 mg of Example 10, yield in 20.1%. $^1$H NMR (CDCl$_3$, 400 MHz): δ 9.15 (s, 2H), 7.65-7.64 (m, 1H), 6.74-6.72 (m, 1H), 6.68-6.67 (m, 1H), 5.57 (s, 2H), 4.10 (t, 4H, J=4.4 Hz), 3.88 (t, 4H, J=4.8 Hz). ESI-MS (M+H)$^+$: 298.

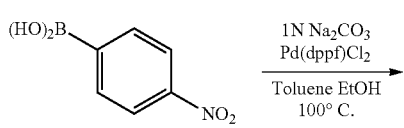

Synthesis of Example 11 (Method A)
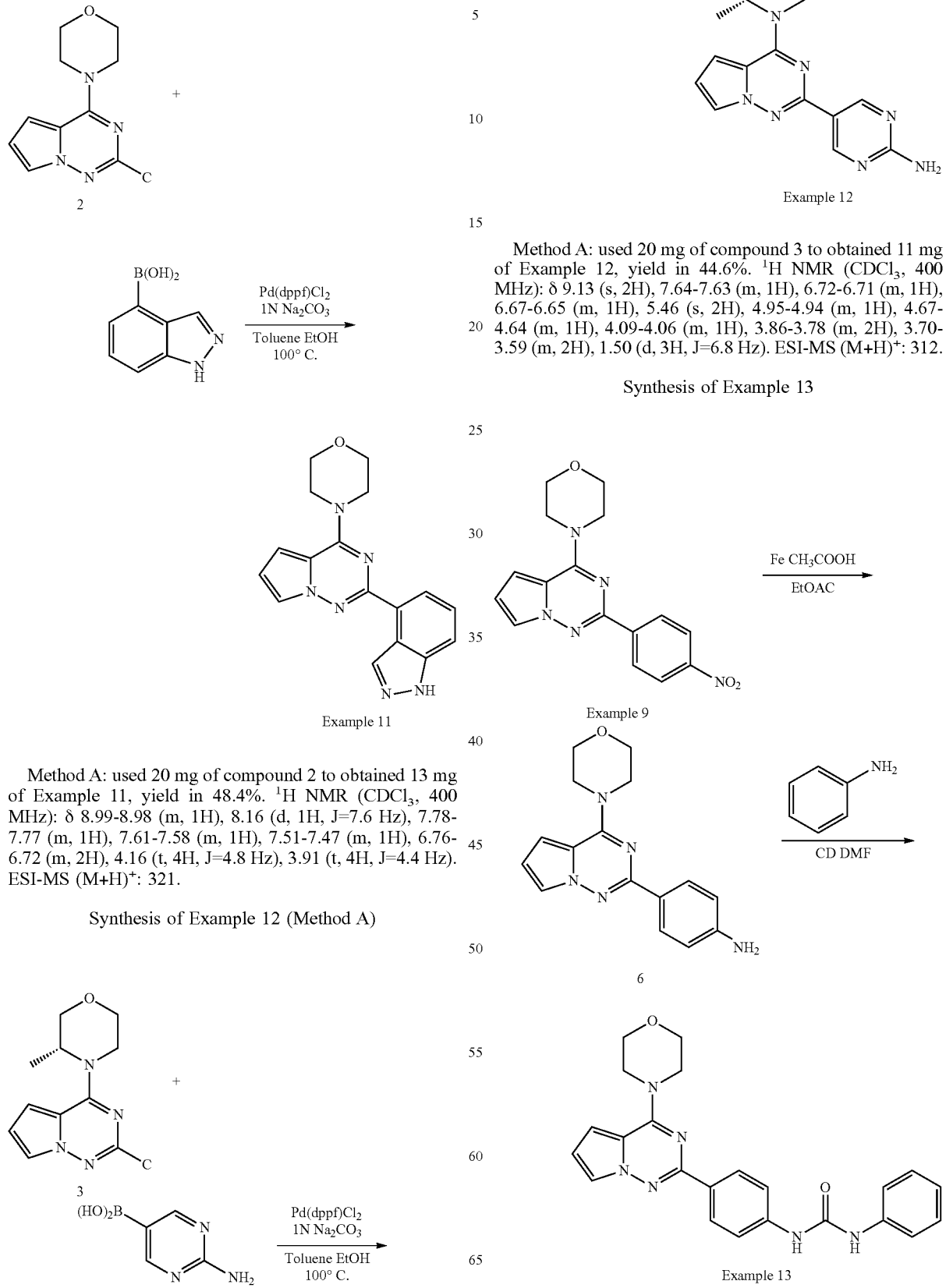
Method A: used 20 mg of compound 2 to obtained 13 mg of Example 11, yield in 48.4%. $^1$H NMR (CDCl$_3$, 400 MHz): δ 8.99-8.98 (m, 1H), 8.16 (d, 1H, J=7.6 Hz), 7.78-7.77 (m, 1H), 7.61-7.58 (m, 1H), 7.51-7.47 (m, 1H), 6.76-6.72 (m, 2H), 4.16 (t, 4H, J=4.8 Hz), 3.91 (t, 4H, J=4.4 Hz). ESI-MS (M+H)$^+$: 321.
Synthesis of Example 12 (Method A)
Method A: used 20 mg of compound 3 to obtained 11 mg of Example 12, yield in 44.6%. $^1$H NMR (CDCl$_3$, 400 MHz): δ 9.13 (s, 2H), 7.64-7.63 (m, 1H), 6.72-6.71 (m, 1H), 6.67-6.65 (m, 1H), 5.46 (s, 2H), 4.95-4.94 (m, 1H), 4.67-4.64 (m, 1H), 4.09-4.06 (m, 1H), 3.86-3.78 (m, 2H), 3.70-3.59 (m, 2H), 1.50 (d, 3H, J=6.8 Hz). ESI-MS (M+H)$^+$: 312.
Synthesis of Example 13

Synthesis of Compound 6

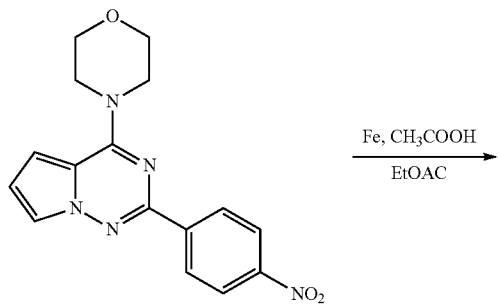

Example 9

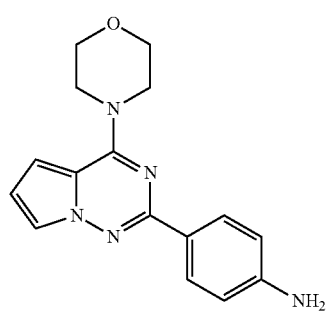

6

A mixture of Example 9 (20 mg, 0.06 mmol) and Fe (20 mg, 0.37 mmol) in EA (1.5 mL) and acetic acid (1.5 mL) was stirred at reflux for overnight. After adjusted pH to 8 with Na$_2$CO$_3$ (aq.), the mixture was extracted with EA. The combined organic layers were washed with brine, dried over Na$_2$SO$_4$ and concentrated to dryness to give compound 6 (10 mg, 55.1%). The crude product was used directly for the next step without purification. $^1$H NMR (CDCl$_3$, 400 MHz): δ 8.03 (d, 2H, J=8.0 Hz), 7.57-7.55 (m, 1H), 6.65 (d, 2H, J=8.4 Hz), 6.60-6.56 (m, 2H), 4.03 (t, 4H, J=4.8 Hz), 3.80 (t, 4H, J=4.8 Hz). ESI-MS (M+H)$^+$: 326.

Synthesis of Example 13 (Method C)

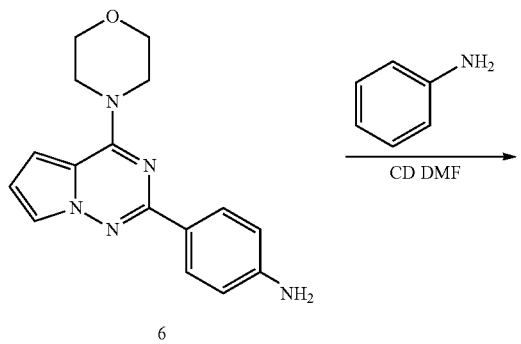

6

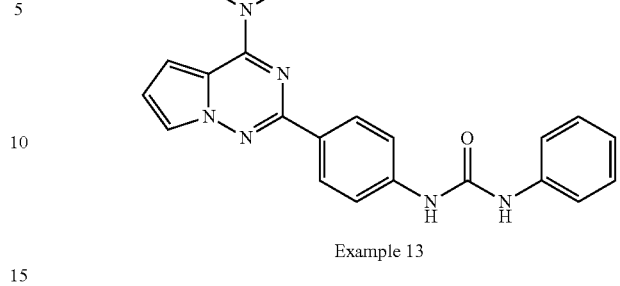

Example 13

A solution of compound 6 (10 mg, 0.03 mmol), CDI (11 mg, 0.06 mmol) and Et$_3$N (0.2 mL) in DMF (1 mL) was stirred at RT for 2 h. Then the aniline (6 uL, 0.06 mmol) was added, the mixture was stirred at RT for overnight. The mixture was quenched with H$_2$O, extracted with DCM. The combined organic layers were washed with brine, dried over Na$_2$SO$_4$ and concentrated to dryness The crude material was purified by Prep-TLC (PE:EA=2:1) affording to Example 13 (9 mg, 25.7%). $^1$H NMR (DMSO-d$_6$, 400 MHz): δ 8.91 (s, 2H), 8.16 (d, 2H, J=8.0 Hz), 7.80 (s, 1H), 7.56 (d, 2H, J=8.0 Hz), 7.47 (d, 2H, J=7.6 Hz), 7.30 (t, 2H, J=7.6 Hz) 7.01-6.99 (m, 2H), 6.73-6.72 (m, 1H), 4.08 (t, 4H, J=4.8 Hz), 3.80 (t, 4H, J=4.8 Hz). ESI-MS (M+H)$^+$: 415.

Synthesis of Example 14 (Method C)

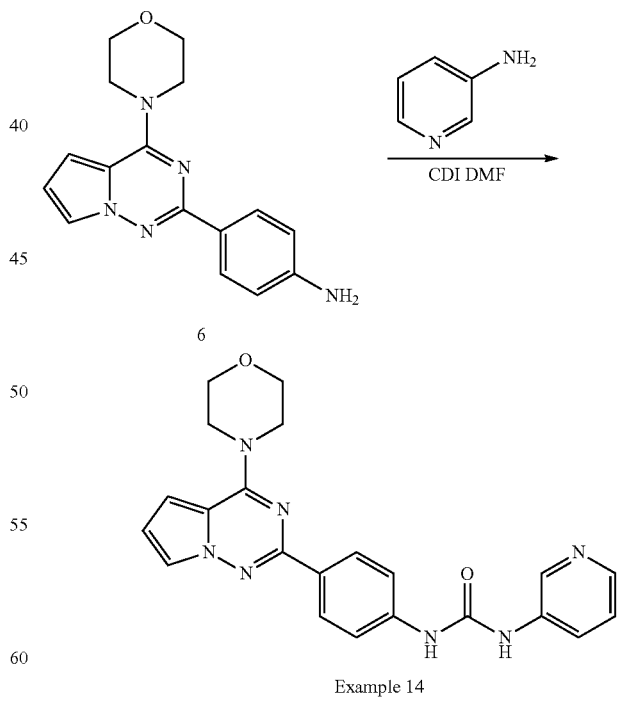

Example 14

Method C: used 15 mg of compound 6 to obtained 10 mg of Example 14, yield in 47.4%. $^1$H NMR (DMSO-d$_6$, 400 MHz): δ 9.15 (s, 1H), 9.03 (s, 1H), 8.69 (s, 1H), 8.24-8.22 (m, 3H), 8.02 (d, 1H, J=7.6 Hz), 7.86 (s, 1H), 7.63 (d, 2H, J=8.4 Hz), 7.41-7.38 (m, 2H), 6.79-6.78 (m, 1H), 4.13 (t, 4H, J=4.8 Hz), 3.85 (t, 4H, J=4.8 Hz). ESI-MS (M+H)+: 416.

Synthesis of Example 15

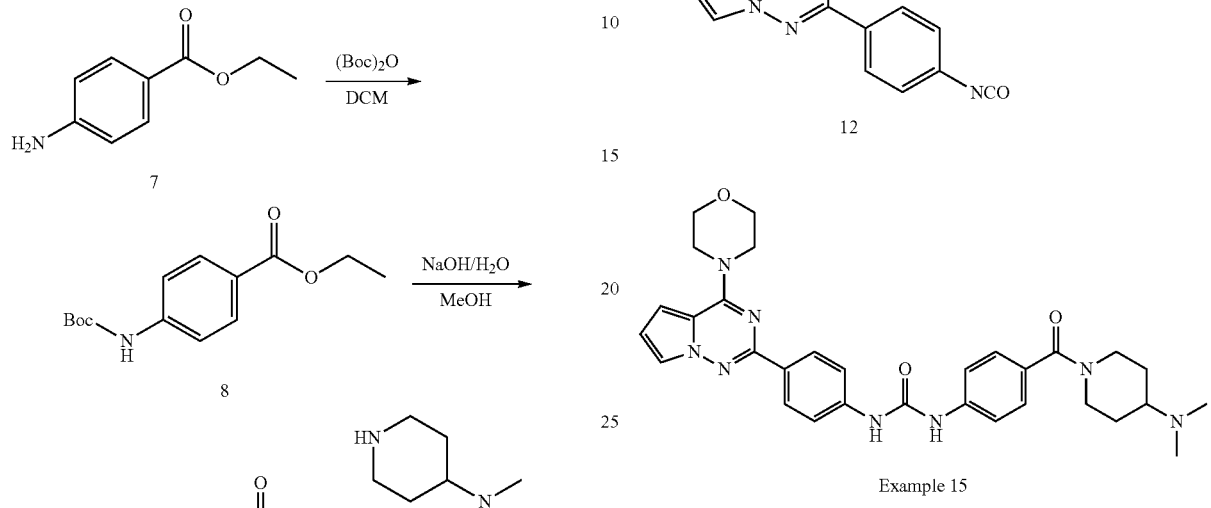

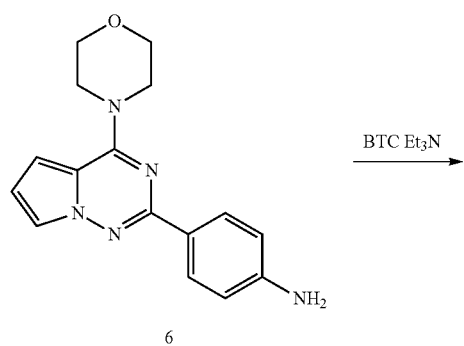

-continued

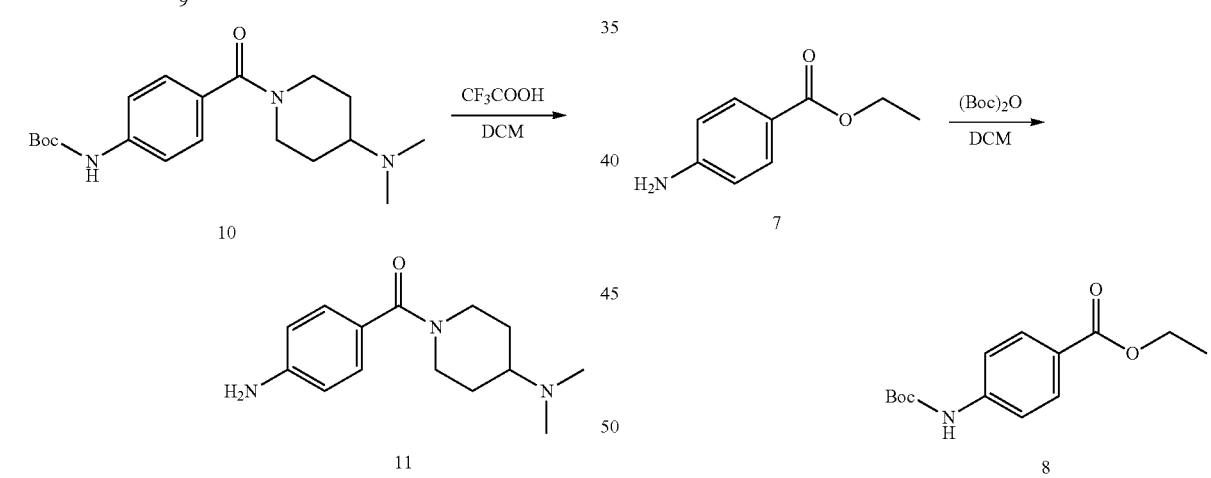

Example 15

Synthesis of Compound 8

A solution of compound 7 (300 mg, 1.8 mmol) and Et$_3$N (0.5 mL, 3.6 mmol) in DCM (5 mL), was added (Boc)$_2$O (427 uL, 2 mmol). The mixture was stirred at room temperature for overnight. Then the reaction was quenched with H$_2$O and extracted with DCM. The organic phase was washed with brine, dried over Na$_2$SO$_4$, filtered and concentrated, the crude product was purified by column chromatography (PE/EA=50:1) to give compound 8 (300 mg, yield: 61.2%). $^1$H NMR (CDCl$_3$, 400 MHz): δ 7.97 (d, 2H, J=8.8 Hz), 7.42 (d, 2H, J=8.4 Hz), 4.37-4.32 (m, 2H), 1.52 (s, 9H), 1.38 (t, 3H, J=7.2 Hz).

Synthesis of Compound 9

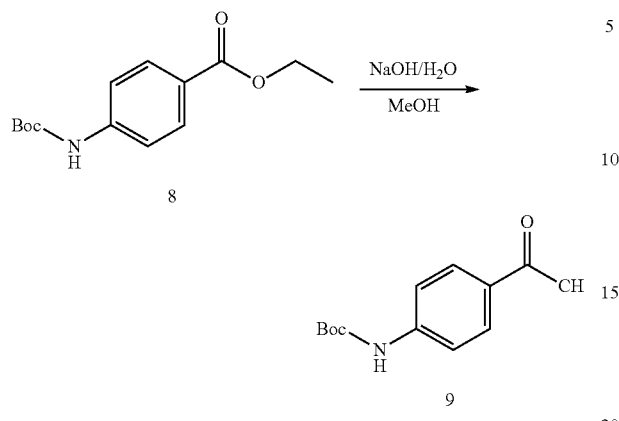

A mixture of compound 8 (300 mg, 1.13 mmol) and NaOH (1M, 7 mL) in MeOH (5 mL) was stirred at room temperature for overnight. After concentrated, the residue was dissolved in H$_2$O, 1 N HCl was added until pH=2, and the mixture was extracted with EA. The organic layer was washed with brine, dried over Na$_2$SO$_4$ and concentrated to provide the product compound 9 (200 mg, yield: 74.5%). It was used for the next step without further purification. $^1$H NMR (DMSO-d$_6$, 400 MHz): δ 12.64 (s, 1H), 9.77 (s, 1H), 7.89 (d, 2H, J=8.4 Hz), 7.61 (d, 2H, J=8.8 Hz), 1.54 (s, 9H).

Synthesis of Compound 10

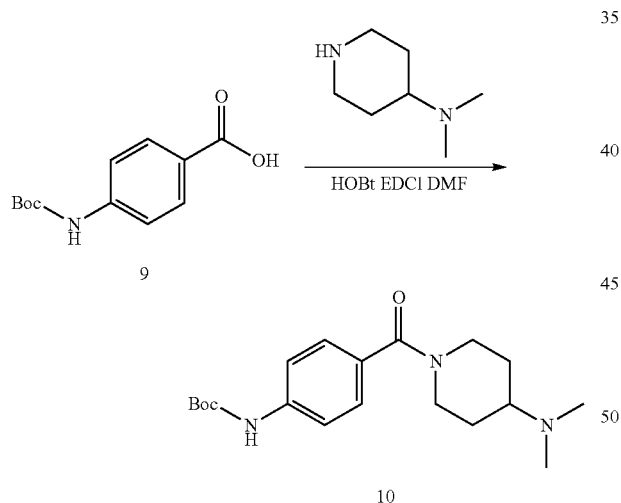

A solution of compound 9 (160 mg, 0.67 mmol), HOBT (136.7 mg, 1.01 mmol), EDCI (193.6 mg, 1.01 mmol) and Et$_3$N (0.3 mL, 2.01 mmol) in DMF (5 mL) was stirred for 3 h at ambient temperature. Then N,N-dimethylpiperidin-4-amine (113 μL, 0.80 mmol) was added. After stirred for overnight at ambient temperature, the mixture was dissolved in DCM and H$_2$O. The organic phase was washed with brine, dried over Na$_2$SO$_4$ and concentrated. The crude product was purified by column chromatography (PE/EA=5:1 to EA) to give compound 10 (200 mg, yield: 85%). $^1$H NMR (CDCl$_3$, 400 MHz): δ 7.40-7.34 (m, 4H), 6.59 (s, 1H), 2.80-2.77 (m, 3H), 2.48-2.45 (m, 2H), 2.33 (s, 6H), 1.88-1.84 (m, 2H), 1.52 (s, 9H), 1.48-1.45 (m, 2H).

Synthesis of Compound 11

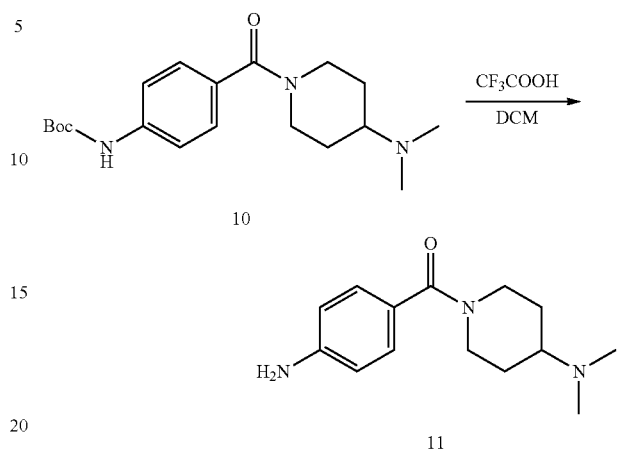

A mixture of compound 10 (260 mg 0.7 mmol) and TFA (1 mL) in DCM (5 mL) was stirred at room temperature for overnight. Then the reaction was quenched with NaHCO$_3$ (aq.) and extracted with DCM. The organic layer was washed with brine, dried over Na$_2$SO$_4$ and concentrated to provide the product compound 11 (200 mg). It was used for the next step without further purification.

Synthesis of Compound 12

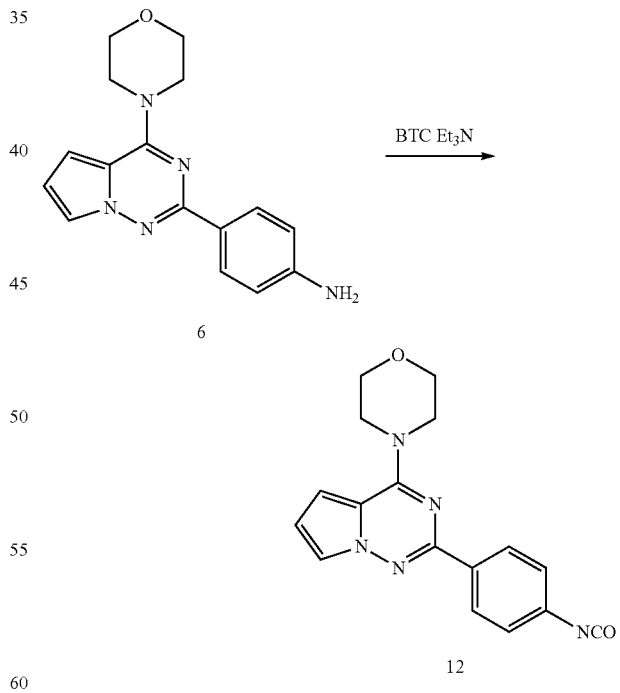

A solution of BTC (40.2 mg, 0.14 mmol) in DCM (3 mL) was added dropwise to a mixture of compound 6 (10 mg, 0.03 mmol) and Et$_3$N (44 μL, 0.3 mmol) in DCM (3 mL) with stirring at 0° C. under N$_2$. After addition, the reaction mixture was stirred at 0° C. for 30 min. The reaction mixture was diluted with NaHCO$_3$ (aq.) and extracted with DCM.

The combined organic layers were washed with brine, dried over Na$_2$SO$_4$ and concentrated to give compound 12 (11 mg). The crude product was used directly for the next step without purification.

Synthesis of Example 15

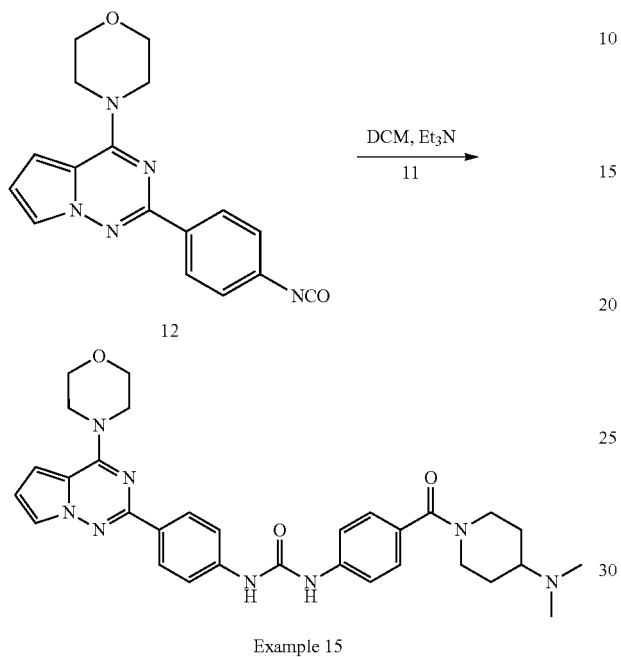

To a solution of compound 12 (11 mg, 0.03 mmol) in DCM (2 mL) was added dropwise a solution of compound 11 (139 mg, 1.01 mmol) in THF (3 ml) with stirring at room temperature. After addition, the reaction mixture was stirred at room temperature for 16 h. The reaction mixture was concentrated and the crude material was purified by Pre-TLC (EA/NH$_3$H$_2$O) affording to Example 15 (5 mg, yield: 25.6%). $^1$H NMR (MeOD-d$_4$, 400 MHz): δ 8.13-8.11 (m, 2H), 7.58-7.57 (m, 1H), 7.50 (s, 1H), 7.48 (s, 1H), 7.45 (s, 1H), 7.43 (s, 1H), 7.34-7.32 (m, 2H), 6.81-6.80 (m, 1H), 6.61-6.59 (m, 1H), 4.04 (t, 4H, J=4.8 Hz), 3.77 (t, 4H, J=4.8 Hz), 3.50 (s, 1H), 3.40-3.36 (m, 2H), 2.78 (s, 6H), 2.05-2.00 (m, 2H), 1.62-1.58 (m, 2H), 1.53-1.49 (m, 2H). ESI-MS (M+H)$^+$: 569.

Synthesis of Example 16

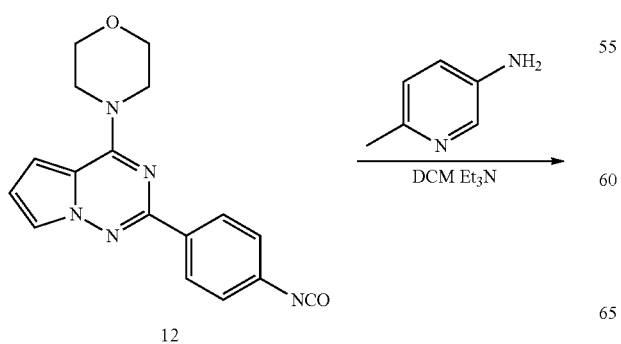

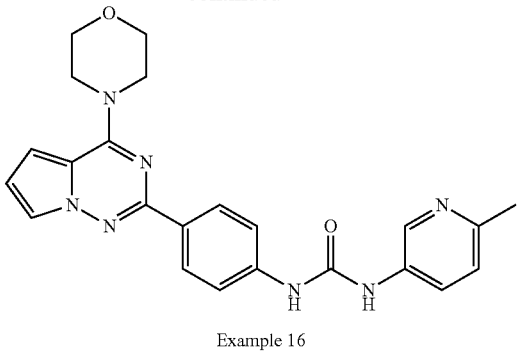

The procedure of Example 16 (5.0 mg, yield: 23.4%) was similar to that of Example 15. $^1$H NMR (MeOD-d$_4$, 400 MHz): δ 8.84-8.83 (m, 1H), 8.12 (d, 2H, J=8.8 Hz), 8.09-8.06 (m, 1H), 7.58-7.57 (m, 1H), 7.53-7.51 (m, 1H), 7.47 (d, 2H, J=8.8 Hz), 6.81-6.80 (m, 1H), 6.61-6.59 (m, 1H), 4.04 (t, 4H, J=4.8 Hz), 3.77 (t, 4H, J=4.8 Hz), 2.54 (s, 3H). ESI-MS (M+H)$^+$: 430.

Synthesis of Example 17

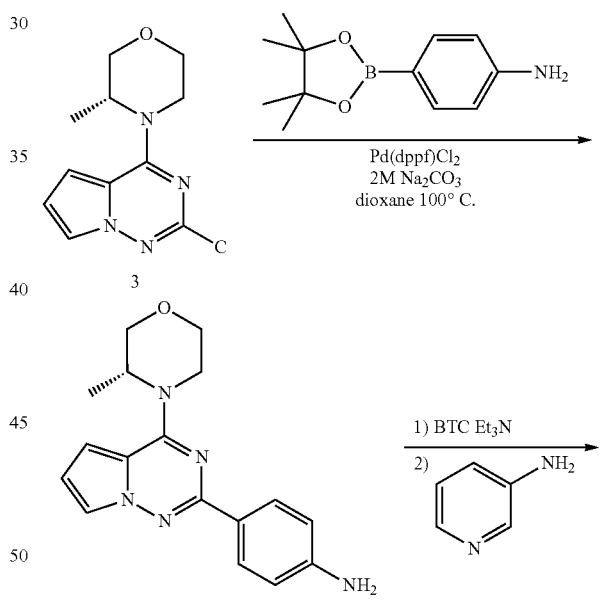

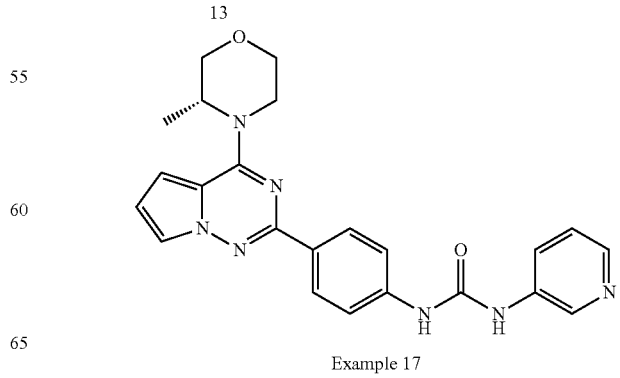

Synthesis of Compound 13 (Method B)

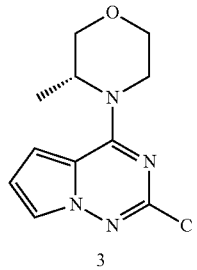

3

+

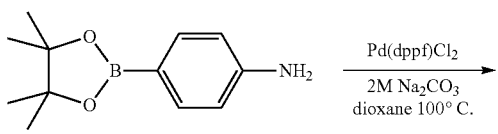

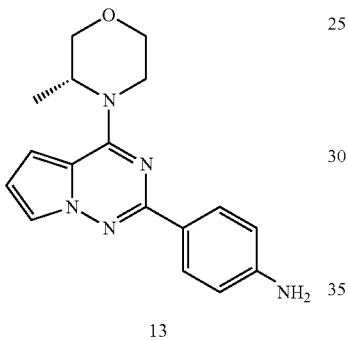

13

Method B: used 30 mg of compound 3 to obtained 20 mg of compound 13, yield in 54.5%. $^1$H NMR (CDCl$_3$, 400 MHz): δ 8.01 (d, 2H, J=8.4 Hz), 7.55 (dd, 1H, J=2.8, 1.6 Hz), 6.63 (d, 2H, J=8.4 Hz), 6.58 (dd, 1H, J=4.4, 1.2 Hz), 6.53 (dd, 1H, J=4.4, 2.4 Hz), 4.88 (d, 1H, J=6.0 Hz), 4.60 (d, 1H, J=12.6 Hz), 3.98-3.95 (m, 1H), 3.73 (d, 2H, J=3.2 Hz), 3.63-3.55 (m, 1H), 3.52-3.45 (m, 1H), 1.41 (d, 3H, J=6.8 Hz).

Synthesis of Example 17

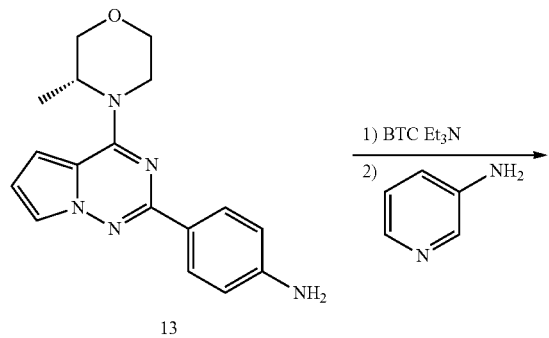

13

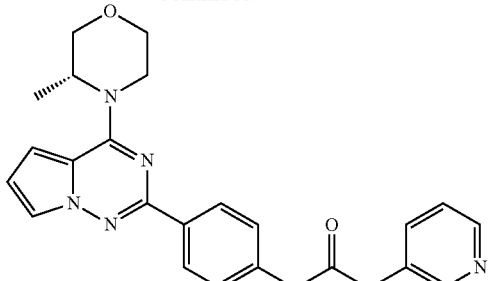

Example 17

The procedure of Example 17 (6.0 mg, yield: 21.3%) was similar to that of Example 15. $^1$H NMR (CDCl$_3$, 400 MHz): δ 8.43 (s, 1H), 8.23-8.11 (m, 5H), 8.02 (s, 1H), 7.63 (s, 1H), 7.47 (d, 2H, J=8.4 Hz), 7.25-7.21 (m, 1H), 6.68-6.63 (m, 2H), 4.94-4.93 (m, 1H), 4.66 (d, 1H, J=12.4 Hz), 4.07-4.04 (m, 1H), 3.84-3.75 (m, 2H), 3.69-3.57 (m, 2H), 1.48 (d, 3H, J=6.8 Hz). ESI-MS (M+H)$^+$: 430.

Synthesis of Example 18

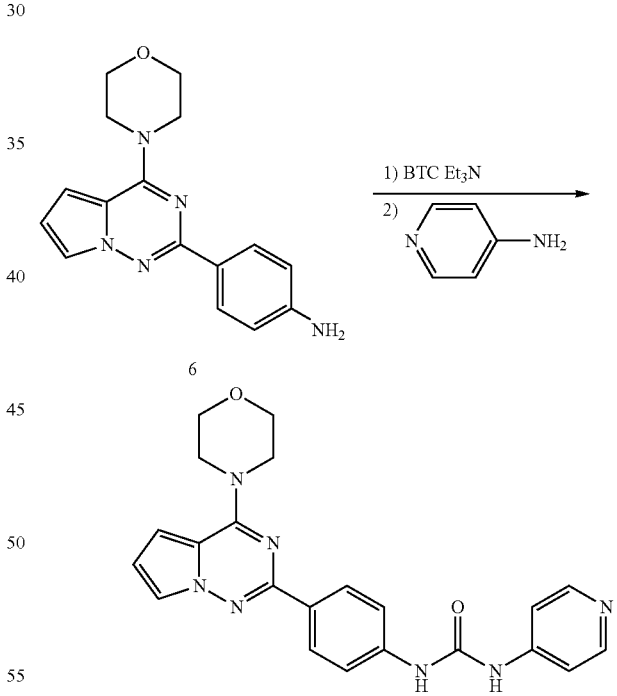

Example 18

The procedure of Example 18 (5.0 mg, yield: 23.7%) was similar to that of Example 15. $^1$H NMR (DMSO-d$_6$, 400 MHz): δ 11.29-11.28 (m, 1H), 10.28 (s, 1H), 8.51 (d, 2H, J=6.4 Hz), 8.19 (d, 2H, J=8.4 Hz), 7.80-7.75 (m, 3H), 7.59 (d, 2H, J=8.4 Hz), 7.00-6.99 (m, 1H), 6.73-6.71 (m, 1H), 4.07 (t, 4H, J=4.4 Hz), 3.79 (t, 4H, J=4.0 Hz). ESI-MS (M+H)$^+$: 416.

Synthesis of Example 19

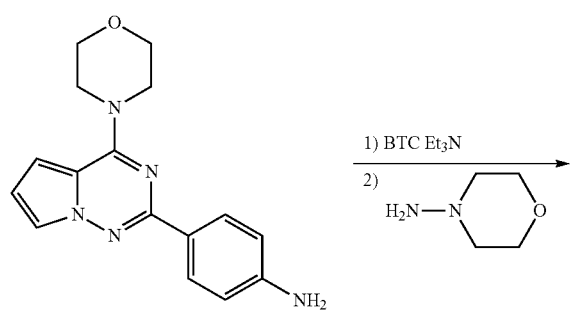

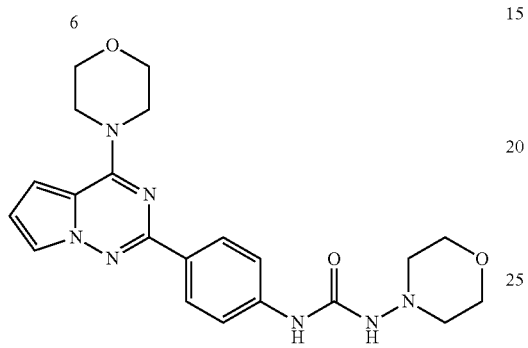

Example 19

The procedure of Example 19 (20 mg, yield: 69.5%) was similar to that of Example 15. $^1$H NMR (CDCl$_3$, 400 MHz): δ 8.25 (d, 2H, J=8.4 Hz), 8.16 (s, 1H), 7.67-7.66 (m, 1H), 7.56 (d, 2H, J=8.8 Hz), 6.69-6.65 (m, 2H), 5.70 (s, 1H), 4.12 (t, 4H, J=5.2 Hz), 3.89-3.83 (m, 8H), 2.94-2.80 (m, 4H). ESI-MS (M+H)$^+$: 424.

Synthesis of Example 20

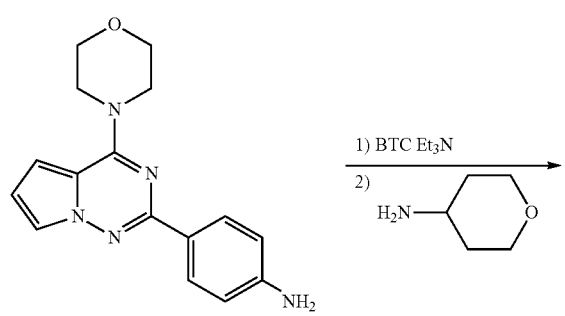

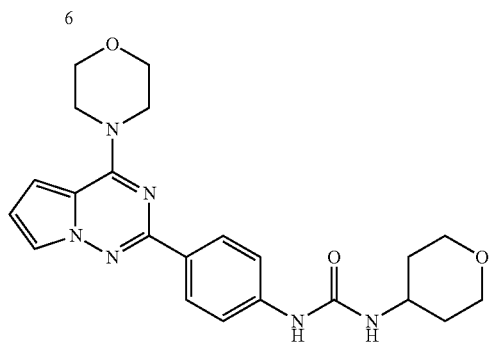

Example 20

The procedure of Example 20 (6.9 mg, yield: 22.6%) was similar to that of Example 15. $^1$H NMR (CDCl$_3$, 400 MHz): δ 8.22 (d, 2H, J=8.0 Hz), 7.67 (s, 1H), 7.35 (d, 2H, J=8.0 Hz), 6.72-6.66 (m, 2H), 6.37-6.35 (m, 1H), 5.29 (s, 1H), 4.12-4.11 (m, 4H), 3.96-3.89 (m, 5H), 3.49 (t, 4H, J=9.6 Hz), 1.98-1.95 (m, 2H), 1.47-1.43 (m, 2H). ESI-MS (M+H)$^+$: 423.

Synthesis of Example 21

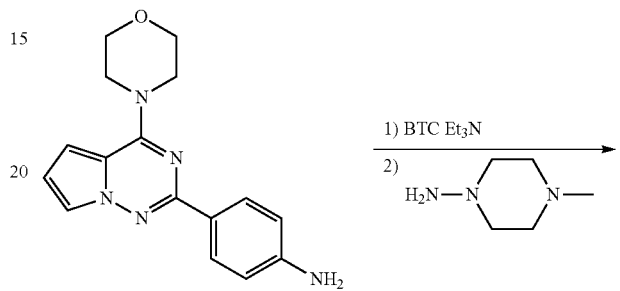

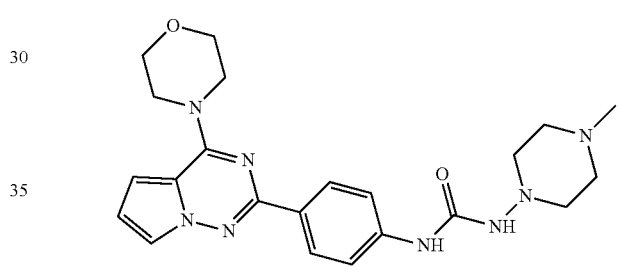

Example 21

The procedure of Example 21 (15.0 mg, yield: 53.5%) was similar to that of Example 15. $^1$H NMR (CDCl$_3$, 400 MHz): δ 8.24 (d, 2H, J=8.8 Hz), 8.19 (s, 1H), 7.66 (s, 1H), 7.55 (d, 2H, J=8.8 Hz), 6.89-6.64 (m, 2H), 5.83-5.74 (m, 1H), 4.11 (t, 4H, J=4.8 Hz), 3.88 (t, 4H, J=4.8 Hz), 3.11-2.73 (m, 8H), 2.36 (s, 3H). ESI-MS (M+H)$^+$: 437.

Synthesis of Example 22

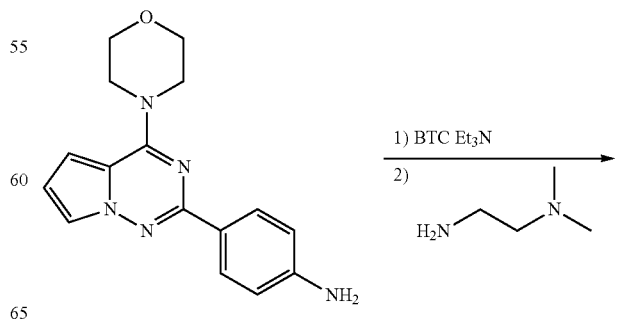

-continued

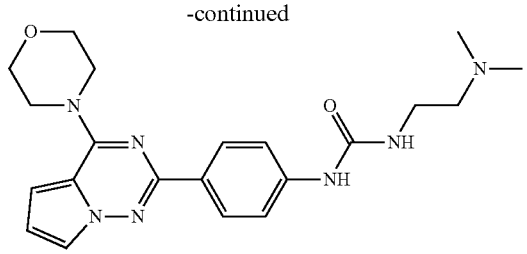

Example 22

The procedure of Example 22 (15.0 mg, yield: 56.7%) was similar to that of Example 15. $^1$H NMR (CDCl$_3$, 400 MHz): δ 8.42-8.26 (m, 1H), 8.10 (d, 2H, J=8.8 Hz), 7.56 (s, 1H), 7.39 (d, 2H, J=8.8 Hz), 6.59-6.55 (m, 2H), 6.22 (s, 1H), 4.00 (t, 4H, J=4.4 Hz), 3.78 (t, 4H, J=4.8 Hz), 3.37 (d, 2H, J=5.2 Hz), 2.65 (t, 2H, J=5.2 Hz), 2.39 (s, 6H). ESI-MS (M+H)$^+$: 410.

Synthesis of Example 23

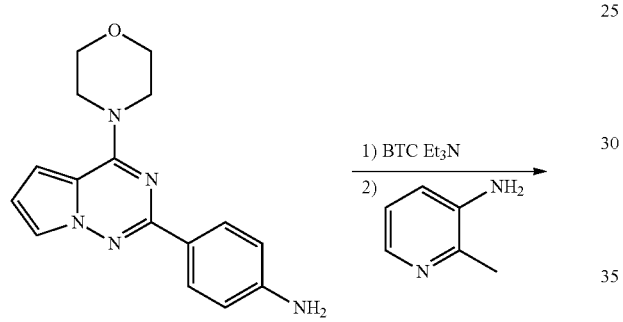

Example 23

The procedure of Example 23 (20.0 mg, yield: 72.8%) was similar to that of Example 15. $^1$H NMR (MeOD-d$_4$, 400 MHz): δ 8.49-8.45 (m, 1H), 8.23-8.21 (m, 3H), 7.67 (s, 1H), 7.60-7.57 (m, 2H), 7.45-7.41 (m, 1H), 6.90-6.89 (m, 1H), 6.71-6.69 (m, 1H), 4.14 (t, 4H, J=4.4 Hz), 3.87 (t, 4H, J=4.0 Hz), 2.64 (s, 3H). ESI-MS (M+H)$^+$: 430.

Synthesis of Example 24

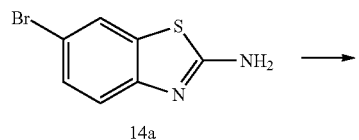

-continued

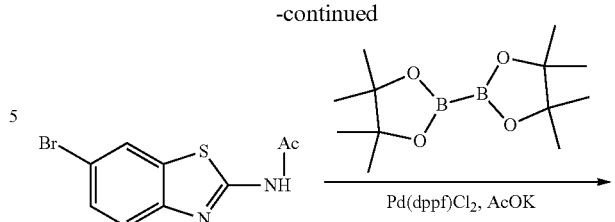

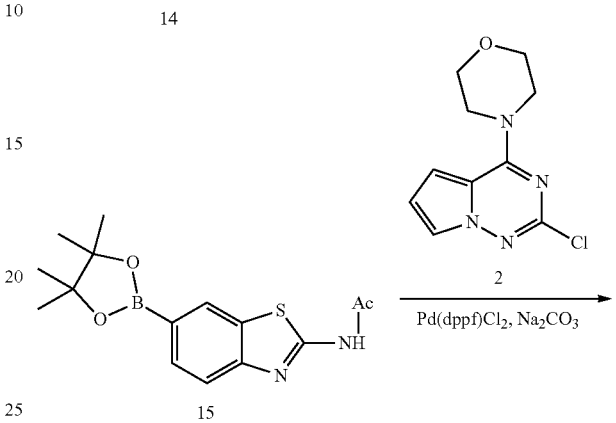

Example 24

Synthesis of Compound 14

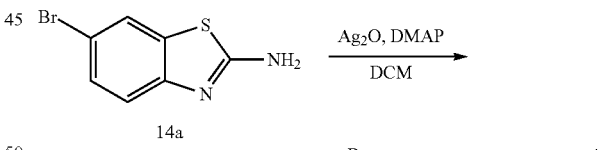

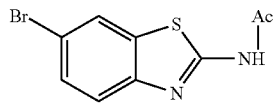

To a solution of compound 14a (50 mg, 0.218 mmol) and DMAP (31 mg, 0.250 mmol) in DCM (0.85 mL) was added Ac$_2$O (23 μL, 0.244 mmol) at 0° C. with stirring. Then the mixture was stirred at room temperature for overnight. The mixture was washed with 3M HCl, and extracted with DCM. The combined organic layers were washed with brine, dried over Na$_2$SO$_4$ and concentrated to give compound 14 (50 mg, 83.5%). The crude product was used directly for the next step without further purification. $^1$H NMR (400 MHz, CDCl$_3$) δ11.65 (s, 1H), 7.91 (d, 1H, J=1.6 Hz), 7.52~7.45 (m, 2H), 2.26 (s, 3H).

Synthesis of Compound 15

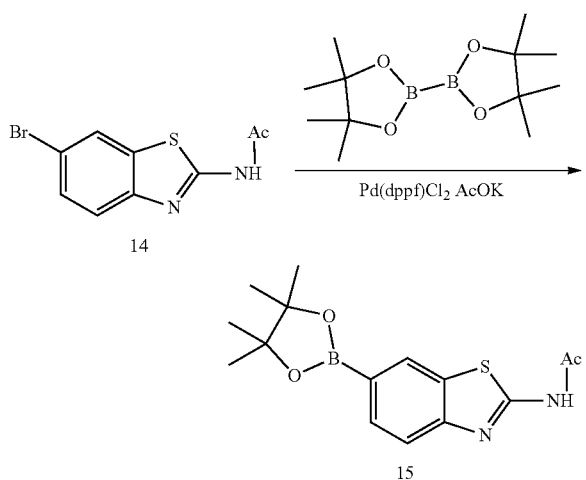

To a solution of compound 14 (20 mg, 0.078 mmol) and bis(pinacolato)diboron (39.8 mg, 0.156 mmol) in DMSO (0.5 mL) was added Pd(dppf)Cl₂ (300 mg) and AcOK (38 g, 0.392 mmol) under N₂ protection. The resulting mixture was stirred at 100° C. for 5 hours. The mixture was dissolved in DCM and filtrated over celite. The organic phase was washed with H₂O and brine. After dried over Na₂SO₄, filtered and concentrated, the crude product was purified by Pre-TLC (PE/EA=1:1) to give compound 15 (6 mg, yield: 25.3%) as solid. ¹H-NMR (CDCl₃, 400 MHz) δ 7.89 (s, 1H), 7.77 (d, 1H, J=7.6 Hz), 7.57 (d, 1H, J=7.2 Hz), 2.52 (s, 3H), 1.36 (s, 12H).

Synthesis of Example 24

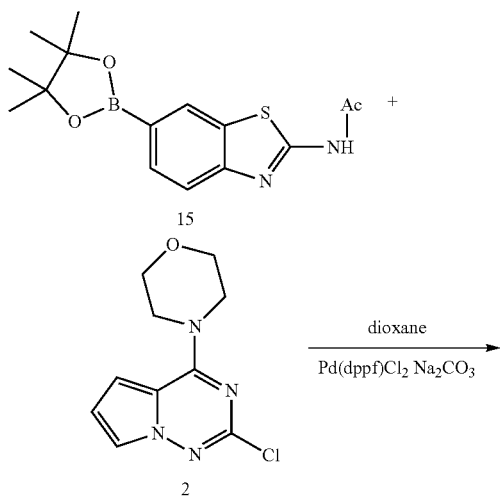

A mixture of compound 15 (30 mg, 0.094 mmol) and 2 (22.5 mg, 0.094 mmol) in 1,4-dioxane (1.5 mL) and H₂O (0.5 mL) was added Pd(dppf)Cl₂ (4.0 mg) and Na₂CO₃ (50 mg) under N₂ protection. The resulting mixture was stirred at 100° C. for overnight. The mixture was dissolved in DCM and filtrated over celite. The filtrate was washed with water, brine, dried over Na₂SO₄ and concentrated to give the crude product. After purified by Pre-HPLC to afford compound Example 24 (4.5 mg, yield: 11.9%). ¹H NMR (400 MHz, CDCl₃) δ 8.74 (d, 1H, J=1.2 Hz), 8.37~8.35 (m, 1H), 7.79 (d, 1H, J=4.8 Hz), 7.70~7.69 (m, 1H), 6.85~6.83 (m, 1H), 6.72~6.70 (m, 1H), 4.19~4.17 (m, 4H), 3.93~3.90 (m, 4H), 2.30 (s, 3H). ESI-MS (M+H)⁺: 395.2

Synthesis of Example 25

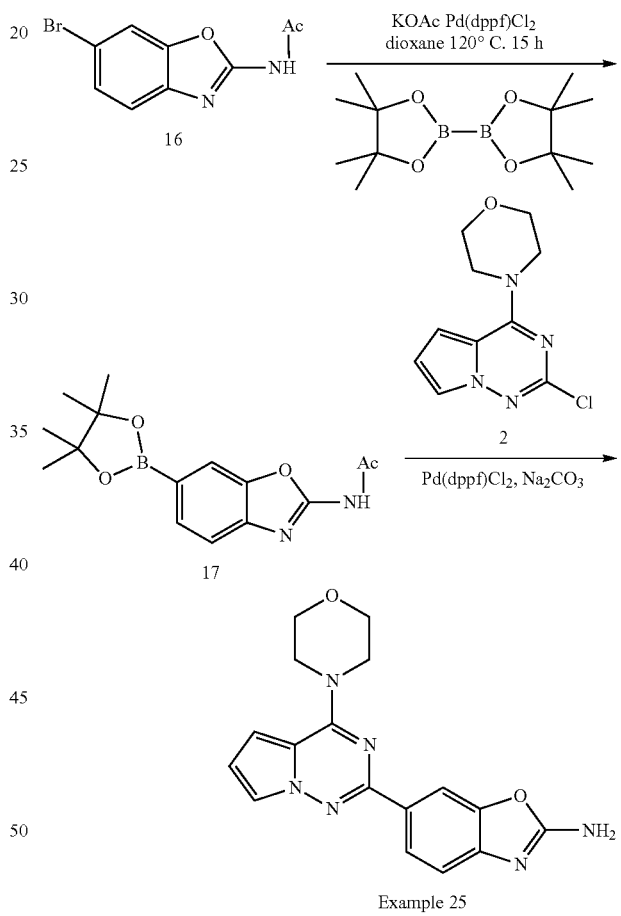

Synthesis of Compound 17

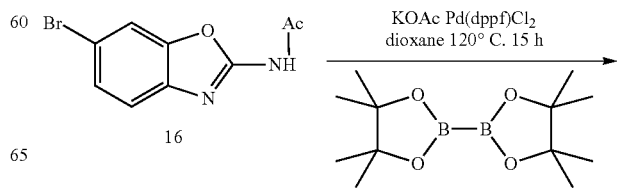

-continued

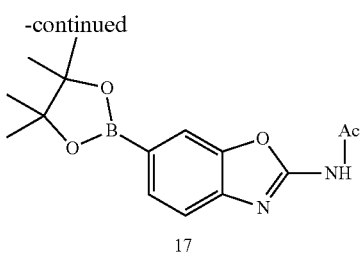

17

To a solution of compound 16 (150 mg, 0.58 mmol) and bis(pinacolato)diboron (448 mg, 1.76 mmol) in dioxane (5.0 mL) was added Pd(dppf)Cl$_2$ (15 mg) and AcOK (288 mg, 2.94 mmol) under N$_2$ protection. The resulting mixture was stirred at 120° C. for overnight. The mixture was dissolved in DCM and filtrated over celite. The organic phase was washed with H$_2$O and brine. After dried over Na$_2$SO$_4$, filtered and concentrated, the crude product was purified by Pre-TLC (PE/EA=1:1) to give compound 17 (80 mg, yield: 45.0%) as solid. $^1$H-NMR (CDCl$_3$, 400 MHz) δ 7.88 (s, 1H), 7.77 (d, 1H, J=7.6 Hz), 7.56 (d, 1H, J=8.0 Hz), 2.52 (s, 3H), 1.36 (s, 12H).

Synthesis of Example 25

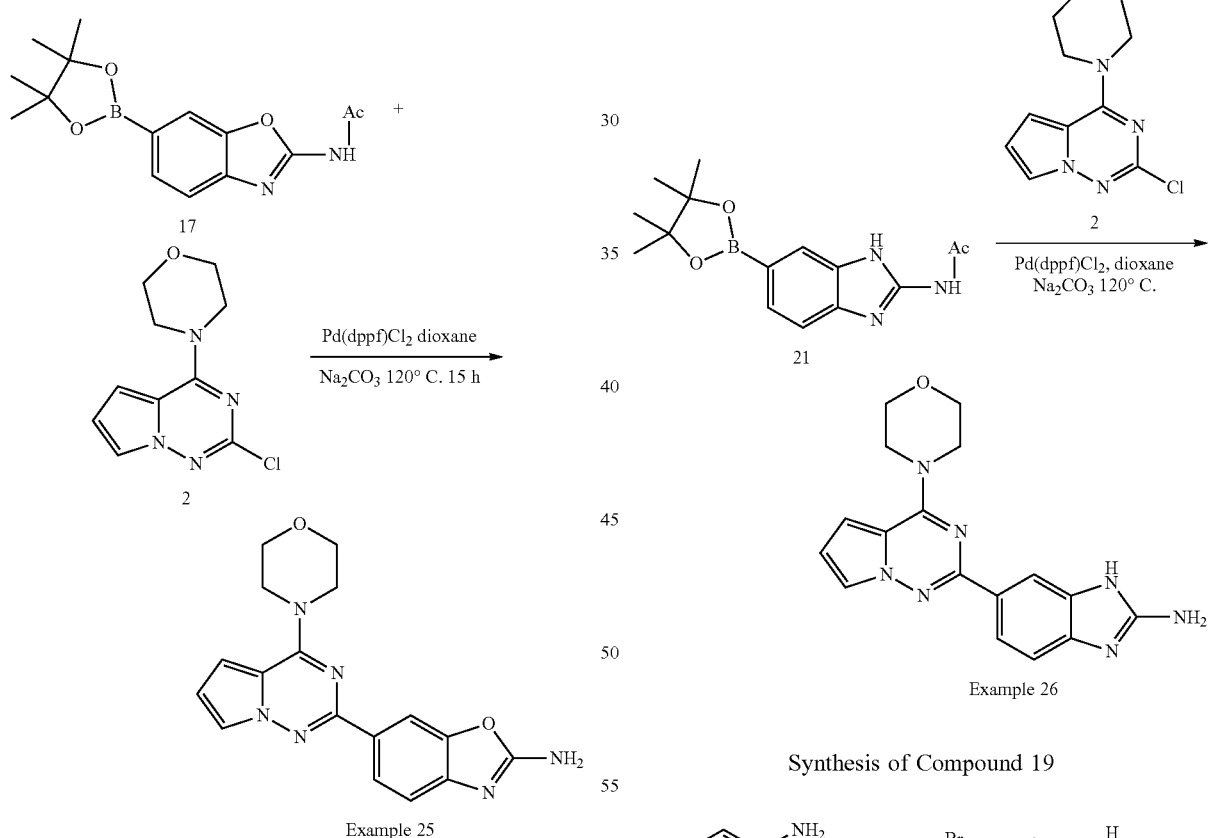

Example 25

A mixture of compound 17 (40 mg, 0.132 mmol) and compound 2 (31.5 mg, 0.132 mmol) in 1,4-dioxane (2.0 mL) and H$_2$O (1.0 mL) was added Pd(dppf)Cl$_2$ (10 mg) and Na$_2$CO$_3$ (100 mg) under N$_2$ protection. The resulting mixture was stirred at 120° C. for overnight. The mixture was dissolved in DCM and filtrated over celite. The filtrate was washed with water, brine, dried over Na$_2$SO$_4$ and concentrated to give the crude product. After purified by Pre-HPLC to afford compound Example 25 (5.0 mg, yield: 11.2%). $^1$H NMR (400 MHz, DMSO) δ 8.16~8.14 (m, 2H), 7.67~7.66 (m, 1H), 7.26 (d, 1H, J=4.8 Hz), 6.90~6.88 (m, 1H), 6.69~6.68 (m, 1H), 4.14~4.11 (m, 4H), 3.87~3.65 (m, 4H). ESI-MS (M+H)$^+$: 337.79.

Synthesis of Example 26

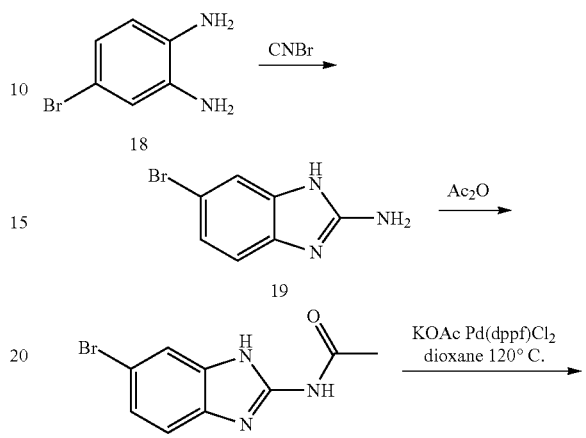

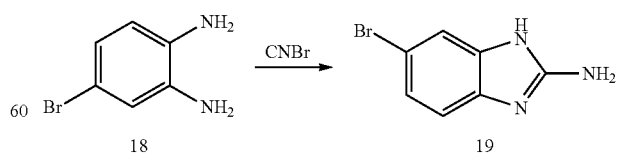

Example 26

Synthesis of Compound 19

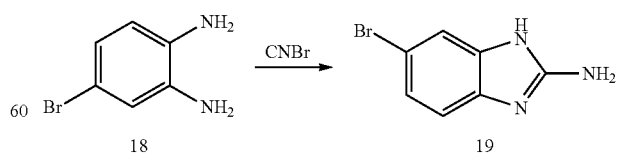

To a stirred solution of compound 18 (1.0 g, 10.7 mmol) in THF (10 mL) and water (2 mL) at 0° C., was added cyanogen bromide (650 mg, 11.7 mmol) in THF (3 mL), the reaction mixture was stirred for 16 h at ambient temperature. Later than reaction was quenched with saturated aqueous sodium hydrogen carbonate (50 mL) and shaken the resulting solid was filtered off, was washed with water and dried under reduced pressure to afford compound 19 (700 mg, 67.7%). ¹H-NMR (400 MHz, DMSO) δ 7.21 (d, 1H, J=1.6 Hz,) 7.03~7.01 (m, 1H), 6.96 (d, 1H, J=1.2 Hz), 6.23 (s, 2H), 5.75 (s, 1H).

Synthesis of Compound 20

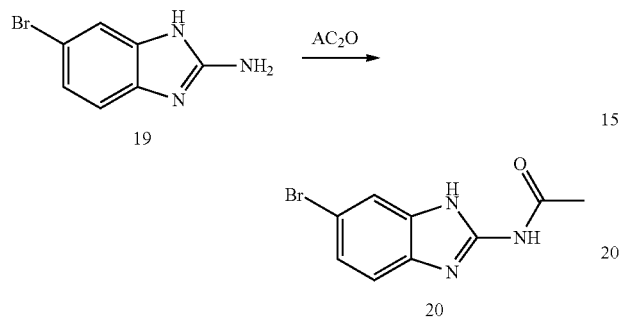

The solution of compound 19 (200 mg, 0.94 mmol) in Ac₂O (2 mL) was stirred at room temperature for overnight. After removed the most Ac₂O, the residue was washed with NaHCO₃, and extracted with DCM. The combined organic layers were washed with brine, dried over Na₂SO₄ and concentrated to give compound 20 (120 mg, 50.1%). The crude product was used directly for the next step without further purification. ¹H NMR (400 MHz, DMSO) δ 12.15~12.11 (m, 1H), 11.58 (s, 1H), 7.62~7.57 (m, 1H), 7.42~7.39 (m, 1H), 7.21~7.19 (m, 1H), 2.16 (s, 3H)

Synthesis of Compound 21

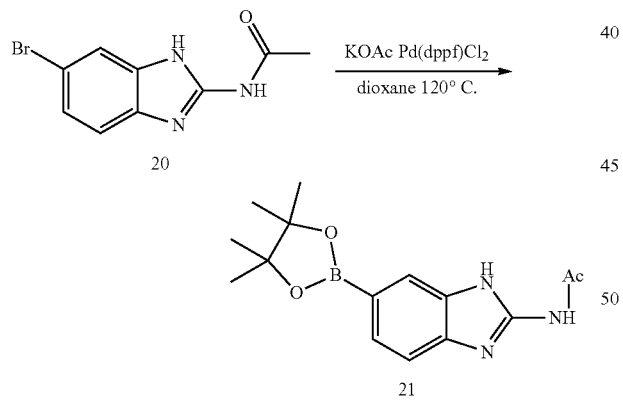

To a solution of compound 20 (100 mg, 0.39 mmol) and bis(pinacolato)diboron (300 mg, 1.18 mmol) in dioxane (5.0 mL) was added Pd(dppf)Cl₂ (15 mg) and AcOK (190 mg, 1.77 mmol) under N₂ protection. The resulting mixture was stirred at 120° C. for overnight. The mixture was dissolved in DCM and filtrated over celite. The organic phase was washed with H₂O and brine. After dried over Na₂SO₄, filtered and concentrated, the crude product was purified by Pre-TLC (PE/EA=1:1) to give compound 21 (52 mg, yield: 43.0%) as solid. ¹H-NMR (400 MHz, CDCl₃) δ 7.94 (s, 1H), 7.73~7.71 (m, 1H), 7.52~7.48 (m, 2H), 2.41 (s, 3H), 1.35 (s, 12H).

Synthesis of Example 26

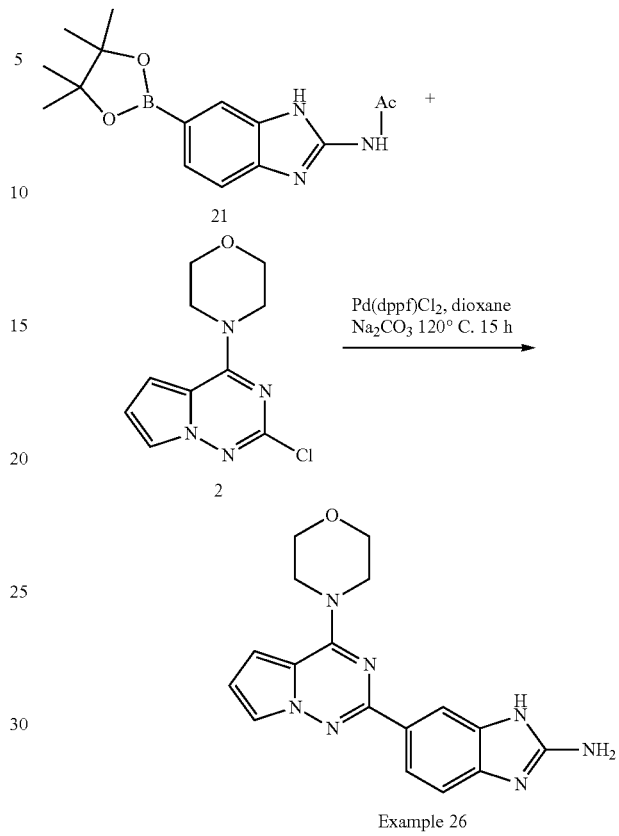

Example 26

The procedure of Example 26 (5.0 mg, yield: 12.4%) was similar to that of Example 24. ¹H NMR (400 MHz, MeOD) δ 8.19 (s, 1H), 8.07 (d, 1H, J=8.0 Hz), 7.63 (d, 1H, J=0.8 Hz), 7.30 (d, 1H, J=8.4 Hz), 6.85 (d, 1H, J=3.6 Hz), 6.67~6.65 (m, 1H), 4.09~4.06 (m, 4H), 3.84~3.81 (m, 4H). ESI-MS (M+H)⁺: 337.6.

Synthesis of Example 27

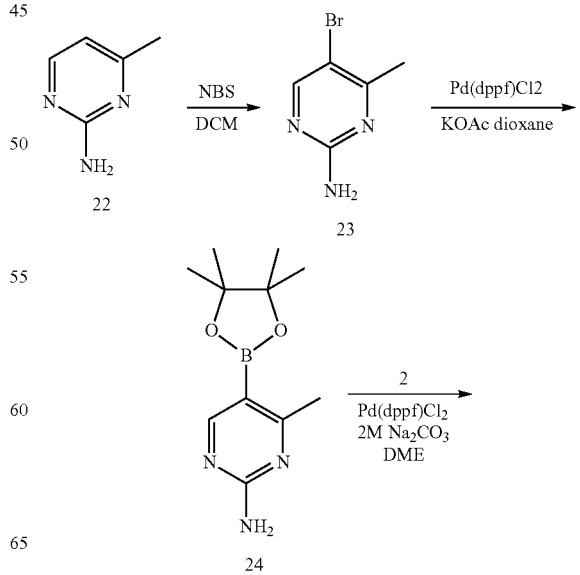

-continued

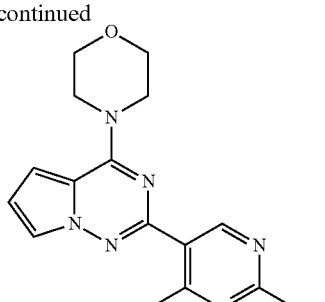

Example 27

Synthesis of Compound 23

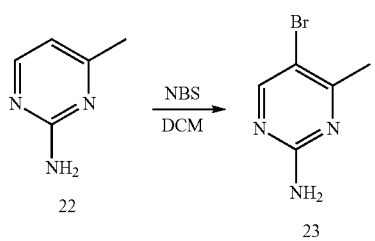

To a solution of compound 22 (500 mg, 4.6 mmol) in DCM (50 mL) was added NBS (820 mg, 4.6 mmol). The mixture was stirred in the dark for 16 hours at room temperature. The reaction was quenched with DCM (50 mL) and 1N NaOH (50 mL). The organic layer was washed with brine, dried over $Na_2SO_4$, filtered and concentrated to give the title compound 23 as a white solid (700 mg, 81% yield), which was used directly in the next step without further purification.

$^1$H NMR (CDCl3): δ 8.23 (s, 1H), 4.98 (bs, 2H), 2.45 (s, 3H).

Synthesis of Compound 24

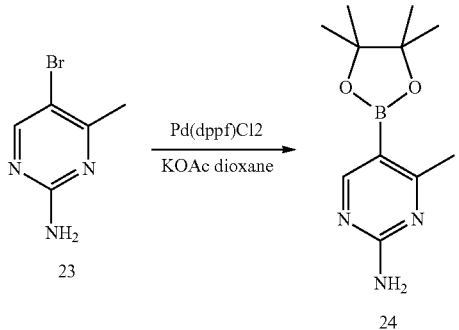

To a dry flask was added compound 23 (50 mg, 0.27 mmol), potassium acetate (79 mg, 0.81 mmol), bis(pinacolato)diboron (81 mg, 0.32 mmol) and dioxane (1.5 mL). $N_2$ was bubbled through the solution for 1.5 minutes, at which time 1,1-bis(diphenylphosphino)ferrocene-palladium(II) (22 mg, 30 μmol) was added. The reaction was stirred at 115° C. for 16 hours under $N_2$. After cooling to room temperature, the dioxane was removed in vacuo. EA was added and the resulting slurry was sonicated and filtered. Additional EA was used to wash the solid. The combined organic was concentrated and the crude was purified by prep-TLC affording to a white solid (40 mg). By $^1$H NMR the material was a 2:1 mixture of compound 24 and compound 22 byproduct. The mixture was used in the subsequent Suzuki reactions. $^1$H NMR (400 MHz, $CDCl_3$): δ 8.53 (s, 1H), 5.77 (bs, 2H), 2.56 (s, 3H), 1.32 (s, 12H)

Synthesis of Example 27

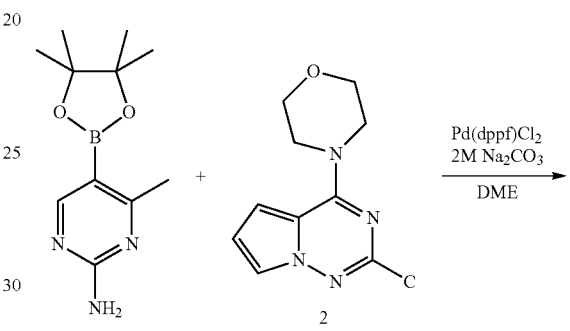

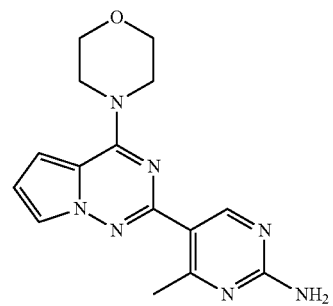

Example 27

To a mixture of compound 24 (40 mg, 0.17 mmol), compound 2 (15 mg, 0.06 mmol) and 2M $Na_2CO_3$ (0.5 ml) was added DME (1.5 ml). $N_2$ was bubbled through the solution for 1.5 minutes, at which time 1,1-bis(diphenylphosphino)ferrocene-palladium(II) dichloromethane adduct (5 mg, 6 μmol) was added. The reaction was stirred at 95° C. for 16 hours under $N_2$. After cooling to room temperature, EA was added and the resulting slurry was sonicated and filtered. Additional EA was used to wash the solid. The combined organic was concentrated and the crude material was purified by Prep-TLC (PE:EA:TEA=1:1:1d) to give Example 27 (12 mg) as a white solid. $^1$H NMR (400 MHz, $CDCl_3$): δ 8.54 (s, 1H), 7.68-7.64 (m, 1H), 6.84 (s, 1H), 6.72-6.76 (m, 1H), 6.68-6.72 (m, 1H), 5.03 (bs, 2H), 4.11-4.03 (m, 4H), 3.87-3.80 (m, 4H). ESI-MS (M+H)$^+$: 312.67

Synthesis of Compound 28

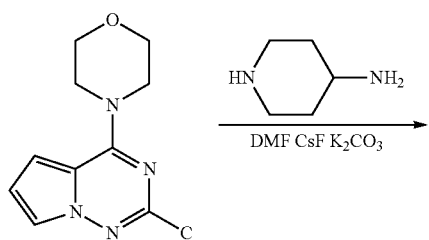

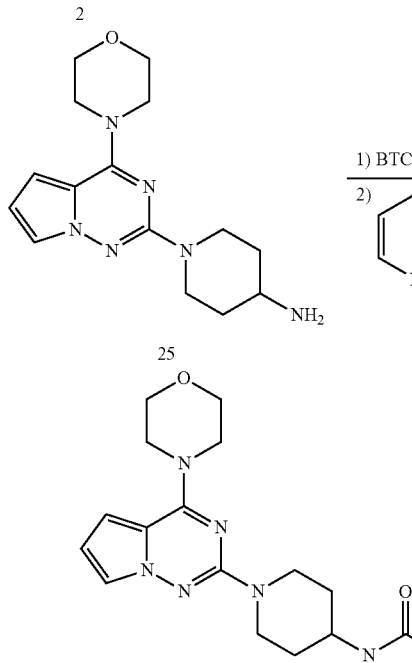

A mixture of compound 2 (15 mg, 0.06 mmol), CsF (27 mg, 0.20 mmol), K$_2$CO$_3$ (16 mg, 0.1 mm) and piperidin-4-amine (33 μL, 0.3 mmol) in DMSO (2.0 mL) was stirred at 140° C. for overnight. The mixture was dissolved in DCM and washed with water, brine, dried over Na$_2$SO$_4$ and concentrated to give the crude product. After purified by Pre-HPLC to afford compound 25 (3.0 mg, yield: 30.9%).

Synthesis of Example 28

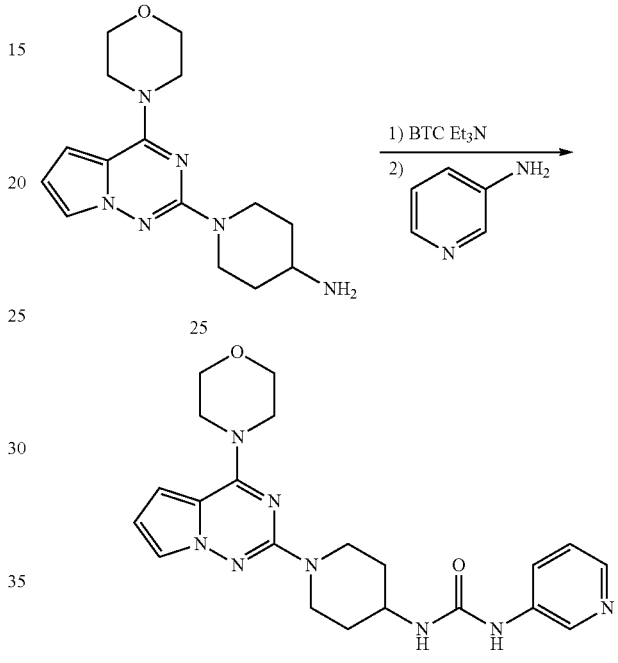

The procedure of Example 28 (4.0 mg, yield: 9.5%) was similar to that of Example 15. $^1$H NMR (MeOD-d$_4$, 400 MHz): δ 8.53 (s, 1H), 8.06-8.05 (m, 1H), 7.87-7.85 (m, 1H), 7.29-7.26 (m, 2H), 6.26-6.21 (m, 1H), 6.38-6.36 (m, 1H), 4.27-4.22 (m, 1H), 3.87 (t, 4H, J=4.8 Hz), 3.71 (t, 4H, J=4.8 Hz), 3.56-3.52 (m, 2H), 2.99-2.90 (m, 2H), 1.52-1.49 (m, 2H), 1.43-1.39 (m, 2H). ESI-MS (M+H)$^+$: 423.

Synthesis of Example 29

Synthesis of Compound 25

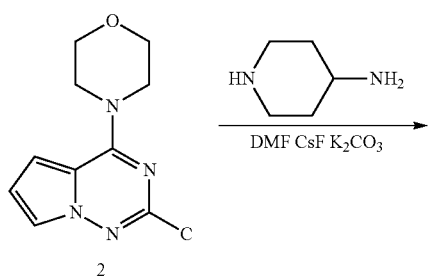

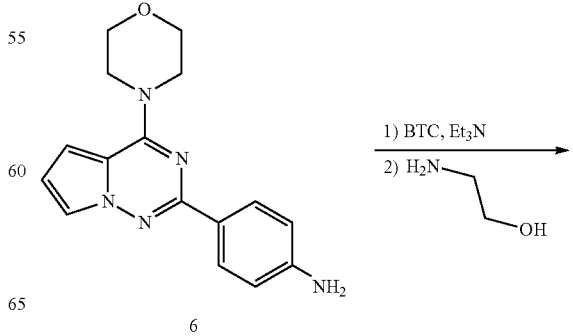

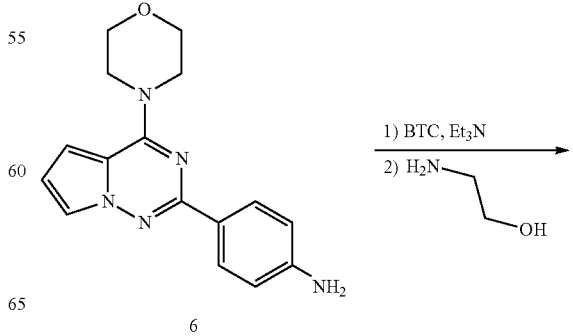

-continued

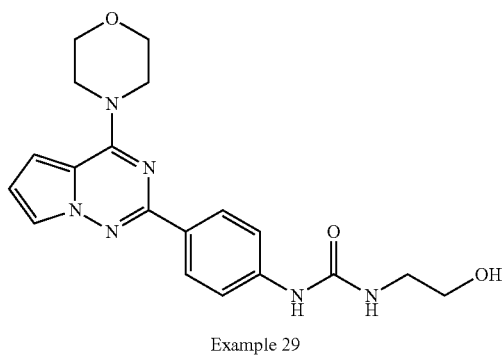

Example 29

The procedure of Example 29 (20.0 mg, yield: 51.5%) was similar to that of Example 15. $^1$H NMR (MeOD-d$_4$, 400 MHz): δ 8.17-8.14 (m, 2H), 7.66-7.65 (m, 1H), 7.46-7.43 (m, 2H), 6.89-6.88 (m, 1H), 6.69-6.67 (m, 1H), 4.12 (t, 4H, J=5.2 Hz), 3.85 (t, 4H, J=4.8 Hz), 3.64 (t, 2H, J=5.6 Hz), 3.33 (t, 2H, J=4.4 Hz). ESI-MS (M+H)$^+$: 383.

Synthesis of Example 30

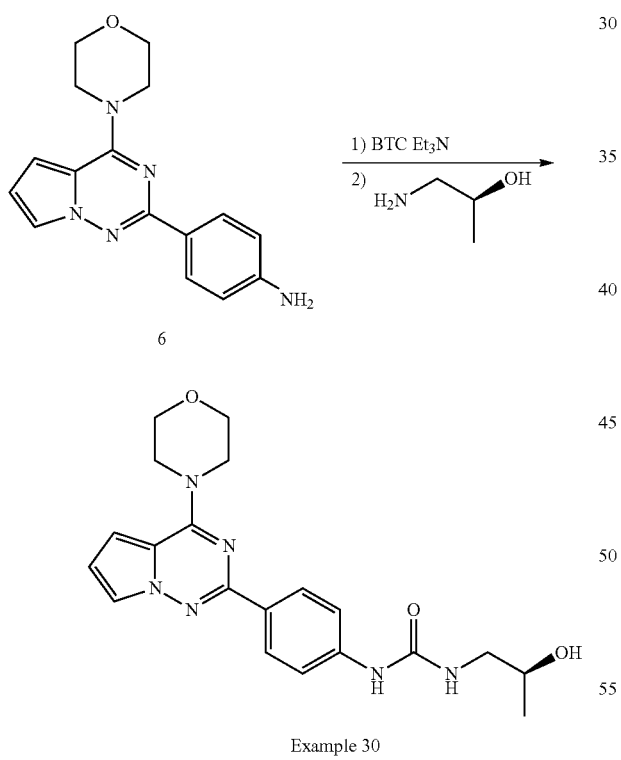

Example 30

The procedure of Example 30 (20.0 mg, yield: 46.5%) was similar to that of Example 15. $^1$H NMR (MeOD-d$_4$, 400 MHz): δ 8.15 (d, 2H, J=8.8 Hz), 7.66-7.65 (m, 1H), 7.44 (d, 2H, J=8.8 Hz), 6.89-6.87 (m, 1H), 6.69-6.67 (m, 1H), 4.12 (t, 4H, J=4.4 Hz), 3.85 (t, 4H, J=4.8 Hz), 3.12-3.07 (m, 1H), 1.32-1.29 (m, 2H), 1.18 (d, 3H, J=6.4 Hz). ESI-MS (M+H)$^+$: 397.

Synthesis of Example 31

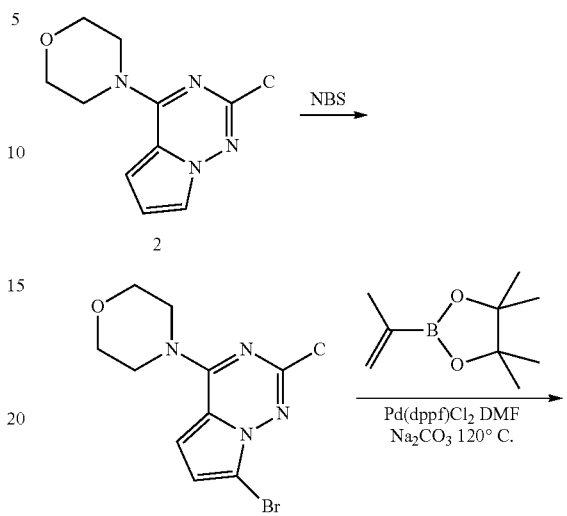

Example 31

Synthesis of Compound 26

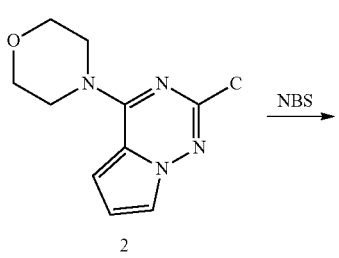

-continued

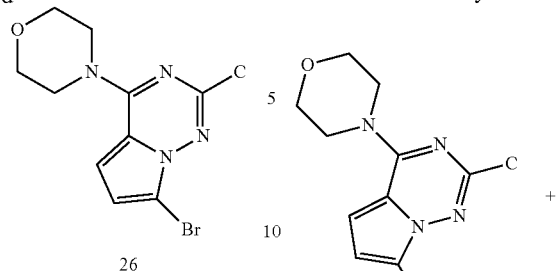

26

To a stirred solution of compound 2 (1.20 g, 5.03 mmol) in DMF (8 mL) was added NBS (940 mg, 5.28 mmol) in DMF (1 mL), the reaction mixture was stirred for 2 h at ambient temperature. Then the reaction was quenched with $H_2O$ and extracted with EA. The organic phase was washed with brine, dried over $Na_2SO_4$, filtered and concentrated, the crude product was purified by column chromatography (PE/EA=10:1) to give compound 26 (1.2 g, yield: 75.2%). $^1$H-NMR (400 MHz, CDCl$_3$) δ 6.79 (d, 1H, J=4.8 Hz), 6.69 (d, 1H, J=4.8 Hz), 4.05~4.03 (m, 4H), 3.85~3.83 (m, 4H).

Synthesis of Compound 27

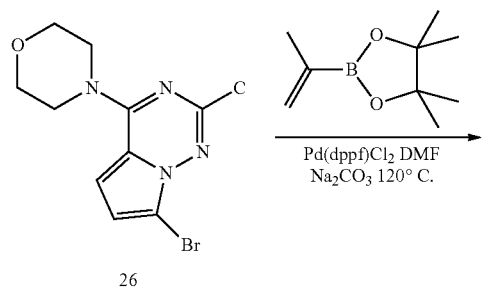

26

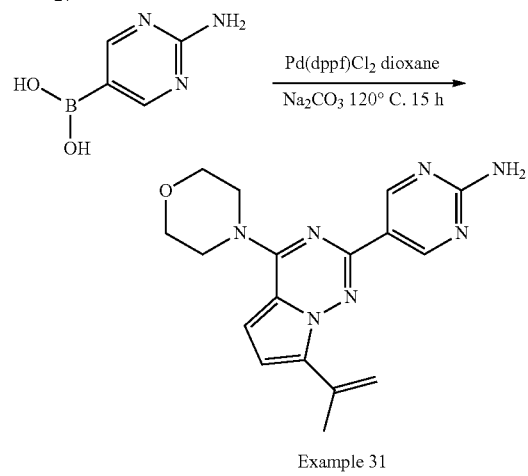

27

A mixture of compound 26 (1.2 g, 3.78 mmol), isopropenylboronic acid pinacol ester (1.07 mL, 5.67 mmol) and $Na_2CO_3$ (50 mg, 472 mmol) in DMF (5.0 mL) and $H_2O$ (1.0 mL) was added Pd(dppf)Cl$_2$ (30 mg) under $N_2$ protection. The resulting mixture was stirred at 95° C. for overnight. The mixture was dissolved in EA and filtrated over celite. The filtrate was washed with water, brine, dried over $Na_2SO_4$ and concentrated to give the crude product. After purified by column chromatography (PE/EA=10:1) to afford compound 27 (340 mg, yield: 32.3%). $^1$H-NMR (400 MHz, CDCl$_3$) δ 6.75 (d, 1H, J=4.8 Hz), 6.66 (d, 1H, J=4.8 Hz), 6.20 (d, 1H, J=0.8 Hz), 5.39 (d, 1H, J=1.6 Hz), 4.05-4.00 (m, 4H), 3.85-3.83 (m, 4H), 2.21 (s, 3H).

Synthesis of Example 31

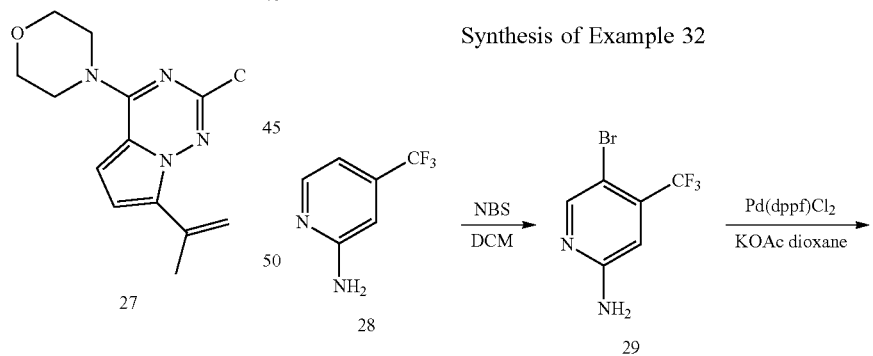

Example 31

The procedure of Example 31 (5.0 mg, yield: 20.1%) was similar to that of Example 24. $^1$H NMR (400 MHz, CDCl$_3$) δ 9.17 (s, 2H), 6.76~6.72 (m, 2H), 6.34 (d, 1H, J=1.6 Hz), 5.77~5.76 (m, 2H), 5.41 (d, 1H, J=1.6 Hz), 4.09~4.08 (m, 4H), 3.89~3.86 (m, 4H), 2.28 (s, 3H). ESI-MS (M+H)$^+$: 338.73.

Synthesis of Example 32

Synthesis of Compound 29

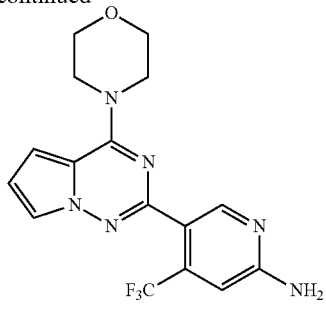

Example 32

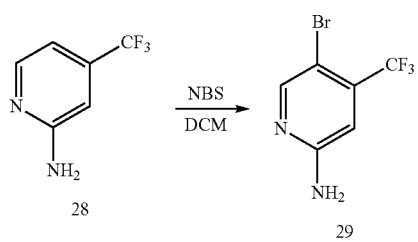

To a solution of compound 28 (500 mg, 3.1 mmol) in DCM (40 mL) was added NBS (600 mg, 3.3 mmol). The solution was stirred in the dark for 2 hours at rt. Then the reaction was quenched with 1N NaOH (50 mL) and extracted with DCM (50 mL). The organic phase was washed with brine (100 mL), dried over $Na_2SO_4$, filtered and concentrated. The residue was purified with silica gel column chromatography using Petroleum ether:Ethyl acetate (10:1) affording to compound 29 (700 mg, 94%) as a light yellow solid. $^1$H NMR (CDCl$_3$): δ 8.28 (s, 1H), 6.77 (s, 1H), 4.78 (bs, 2H).

Synthesis of Compound 30

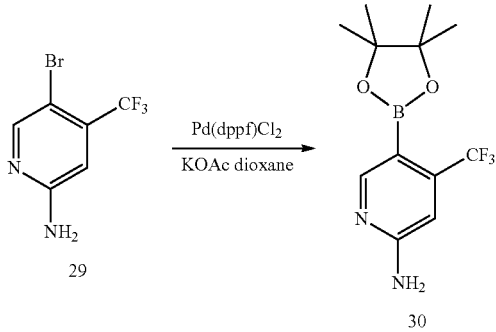 [SMILES: Nc1cc(C(F)(F)F)c(Br)cn1 ; "KOAc dioxane" ; "Pd(dppf)Cl2" ; CC1(C)OB(c2cnc(N)cc2C(F)(F)F)OC1(C)C]

To a dry flask was added 5-bromo-4-(trifluoromethyl)pyridin-2-amine (220 mg, 0.91 mmol), potassium acetate (446 mg, 4.55 mmol), bis(pinacolato)diboron (279 mg, 1.10 mmol, 1.1 eq.) and dioxane (5 mL). $N_2$ was bubbled through the solution for 1.5 minutes, at which time 1,1-bis(diphenylphosphino)ferrocene-palladium(II) (32 mg, 45 mol) was added. The reaction was stirred at 100° C. for 16 hours under $N_2$. After cooling to room temperature, the dioxane was removed in vacuo. EA was added and the resulting slurry was sonicated and filtered. Additional ethyl acetate was used to wash the solid. The combined organic was concentrated and the crude material was purified by silica gel chromatography using Petroleum ether:Ethyl acetate (10:1) affording to compound 30 (60 mg, 23%) as a light yellow solid. $^1$H NMR (400 MHz, CDCl$_3$): δ 8.47 (s, 1H), 6.76 (s, 1H), 5.15 (bs, 2H), 1.34 (s, 12H).

Synthesis of Example 32

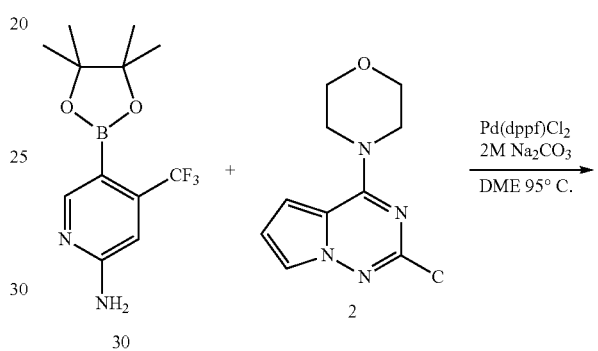

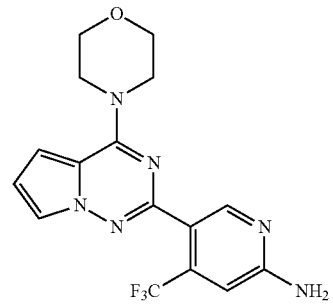

Example 32

To a mixture of compound 30 (60 mg, 0.21 mmol), compound 2 (48 mg, 0.20 mmol) and 2M $Na_2CO_3$ (0.5 ml) was added DME (1.5 ml). $N_2$ was bubbled through the solution for 1.5 minutes, at which time Pd(dppf)Cl$_2$ (10 mg, 10 μmol) was added. The reaction was stirred at 95° C. for 16 hours under $N_2$. After cooling to room temperature, Ethyl acetate was added and the resulting slurry was sonicated and filtered. Additional ethyl acetate was used to wash the solid. The combined organic was concentrated and the crude material was purified by Prep-TLC using Petroleum ether:Ethyl acetate (3:1) affording to Example 32 (5 mg, 7%) as a yellow oil. $^1$H NMR (400 MHz, CDCl$_3$): δ 8.54 (s, 1H), 7.68-7.64 (m, 1H), 6.84 (s, 1H), 6.72-6.76 (m, 1H), 6.68-6.72 (m, 1H), 5.03 (bs, 2H), 4.11-4.03 (m, 4H), 3.87-3.80 (m, 4H). ESI-MS (M+H)$^+$: 365.3.

Synthesis of Example 33

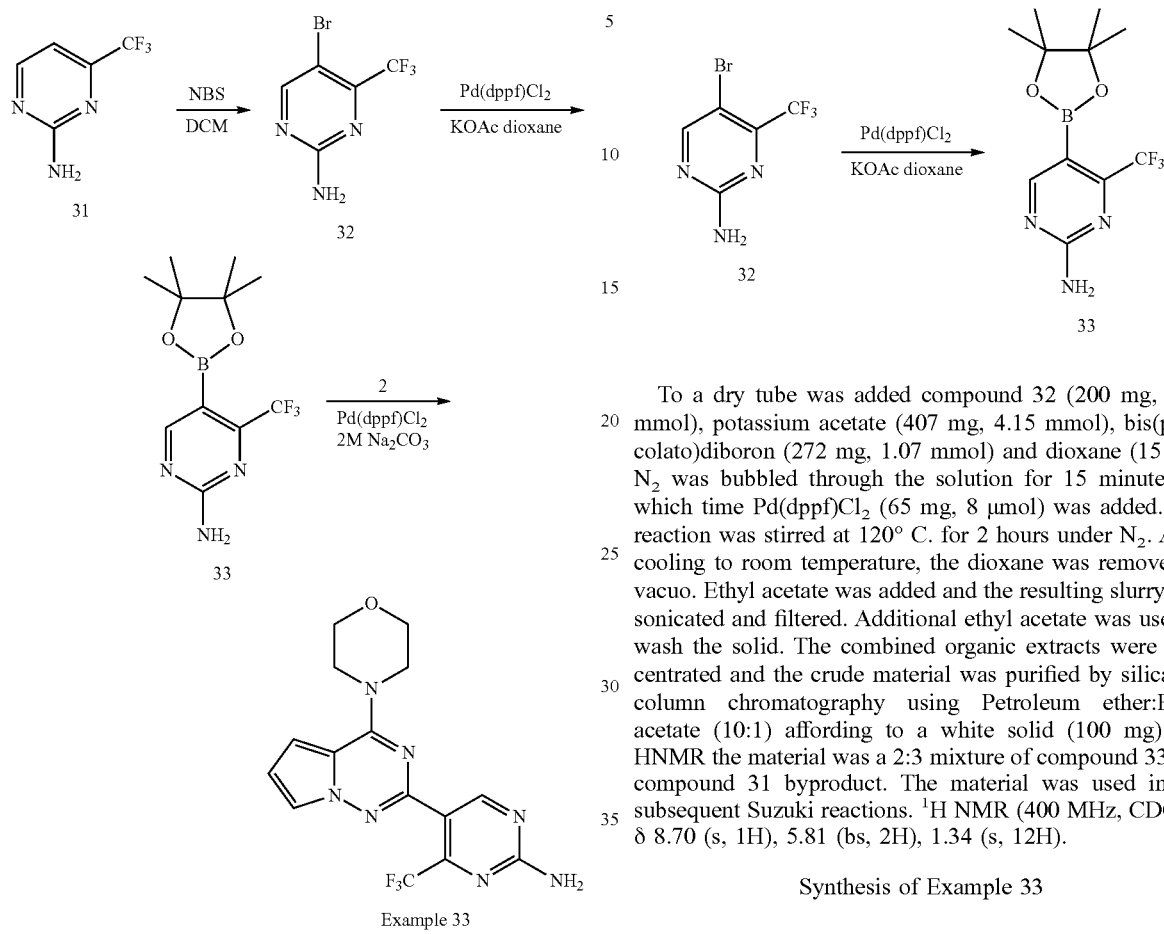

Example 33

Synthesis of Compound 32

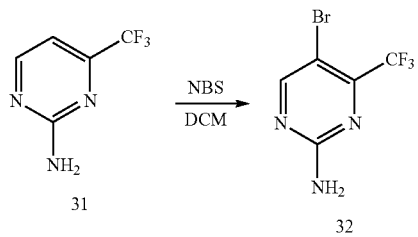

To a solution of compound 31 (500 mg, 3.06 mmol) in DCM (60 mL) was added NBS (1.66 g, 9.32 mmol). The solution was stirred in the dark for 2d at rt. Then the reaction was quenched with 1N NaOH (50 mL) and extracted with DCM (50 mL). The organic phase was washed with brine (100 mL), dried over $Na_2SO_4$, filtered and concentrated to give the title compound 32 as a white solid (530 mg, 73% yield), which was used directly in the next step without further purification. $^1$H NMR (CDCl$_3$): δ 8.52 (s, 1H), 5.29 (bs, 2H).

Synthesis of Compound 33

To a dry tube was added compound 32 (200 mg, 0.83 mmol), potassium acetate (407 mg, 4.15 mmol), bis(pinacolato)diboron (272 mg, 1.07 mmol) and dioxane (15 ml). $N_2$ was bubbled through the solution for 15 minutes, at which time Pd(dppf)Cl$_2$ (65 mg, 8 μmol) was added. The reaction was stirred at 120° C. for 2 hours under $N_2$. After cooling to room temperature, the dioxane was removed in vacuo. Ethyl acetate was added and the resulting slurry was sonicated and filtered. Additional ethyl acetate was used to wash the solid. The combined organic extracts were concentrated and the crude material was purified by silica gel column chromatography using Petroleum ether:Ethyl acetate (10:1) affording to a white solid (100 mg). By HNMR the material was a 2:3 mixture of compound 33 and compound 31 byproduct. The material was used in the subsequent Suzuki reactions. $^1$H NMR (400 MHz, CDCl$_3$): δ 8.70 (s, 1H), 5.81 (bs, 2H), 1.34 (s, 12H).

Synthesis of Example 33

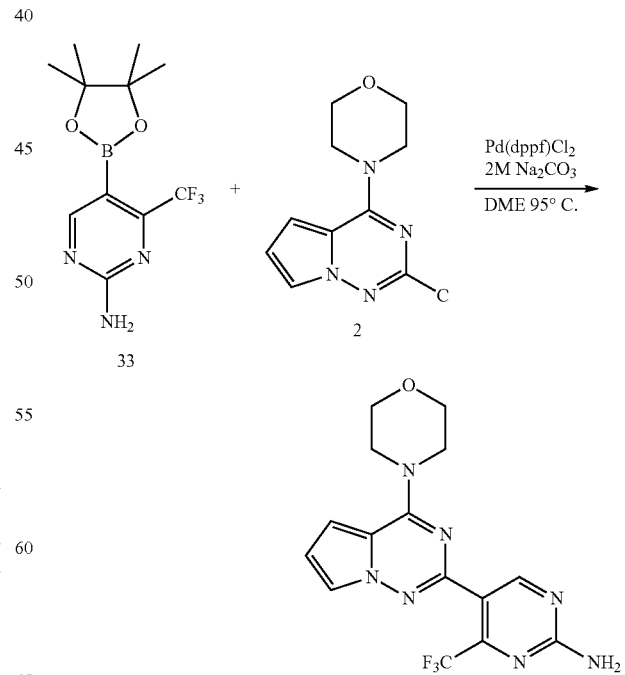

Example 33

To a mixture of compound 33 (80 mg, 0.28 mmol), compound 2 (22 mg, 0.09 mmol) and 2M Na$_2$CO$_3$ (1.2 mL) was added dioxane (6 mL). N$_2$ was bubbled through the solution for 1.5 minutes, at which time Pd(dppf)Cl$_2$ (12 mg, 3 μmol) was added. The reaction was stirred at 100° C. for 1 hour under N$_2$. After cooling to room temperature, Ethyl acetate was added and the resulting slurry was sonicated and filtered. Additional ethyl acetate was used to wash the solid. The combined organic extracts were concentrated and the crude material was purified by Prep-TLC using Petroleum ether:Ethyl acetate (3:1) affording to Example 33 (10 mg), and the compound was unstable. $^1$H NMR (400 MHz, CDCl$_3$): δ 8.83 (s, 1H), 7.68-7.64 (m, 1H), 6.74-6.78 (m, 1H), 6.70-6.73 (m, 1H), 5.53 (bs, 2H), 4.11-4.04 (m, 4H), 3.87-3.82 (m, 4H). ESI-MS (M+H)$^+$: 366.1

Synthesis of Example 34

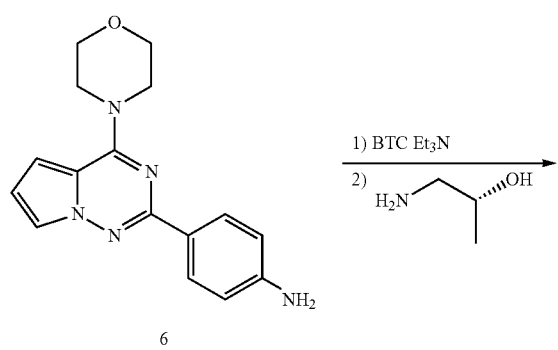

Example 34

The procedure of Example 34 (20.0 mg, yield: 71.4%) was similar to that of Example 15. $^1$H NMR (DMSO-d$_6$, 400 MHz): δ 9.15 (s, 1H), 8.08 (d, 2H, J=8.8 Hz), 7.79-7.78 (m, 1H), 7.49 (d, 2H, J=8.8 Hz), 6.99-6.97 (m, 1H), 6.71-6.69 (m, 1H), 6.51-6.48 (m, 1H), 4.78 (d, 1H, J=4.8 Hz), 4.06 (t, 4H, J=4.4 Hz), 3.78 (t, 4H, J=4.8 Hz), 3.68-3.65 (m, 1H), 3.14-3.08 (m, 1H), 3.01-2.95 (m, 1H), 1.06 (d, 3H, J=6.0 Hz). ESI-MS (M+H)$^+$: 397.

Synthesis of Example 35

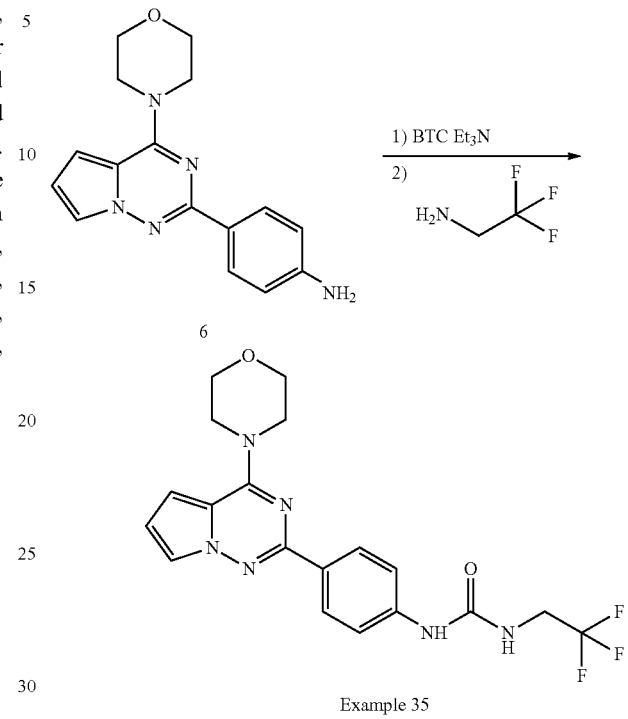

Example 35

The procedure of Example 35 (20.0 mg, yield: 56.2%) was similar to that of Example 15. $^1$H NMR (DMSO-d$_6$, 400 MHz): δ 9.53 (s, 1H), 8.12 (d, 2H, J=8.4 Hz), 7.80-7.79 (m, 1H), 7.52 (d, 2H, J=8.8 Hz), 7.24-7.21 (m, 1H), 6.99-6.98 (m, 1H), 6.72-6.70 (m, 1H), 4.06 (t, 4H, J=4.4 Hz), 3.96-3.89 (m, 2H), 3.78 (t, 4H, J=4.8 Hz). ESI-MS (M+H)$^+$: 421.

Synthesis of Example 36

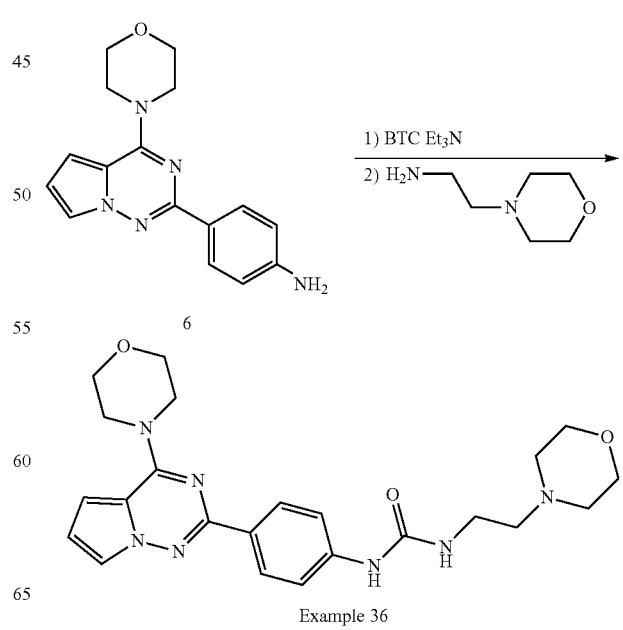

Example 36

The procedure of Example 36 (15.0 mg, yield: 48.5%) was similar to that of Example 15. $^1$H NMR (MeOD-d$_4$, 400 MHz): δ 8.17 (d, 2H, J=8.8 Hz), 7.67-7.66 (m, 1H), 7.48 (d, 2H, J=8.8 Hz), 6.79-6.78 (m, 1H), 6.69-6.68 (m, 1H), 4.15 (t, 4H, J=4.4 Hz), 3.91 (t, 4H, J=4.8 Hz), 3.76 (t, 4H, J=4.4 Hz), 3.39 (t, 2H, J=6.4 Hz), 2.58 (t, 6H, J=6.4 Hz). ESI-MS (M+H)$^+$: 452.

Synthesis of Example 37

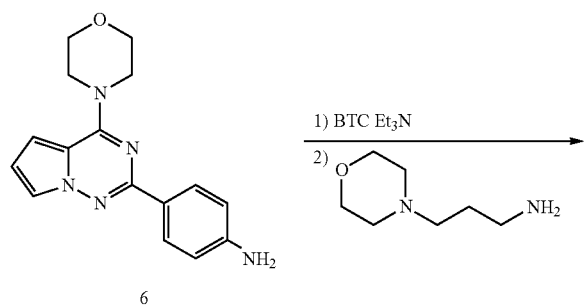

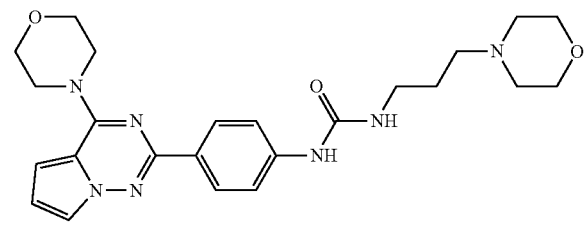

Example 37

The procedure of Example 37 (15.0 mg, yield: 47.4%) was similar to that of Example 15. $^1$H NMR (DMSO-d$_6$, 400 MHz): δ 9.00 (s, 1H), 8.08 (d, 2H, J=8.8 Hz), 7.79-7.78 (m, 1H), 7.49 (d, 2H, J=8.8 Hz), 6.99-6.98 (m, 1H), 6.71-6.69 (m, 1H), 6.47-6.44 (m, 1H), 4.06 (t, 4H, J=4.4 Hz), 3.78 (t, 4H, J=4.8 Hz), 3.58 (t, 4H, J=4.4 Hz), 3.15-3.10 (m, 2H), 2.35-2.29 (m, 6H), 1.59 (t, 2H, J=7.2 Hz). ESI-MS (M+H)$^+$: 466.

Synthesis of Example 38

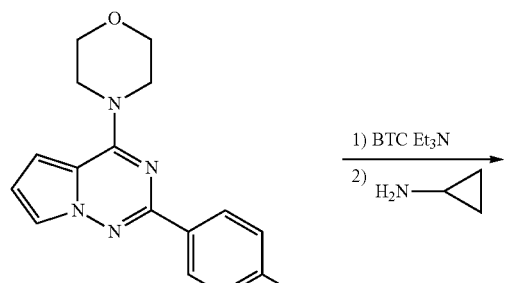

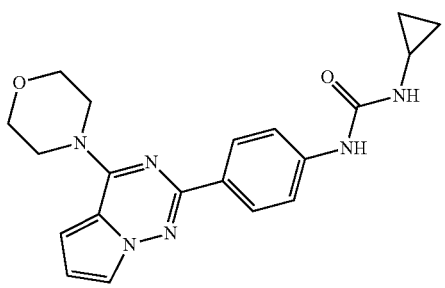

Example 38

The procedure of Example 38 (15.0 mg, yield: 58.3%) was similar to that of Example 15. $^1$H NMR (MeOD-d$_4$, 400 MHz): δ 8.17-8.15 (m, 2H), 7.68-7.65 (m, 1H), 7.50-7.48 (m, 2H), 6.83-6.81 (m, 1H), 6.69-6.67 (m, 1H), 4.15 (t, 4H, J=4.8 Hz), 3.89 (t, 4H, J=4.8 Hz), 2.63-2.60 (m, 1H), 0.78-0.76 (m, 2H), 0.55-0.54 (m, 2H). ESI-MS (M+H)$^+$: 379.

Synthesis of Example 39

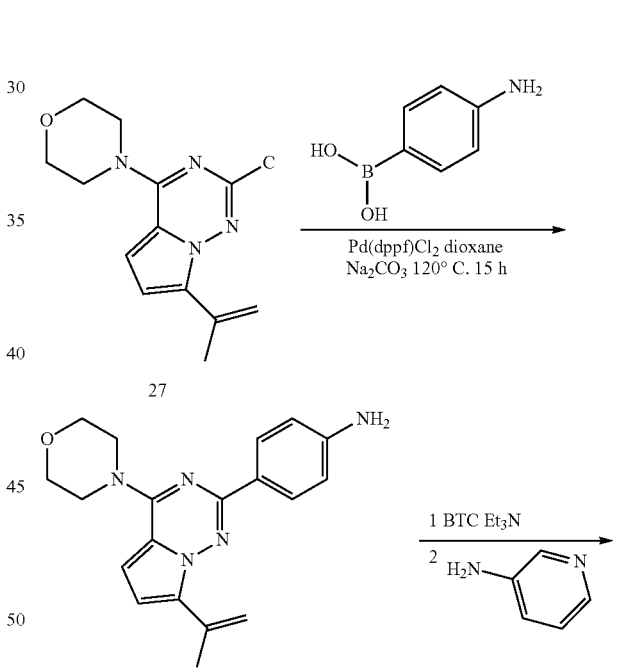

Example 39

Synthesis of Compound 34

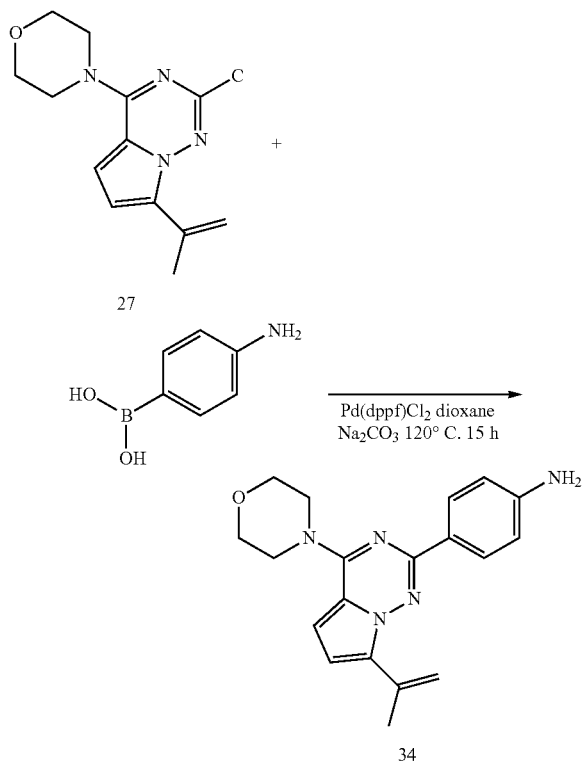

The procedure of compound 34 (16 mg, yield: 44%) was similar to that of Example 24. $^1$H NMR (400 MHz, CDCl$_3$) δ 8.13 (d, 2H, J=4.8 Hz), 6.74~6.68 (m, 4H), 6.49 (d, 1H, J=1.6 Hz), 5.40 (s, 1H), 4.13~4.07 (m, 4H), 3.88~3.78 (m, 4H), 2.29 (s, 3H).

Synthesis of Example 39

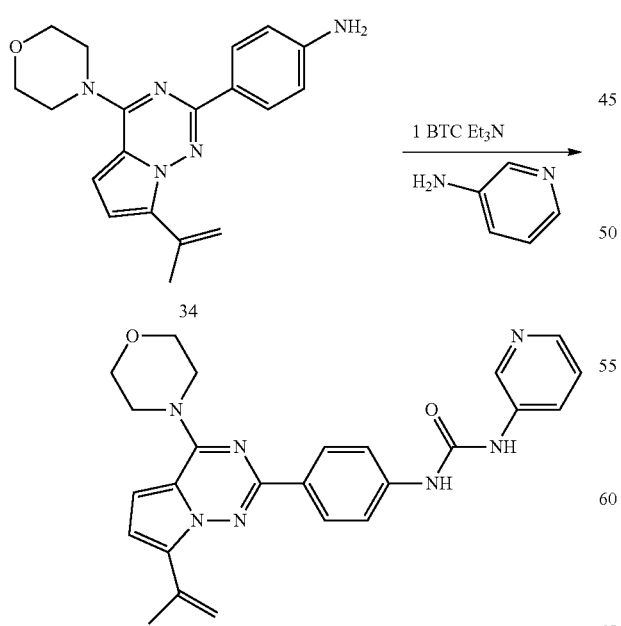

The procedure of Example 9 (5.0 mg, yield: 20.1%) was similar to that of Example 15. $^1$H NMR (400 MHz, MeOD) δ 8.39 (s, 1H), 8.12~8.03 (m, 4H), 7.39 (d, 2H, J=4.8 Hz), 7.26~7.22 (m, 1H), 6.61~6.57 (m, 2H), 6.32 (s, 1H), 5.26 (s, 1H), 3.76~3.74 (m, 4H), 3.20~3.19 (m, 4H), 2.15 (s, 3H). ESI-MS (M+H)$^+$: 456.97.

Synthesis of Example 40

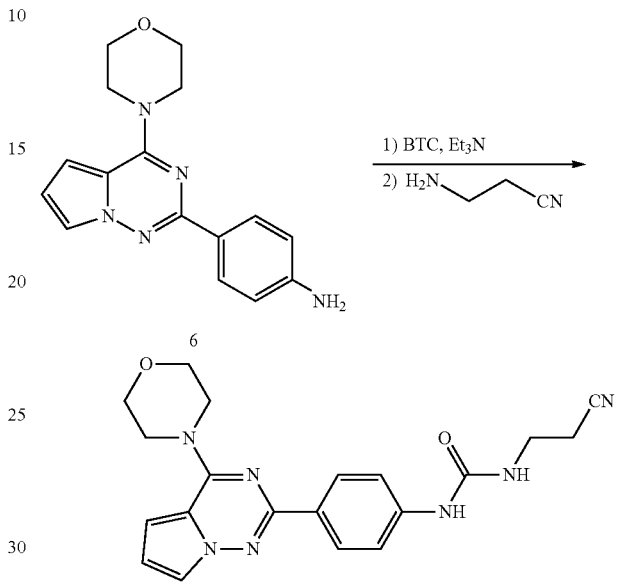

The procedure of Example 40 (10.0 mg, yield: 51.1%) was similar to that of Example 15. $^1$H NMR (MeOD-d$_4$, 400 MHz): δ 8.19-8.17 (m, 2H), 7.67 (s, 1H), 7.49-7.47 (m, 2H), 6.76-6.75 (m, 1H), 6.69-6.68 (m, 1H), 4.16-4.15 (m, 4H), 3.92-3.91 (m, 4H), 3.51 (d, 2H, J=6.0 Hz), 2.69 (t, 2H, J=6.4 Hz). ESI-MS (M+H)$^+$: 392.

Synthesis of Example 41

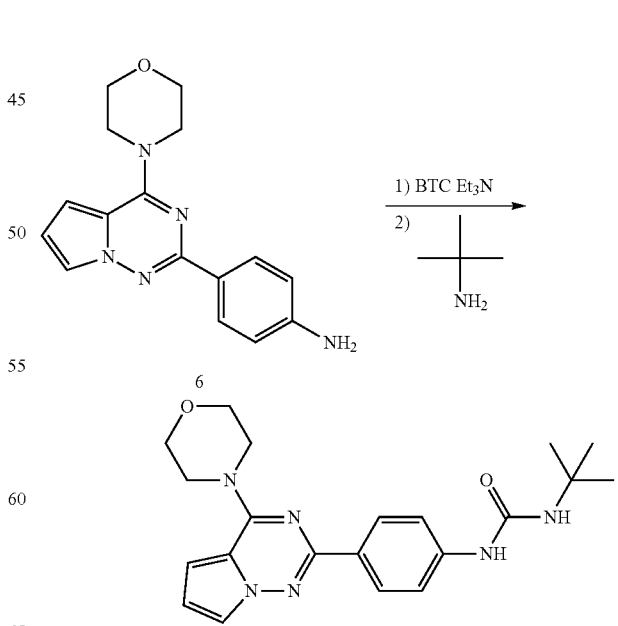

The procedure of Example 41 (10.0 mg, yield: 50.7%) was similar to that of Example 15. $^1$H NMR (CDCl$_3$, 400 MHz): δ 8.21 (d, 2H, J=8.0 Hz), 7.67 (s, 1H), 7.34 (d, 2H, J=8.0 Hz), 6.71-6.66 (m, 2H), 6.40 (s, 1H), 4.74-4.70 (m, 1H), 4.12 (t, 4H, J=4.4 Hz), 3.89 (t, 4H, J=4.4 Hz), 1.39 (m, 9H). ESI-MS (M+H)$^+$: 395.

Synthesis of Example 42

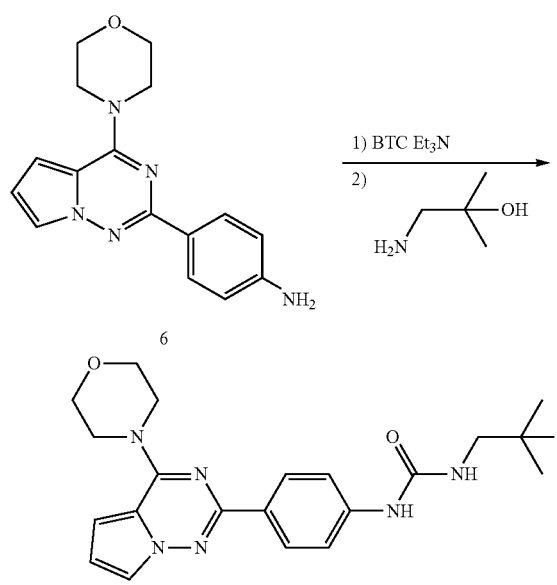

Example 42

The procedure of Example 42 (10.0 mg, yield: 48.7%) was similar to that of Example 15. $^1$HNMR (MeOD-d$_4$, 400 MHz): δ 7.88 (d, 2H, J=8.8 Hz), 7.39 (s, 1H), 7.20 (d, 2H, J=8.8 Hz), 6.53-6.52 (m, 1H), 6.42-6.40 (m, 1H), 3.88 (t, 4H, J=4.4 Hz), 3.63 (t, 4H, J=4.8 Hz), 2.95 (s, 2H), 0.96 (s, 6H). ESI-MS (M+H)$^+$: 411.

Synthesis of Example 43

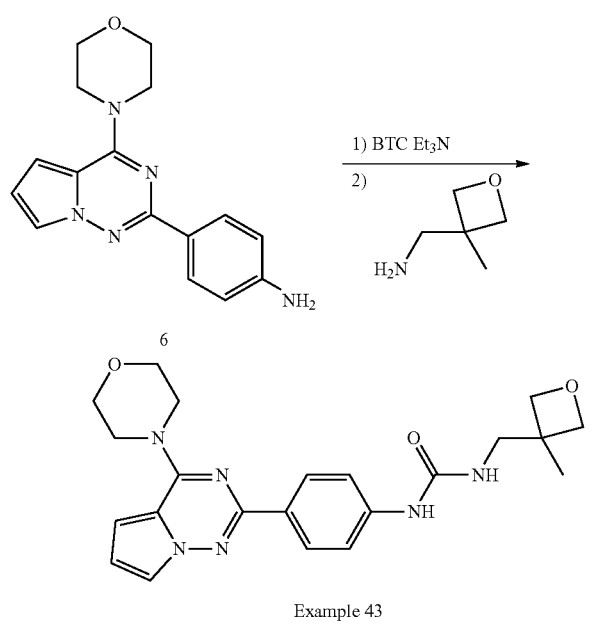

Example 43

The procedure of Example 43 (10.0 mg, yield: 47.3%) was similar to that of Example 15. 1H NMR (MeOD-d4, 400 MHz): δ 8.54 (d, 2H, J=8.4 Hz), 8.04 (s, 1H), 7.87-7.85 (m, 2H), 7.15-7.14 (m, 1H), 7.06-7.05 (m, 1H), 4.95 (d, 2H, J=4.8 Hz), 4.80-4.78 (m, 2H), 4.53-4.52 (m, 4H), 4.29-4.28 (m, 4H), 3.79 (s, 2H), 1.74 (s, 3H). ESI-MS (M+H)+: 423.

Synthesis of Example 44

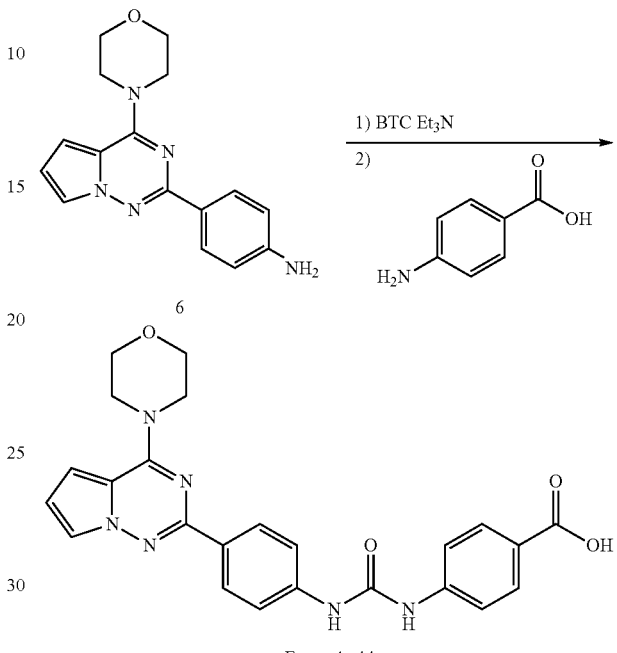

Example 44

The procedure of Example 44 (160.0 mg, yield: 51.5%) was similar to that of Example 15. $^1$H NMR (DMSO-d$_6$, 400 MHz): δ 12.65-12.60 (m, 1H), 9.11 (s, 1H), 9.03 (s, 1H), 8.17 (d, 2H, J=8.4 Hz), 7.88 (d, 2H, J=8.4 Hz), 7.81-7.80 (m, 1H), 7.59-7.57 (m, 4H), 7.01-7.00 (m, 1H), 6.73-6.71 (m, 1H), 4.07 (t, 4H, J=4.4 Hz), 3.79 (t, 4H, J=4.8 Hz). ESI-MS (M+H)$^+$: 459.

Synthesis of Example 45

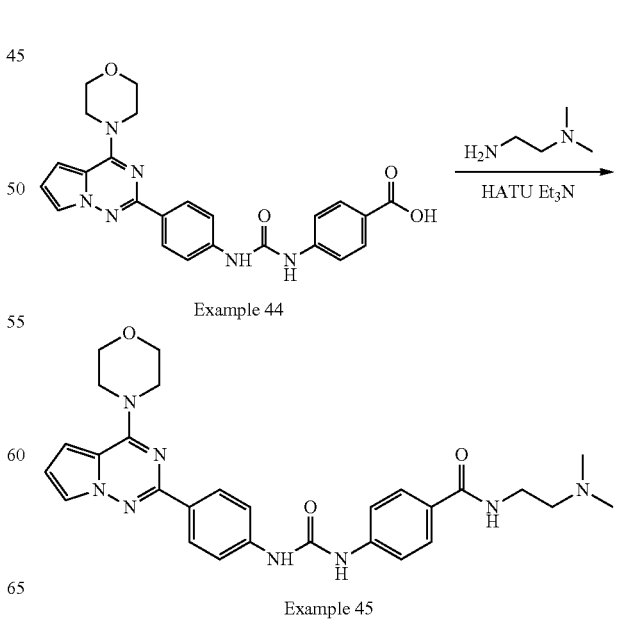

Example 45

A mixture of Example 44 (20 mg, 0.04 mmol) and HATU (25 mg, 0.06 mmol) in DCM (2 mL) was added Et$_3$N (19 uL, 0.13 mmol) at room temperature. After 5 mins, N1,N1-dimethylethane-1,2-diamine (7 μL, 0.06 mmol) was added. The mixture was stirred at RT for 3 h, diluted with H$_2$O, and extracted with DCM. The combined organic layers were washed with brine, dried over Na$_2$SO$_4$ and concentrated. The crude material was purified by Prep-TLC to give Example 45 (7 mg, 30.4%). $^1$H NMR (MeOD-d$_4$, 400 MHz): δ 7.97 (d, 2H, J=8.0 Hz), 7.63 (d, 2H, J=7.6 Hz), 7.43 (s, 1H), 7.35-7.31 (m, 4H), 6.55-6.53 (m, 1H), 6.46-6.44 (m, 1H), 3.92-3.91 (m, 4H), 3.67-3.66 (m, 4H), 3.54-3.52 (m, 2H), 3.14-3.13 (m, 2H), 2.73 (s, 6H). ESI-MS (M+H)$^+$: 529.

Synthesis of Example 46

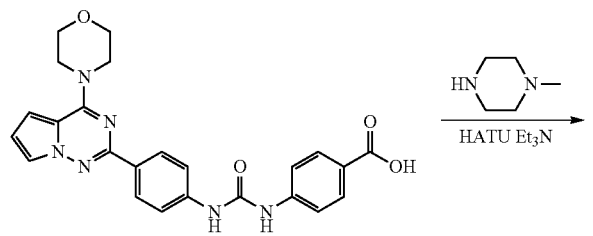

Example 44

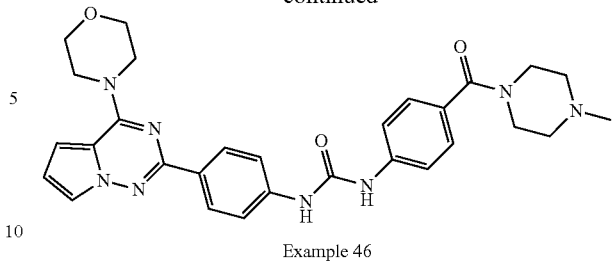

Example 46

The procedure of Example 46 (9.0 mg, yield: 41.7%) was similar to that of Example 45. $^1$H NMR (MeOD-d$_4$, 400 MHz): δ 8.21 (d, 2H, J=8.4 Hz), 7.67 (s, 1H), 7.57-7.55 (m, 4H), 7.39 (d, 2H, J=8.4 Hz), 6.81-6.80 (m, 1H), 6.70-6.69 (m, 1H), 4.16-4.15 (m, 4H), 3.91-3.90 (m, 4H), 3.77-3.60 (m, 4H), 2.61-2.60 (m, 4H), 2.44 (s, 3H). ESI-MS (M+H)$^+$: 541.

Synthesis of Example 47

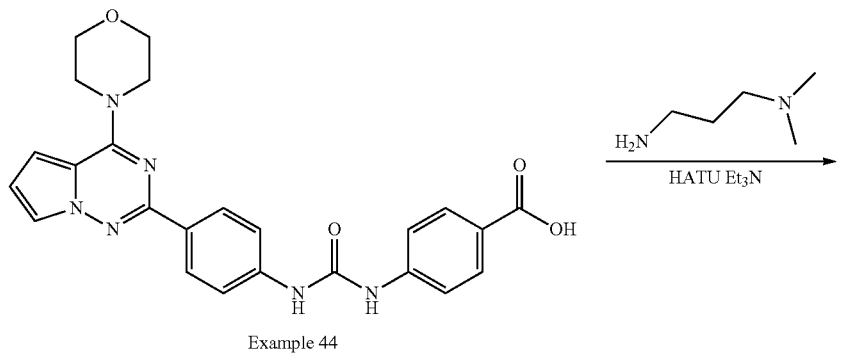

Example 44

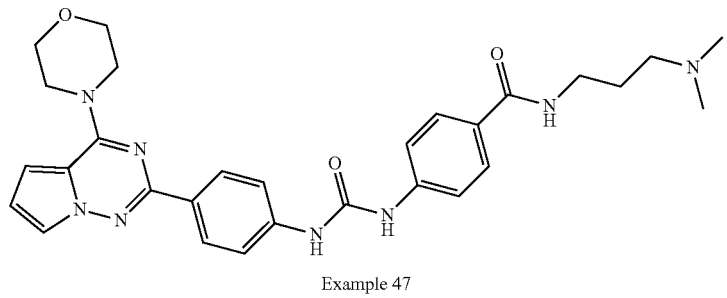

Example 47

The procedure of Example 47 (9.0 mg, yield: 41.5%) was similar to that of Example 45. $^1$H NMR (MeOD-d$_4$, 400 MHz): δ 8.21 (d, 2H, J=8.4 Hz), 7.83 (d, 2H, J=8.8 Hz), 7.68 (s, 1H), 7.59-7.53 (m, 4H), 6.79-6.78 (m, 1H), 6.70-6.69 (m, 1H), 4.16-4.15 (m, 4H), 3.91 (s, 4H), 3.53-3.50 (m, 2H), 3.18-3.15 (m, 2H), 2.90 (s, 6H), 2.10-2.04 (m, 2H). ESI-MS (M+H)$^+$: 543.

Synthesis of Example 48
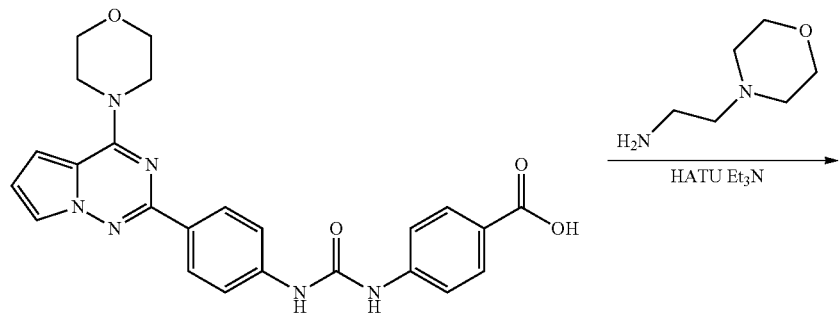
Example 44
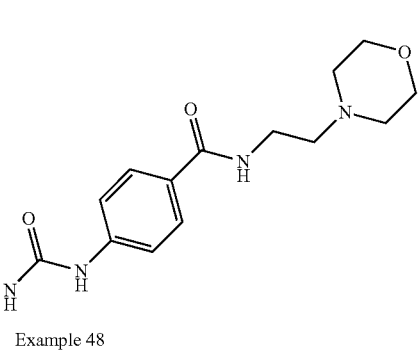
Example 48
The procedure of Example 48 (5.0 mg, yield: 21.9%) was similar to that of Example 45. $^1$H NMR (DMSO-d$_6$, 400 MHz): δ 9.19 (s, 1H), 8.28 (s, 1H), 8.17 (d, 2H, J=8.8 Hz), 7.79 (d, 2H, J=8.8 Hz), 7.58-7.53 (m, 4H), 7.01-7.00 (m, 3H), 6.73-6.71 (m, 1H), 4.07 (t, 4H, J=4.0 Hz), 3.79 (t, 4H, J=4.4 Hz), 3.57 (t, 4H, J=4.0 Hz), 3.38-3.34 (m, 2H), 2.47-2.41 (m, 6H). ESI-MS (M+H)$^+$: 571.
Synthesis of Example 49
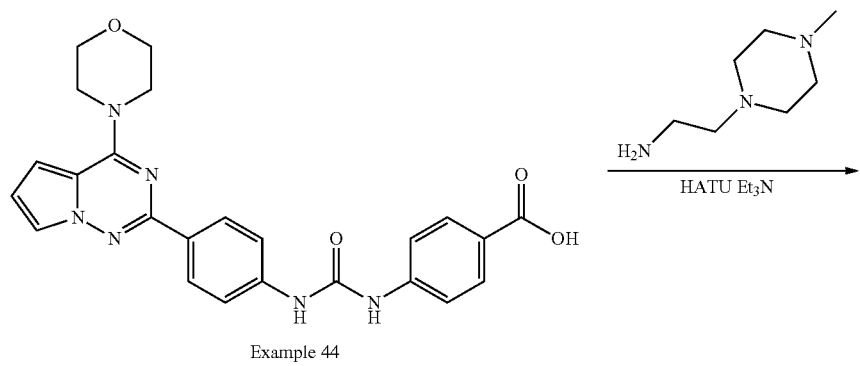
Example 44
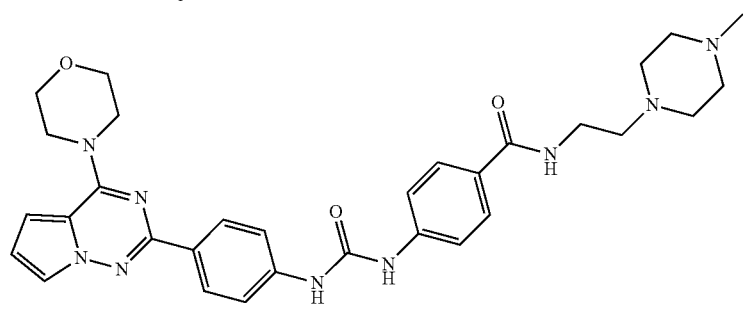
Example 49

The procedure of Example 49 (10.0 mg, yield: 42.9%) was similar to that of Example 45. $^1$H NMR (MeOD-d$_4$, 400 MHz): δ 8.21 (d, 2H, J=8.8 Hz), 7.80 (d, 2H, J=8.8 Hz), 7.68 (s, 1H), 7.58-7.55 (m, 4H), 6.82-6.81 (m, 1H), 6.70-6.69 (m, 1H), 4.16 (s, 4H), 3.91 (s, 4H), 3.58-3.55 (m, 2H), 2.91-2.73 (m, 10H), 2.58 (s, 3H). ESI-MS (M+H)$^+$: 584.

Synthesis of Example 50

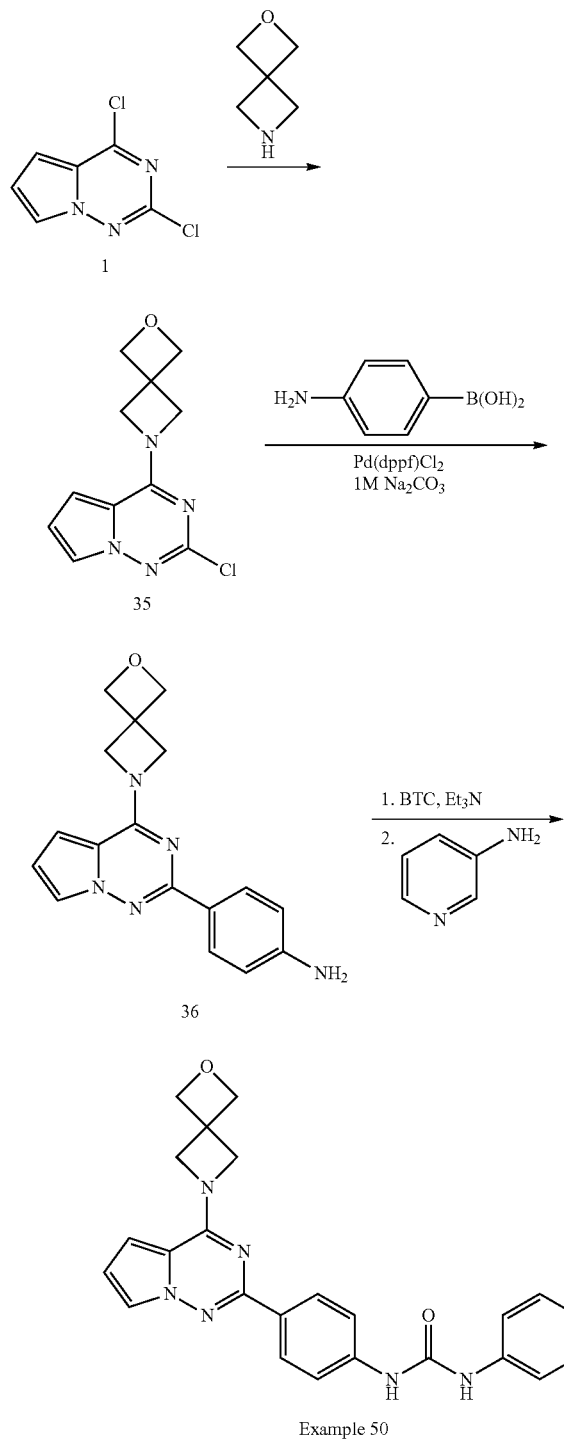

Example 50

Synthesis of Compound 35

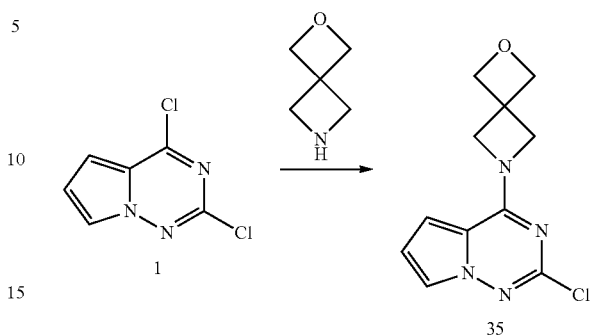

A mixture of 2,4-dichloropyrrolo[1,2-f][1,2,4]triazine (150 mg, 0.8 mmol), 2-oxa-6-azaspiro[3.3]heptane (103 mg, 1.04 mmol) and K$_2$CO$_3$ (221 mg, 1.6 mmol) in DMF (4.5 mL) was stirred at room temperature for 2 h. TLC showed the starting material was completely consumed and DCM (10 mL) was added to the mixture, and the mixture was washed with water (5 mL) and brine. The organic layer was dried over anhydrous Na$_2$SO$_4$ and concentrated in vacuo to give compound 35 (160 mg, 81%).

Synthesis of Compound 36

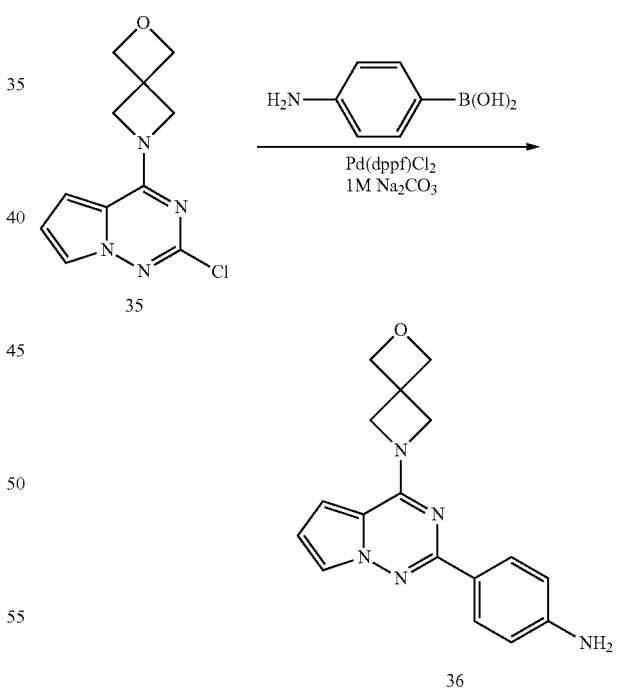

To a mixture of compound 35 (161 mg, 0.64 mmol), (4-aminophenyl)boronic acid (212 mg, 0.97 mmol) and 1.8M Na2CO3 (1.5 ml) was added dioxane (6 ml). N2 was bubbled through the solution for 1.5 minutes, at which time Pd(dppf)Cl$_2$ (44 mg, 60 μmol) was added. The reaction was stirred at 120° C. for 20 hours under N2. After cooling to room temperature, Ethyl acetate (20 mL) was added and the resulting slurry was sonicated and filtered. Additional ethyl acetate was used to wash the solid. The combined organic extracts were concentrated and the crude material was purified by silica gel column chromatography (Petroleum ether:Ethyl acetate=4:1) affording to compound 36 (30 mg) as a white solid.

Synthesis of Example 50

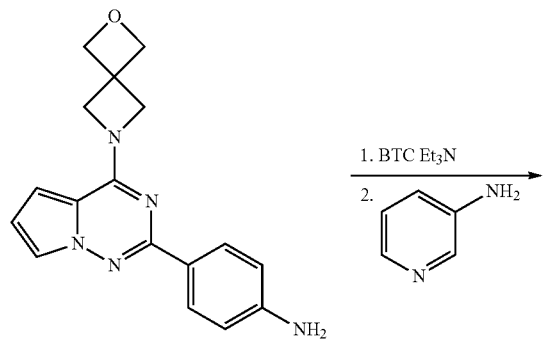

Example 50

The procedure of Example 50 (15.0 mg, yield: 30.0%) was similar to that of Example 15. $^1$H NMR (400 MHz, DMSO): δ 9.05 (s, 1H), 8.93 (s, 1H), 8.62 (d, 1H, J=2.2 Hz), 8.25-8.19 (m, 1H), 8.15 (d, 2H, J=8.6 Hz), 8.00-7.94 (m, 1H), 7.75-7.70 (m, 1H), 7.57 (d, 2H, J=8.6 Hz), 7.37-7.30 (m, 1H), 6.73-6.65 (m, 2H), 4.35-5.04 (m, 8H). ESI-MS (M+H)$^+$: 428.1.

Synthesis of Example 51

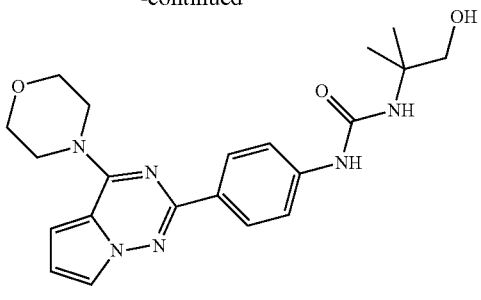

Example 51

The procedure of Example 51 (5.0 mg, yield: 17.9%) was similar to that of Example 15. $^1$H NMR (MeOD-d$_4$, 400 MHz): δ 8.15 (d, 2H, J=8.4 Hz), 7.65 (s, 1H), 7.43 (d, 2H, J=8.8 Hz), 6.81-6.80 (m, 1H), 6.69-6.68 (m, 1H), 4.14 (s, 4H), 3.91-3.90 (m, 4H), 3.61 (s, 2H), 1.34 (s, 6H). ESI-MS (M+H)$^+$: 411.

Synthesis of Example 52

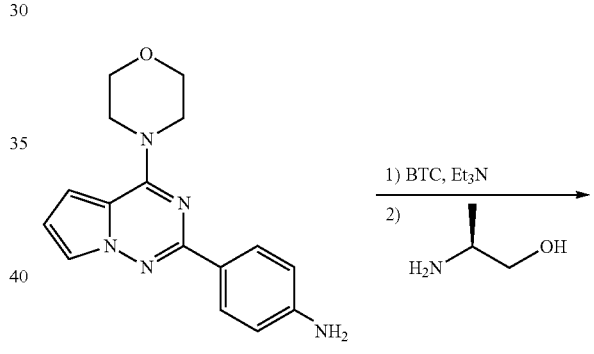

Example 52

The procedure of Example 52 (5.0 mg, yield: 18.6%) was similar to that of Example 15. $^1$H NMR (MeOD-d$_4$, 400 MHz): δ 8.15 (d, 2H, J=8.8 Hz), 7.66 (s, 1H), 7.45 (d, 2H, J=8.8 Hz), 6.84-6.83 (m, 1H), 6.69-6.67 (m, 1H), 4.14 (t, 4H, J=4.4 Hz), 3.89 (t, 5H, J=4.8 Hz), 3.56-3.55 (m, 2H), 1.21 (d, 3H, J=6.8 Hz). ESI-MS (M+H)+: 397

Synthesis of Example 53

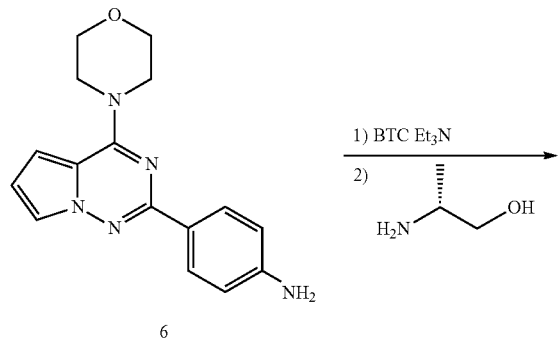

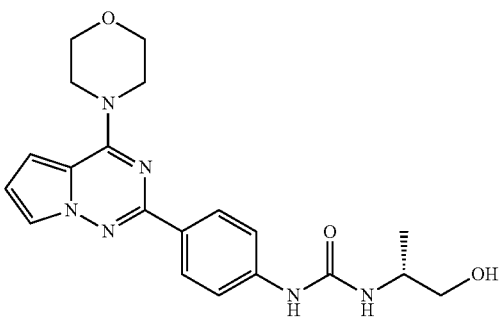

Example 53

The procedure of Example 53 (5.0 mg, yield: 18.6%) was similar to that of Example 15. ¹HNMR (MeOD-d₄, 400 MHz): δ 8.17 (d, 2H, J=6.8 Hz), 7.67 (s, 1H), 7.51-7.45 (m, 2H), 6.76 (s, 1H), 6.69 (s, 1H), 4.15 (s, 4H), 3.91 (s, 5H), 3.61-3.52 (m, 2H), 1.21-1.19 (m, 3H). ESI-MS (M+H)+: 397.

Synthesis of Example 54

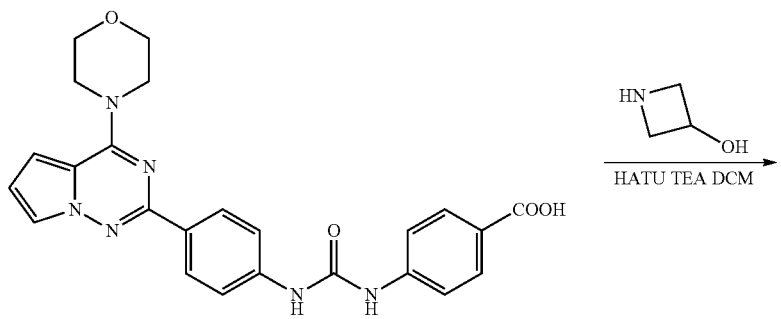

Example 44

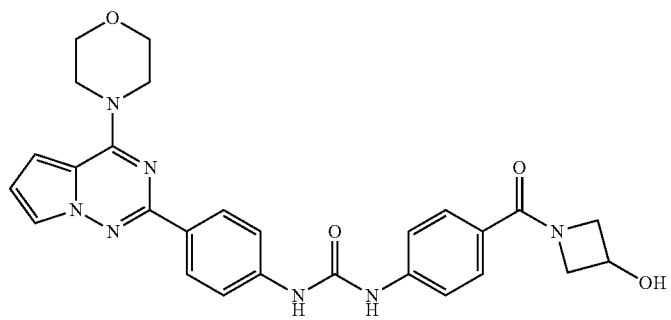

Example 54

The procedure of Example 54 (18 mg, 85%) was similar to that of Example 45. ¹HNMR (400 MHz, DMSO) δ 9.01 (d, 2H, J=4.2 Hz), 8.17 (d, 2H, J=8.7 Hz), 7.78-7.83 (m, 1H), 7.0-7.64 (m, 6H), 7.00 (dd, 1H, J=4.4, 1.1 Hz), 6.72 (dd, 1H, J=4.5, 2.7 Hz), 5.73 (d, 1H, J=6.0 Hz), 4.43-4.55 (m, 2H), 4.23 (bs, 1H), 4.13-3.97 (m, 5H), 3.86-3.70 (m, 5H). ESI-MS (M+H)+: 514.2

Synthesis of Example 55
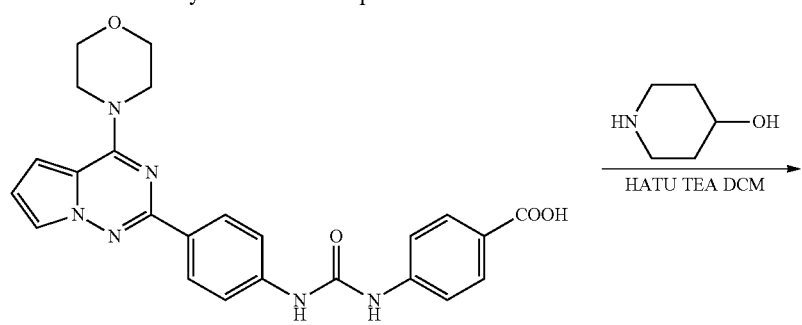
Example 44
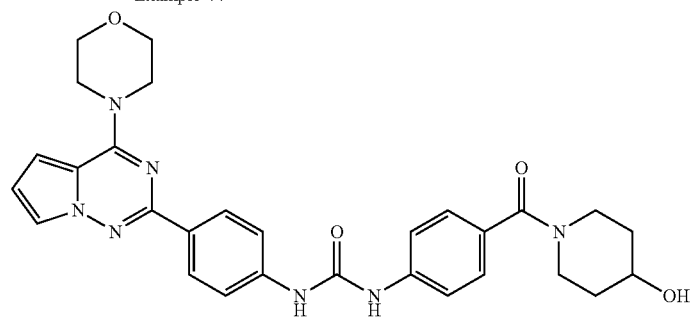
Example 55
The procedure of Example 55 (16 mg, 72%) was similar to that of Example 45. HNMR (400 MHz, CDCl$_3$) δ 8.37 (s, 1H), 8.30 (s, 1H), 8.14 (d, 2H, J=8.4 Hz), 7.63-7.68 (m, 1H), 7.20 (s, 4H), 6.72-6.61 (m, 2H), 4.00-4.22 (m, 5H), 3.98-3.79 (m, 6H), 3.55-3.78 (m, 2H), 3.10-3.50 (m, 3H), 3.00-3.10 (m, 1H). ESI-MS (M+H)$^+$: 542.3
Synthesis of Example 56
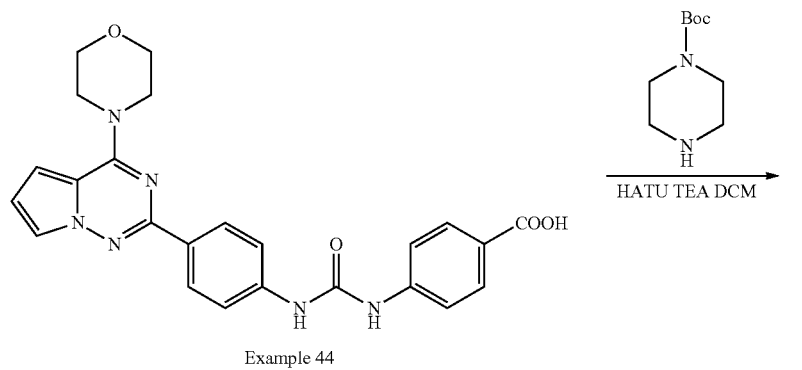
Example 44
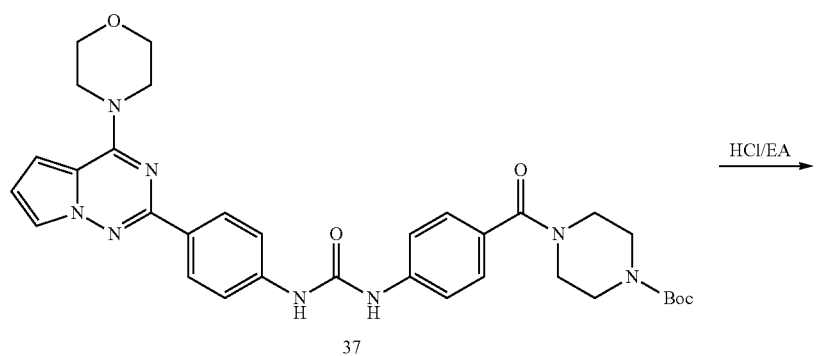

-continued
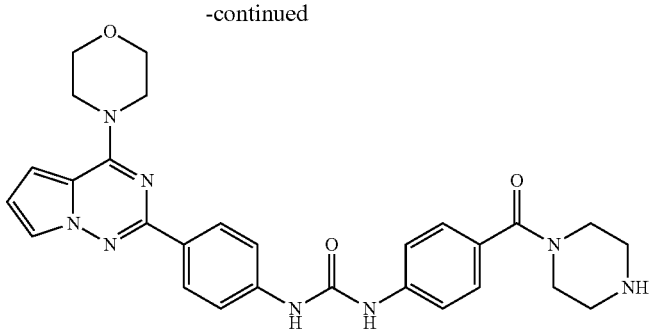
Example 56
Synthesis of Compound 37
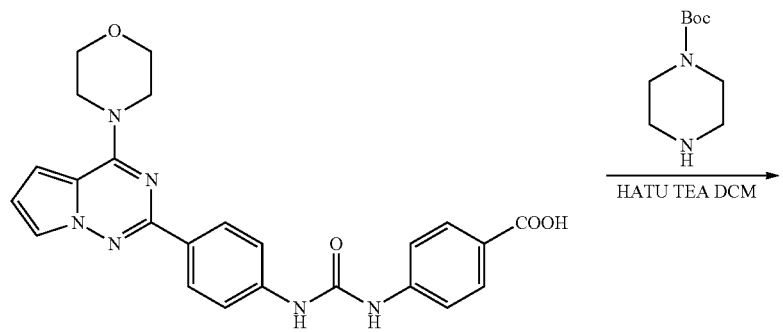
37
The procedure of compound 37 (40 mg) was similar to that of Example 45.
Synthesis of Example 56
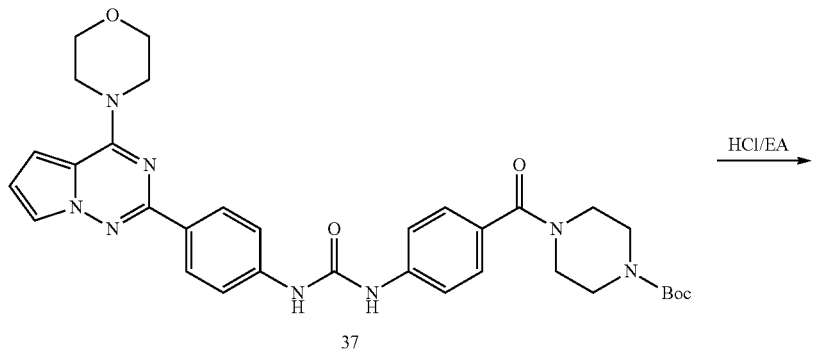
37

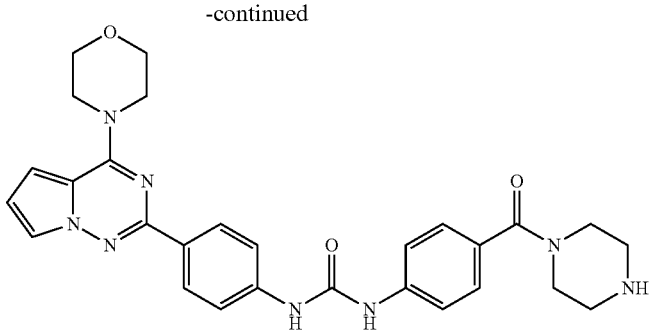

Example 56

A mixture of compound 37 (40 mg, 0.064 mmol) in HCl/EA (5 mL) was stirred for 30 min at room temperature. The reaction mixture was filtered and the filter cake was diluted with NaHCO$_3$ (aq.) and DCM, separated and the aqueous layer was extracted with DCM (3×50 mL). The combined organic layers were washed with brine, dried over Na$_2$SO$_4$ and concentrated. The crude material was purified by Prep-TLC (EA:CH$_3$OH:NH$_4$OH=2:1:0.1) affording to Example 56 (10 mg, 30%) as a white solid. $^1$HNMR (400 MHz, CDCl$_3$+CD$_3$OD) δ 8.10-8.17 (m, 1H), 7.59-7.64 (m, 1H), 7.51-7.42 (m, 5H), 7.27-7.32 (m, 2H), 6.59-6.68 (m, 2H), 4.02-4.12 (m, 4H), 3.79-3.89 (m, 4H), 3.55-3.75 (m, 4H), 2.85-3.00 (m, 4H). ESI-MS (M+H)$^+$: 527.3

Synthesis of Example 57

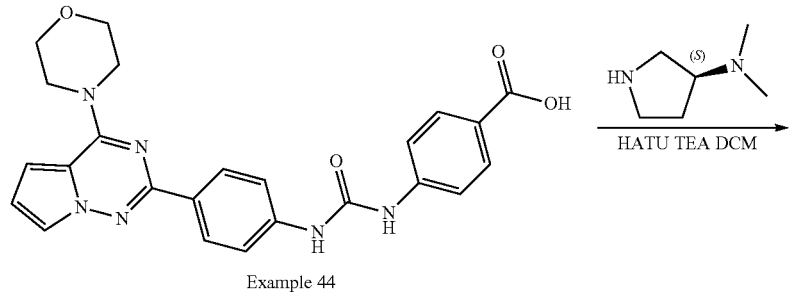

Example 44

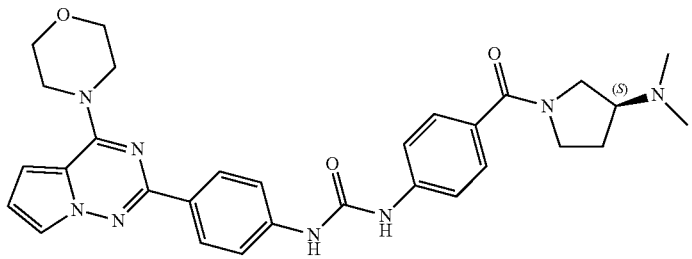

Example 57

The procedure of Example 57 (12 mg, 54%) was similar to that of Example 45. $^1$HNMR (400 MHz, CDCl$_3$) δ 8.64-8.9 (m, 2H), 8.19 (d, J=8.4 Hz, 2H), 7.69-7.61 (m, 1H), 7.57 (d, J=8.4 Hz, 2H), 7.25-7.45 (m, 2H), 6.60-6.70 (m, 2H), 4.02-4.13 (m, 4H), 3.80-3.90 (m, 4H), 3.80-3.20 (m, 5H), 2.54 (s, 6H), 1.5-2.4 (m, 2H). ESI-MS (M+H)$^+$:555.3

Synthesis of Example 58
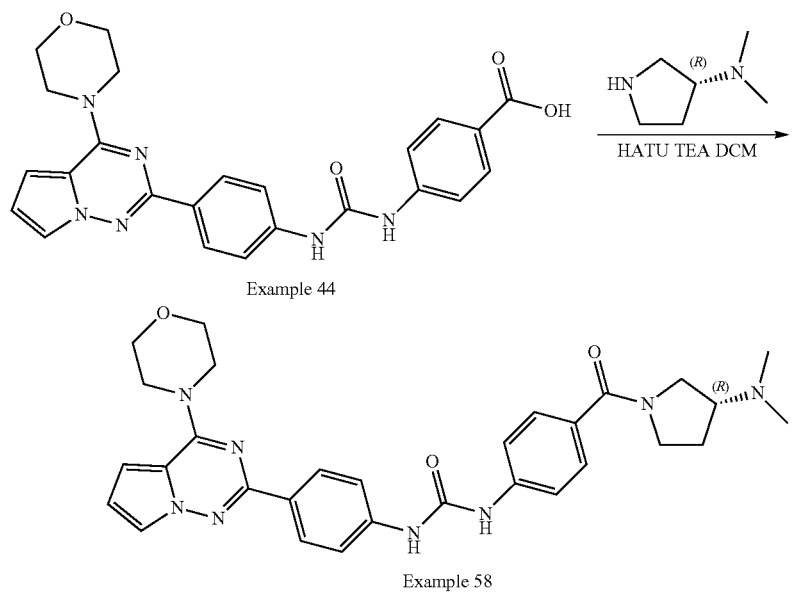
Example 44
Example 58
The procedure of Example 58 (12 mg, 50%) was similar to that of Example 45. $^1$HNMR (400 MHz, CDCl$_3$) δ 8.64-8.9 (m, 2H), 8.19 (d, J=8.4 Hz, 2H), 7.69-7.61 (m, 1H), 7.57 (d, J=8.4 Hz, 2H), 7.25-7.45 (m, 2H), 6.60-6.70 (m, 2H), 4.02-4.13 (m, 4H), 3.80-3.90 (m, 4H), 3.80-3.20 (m, 5H), 2.54 (s, 6H), 1.5-2.4 (m, 2H). ESI-MS (M+H)$^+$:555.3
Synthesis of Example 59
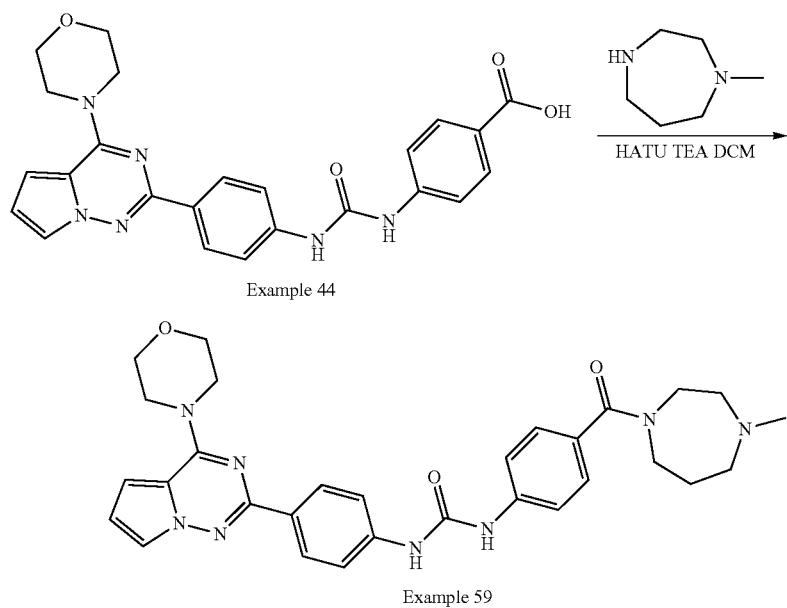
Example 44
Example 59
The procedure of Example 59 (12 mg, 54%) was similar to that of Example 45. $^1$HNMR (400 MHz, CDCl3) δ 8.65 (bs, 1H), 8.55 (bs, 1H), 8.19 (d, J=8.5 Hz, 2H), 7.64 (s, 1H), 7.54 (d, J=8.5 Hz, 2H), 7.30-7.44 (m, 2H), 6.60-6.70 (m, 2H), 4.02-4.14 (m, 4H), 3.80-3.90 (m, 4H), 2.80-3.75 (m, 8H), 2.63 (s, 3H), 2.03-2.25 (m, 2H). ESI-MS (M+H)$^+$:555.3

Synthesis of Example 60
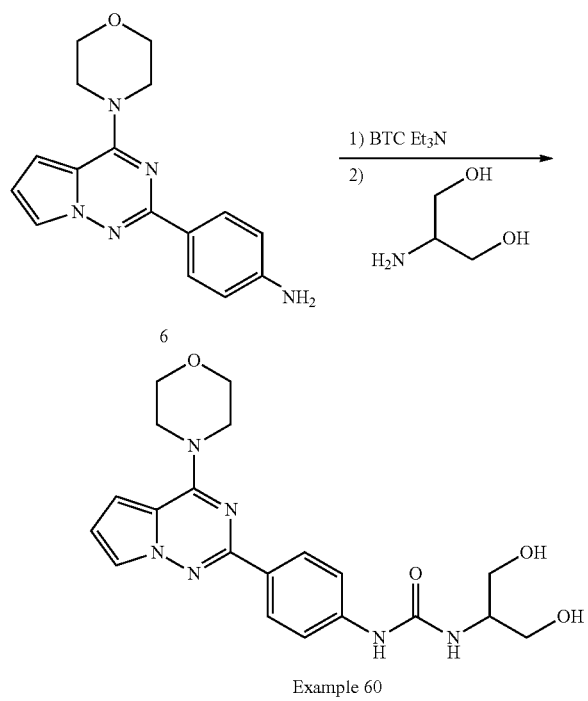
Example 60
The procedure of Example 60 (8.0 mg, yield: 22.9%) was similar to that of Example 15. ¹HNMR (MeOD-d₄, 400 MHz): δ 8.15 (d, 2H, J=8.8 Hz), 7.65-7.64 (m, 1H), 7.44 (d, 2H, J=8.8 Hz), 6.88-6.87 (m, 1H), 6.69-6.67 (m, 1H), 4.11 (t, 4H, J=4.8 Hz), 3.86-3.81 (m, 5H), 3.72-3.63 (m, 4H). ESI-MS (M+H)⁺: 413.
Synthesis of Example 61
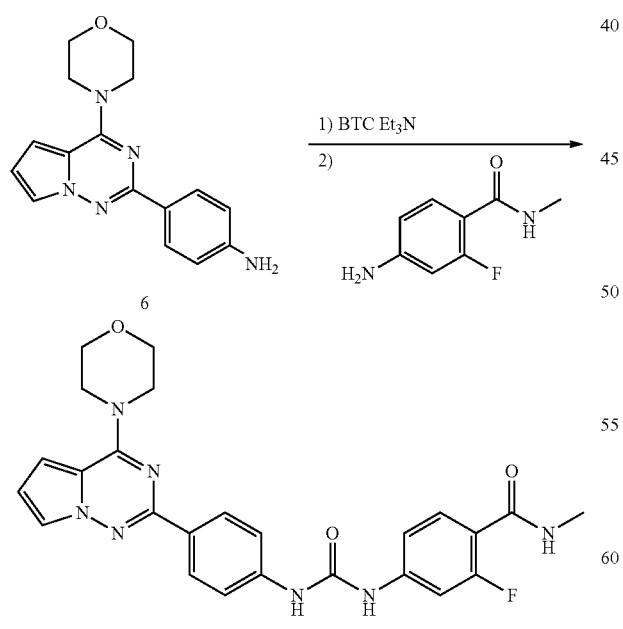
Example 61
The procedure of Example 61 (4.0 mg, yield: 6.2%) was similar to that of Example 15. ¹H NMR (MeOD-d₄, 400 MHz): δ 9.22 (s, 1H), 9.10 (s, 1H), 8.18 (d, 2H, J=8.8 Hz), 8.02-8.00 (m, 1H), 7.81 (s, 1H), 7.65-7.56 (m, 1H), 7.19-7.17 (m, 1H), 7.01-7.00 (m, 1H), 6.73-6.72 (m, 1H), 4.07-4.06 (m, 4H), 3.80-3.79 (m, 4H), 2.78-2.77 (m, 3H). ESI-MS (M+H)⁺: 490.
Synthesis of Example 62
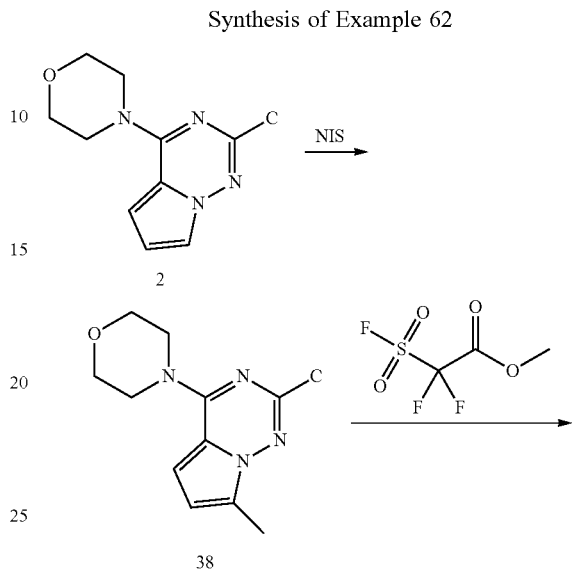
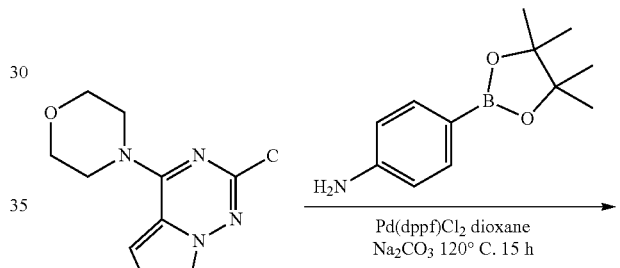
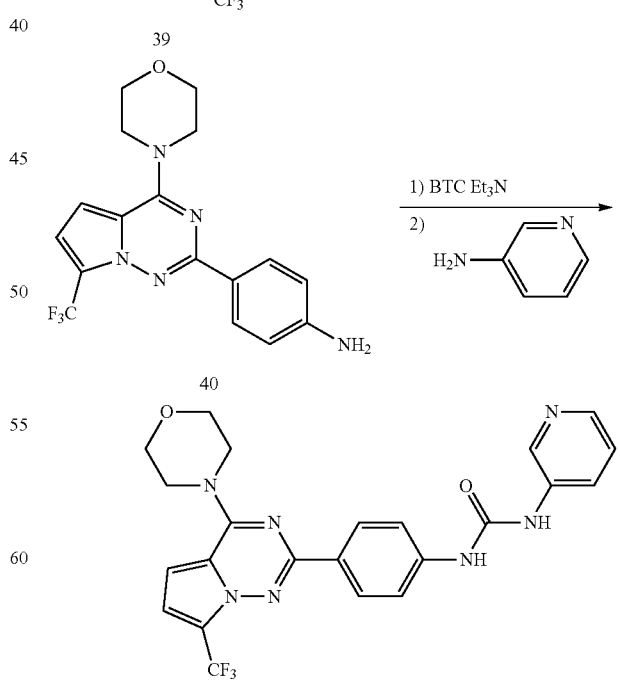
Example 62

Synthesis of Compound 38

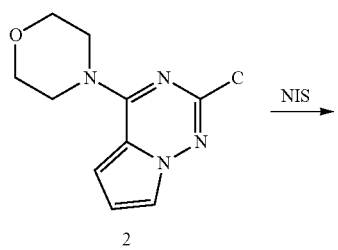

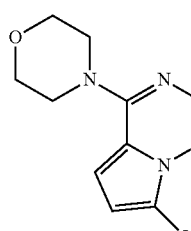

To a stirred solution of compound 2 (20 mg, 0.084 mmol) in DCM (3 mL) was added NIS (60 mg, 0.251 mmol) in DCM (1 mL), the reaction mixture was stirred for one week at ambient temperature. Later than reaction was quenched with H$_2$O and extracted with EA. The organic phase was washed with brine, dried over Na$_2$SO$_4$, filtered and concentrated, the crude product was purified by Pre-TLC (PE/EA=3:1) to give compound 38 (17 mg, yield: 56%). $^1$H-NMR (400 MHz, CDCl$_3$) δ 6.85 (d, 1H, J=4.8 Hz), 6.82 (d, 1H, J=4.8 Hz), 4.03~4.02 (m, 4H), 3.85~3.83 (m, 4H).

Synthesis of Compound 39

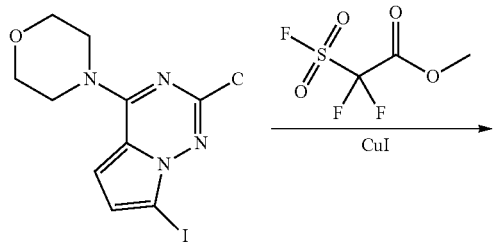

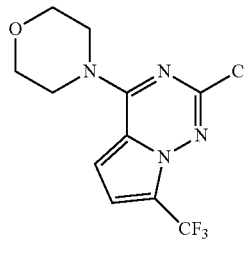

A mixture of compound 38 (100 mg, 0.274 mmol), CuI (62 mg, 0.329 mmol) in DMF (5.0 mL) was added methyl 2,2-difluoro-2-(fluorosulfonyl)acetate (316 mg, 1.65 mmol) under N$_2$ protection. The resulting mixture was stirred at 100° C. for 1 h. After cooled to room temperature, the mixture was dissolved in EA and H$_2$O. The organic phase was washed with brine, dried over Na$_2$SO$_4$ and concentrated to give the crude product. After purified by Pre-HPLC (PE:EA=3:1) to afford compound 39 (50 mg, yield: 59.4%). $^1$H-NMR (400 MHz, CDCl$_3$) δ 6.96 (d, 1H, J=4.8 Hz), 6.73 (d, 1H, J=5.2 Hz), 4.08~4.06 (m, 4H), 3.87~3.84 (m, 4H).

Synthesis of Compound 40

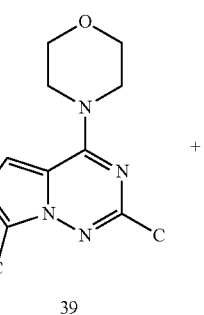

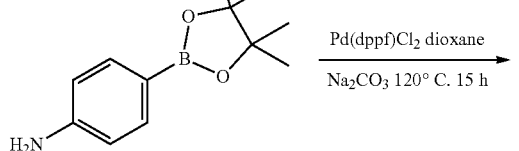

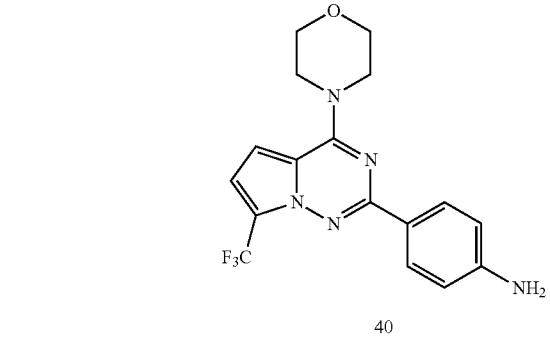

The procedure of compound 40 (12.0 mg, yield: 50.6%) was similar to that of Example 24. $^1$H NMR (400 MHz, CDCl$_3$) δ 8.16 (d, 2H, J=8.8 Hz), 6.95 (d, 1H, J=4.8 Hz), 6.80 (d, 2H, J=8.8 Hz), 6.66 (d, 1H, J=4.8 Hz), 4.13~4.10 (m, 4H), 3.90~3.88 (m, 4H).

Synthesis of Example 62

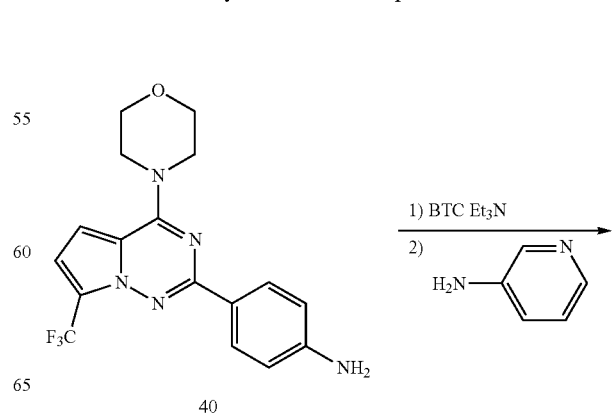

117

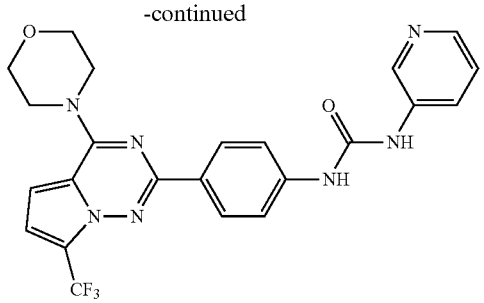

Example 62

The procedure of Example 62 (7.0 mg, yield: 52.6%) was similar to that of Example 15. ¹H NMR (400 MHz, MeOD) δ 8.34 (s, 1H), 8.04~8.02 (m, 2H), 7.98~7.95 (m, 1H), 7.91~7.89 (m, 1H), 7.30 (d, 2H, J=8.8 Hz), 7.16~7.13 (m, 1H), 6.75 (d, 1H, J=4.4 Hz), 6.54 (d, 1H, J=4.4 Hz), 3.91~3.90 (m, 4H), 3.68~3.66 (m, 4H). ESI-MS (M+H)⁺: 484.26

Synthesis of Example 63

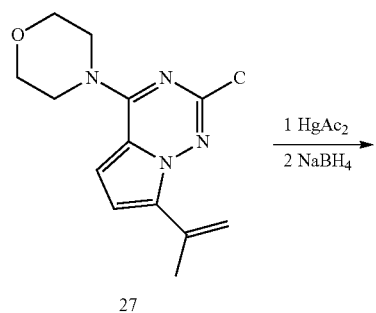

27

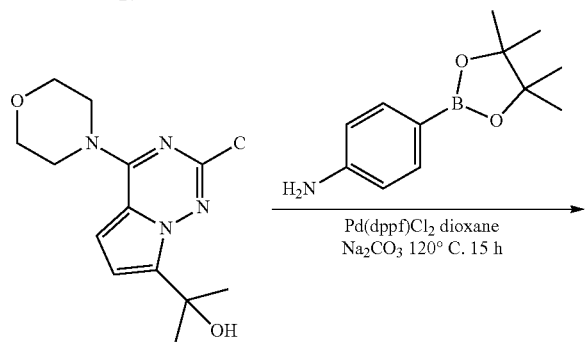

42

118

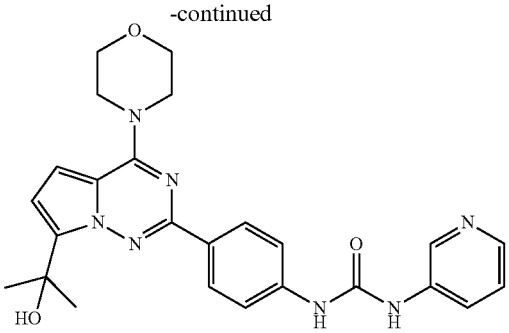

Example 63

Synthesis of Compound 41

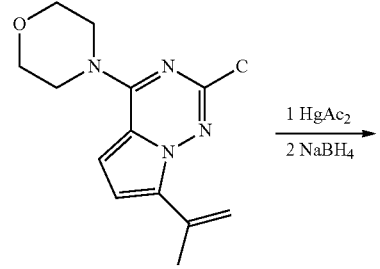

27

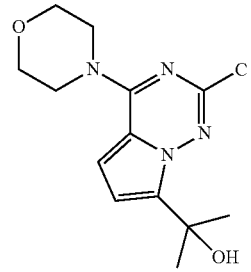

41

A solution of mercuric acetate (384 mg, 1.34 mmol) in H₂O (1.5 mL) was added compound 27 (340 mg, 1.22 mmol) in THF (1.5 mL) under N₂ protection. After stirred at RT for 3 h, the mixture was added 3N NaOH (1.5 mL) and 0.5N NaBH₄ (1.5 mL). The resulting mixture was stirred at RT for another 3 h. Then the reaction was extracted with EA. The organic phase was washed with brine, dried over Na₂SO₄, filtered and concentrated, the crude product was purified by column chromatography (PE/EA=10:1) to give compound 41 (110 mg, yield: 30.4%). ¹H-NMR (400 MHz, CDCl₃) δ 6.69 (d, 1H, J=4.8 Hz), 6.48 (d, 1H, J=4.8 Hz), 4.06~4.03 (m, 4H), 3.85~3.82 (m, 4H), 1.68 (s, 6H).

Synthesis of Compound 42

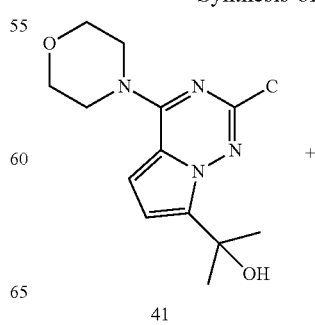 +

41

-continued

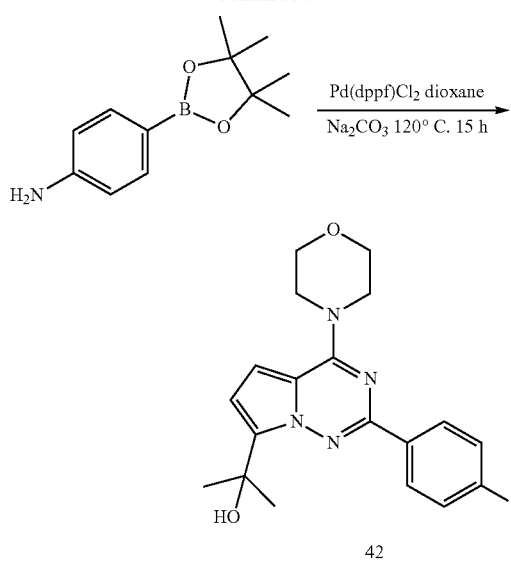

42

The procedure of compound 42 (90 mg, yield: 68.7%) was similar to that of Example 24. ¹H NMR (400 MHz, CDCl₃) δ 8.06 (d, 2H, J=8.4 Hz), 6.73 (d, 2H, J=8.4 Hz), 6.63 (d, 1H, J=4.8 Hz), 6.47 (d, 1H, J=4.4 Hz), 4.12~4.10 (m, 4H), 3.88~3.85 (m, 4H), 1.74 (s, 6H).

Synthesis of Example 63

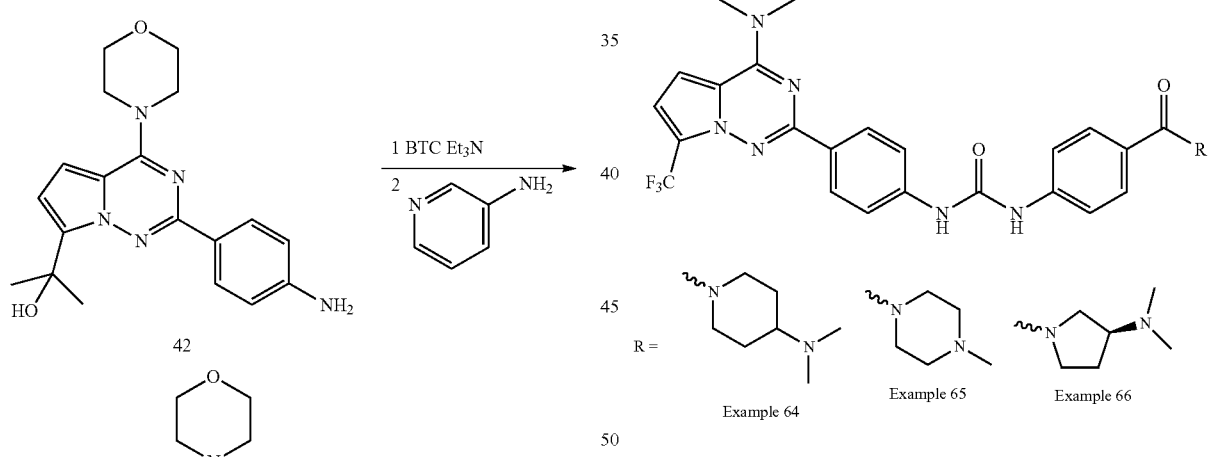

Example 63

The procedure of Example 63 (2.0 mg, yield: 24.9%) was similar to that of Example 15. ¹H NMR (400 MHz, MeOD) δ 8.31 (brs, 1H), 8.29~8.28 (m, 1H), 8.27~8.26 (m, 1H), 8.20~8.17 (m, 3H), 7.57 (d, 2H, J=8.8 Hz), 6.70 (d, 1H, J=4.8 Hz), 6.53 (d, 1H, J=4.8 Hz), 4.16~4.14 (m, 4H), 3.91~3.89 (m, 4H), 1.77 (s, 6H). ESI-MS (M−H)⁻: 472.34

Synthesis of Example 64, Example 65, Example 66

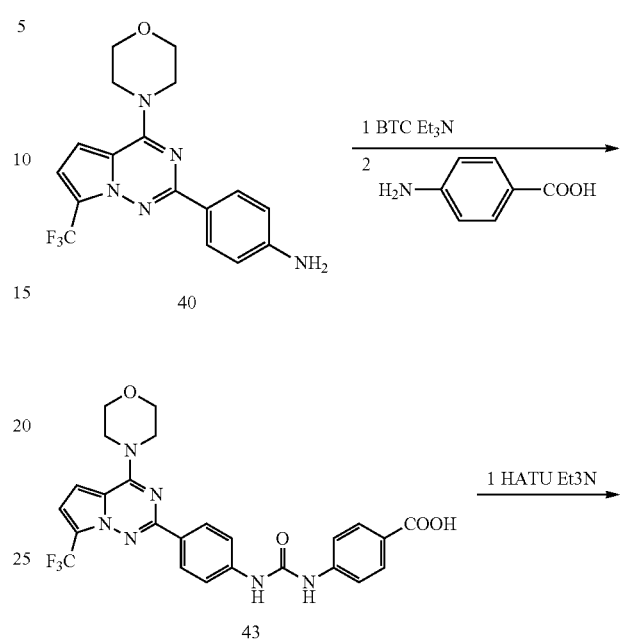

Synthesis of Compound 43

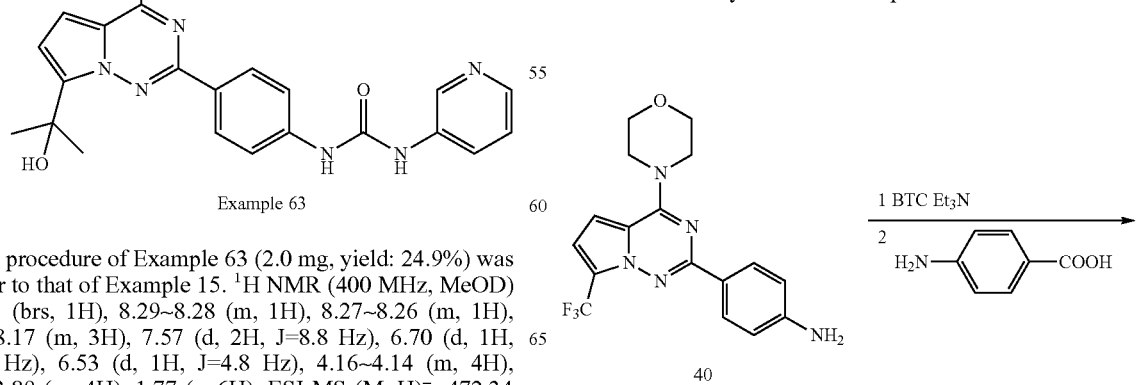

40

-continued
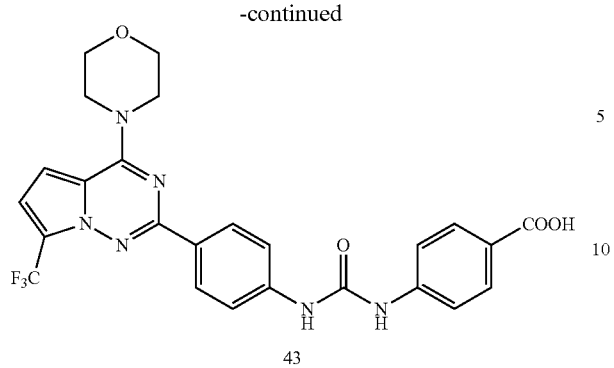
43
The procedure of compound 43 (22.0 mg, yield: 56.2%) was similar to that of Example 15. ¹HNMR (400 MHz, MeOD) δ 8.14 (d, 2H, J=8.8 Hz), 7.87~7.85 (m, 2H), 7.42~7.40 (m, 4H), 6.86 (d, 1H, J=4.4 Hz), 6.60 (d, J=4.8 Hz, 1H), 4.03~4.00 (m, 4H), 3.83~3.79 (m, 4H).
Synthesis of Example 64
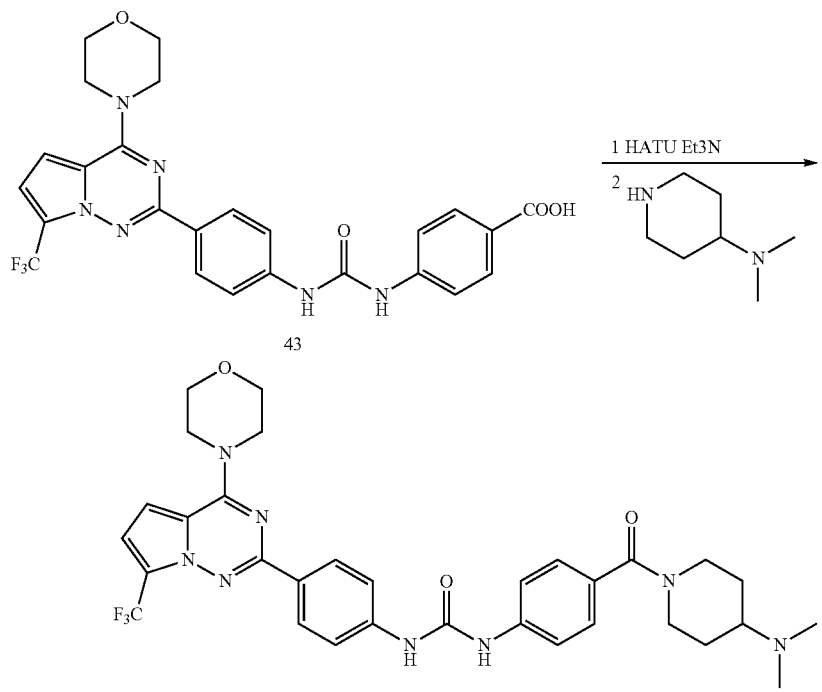
Example 64
The procedure of Example 64 (7.0 mg, yield: 82.7%) was similar to that of Example 45. ¹H NMR (400 MHz, MeOD) δ 8.11 (d, 2H, J=8.4 Hz), 7.41~7.38 (m, 4H), 7.24 (t, 2H, J=8.8 Hz), 6.85 (d, 1H, J=4.8 Hz), 6.58 (d, 1H, J=4.8 Hz), 4.03~3.98 (m, 4H), 3.80~3.75 (m, 4H), 3.31~3.21 (m, 5H), 2.69 (s, 6H), 2.06~1.94 (m, 2H), 1.58~1.48 (m, 2H). ESI-MS (M+H)⁺: 637.16
Synthesis of Example 65
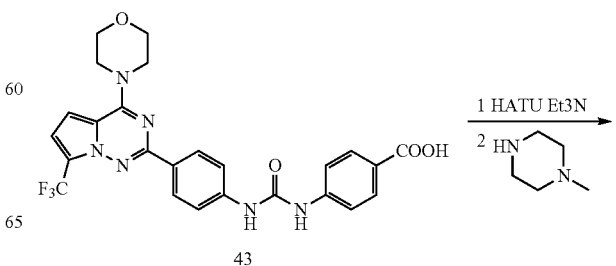
43

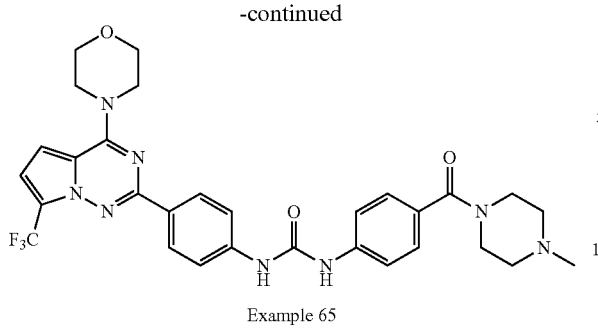

Example 65

The procedure of Example 65 (4.0 mg, yield: 34.6%) was similar to that of Example 45. ¹H NMR (400 MHz, MeOD) δ 8.17 (d, 2H, J=8.4 Hz), 7.43 (d, 2H, J=8.8 Hz), 7.38 (d, 2H, J=8.0 Hz), 7.28 (s, 2H), 6.91 (d, 1H, J=4.4 Hz), 6.61 (d, 1H, J=4.8 Hz), 4.07~4.05 (m, 4H), 3.85~3.84 (m, 4H), 3.69~3.62 (m, 4H), 2.62~2.55 (m, 4H), 2.39 (s, 3H). ESI-MS (M+H)⁺: 609.14

Synthesis of Example 66

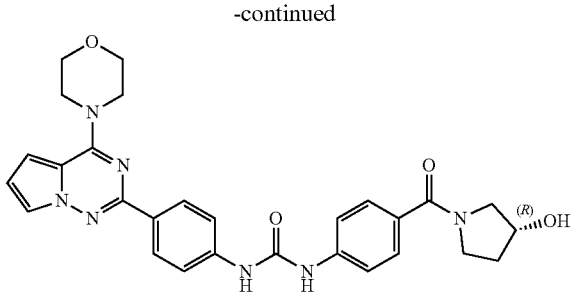

Example 67

The procedure of Example 67 (20 mg, 71%) was similar to that of Example 45. ESI-MS (M+H)⁺: 528.17

Synthesis of Example 68

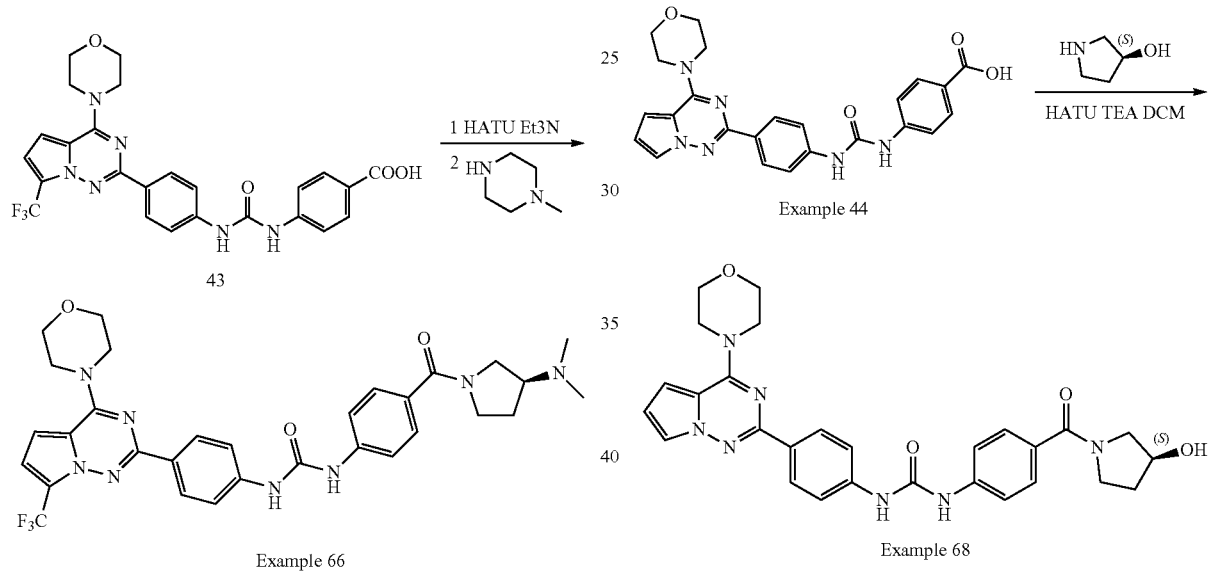

Example 66

The procedure of Example 66 (4.0 mg, yield: 33.8%) was similar to that of Example 45. ¹H NMR (400 MHz, CDCl₃) δ 8.59~8.58 (m, 2H), 8.18 (d, 2H, J=8.4 Hz), 7.50 (d, 2H, J=7.6 Hz), 7.32~7.30 (m, 1H), 7.26~7.24 (m, 1H), 6.93 (d, J=4.4 Hz, 1H), 6.62 (d, 1H, J=4.8 Hz), 4.08~4.06 (m, 4H), 3.87~3.84 (m, 4H), 3.81~3.78 (m, 1H), 3.64~3.62 (m, 1H), 3.53~3.51 (m, 2H), 2.90 (s, 1H), 2.35~2.33 (m, 6H), 1.90~1.87 (m, 1H), 1.28~1.23 (m, 1H). ESI-MS (M+H)⁺: 623.12

Synthesis of Example 67

Example 68

The procedure of Example 68 (20 mg, 71%) was similar to that of Example 45. ESI-MS (M+H)⁺: 528.17

Synthesis of Example 69

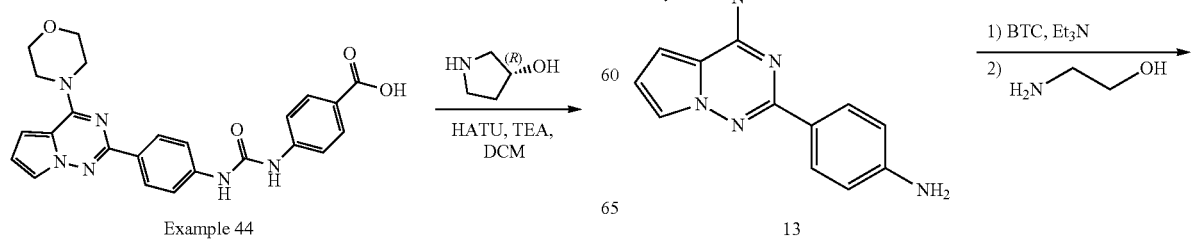

-continued

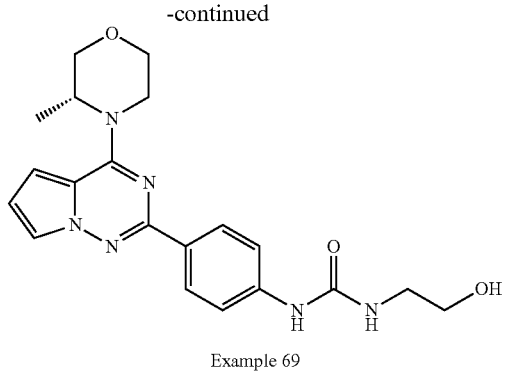

Example 69

The procedure of Example 69 (20 mg, 52%) was similar to that of Example 15. $^1$H NMR (DMSO-d$_6$, 400 MHz): δ 8.86 (s, 1H), 8.08 (d, 2H, J=8.8 Hz), 7.78 (s, 1H), 7.48 (d, 2H, J=8.8 Hz), 6.97-6.95 (m, 1H), 6.71-6.70 (m, 1H), 6.32-6.31 (m, 1H), 4.98-4.95 (m, 1H), 4.78-4.75 (m, 1H), 4.67-4.62 (m, 1H), 4.01 (d, 1H, J=8.0 Hz), 3.80-3.70 (m, 2H), 3.61-3.43 (m, 4H), 3.19-3.15 (m, 2H), 1.38 (d, 3H, J=6.8 Hz). ESI-MS (M+H)$^+$: 397.

Synthesis of Example 70

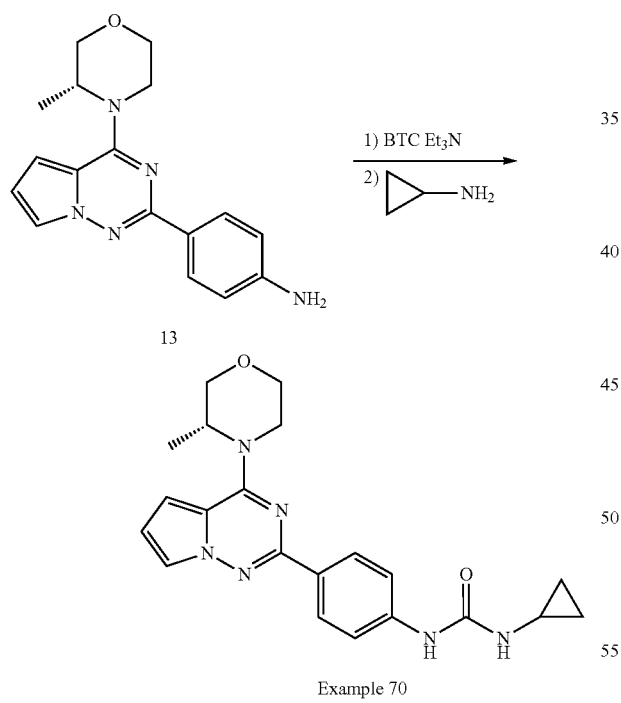

Example 70

The procedure of Example 70 (30 mg, 78%) was similar to that of Example 15. $^1$H NMR (DMSO-d$_6$, 400 MHz): δ 8.66 (s, 1H), 8.09 (d, 2H, J=8.8 Hz), 7.78 (s, 1H), 7.50 (d, 2H, J=8.8 Hz), 6.97-6.95 (m, 1H), 6.72-6.70 (m, 1H), 6.55-6.54 (m, 1H), 4.98-4.94 (m, 1H), 4.68-4.62 (m, 1H), 4.01 (d, 1H, J=8.0 Hz), 3.80-3.70 (m, 2H), 3.61-3.48 (m, 2H), 2.57-2.54 (m, 1H), 1.38 (d, 3H, J=6.8 Hz), 0.65-0.62 (m, 2H), 0.43-0.40 (m, 2H). ESI-MS (M+H)$^+$: 393.

Synthesis of Example 71

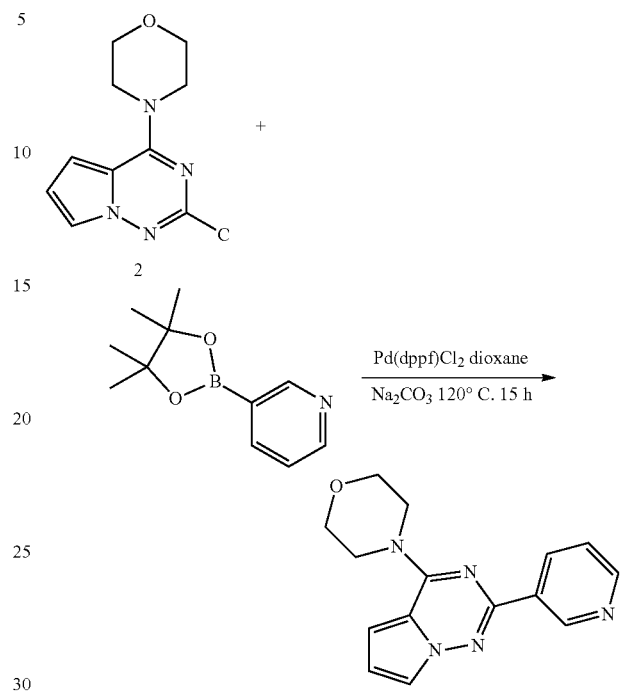

Example 71

A mixture of compound 2 (20 mg, 0.083 mmol) and 3-(4,4,5,5-tetramethyl-1,3,2-dioxaborolan-2-yl)pyridine (34.0 mg, 0.167 mmol) in 1,4-dioxane (2.0 mL) and H$_2$O (0.5 mL) was added Pd(dppf)Cl$_2$ (10 mg) and Na$_2$CO$_3$ (35 mg, 0.325 mmol) under N$_2$ protection. The resulting mixture was stirred at 120° C. for overnight. The mixture was dissolved in DCM and filtrated over celite. The filtrate was washed with water, brine, dried over Na$_2$SO$_4$ and concentrated to give the crude product. After purified by Pre-HPLC to afford compound Example 71 (15.0 mg, yield: 63.6%). $^1$H NMR (400 MHz, CDCl$_3$) δ 9.51 (s, 1H), 8.67 (d, 1H, J=3.2 Hz), 8.60 (d, 1H, J=8.0 Hz), 7.70 (dd, 1H, J=2.4, 1.6 Hz), 7.42 (dd, 1H, J=7.6, 4.8 Hz), 6.75 (dd, 1H, J=4.4, 1.2 Hz), 6.71 (dd, 1H, J=4.4, 2.8 Hz), 4.18~4.11 (m, 4H), 3.93~3.86 (m, 4H).

Synthesis of Example 72

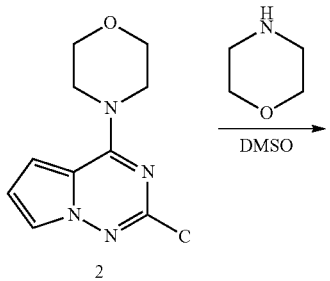

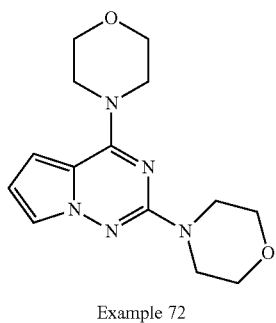

Example 72

A mixture of compound 2 (8 mg, 0.03 mm), CsF (40 mg, 0.26 mm) and morpholine (34.0 mg, 0.167 mmol) in DMSO (2.0 mL) was stirred at 140° C. for overnight. The mixture was dissolved in DCM and washed with water, brine, dried over $Na_2SO_4$ and concentrated to give the crude product. After purified by Pre-HPLC to afford compound Example 72 (3.0 mg, yield: 30.9%). $^1$H NMR ($CDCl_3$, 400 MHz): δ 7.54 (s, 1H), 6.61-6.60 (m, 1H), 6.50-6.49 (m, 1H), 3.98 (t, 4H, J=4.8 Hz), 3.84 (t, 4H, J=4.8 Hz), 3.79 (t, 4H, J=4.4 Hz), 3.64 (t, 4H, J=4.8 Hz). ESI-MS $(M+H)^+$: 290.

Synthesis of Example 73

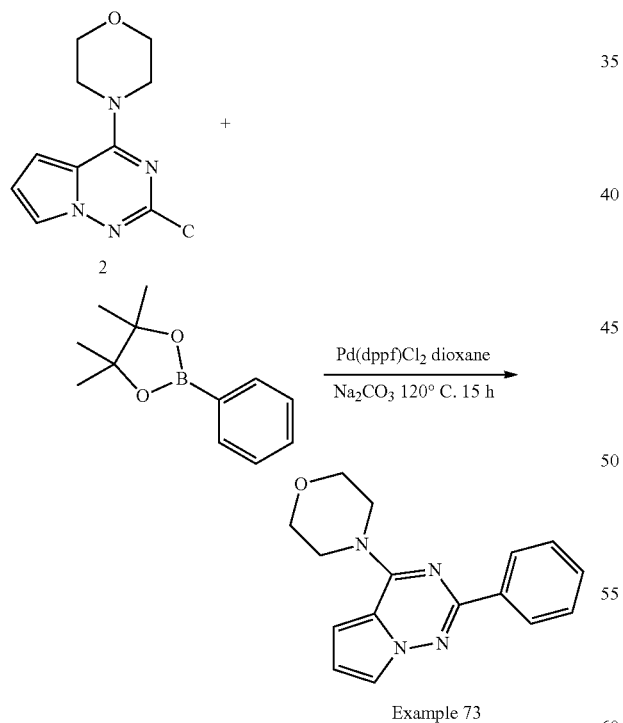

Example 73

The procedure of Example 73 (14 mg, 60%) was similar to that of Example 6. $^1$H NMR ($CDCl_3$, 400 MHz): δ 8.30-8.28 (m, 2H), 7.70-7.69 (m, 1H), 7.47-7.44 (m, 3H), 6.73-6.68 (m, 2H), 4.14 (t, 4H, J=4.4 Hz), 3.89 (t, 4H, J=4.8 Hz). ESI-MS $(M+H)^+$: 281.

Synthesis of Example 74

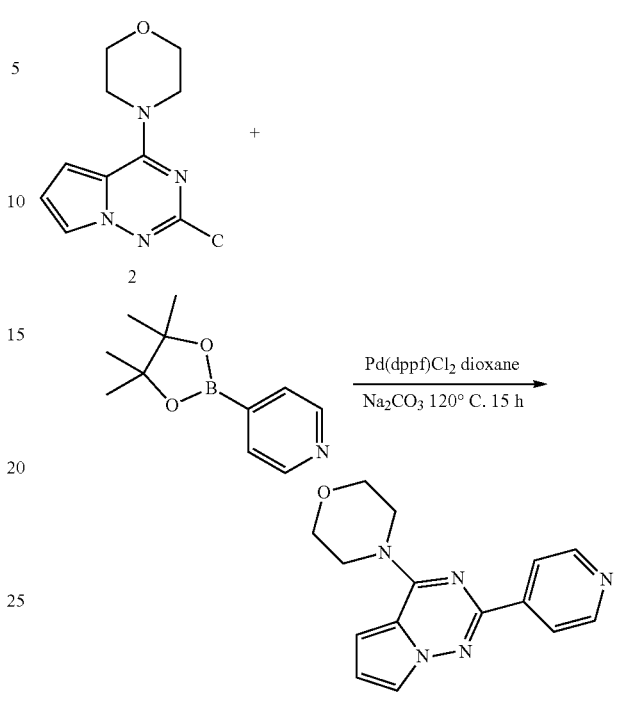

Example 74

The procedure of Example 74 (15 mg, 64%) was similar to that of Example 6. $^1$H NMR ($CDCl_3$, 400 MHz): δ 8.72 (d, 2H, J=1.2 Hz), 8.18 (d, 2H, J=3.6 Hz), 7.72-7.71 (m, 1H), 6.77-6.72 (m, 2H), 4.15 (t, 4H, J=4.8 Hz), 3.90 (t, 4H, J=5.2 Hz). ESI-MS $(M+H)^+$: 282.

Synthesis of Example 75

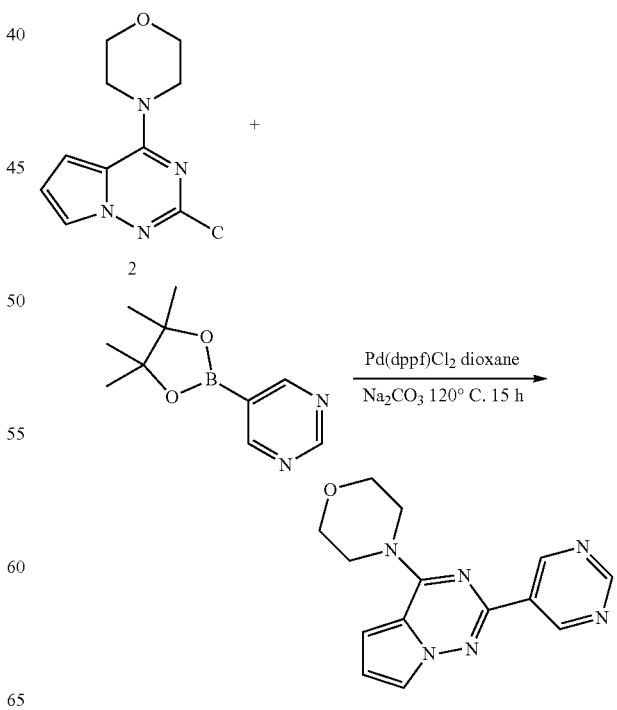

Example 75

The procedure of Example 75 (10 mg, 42%) was similar to that of Example 6. $^1$H NMR (CDCl$_3$, 400 MHz): δ 9.56 (s, 2H), 9.28 (s, 1H), 7.71-7.70 (m, 1H), 6.78-6.77 (m, 1H), 6.74-6.72 (m, 1H), 4.14 (t, 4H, J=4.4 Hz), 3.89 (t, 4H, J=5.2 Hz). ESI-MS (M+H)$^+$: 283.

Synthesis of Example 76

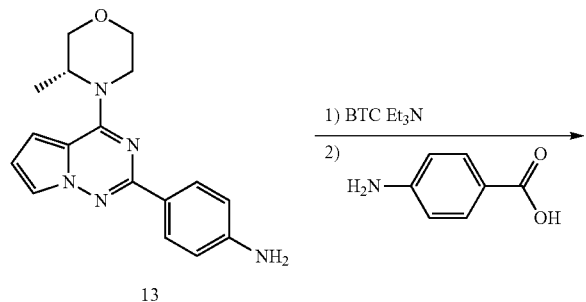

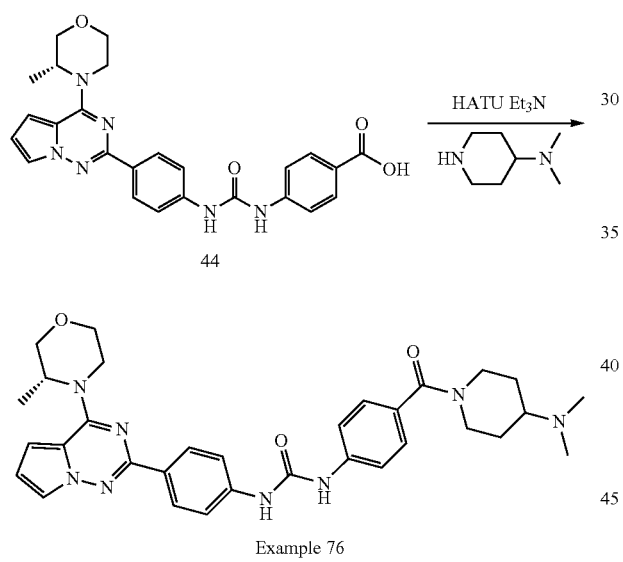

Synthesis of Compound 44

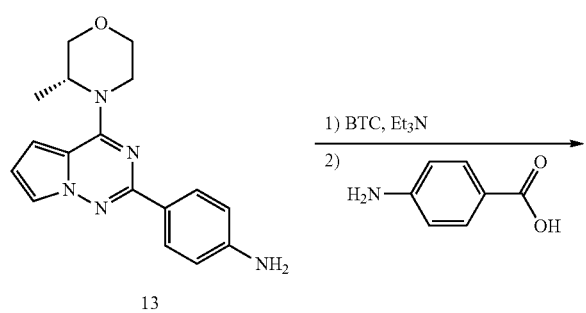

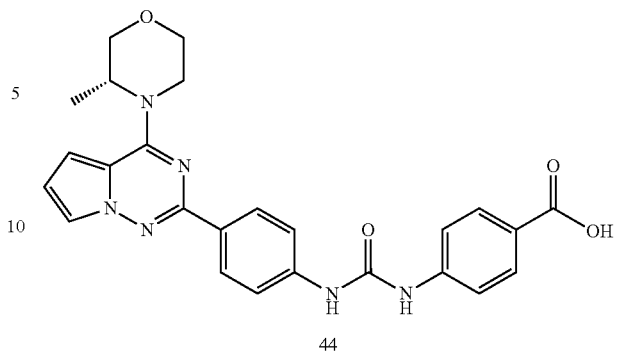

44

The procedure of compound 44 (20 mg, 43.7%) was similar to that of Example 15. $^1$H NMR (DMSO, 400 MHz): δ 12.59 (brs, 1H), 9.43 (s, 1H), 9.32 (s, 1H), 8.16 (d, 2H, J=8.8 Hz), 7.88 (d, 2H, J=8.8 Hz), 7.81-7.80 (m, 1H), 7.59-7.56 (m, 4H), 6.97 (d, 1H, J=3.6 Hz), 6.72-6.71 (m, 1H), 4.98-4.96 (m, 1H), 4.67-4.64 (m, 1H), 4.03-4.00 (m, 2H), 3.71-3.70 (m, 2H), 3.58-3.55 (m, 1H), 1.39 (d, 3H, J=4.8 Hz).

Synthesis of Example 76

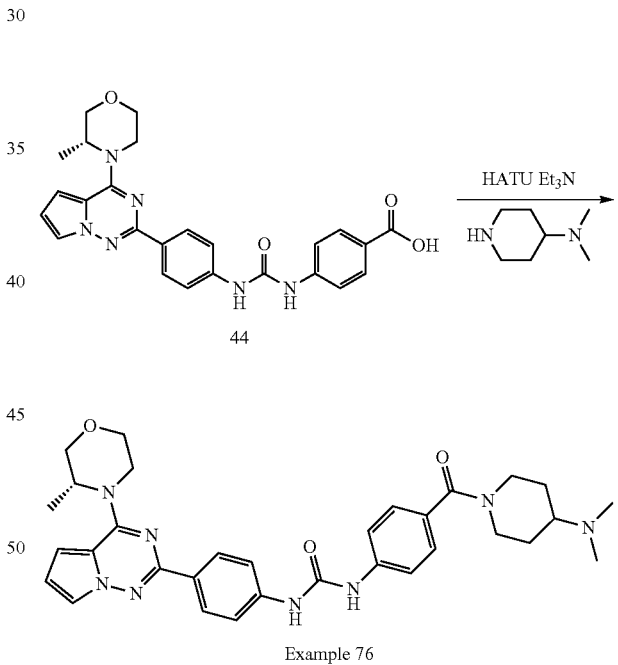

The procedure of Example 76 (15 mg, 51%) was similar to that of Example 45. $^1$H NMR (DMSO-d$_6$, 400 MHz): δ 9.41 (s, 1H), 9.37 (s, 1H), 8.16 (d, 2H, J=8.8 Hz), 7.80 (s, 1H), 7.59-7.54 (m, 4H), 7.38 (d, 2H, J=8.8 Hz), 6.98 (d, 1H, J=8.0 Hz), 6.73-6.71 (m, 1H), 5.00-4.97 (m, 1H), 4.69-4.63 (m, 2H), 4.02 (d, 1H, J=8.4 Hz), 3.81-3.71 (m, 2H), 3.62-3.49 (m, 2H), 3.10-3.04 (m, 2H), 2.70 (s, 6H), 2.03-2.01 (m, 2H), 1.65-1.55 (m, 2H), 1.39 (d, 3H, J=6.4 Hz), 1.19 (t, 2H, J=7.2 Hz). ESI-MS (M+H)$^+$: 583.

Synthesis of Example 77

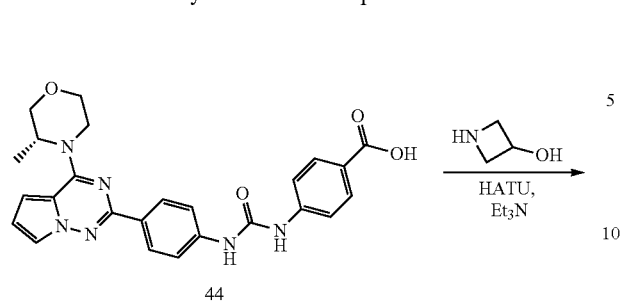

44

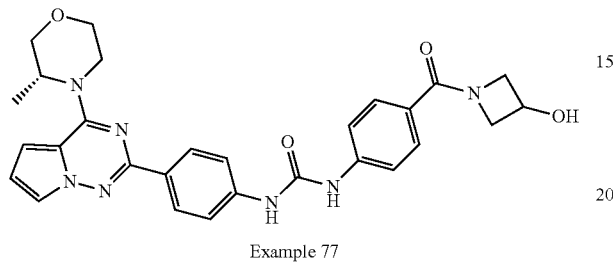

Example 77

The procedure of Example 77 (10 mg, 72%) was similar to that of Example 45. HNMR (400 MHz, MeOD) δ 8.10-8.25 (m, 2H), 7.46-7.70 (m, 7H), 6.75-6.85 (m, 1H), 6.62-6.72 (m, 1H), 4.96-5.08 (m, 1H), 4.46-4.80 (m, 3H), 4.34-4.44 (m, 1H), 4.15-4.25 (m, 1H), 4.03-4.13 (m, 1H), 3.93-4.12 (m, 1H), 3.80-3.92 (m, 2H), 3.55-3.75 (m, 2H), 1.45-1.58 (m, 3H). ESI-MS (M+H)+: 528.17

Synthesis of Example 78

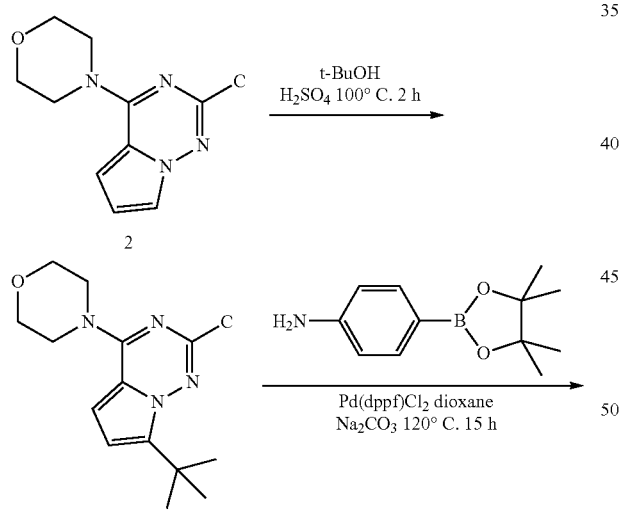

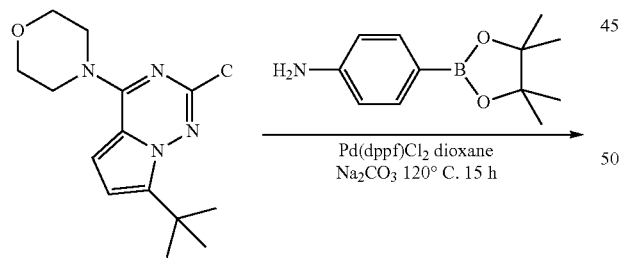

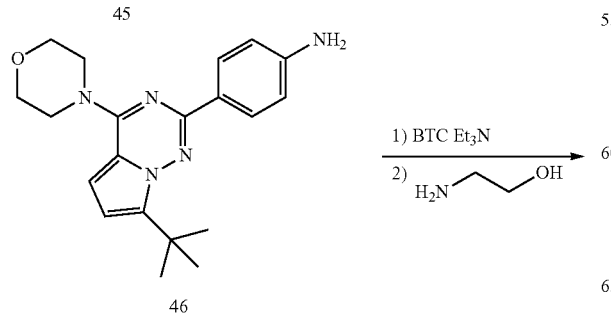

46

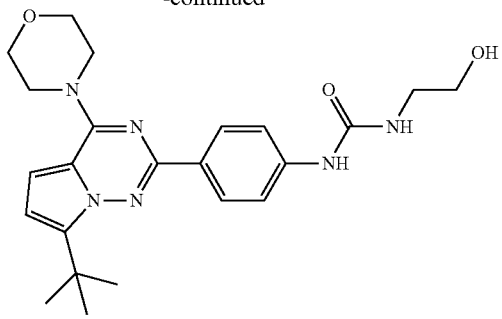

Example 78

Synthesis of Compound 45

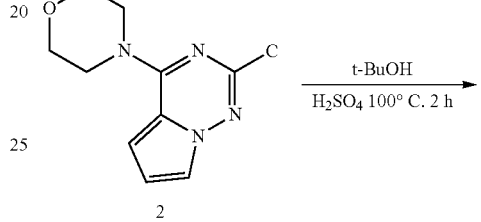

2

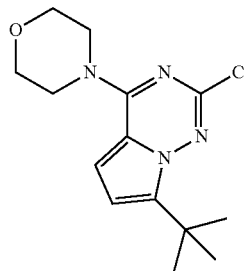

45

A mixture of compound 2 (100 mg, 0.419 mmol) and 2-methylpropan-2-ol (383 mL, 4.19 mmol) in H$_2$SO$_4$ (2.0 mL) was stirred at 100° C. for 2 h. After cooled to room temperature, the mixture was dissolved in EA and H$_2$O. The organic phase was washed with NaHCO$_3$, brine, dried over Na$_2$SO$_4$ and concentrated to give the crude product. After purified by Pre-HPLC (PE:EA=8:1) to afford compound 45 (100 mg, yield: 80.9%). $^1$H-NMR (400 MHz, CDCl$_3$) δ 6.68 (d, 1H, J=4.8 Hz), 6.44 (d, 1H, J=4.8 Hz), 4.03~4.00 (m, 4H), 3.86~3.81 (m, 4H), 1.48 (s, 9H).

Synthesis of Compound 46

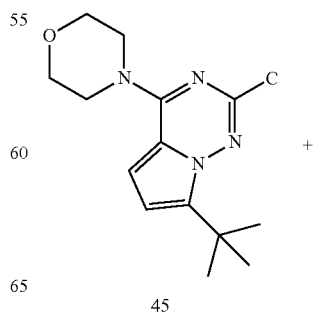 +

45

133
-continued

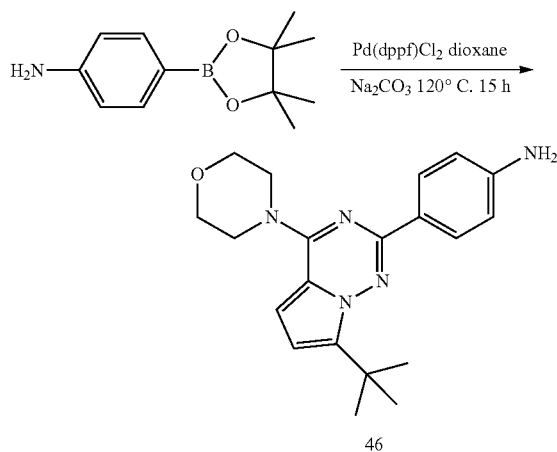

46

The procedure of compound 44 (50.0 mg, yield: 41.9%) was similar to that of Example 24. ¹H NMR (400 MHz, CDCl₃) δ 8.16 (d, 2H, J=8.4 Hz), 6.75 (d, 2H, J=8.0 Hz), 6.63 (d, 1H, J=4.4 Hz), 6.45 (d, 1H, J=4.4 Hz), 4.09~4.07 (m, 4H), 3.88~3.85 (m, 4H), 1.50 (s, 9H).

Synthesis of Example 78

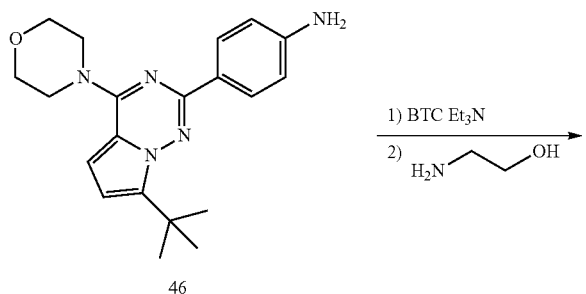

Example 78

The procedure of Example 78 (7.0 mg, yield: 37.4%) was similar to that of Example 15. ¹H NMR (400 MHz, CDCl₃) δ 8.19 (d, 2H, J=8.4 Hz), 7.41 (d, 2H, J=7.6 Hz), 6.62 (d, 1H, J=4.4 Hz), 6.43 (d, 1H, J=4.4 Hz), 4.09~4.05 (m, 4H), 3.84~3.83 (m, 4H), 3.66~3.63 (m, 2H), 3.36~3.33 (m, 2H), 1.52 (s, 9H).

134

Synthesis of Example 79

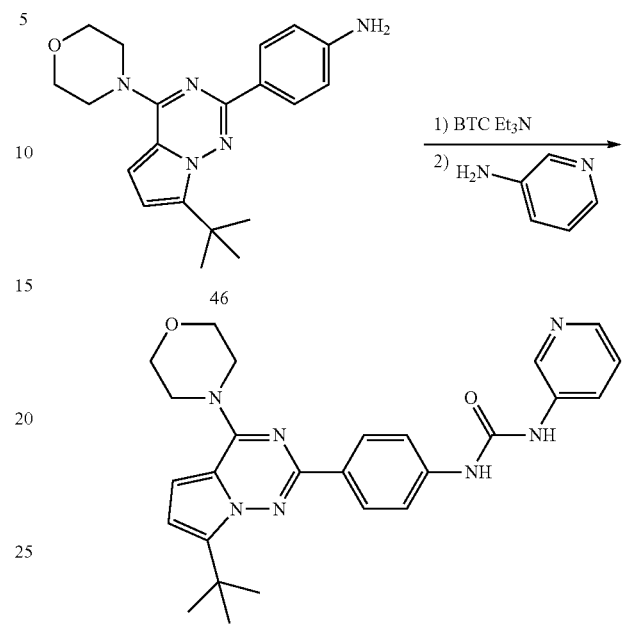

Example 79

The procedure of Example 79 (8.0 mg, yield: 39.7%) was similar to that of Example 15. ¹H NMR (400 MHz, MeOD) δ 8.34 (s, 1H), 8.29-8.27 (m, 3H), 8.16 (d, 1H, J=4.0 Hz), 7.53 (d, 2H, J=4.8 Hz), 7.31-7.29 (m, 1H), 6.65 (d, 1H, J=4.8 Hz), 6.47 (d, 1H, J=4.4 Hz), 4.10-4.08 (m, 4H), 3.88-3.86 (m, 4H), 1.52 (s, 9H).

Synthesis of Example 80

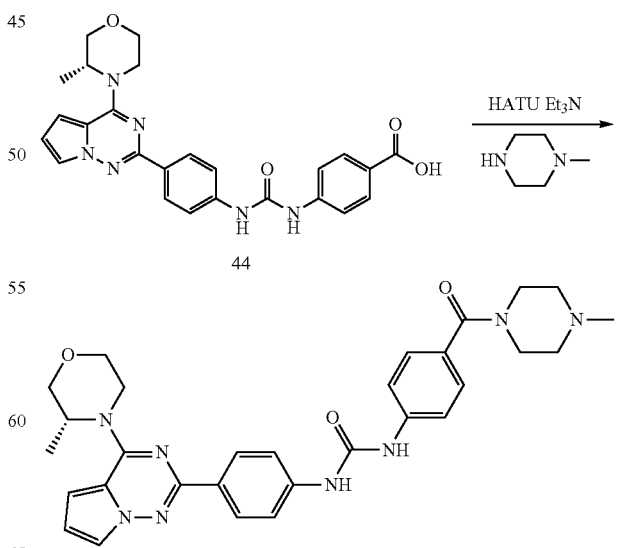

Example 80

The procedure of Example 80 (10 mg, 36%) was similar to that of Example 45. $^1$H NMR (MeOD-d$_4$, 400 MHz): δ 8.21 (d, 2H, J=8.8 Hz), 7.67 (s, 1H), 7.60 (d, 2H, J=8.4 Hz), 7.54 (d, 2H, J=8.4 Hz), 7.45 (d, 2H, J=8.4 Hz), 6.90 (d, 1H, J=4.0 Hz), 6.70-6.68 (m, 1H), 5.05-5.03 (m, 1H), 4.75-4.72 (m, 1H), 4.09-4.06 (m, 1H), 3.88-3.80 (m, 4H), 3.71-3.60 (m, 2H), 3.12-3.04 (m, 3H), 2.75 (s, 3H), 1.49 (d, 3H, J=6.8 Hz), 1.33-1.29 (m, 3H). ESI-MS (M+H)$^+$: 555.
Synthesis of Example 81
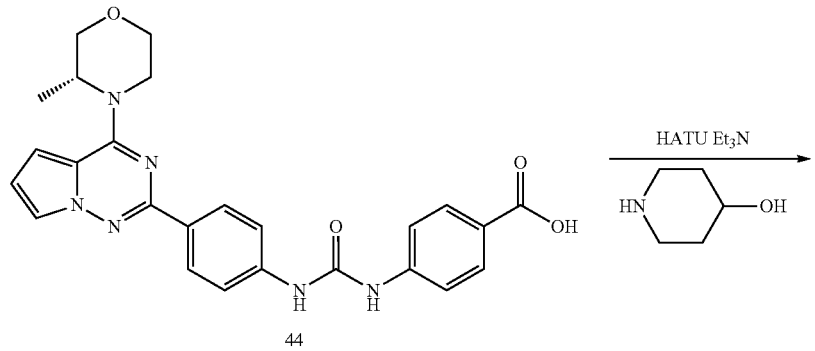
44
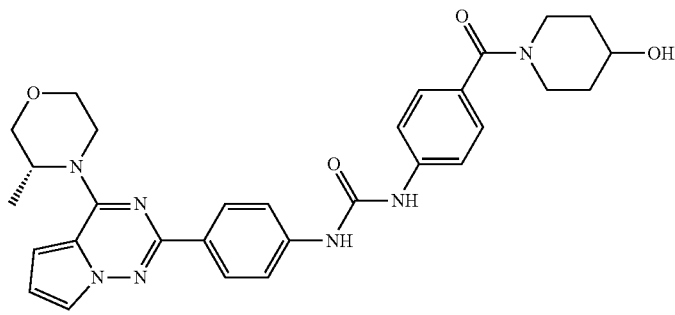
Example 81
The procedure of Example 81 (15 mg, 53%) was similar to that of Example 45. $^1$H NMR (MeOD-d$_4$, 400 MHz): δ 8.21 (d, 2H, J=8.8 Hz), 7.67-7.66 (m, 1H), 7.58-7.52 (m, 4H), 7.38 (d, 2H, J=8.8 Hz), 6.90-6.88 (m, 1H), 6.70-6.68 (m, 1H), 5.04-5.01 (m, 1H), 4.75-4.71 (m, 1H), 4.20-4.05 (m, 2H), 3.92-3.56 (m, 6H), 1.94-1.85 (m, 2H), 1.56-1.48 (m, 5H), 1.33-1.28 (m, 2H). ESI-MS (M+H)$^+$: 556.
Synthesis of Compound 47
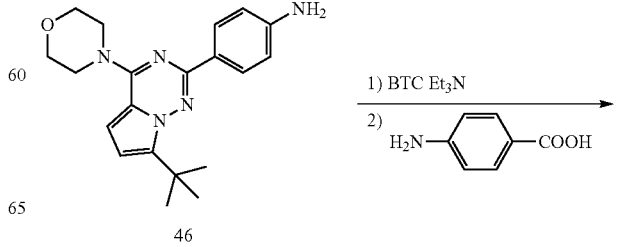
46

-continued

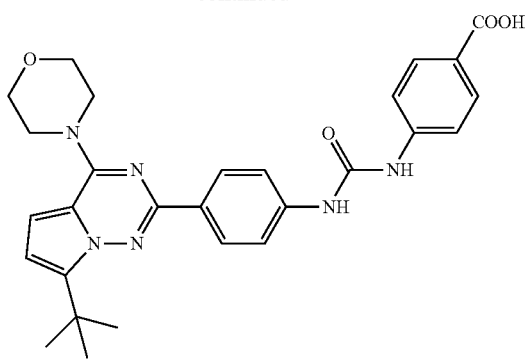

47

The procedure of compound 47 (20.0 mg, yield: 68.3%) was similar to that of Example 15. $^1$H NMR (400 MHz, MeOD) δ 8.20-8.18 (m, 2H), 7.90-7.88 (m, 2H), 7.48-7.44 (m, 4H), 6.60-6.57 (m, 1H), 6.40-6.38 (m, 1H), 4.06-4.03 (m, 4H), 3.86-3.84 (m, 4H), 1.48 (s, 9H).

Synthesis of Example 82

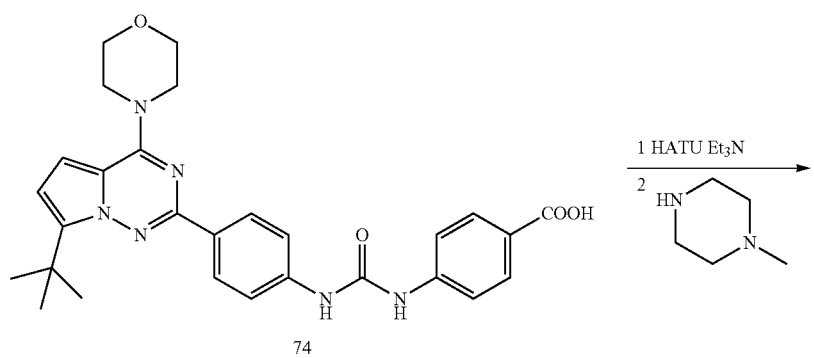

74

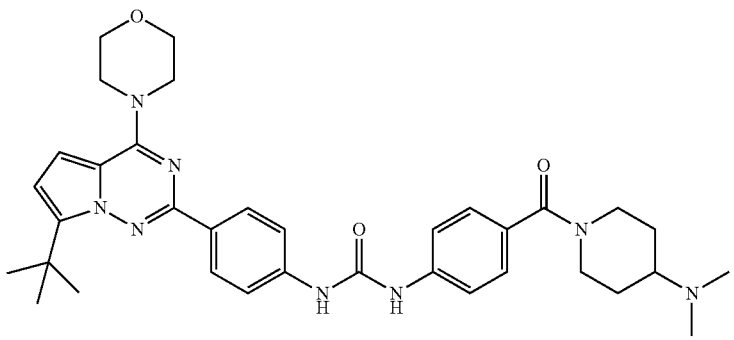

Example 82

A solution of compound 47 (10 mg, 0.019 mmol), HATU (11.1 mg, 0.029 mmol), and Et$_3$N (7.37 mmL, 0.058 mmol) in DCM (2 mL) was stirred for 30 min at ambient temperature. Then N,N-dimethylpiperidin-4-amine (3.74 mg, 0.029 mmol) was added. After stirred for overnight at ambient temperature, the mixture was dissolved in DCM and H$_2$O. The organic phase was washed with brine, dried over Na$_2$SO$_4$ and concentrated to give the crude product. After purified by Pre-HPLC (DCM:MeOH=10:1) to afford Example 82 (7.0 mg, yield: 57.7%). $^1$H NMR (400 MHz, MeOD) δ 8.19-8.15 (m, 2H), 7.52~7.50 (m, 4H), 7.35~7.32 (m, 2H), 6.75~6.73 (m, 1H), 6.49~6.46 (m, 1H), 4.06~4.03 (m, 4H), 3.86~3.84 (m, 4H), 3.46~3.44 (m, 1H), 2.78 (s, 6H), 2.13~2.10 (m, 2H), 1.67~1.65 (m, 2H), 1.51 (s, 9H), 1.23~1.20 (m, 2H), 1.16~1.13 (m, 2H). ESI-MS (M+H)$^+$: 625.46

Synthesis of Example 83

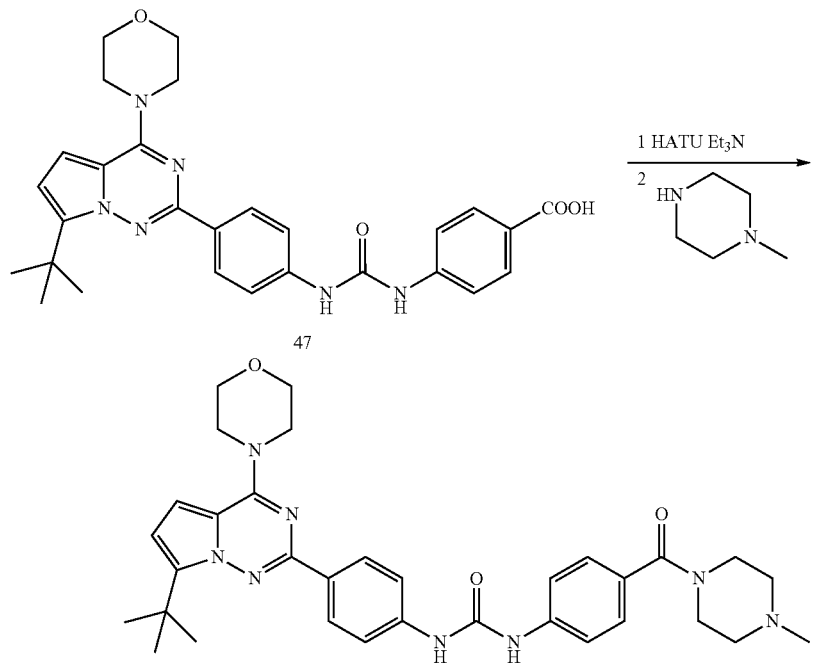

Example 83

The procedure of Example 83 (6.0 mg, yield: 51.7%) was similar to that of Example 45. $^1$H NMR (400 MHz, DMSO) δ 9.16-9.13 (m, 2H), 8.18 (d, J=8.4 Hz, 2H), 7.60~7.53 (m, 4H), 7.38 (d, J=8.4 Hz, 2H), 6.93 (d, J=4.8 Hz, 1H), 6.51 (d, J=4.8 Hz, 1H), 4.05~4.03 (m, 4H), 3.78~3.76 (m, 4H), 3.09~3.07 (m, 4H), 2.47 (s, 3H), 2.44~2.42 (m, 2H), 2.02~1.95 (m, 2H), 1.53 (s, 9H). ESI-MS (M+H)$^+$: 625.46. ESI-MS (M+H)$^+$: 597.34

Synthesis of Example 84

The procedure of Example 84 (9 mg, 31%) was similar to that of Example 45. $^1$H NMR (MeOD-d$_4$, 400 MHz): δ 8.21 (d, 2H, J=8.8 Hz), 7.67-7.66 (m, 1H), 7.59-7.51 (m, 6H), 6.90-6.88 (m, 1H), 6.70-6.68 (m, 1H), 5.04-5.02 (m, 1H), 4.75-4.71 (m, 1H), 4.09-4.02 (m, 1H), 3.88-3.80 (m, 4H), 3.71-3.60 (m, 4H), 3.52-3.47 (m, 1H), 2.47-2.19 (m, 8H), 1.49 (d, 3H, J=6.8 Hz). ESI-MS (M+H)$^+$: 569.

Synthesis of Example 85

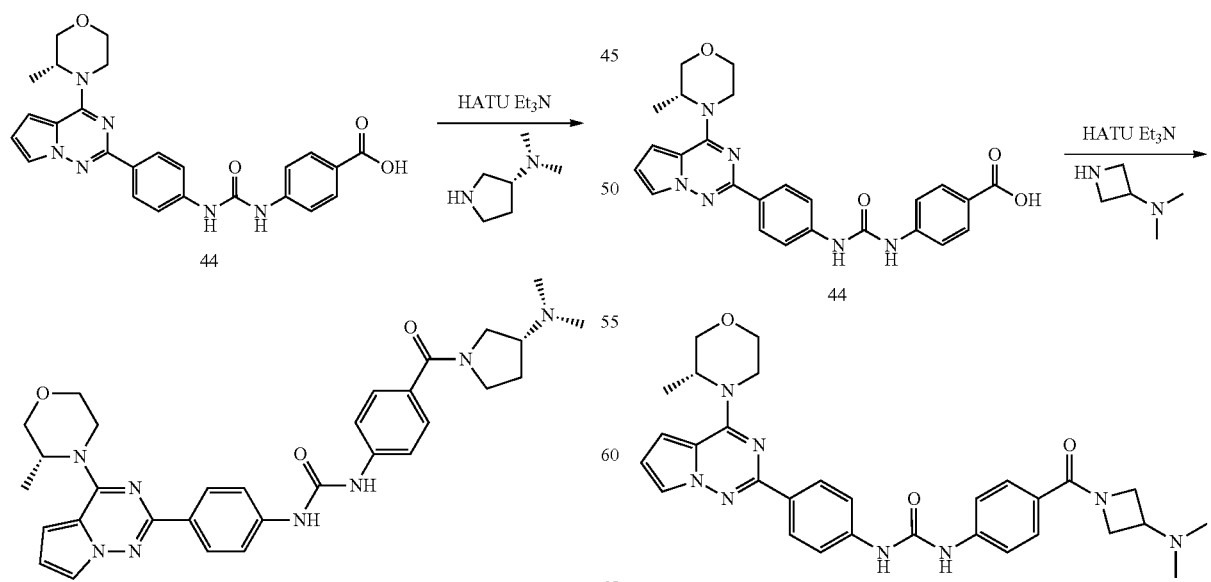

Example 84

Example 85

The procedure of Example 85 (9 mg, 31%) was similar to that of Example 45. ¹H NMR (MeOD-d₄, 400 MHz): δ 8.21 (d, 2H, J=8.8 Hz), 7.67-7.59 (m, 5H), 7.54 (d, 2H, J=8.8 Hz), 6.90-6.88 (m, 1H), 6.70-6.68 (m, 1H), 5.04-5.02 (m, 1H), 4.74-4.71 (m, 1H), 4.54-4.23 (m, 4H), 4.08-4.05 (m, 1H), 3.98-3.96 (m, 1H), 3.87-3.79 (m, 2H), 3.71-3.56 (m, 2H), 2.76 (s, 6H), 1.48 (d, 3H, J=6.8 Hz). ESI-MS (M+H)⁺: 555.

Synthesis of Example 86

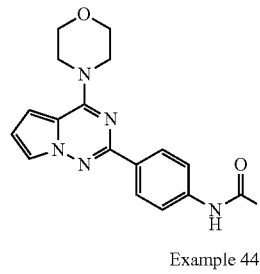

Example 44

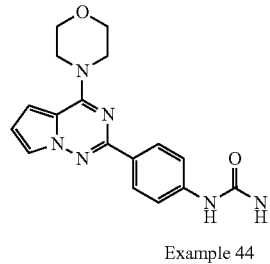

Example 86

The procedure of Example 86 (15 mg, 69%) was similar to that of Example 45. ¹HNMR (MeOD-d₄, 400 MHz): δ 8.22 (d, 2H, J=8.4 Hz), 7.67-7.59 (m, 5H), 7.54 (d, 2H, J=8.8 Hz), 6.91-6.90 (m, 1H), 6.70-6.69 (m, 1H), 4.69-4.25 (m, 4H), 4.13 (t, 4H, J=4.4 Hz), 4.07-4.04 (m, 1H), 3.86 (t, 4H, J=4.8 Hz), 2.83 (s, 6H). ESI-MS (M+H)⁺: 541.

Synthesis of Example 87

The procedure of Example 87 (5 mg, 24%) was similar to that of Example 45. ¹H NMR (DMSO-d₆, 400 MHz): δ 9.39 (d, 2H, J=9.2 Hz), 8.31-8.28 (m, 2H), 8.17 (d, 2H, J=8.8 Hz), 7.81 (d, 3H, J=8.4 Hz), 7.58-7.53 (m, 4H), 7.00-6.99 (m, 1H), 6.73-6.71 (m, 1H), 4.08-4.06 (m, 4H), 3.80-3.78 (m, 4H), 3.52-3.48 (m, 2H), 3.32-3.31 (m, 2H). ESI-MS (M+H)⁺: 502.

Synthesis of Example 88

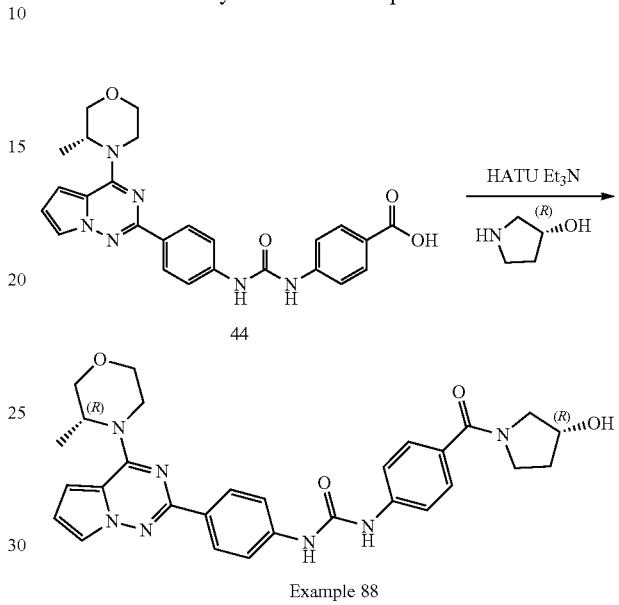

Example 88

The procedure of Example 88 (10 mg, 36%) was similar to that of Example 45. ¹H NMR (DMSO-d₆, 400 MHz): δ 9.66 (s, 1H), 9.62 (s, 1H), 8.15 (d, 2H, J=8.8 Hz), 7.80 (s, 1H), 7.59-7.47 (m, 6H), 6.98-6.97 (m, 1H), 6.73-6.71 (m, 1H), 5.02-4.95 (m, 2H), 4.69-4.63 (m, 1H), 4.32-4.24 (m, 1H), 4.03-4.01 (m, 1H), 3.81-3.71 (m, 2H), 3.65-3.46 (m, 5H), 1.93-1.79 (m, 2H), 1.39 (d, 3H, J=6.8 Hz). ESI-MS (M+H)⁺: 542.

Synthesis of Example 89

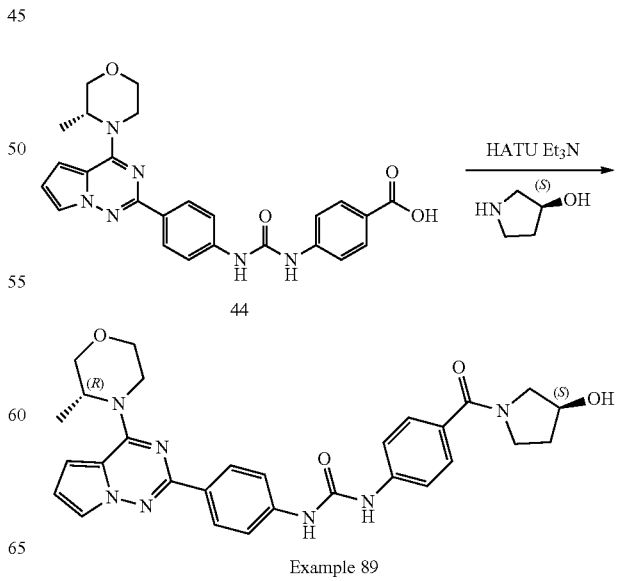

Example 89

The procedure of Example 89 (5 mg, 18%) was similar to that of Example 45. $^1$H NMR (MeOD-d$_4$, 400 MHz): δ 8.20 (d, 2H, J=8.4 Hz), 7.66 (s, 1H), 7.57-7.49 (m, 6H), 6.84-6.83 (m, 1H), 6.70-6.68 (m, 1H), 5.07-5.01 (m, 1H), 4.52-4.40 (m, 1H), 4.12-4.09 (m, 1H), 3.90-3.45 (m, 9H), 2.05-1.97 (m, 2H), 1.53 (d, 3H, J=7.2 Hz). ESI-MS (M+H)$^+$: 542.
Synthesis of Example 90
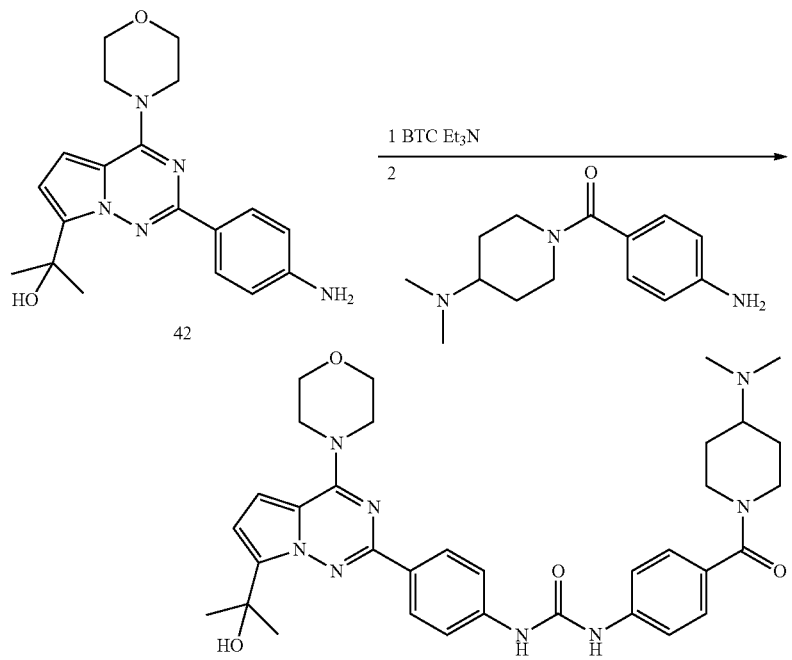
The procedure of Example 90 (2.7 mg, yield: 20.1%) was similar to that of Example 15. $^1$H NMR (400 MHz, MeOD) δ 8.39 (s, 1H), 8.22 (d, J=8.4 Hz, 2H), 7.60~7.44 (m, 4H), 7.43 (d, J=8.8 Hz, 2H), 6.87 (d, J=4.8 Hz, 1H), 6.64 (d, J=4.8 Hz, 1H), 4.14~4.12 (m, 4H), 3.87~3.85 (m, 4H), 3.23~3.18 (m, 5H), 2.85 (s, 6H), 2.19~2.10 (m, 2H), 2.03~2.01 (m, 2H), 1.77 (s, 6H).
Synthesis of Example 91
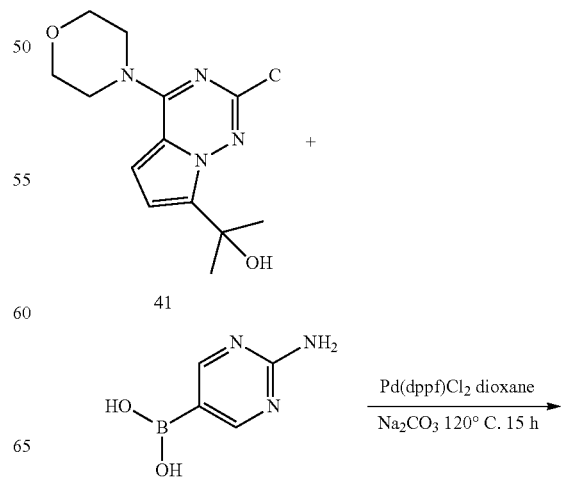

-continued

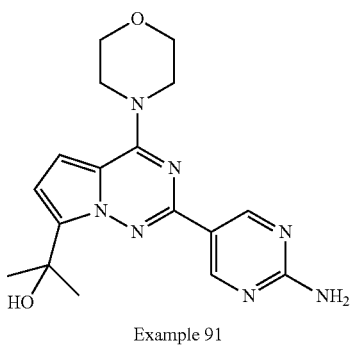

Example 91

The procedure of Example 91 (2.0 mg, yield: 8.35%) was similar to that of Example 24. $^1$H NMR (400 MHz, CDCl$_3$) δ 9.12 (s, 1H), 9.03 (s, 1H), 6.75~6.72 (m, 1H), 6.62~6.53 (m, 1H), 4.08~4.05 (m, 4H), 3.85~3.83 (m, 4H), 1.74 (s, 6H).

Synthesis of Example 92

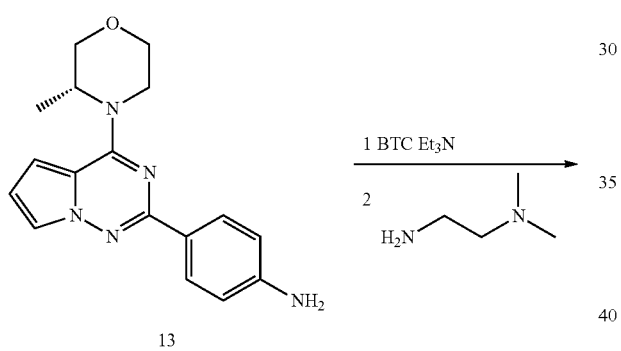

Example 92

The procedure of Example 92 (10 mg, yield: 39%) was similar to that of Example 15. $^1$H NMR (MeOD-d$_4$, 400 MHz): δ 8.16 (d, 2H, J=8.8 Hz), 7.64 (s, 1H), 7.50 (d, 2H, J=8.4 Hz), 6.85-6.84 (m, 1H), 6.67-6.66 (m, 1H), 4.99-4.98 (m, 1H), 4.70-4.67 (m, 1H), 4.05-4.02 (m, 1H), 3.84-3.76 (m, 2H), 3.65-3.56 (m, 4H), 3.29-3.28 (m, 2H), 2.95 (s, 6H), 1.45 (d, 3H, J=6.8 Hz). ESI-MS (M+H)$^+$: 424.

Synthesis of Example 93

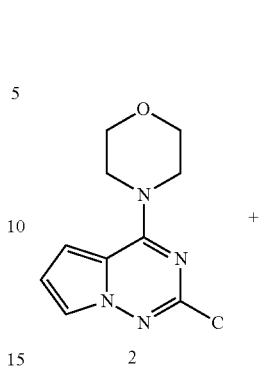

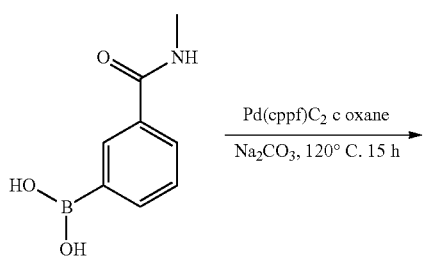

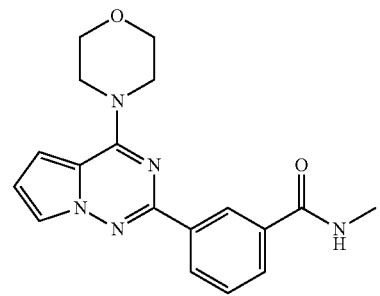

Example 93

The procedure of Example 93 (25 mg, yield: 57%) was similar to that of Example 6. $^1$H NMR (CDCl$_3$, 400 MHz): δ 8.56 (s, 1H), 8.35-8.33 (m, 1H), 7.80-7.78 (m, 1H), 7.62-7.61 (m, 1H), 7.45-7.41 (m, 1H), 6.66-6.61 (m, 2H), 6.29-6.28 (m, 1H), 4.06 (t, 4H, J=4.8 Hz), 3.81 (t, 4H, J=4.8 Hz), 2.98 (d, 3H, J=4.8 Hz). ESI-MS (M+H)$^+$: 338.

Synthesis of Example 94

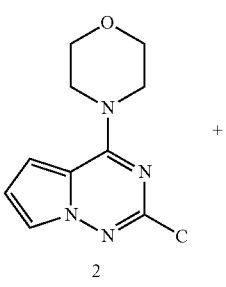

147

-continued

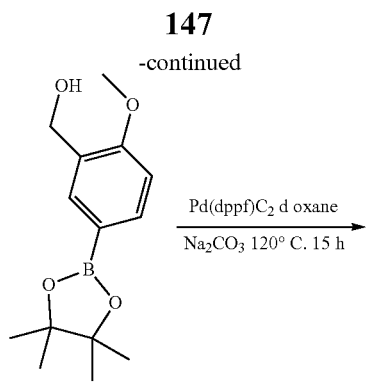

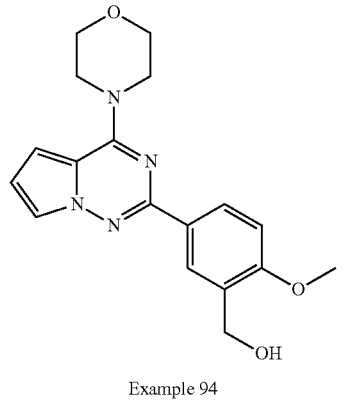

Example 94

The procedure of Example 94 (15 mg, yield: 52%) was similar to that of Example 6. ¹H NMR (CDCl₃, 400 MHz): δ 8.23-8.21 (m, 2H), 7.68-7.67 (m, 1H), 6.95 (d, 1H, J=8.8 Hz), 6.71-6.65 (m, 2H), 4.77 (s, 2H), 4.13 (t, 4H, J=4.4 Hz), 3.93 (s, 3H), 3.89 (t, 4H, J=4.8 Hz). ESI-MS (M+H)⁺: 341.

Synthesis of Example 95

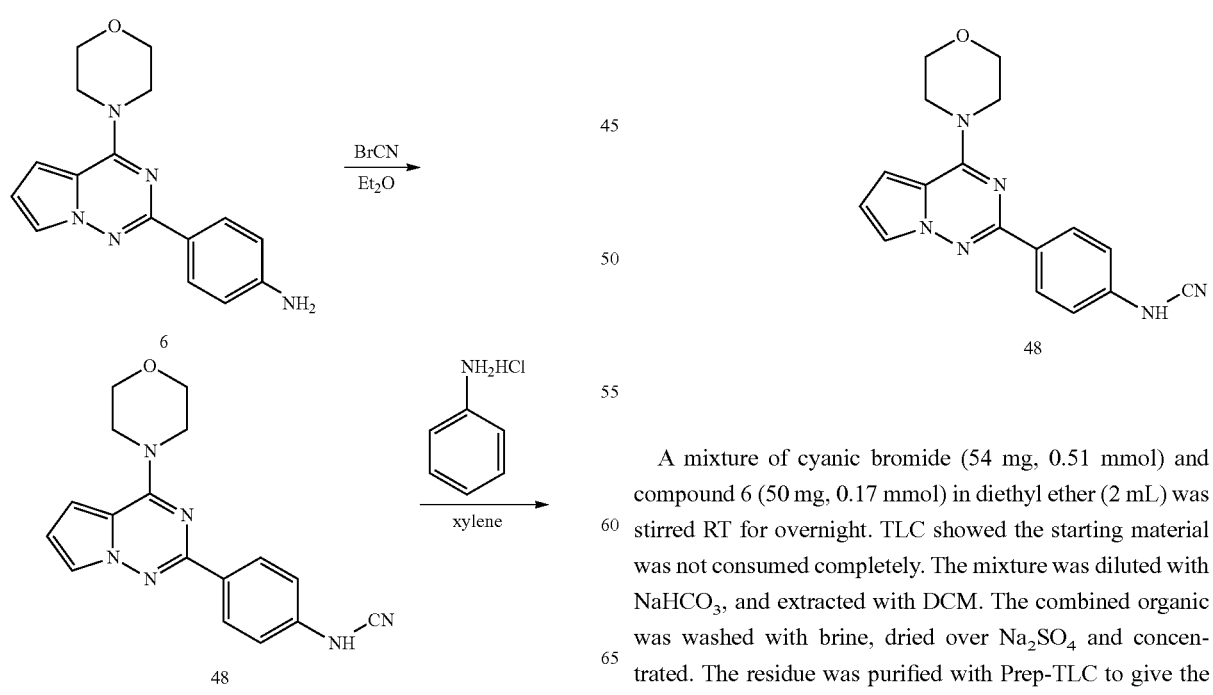

148

-continued

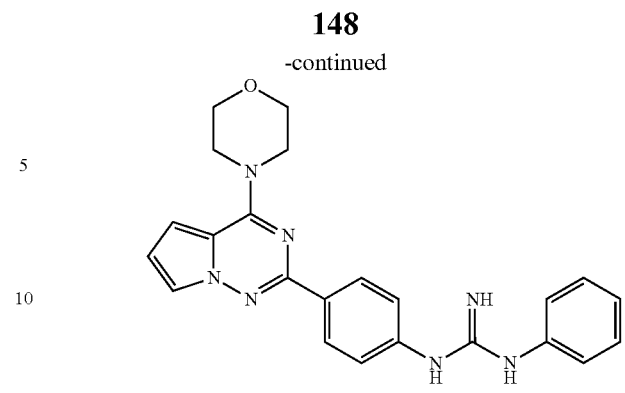

Example 95

Synthesis of Compound 48

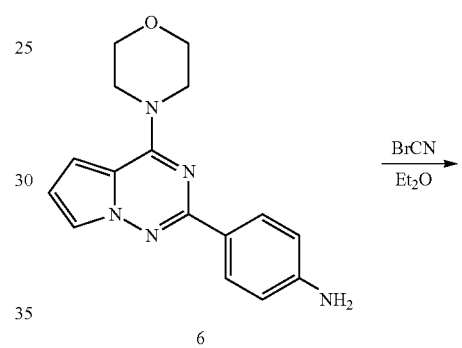

A mixture of cyanic bromide (54 mg, 0.51 mmol) and compound 6 (50 mg, 0.17 mmol) in diethyl ether (2 mL) was stirred RT for overnight. TLC showed the starting material was not consumed completely. The mixture was diluted with NaHCO₃, and extracted with DCM. The combined organic was washed with brine, dried over Na₂SO₄ and concentrated. The residue was purified with Prep-TLC to give the title compound 48 (10 mg, 18.4%).

Synthesis of Example 95

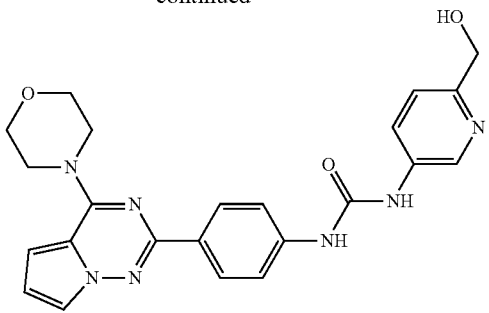

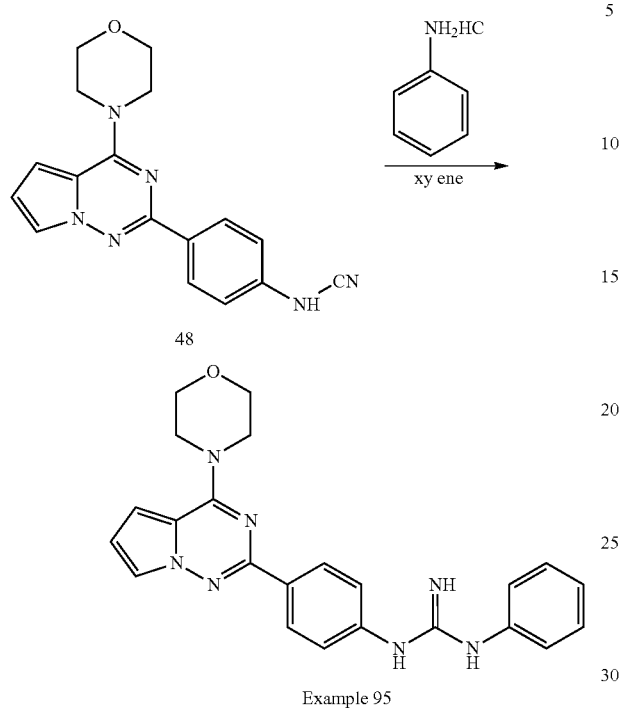

A mixture of compound 48 (10 mg, 0.03 mmol) and aniline hydrochloride (4 mg, 0.03 mmol) in xylene (2 mL) was stirred 135° C. for overnight. After removed the most solvent, the residue was diluted with NaHCO$_3$, and extracted with DCM. The combined organic was washed with brine, dried over Na$_2$SO$_4$ and concentrated. The crude was purified with Prep-TLC to Example 95 (2 mg, 15%). $^1$H NMR (CDCl$_3$, 400 MHz): δ 8.36 (d, 2H, J=8.0 Hz), 7.67 (s, 1H), 7.49-7.47 (m, 2H), 7.41-7.34 (m, 5H), 6.75-6.70 (m, 2H), 4.13 (t, 4H, J=4.8 Hz), 3.89 (t, 4H, J=4.8 Hz). ESI-MS (M+H)$^+$: 414.

Synthesis of Example 96

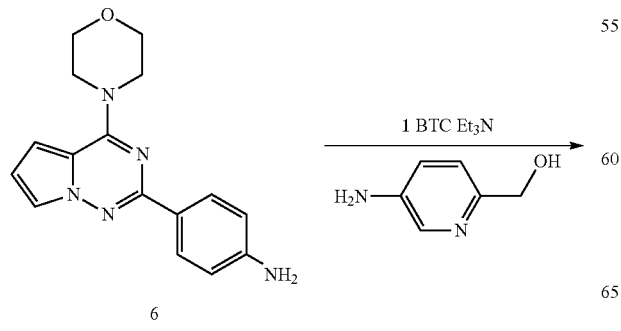

The procedure of Example 96 (7 mg, yield: 9%) was similar to that of Example 15. $^1$H NMR (DMSO-d$_6$, 400 MHz): δ 9.02 (s, 1H), 8.86 (s, 1H), 8.54 (d, 1H, J=2.4 Hz), 8.17 (d, 1H, J=8.8 Hz), 7.95-7.93 (m, 1H), 7.82-7.81 (m, 2H), 7.57 (d, 2H, J=8.8 Hz), 7.40 (d, 1H, J=8.4 Hz), 7.01-7.00 (m, 1H), 6.74-6.72 (m, 1H), 5.33 (t, 1H, J=6.0 Hz), 4.51 (d, 2H, J=6.0 Hz), 4.08 (t, 4H, J=4.8 Hz), 3.80 (t, 4H, J=4.8 Hz). ESI-MS (M+H)$^+$: 446.

Synthesis of Example 97

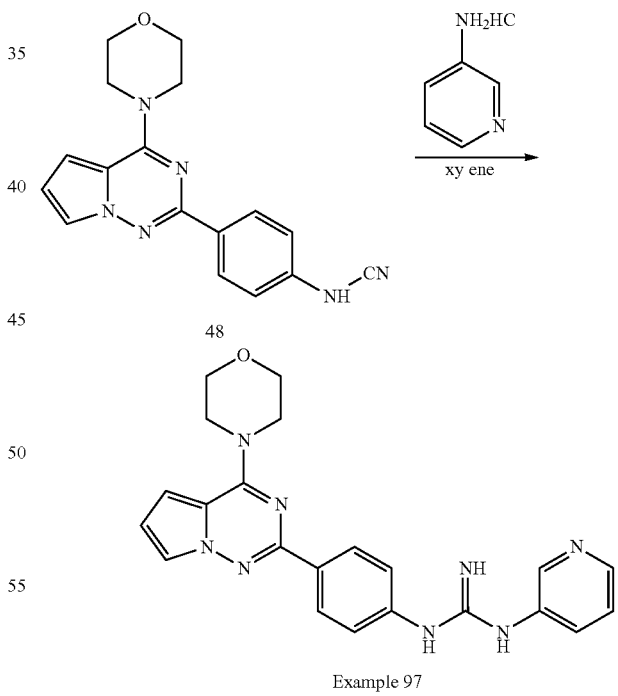

The procedure of Example 97 (7 mg, yield: 21%) was similar to that of Example 95. $^1$H NMR (CDCl$_3$, 400 MHz): δ 8.53 (d, 1H, J=1.2 Hz), 8.33-8.26 (m, 3H), 7.65-7.64 (m, 2H), 7.34-7.28 (m, 3H), 6.70-6.67 (m, 1H), 4.09 (t, 4H, J=4.4 Hz), 3.86 (t, 4H, J=4.8 Hz). ESI-MS (M+H)$^+$: 415.

Synthesis of Example 98

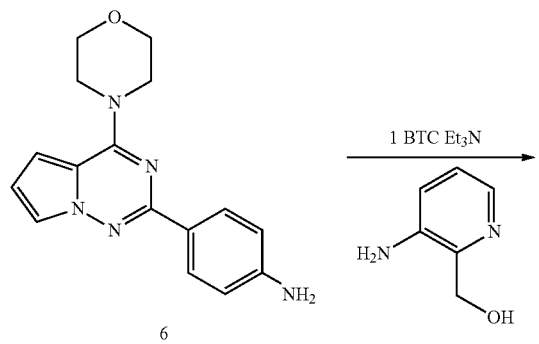

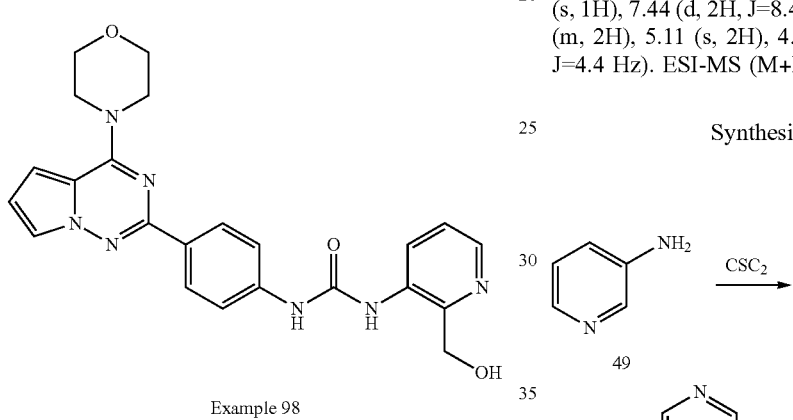

Example 98

The procedure of Example 98 (4 mg, yield: 5%) was similar to that of Example 15. ¹H NMR (MeOD-d$_4$, 400 MHz): δ 8.44-8.42 (m, 1H), 8.24 (d, 2H, J=8.8 Hz), 8.20-8.18 (m, 1H), 7.70-7.69 (m, 1H), 7.59 (d, 2H, J=8.8 Hz), 7.39-7.36 (m, 1H), 6.93-6.92 (m, 1H), 6.73-6.71 (m, 1H), 4.83 (s, 2H), 4.16 (t, 4H, J=4.4 Hz), 3.89 (t, 4H, J=5.2 Hz). ESI-MS (M+H)⁺: 446.

Synthesis of Example 99

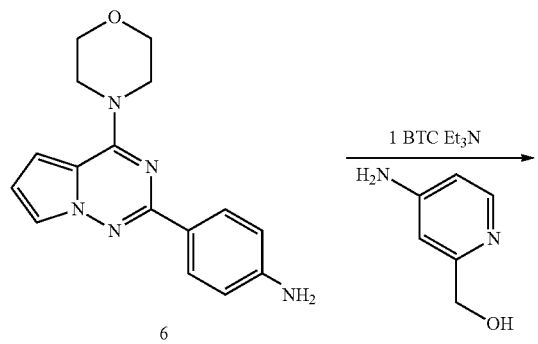

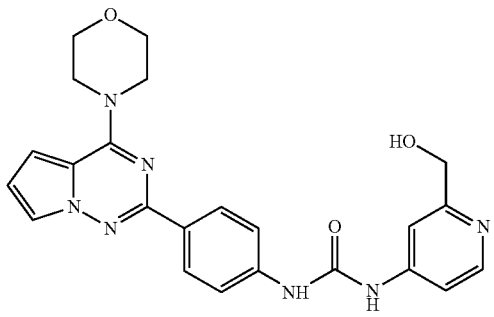

Example 99

The procedure of Example 99 (5 mg, yield: 6%) was similar to that of Example 15. ¹H NMR (MeOD-d$_4$, 400 MHz): δ 8.10 (d, 2H, J=8.4 Hz), 7.90 (d, 1H, J=6.8 Hz), 7.56 (s, 1H), 7.44 (d, 2H, J=8.4 Hz), 6.80-6.76 (m, 2H), 6.65-6.59 (m, 2H), 5.11 (s, 2H), 4.02 (t, 4H, J=4.4 Hz), 3.76 (t, 4H, J=4.4 Hz). ESI-MS (M+H)⁺: 446.

Synthesis of Example 100

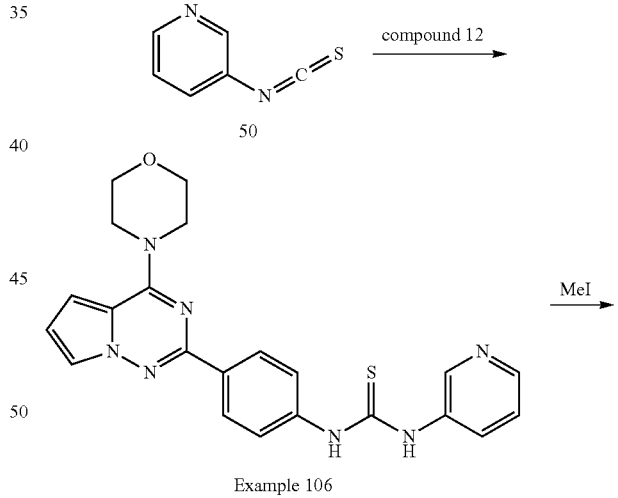

Example 106

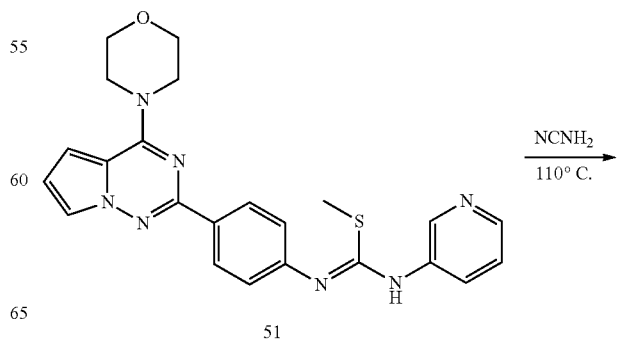

51

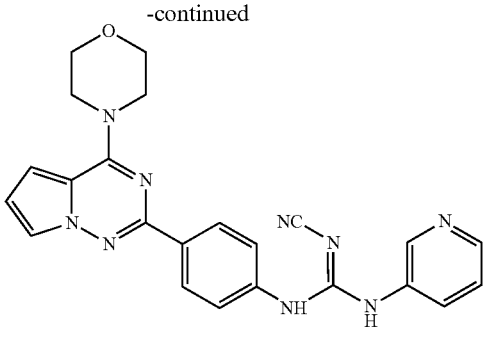

Example 100

Synthesis of Compound 50

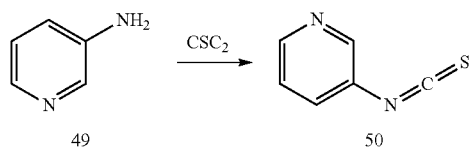

To a solution of 3-aminopyridine (100 mg, 1.1 mmol) in THF (5 mL) was added dropwise a solution of $CSCl_2$ (244 mg, 2.2 mmol) in $H_2O$ (0.5 ml) with stirring at 0° C. under $N_2$. After addition, the reaction mixture was stirred at 0° C. for 1 h. The reaction mixture was diluted with aq. $NaHCO_3$ (5 mL), separated and the aqueous layer was extracted with DCM (3×5 mL). The combined organic layers were washed with brine, dried over $Na_2SO_4$ and concentrated to afford compound 50. The crude was used directly in the next step without further purification.

Synthesis of Example 106

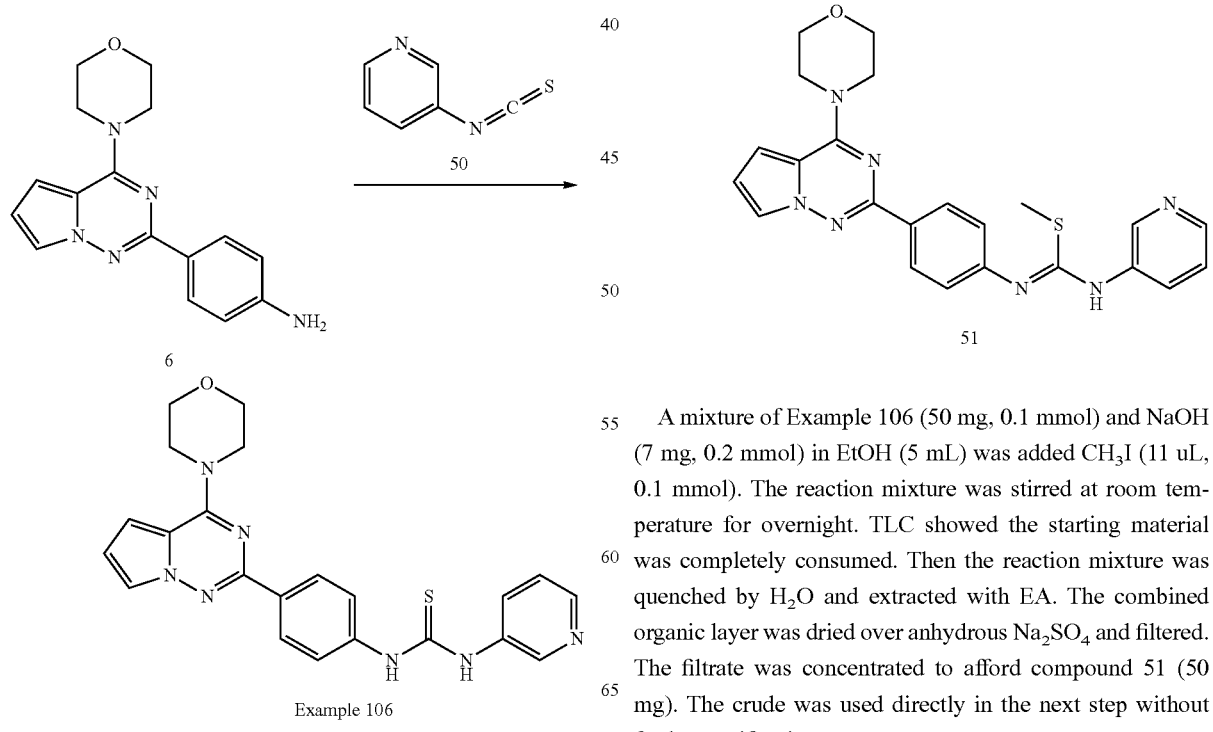

To a stirred solution of compound 50 (140 mg, 1.04 mmol) in DMF (3 mL) was added a solution of compound 6 (102 mg, 0.34 mmol 1) in DMF (1 mL). The reaction mixture was stirred at room temperature for overnight. Then the reaction mixture was quenched by $H_2O$ and extracted with EA. The combined organic layer was dried over anhydrous $Na_2SO_4$ and filtered. The filtrate was concentrated to the residue, which was purified by Pre-TLC to afford Example 106 (48 mg, 38%)₁H NMR (CDCl₃, 400 MHz): δ 8.53 (d, 1H, J=1.2 Hz), 8.33-8.26 (m, 3H), 7.65-7.64 (m, 3H), 7.34-7.28 (m, 3H), 6.70-6.67 (m, 1H), 4.04 (t, 4H, J=4.4 Hz), 3.79 (t, 4H, J=4.8 Hz). ESI-MS (M+H)⁺: 432.

Synthesis of Compound 51

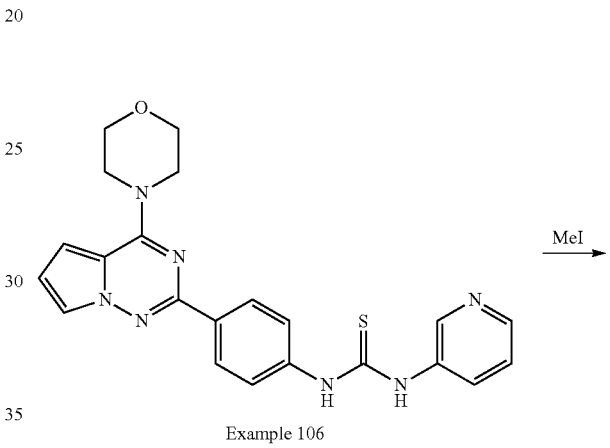

A mixture of Example 106 (50 mg, 0.1 mmol) and NaOH (7 mg, 0.2 mmol) in EtOH (5 mL) was added $CH_3I$ (11 uL, 0.1 mmol). The reaction mixture was stirred at room temperature for overnight. TLC showed the starting material was completely consumed. Then the reaction mixture was quenched by $H_2O$ and extracted with EA. The combined organic layer was dried over anhydrous $Na_2SO_4$ and filtered. The filtrate was concentrated to afford compound 51 (50 mg). The crude was used directly in the next step without further purification.

Synthesis of Example 100

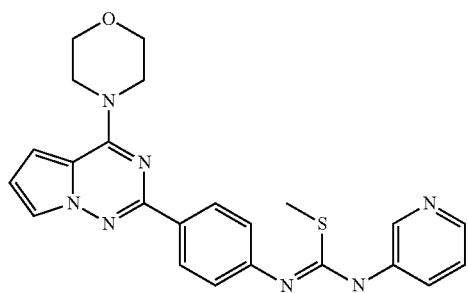

51

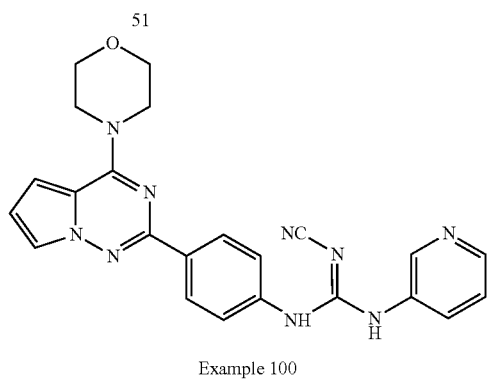

Example 100

A mixture of compound 51 (50 mg, 0.1 mmol) and cyanamide (13 mg, 0.3 mm), triethylenetetramine (2 mg, 0.01 mmol) in EtOH (5 mL) was stirred at 80° C. for 5 h. After filtered, The filtrate was concentrated to the residue, which was purified by Pre-TLC to afford Example 100 (6 mg, 6%). $^1$H NMR (MeOD-$d_4$, 400 MHz): δ 8.44 (d, 1H, J=2.4 Hz), 8.24-8.20 (m, 2H), 7.82-7.79 (m, 1H), 7.59-7.58 (m, 1H), 7.47-7.44 (m, 1H,), 7.36-7.32 (m, 3H), 6.83-6.81 (m, 1H), 6.65-6.60 (m, 1H), 4.04 (t, 4H, J=4.4 Hz), 3.76 (t, 4H, J=4.8 Hz). ESI-MS (M+H)$^+$: 440.

Synthesis of Example 101

Synthesis of Compound 53

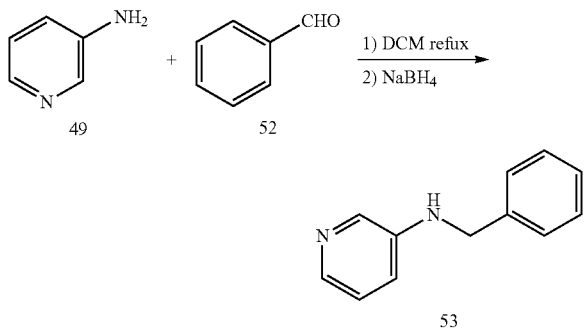

53

3-aminopyridine (100 mg, 1.1 mmol) and benzaldehyde (113 mg, 1.1 mmol) were dissolved in DCM (5 mL) and stirred at reflux for 12 h. The solvent was removed in vacuo. The reside was dissolved in methanol (5 mL), and sodium borohydride (80 mg, 2.2 mmol) was added slowly as a solid to the methanolic solution, and the resulting solution was stirred at room temperature for 1 h. 2 N HCl was then added to destroy the excess sodium borohydride. Once the effervescence had stopped, 2 M NaOH was added until pH 9 was obtained. The yellow solution was extracted with DCM, washed with water (15 mL), separated, dried over MgSO$_4$, filtered and concentrated. The residue was purified by silica gel chromatography using Petroleum ether:Ethyl acetate (2:1) affording to compound 53 (172 mg, 88%). $^1$H NMR (400 MHz, CDCl$_3$) δ 8.10 (d, 1H, J=2.8 Hz), 7.97 (d, 1H, J=5.6 Hz), 7.36 (d, 4H, J=4.4 Hz), 7.33-7.28 (m, 1H), 7.10-7.02 (m, 1H), 6.90 (dd, 1H, J=7.8, 2.2 Hz), 4.33 (s, 2H).

Synthesis of Example 101

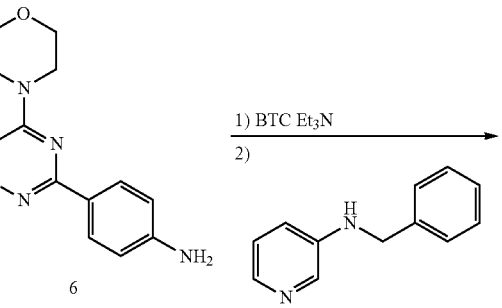

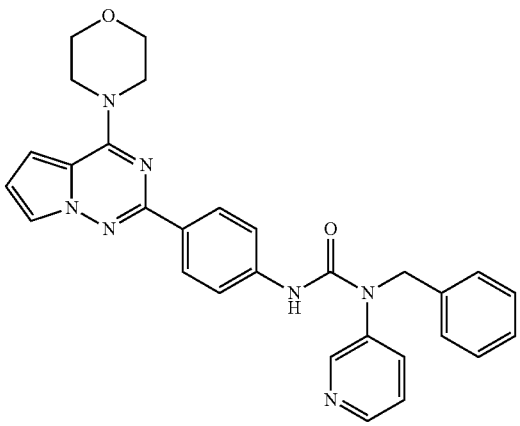

Example 101

The procedure of Example 101 (6 mg, yield: 8%) was similar to that of Example 15. $^1$H NMR (400 MHz, CDCl$_3$) δ 8.54 (s, 2H), 8.19 (d, 2H, J=8.2 Hz), 7.70 (d, 1H, J=8.4), 7.65 (s, 1H), 7.43 (d, 3H, J=8.4 Hz), 7.35-7.27 (m, 5H), 6.69 (d, 1H, J=4.2 Hz), 6.67-6.64 (m, 1H), 5.00 (s, 2H), 4.14-4.07 (m, 4H), 3.91-3.84 (m, 4H).

Synthesis of Example 102

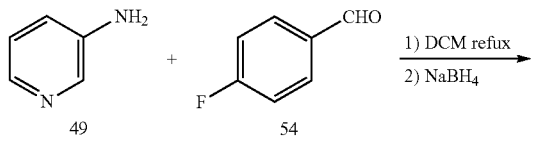

-continued
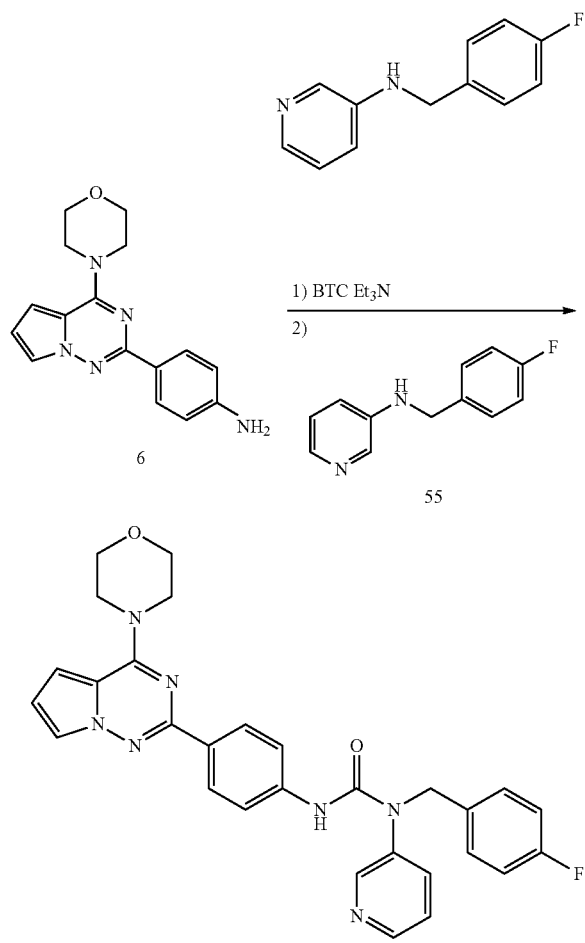
Synthesis of Compound 55
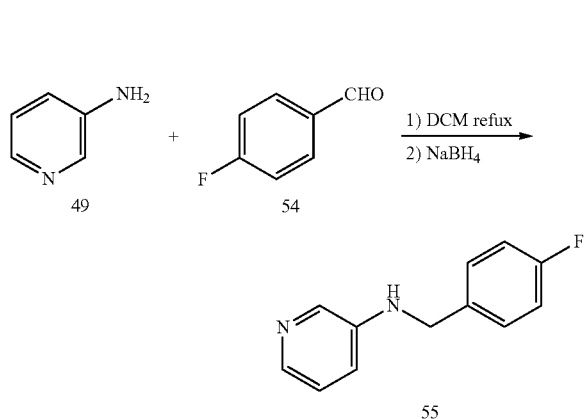
The procedure of compound 55 (35 mg, 75%) was similar to that of compound 53. ¹H NMR (400 MHz, CDCl₃) δ 8.08 (d, 1H, J=2.8 Hz), 7.98 (dd, 1H, J=4.8 1.2 Hz), 7.43-7.28 (m, 2H), 7.12-6.95 (m, 3H), 6.89-6.85 (m, 1H), 4.32 (d, 2H, J=4.2 Hz).
Synthesis of Example 102
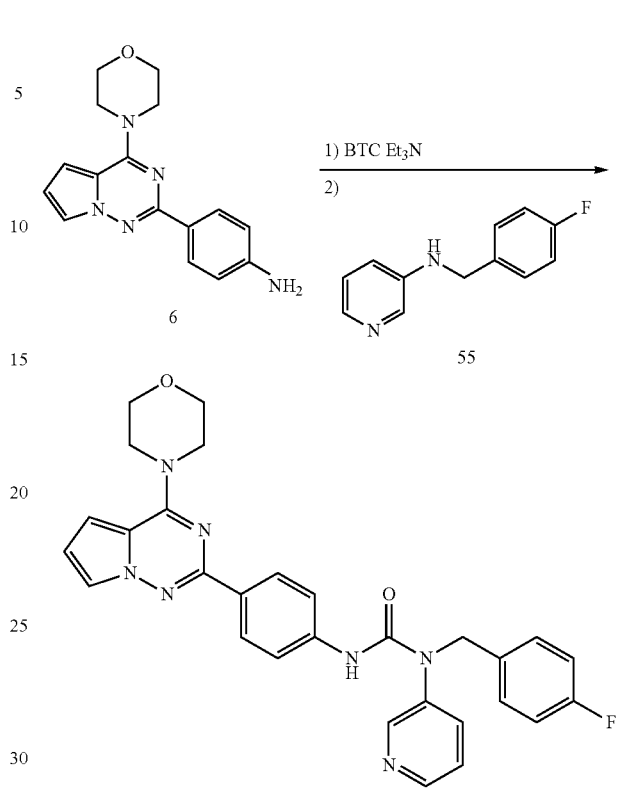
Example 102
The procedure of Example 102 (8 mg, 10%) was similar to that of Example 15. ¹H NMR (400 MHz, MeOD) δ 8.44 (d, 1H, J=4.8 Hz), 8.41 (d, 1H, J=2.4 Hz), 8.18 (d, 2H, J=8.6 Hz), 7.72 (d, 1H, J=8.0 Hz), 7.66 (s, 1H), 7.46 (d, J=8.8 Hz, 3H), 7.34-7.30 (m, 2H), 7.03 (t, 2H, J=8.8 Hz), 6.90 (d, 1H, J=5.6 Hz), 6.70-6.68, (m, 1H), 5.00 (s, 2H), 4.16-4.09 (m, 4H), 3.93-3.81 (m, 4H).
Synthesis of Example 103
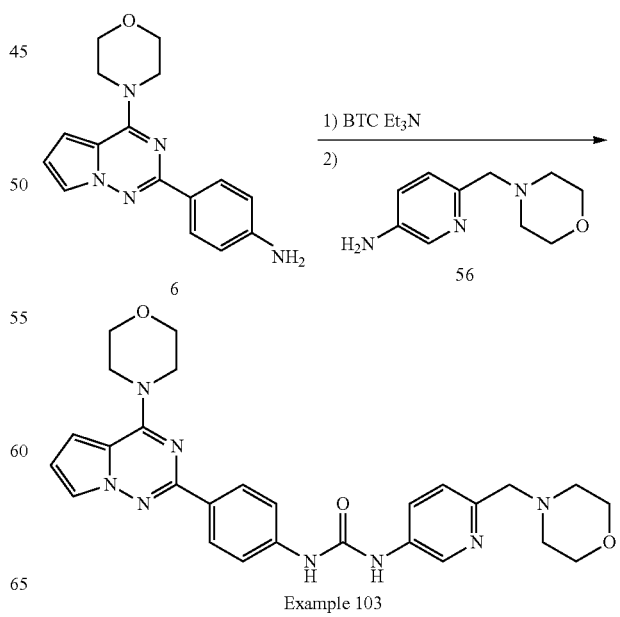
Example 103

The procedure of Example 103 (6 mg, 6.8%) was similar to that of Example 15. ¹H NMR (400 MHz, DMSO) δ 9.07 (s, 1H), 8.93 (s, 1H), 8.57 (s, 1H), 8.17 (d, 2H, J=8.7 Hz), 7.96 (d, 1H, J=7.4 Hz), 7.84-7.77 (m, 1H), 7.57 (d, 2H, J=8.7 Hz), 7.40 (d, 1H, J=5.1 Hz,) 7.04-6.96 (m, 1H), 6.73 (dd, 1H, J=4.5, 2.6 Hz), 4.14-4.00 (m, 4H), 3.85-3.73 (m, 4H), 3.62 (dd, 6H, J=5.6, 3.2 Hz), 2.44-2.31 (m, 4H).

Synthesis of Example 104

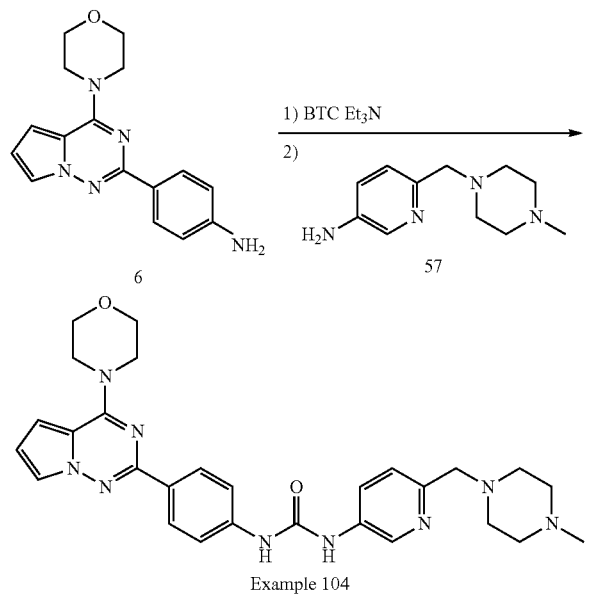

Example 104

The procedure of Example 104 (8 mg, 8.9%) was similar to that of Example 15.

¹H NMR (400 MHz, DMSO) δ 9.09 (s, 1H), 8.97 (s, 1H), 8.59-8.53 (m, 1H), 8.17 (d, 2H, J=8.8 Hz), 7.95 (dd, 1H, J=8.4, 2.5 Hz), 7.80 (dd, 1H, J=3.8, 2.6 Hz), 7.57 (d, 2H, J=8.8 Hz), 7.36 (d, 1H, J=8.2 Hz), 7.01 (dd, 1H, J=4.5, 1.3 Hz), 6.73 (dd, 1H, J=4.6, 2.6 Hz), 4.12-4.02 (m, 4H), 3.84-3.75 (m, 4H), 3.65-3.55 (m, 2H), 2.71 (dd, 4H, J=17.5, 5.5 Hz), 2.31 (dd, 4H, J=14.2, 7.8 Hz), 2.00 (dd, 3H, J=10.2, 4.7 Hz).

Synthesis of Example 105

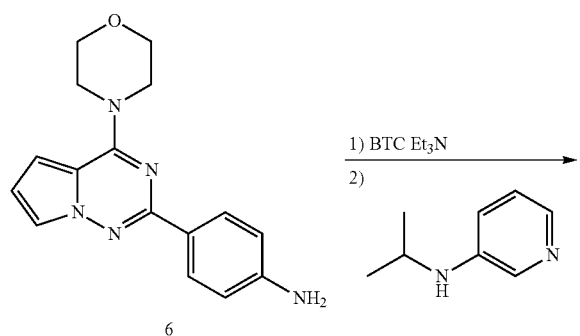

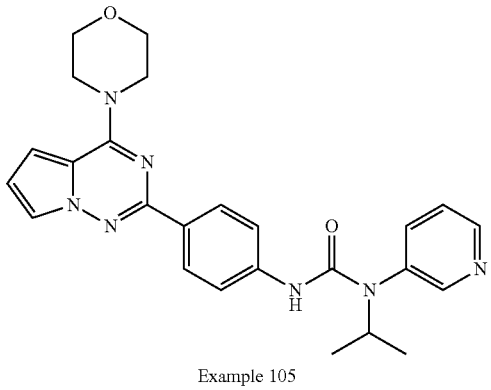

Example 105

The procedure of Example 105 (32 mg, 21%) was similar to that of Example 15. ¹H NMR (CDCl₃, 400 MHz): δ 8.70 (d, 1H, J=4.4 Hz), 8.58 (d, 1H, J=2.0 Hz), 8.16 (d, 2H, J=8.8 Hz), 7.77 (d, 1H, J=8.4 Hz), 7.65 (dd, 1H, J=2.4, 1.6 Hz), 7.60-7.57 (m, 1H), 7.38 (d, 2H, J=8.8 Hz), 6.70-6.64 (m, 2H), 6.13-6.11 (m, 1H), 5.00-4.94 (m, 1H), 4.11 (t, 4H, J=5.0 Hz), 3.88 (t, 4H, J=5.2 Hz), 1.14 (d, 6H, J=6.8 Hz). ESI-MS (M+H)⁺: 458.

Synthesis of Example 107

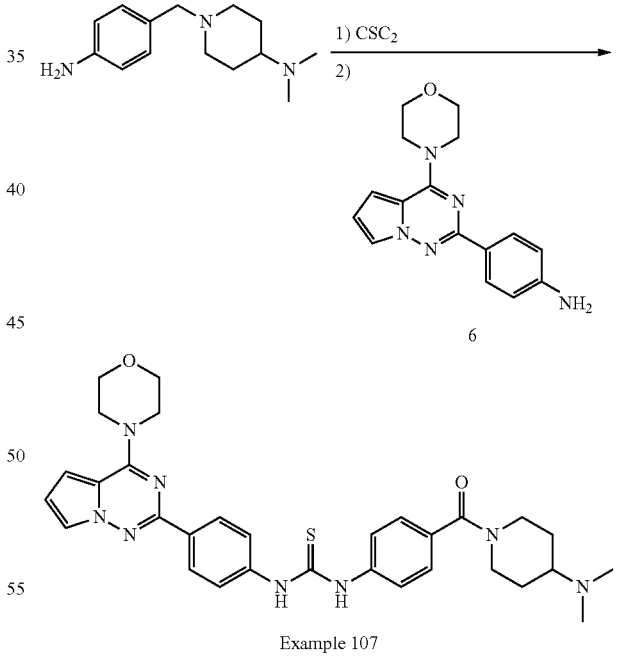

Example 107

The procedure of Example 107 (35 mg, 33%) was similar to that of Example 15. ¹H NMR (400 MHz, DMSO) δ 10.16 (s, 1H), 10.11 (s, 1H), 8.19 (d, 2H, J=8.8 Hz), 7.82 (d, 1H, J=2.6 Hz), 7.60 (dd, 4H, J=12.6, 8.6 Hz), 7.36 (d, 2H, J=8.6 Hz), 7.01 (dd, 1H, J=4.6, 1.2 Hz), 6.74 (dd, 1H, J=4.6, 2.8 Hz), 4.15-4.00 (m, 4H), 3.87-3.70 (m, 4H), 2.93-2.91 (m, 4H), 2.24 (s, 6H), 1.77 (s, 2H), 1.36 (d, 3H, J=9.4 Hz).

Synthesis of Example 108

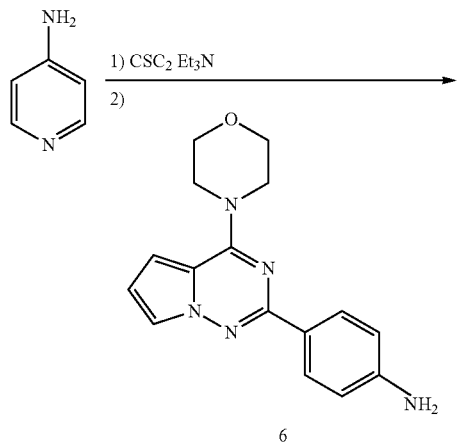

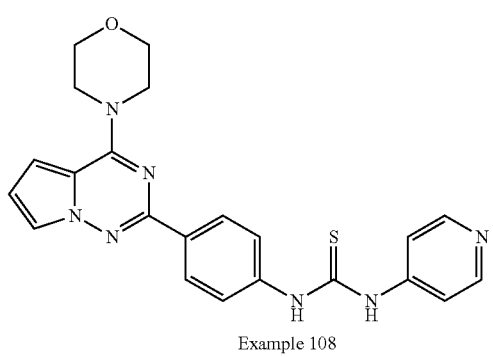

Example 108

The procedure of Example 108 (10 mg, 8%) was similar to that of Example 106. Analytical data: $^1$H NMR (400 MHz, DMSO) δ 10.40 (s, 1H), 10.28 (s, 1H), 8.44 (d, 2H, J=6.2 Hz), 8.21 (d, 2H, J=8.6 Hz), 7.82 (dd, 1H, J=2.6, 1.4 Hz), 7.66 (d, 2H, J=6.4 Hz), 7.63 (d, 2H, J=8.6 Hz), 7.01 (dd, 1H, J=4.6, 1.4 Hz), 6.74 (dd, 1H, J=4.6, 2.8 Hz), 4.15-4.03 (m, 4H), 3.84-3.73 (m, 4H), 1.24 (s, 3H).

Synthesis of Example 109

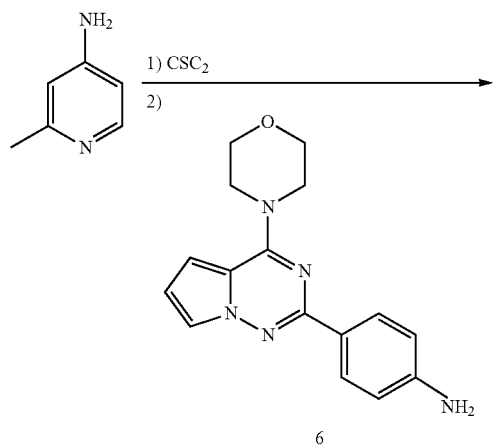

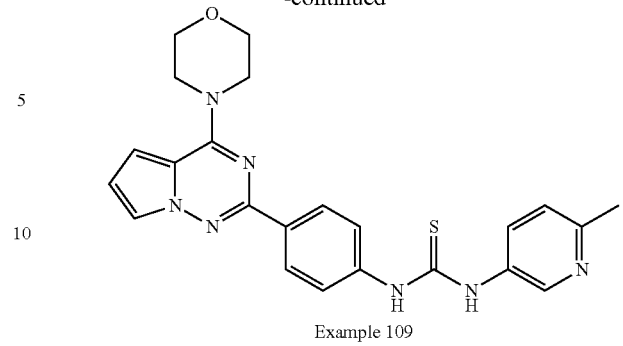

Example 109

The procedure of Example 109 (21 mg, 16%) was similar to that of Example 106. $^1$H NMR (400 MHz, DMSO) δ 10.09 (s, 1H), 9.84 (s, 1H), 8.47 (d, 1H, J=2.6 Hz), 8.20 (d, 2H, J=8.8 Hz), 7.82 (d, 2H, J=2.6 Hz), 7.62 (d, 2H, J=8.8 Hz), 7.24 (d, 1H, J=8.4 Hz), 7.01 (dd, 1H, J=4.6, 1.4 Hz), 6.74 (dd, 1H, J=4.6, 2.8 Hz), 4.14-4.01 (m, 4H), 3.90-3.66 (m, 4H), 2.45 (s, 3H).

Synthesis of Example 110

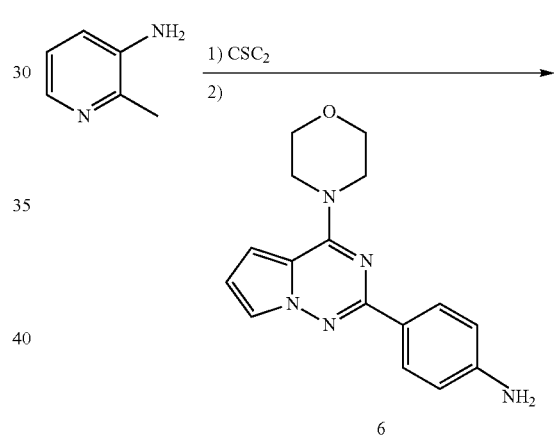

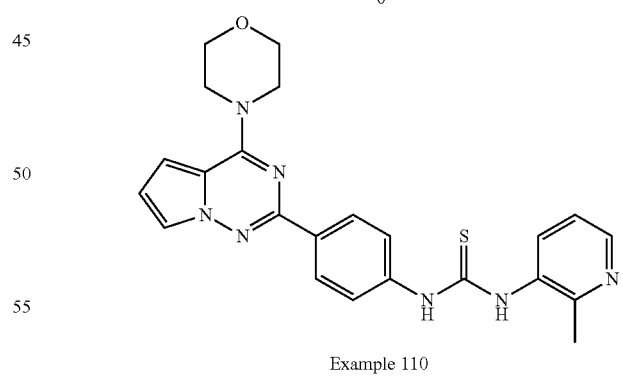

Example 110

The procedure of Example 110 (38 mg, 27%) was similar to that of Example 106. $^1$H NMR (400 MHz, DMSO) δ 10.09 (s, 1H), 9.52 (s, 1H), 8.34 (dd, 1H, J=4.8, 1.6 Hz), 8.21 (d, 2H, J=8.8 Hz), 7.82 (dd, 1H, J=2.6, 1.4 Hz), 7.69 (dd, 1H, J=7.8, 1.6 Hz), 7.66 (s, 1H), 7.64 (s, 1H), 7.25 (dd, 1H, J=7.8, 4.8 Hz), 7.01 (dd, 1H, J=4.6, 1.4 Hz), 6.74 (dd, 1H, J=4.6, 2.8 Hz), 4.14-3.99 (m, 4H), 3.87-3.72 (m, 4H), 2.46 (s, 3H).

Synthesis of Compound 58

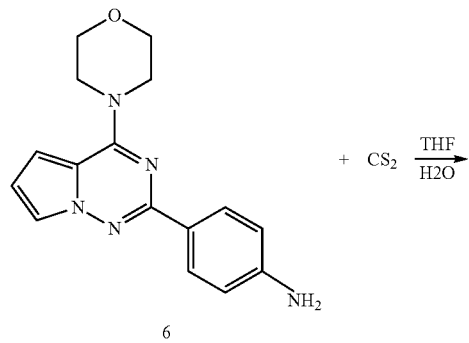

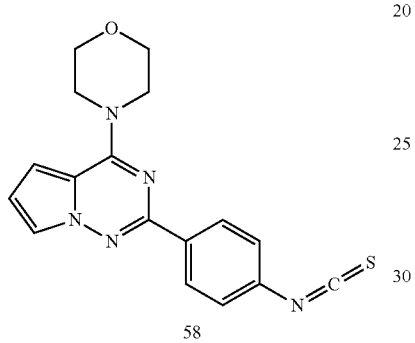

To a solution of Compound 6 (500 mg, 1.7 mmol) in THF (15 ml) was added dropwise a solution of CSCl$_2$ (393 mg, 3.4 mmol) in H$_2$O (5 ml) with stirring at 0° C. under N$_2$. After addition, the reaction mixture was stirred at 0° C. for 2 h. The reaction mixture was diluted with aq. NaHCO$_3$ (15 ml), separated and the aqueous layer was extracted with DCM (3×15 mL). The combined organic layers were washed with brine, dried over Na$_2$SO$_4$ and concentrated to give the compound 58 as a light yellow solid (390 mg, 71% yield), which was used directly in the next step without further purification.

Synthesis of Example 111

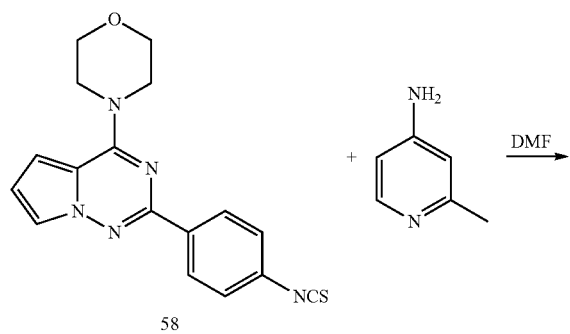

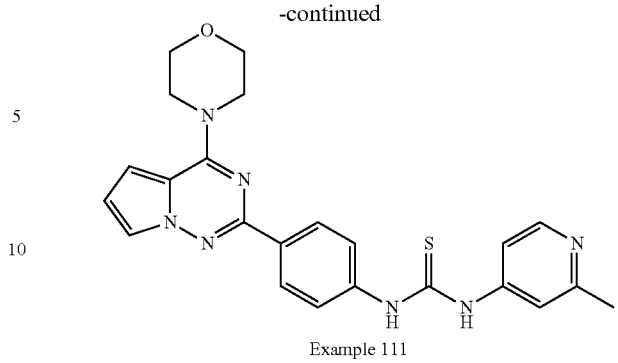

Example 111

2-Methylpyridin-4-amine (50 mg, 0.15 mmol) and compound 58 (13 mg, 0.12 mmol) were dissolved in DMF (5 mL) and stirred at 40° C. for 12 h. The reaction mixture was concentrated and the crude material was purified by silica gel column chromatography (EA) affording to Example 111 (10 mg, 19%) as a light yellow solid. $^1$H NMR (400 MHz, DMSO) δ 10.33 (s, 1H), 10.16 (s, 1H), 8.31 (d, 1H, J=6.4 Hz), 8.21 (d, 2H, J=8.8 Hz), 7.82 (d, 1H, J=4.0 Hz), 7.63 (d, 2H, J=8.6 Hz), 7.49 (s, 1H), 7.46 (d, 1H, J=5.6 Hz), 7.02 (dd, 1H, J=4.6, 1.4 Hz), 6.74 (dd, 1H, J=4.6, 2.8 Hz), 4.13-4.04 (m, 4H), 3.82-3.76 (m, 4H), 2.43 (s, 3H).

Synthesis of Example 112

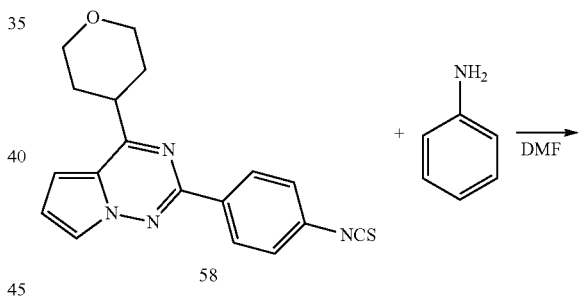

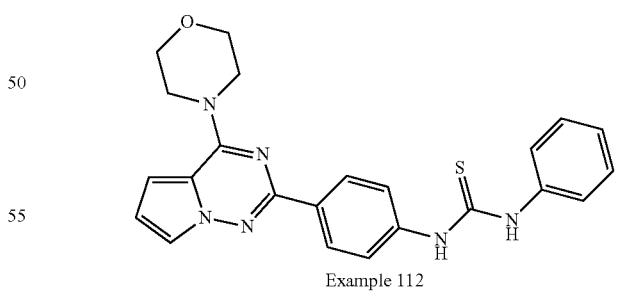

Example 112

The procedure of Example 112 (24 mg, 47.0%) was similar to that of Example 111. $^1$H NMR (400 MHz, DMSO) δ 9.96 (s, 1H), 9.88 (s, 1H), 8.19 (d, 2H, J=8.4 Hz,) 7.82-7.81 (m, 1H), 7.63 (d, 2H, J=8.8 Hz), 7.51 (d, 2H, J=7.6 Hz), 7.36-7.33 (m, 2H), 7.16-7.12 (m, 1H), 7.02-7.00 (m, 1H), 6.74-6.72 (m, 1H), 4.09-4.06 (m, 4H), 3.80-3.71 (m, 4H).

Synthesis of Example 113

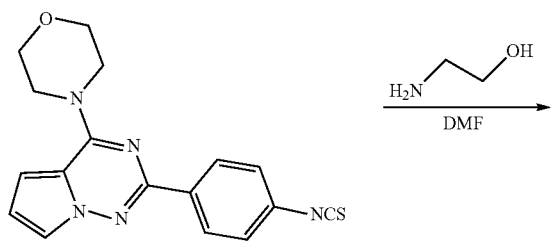

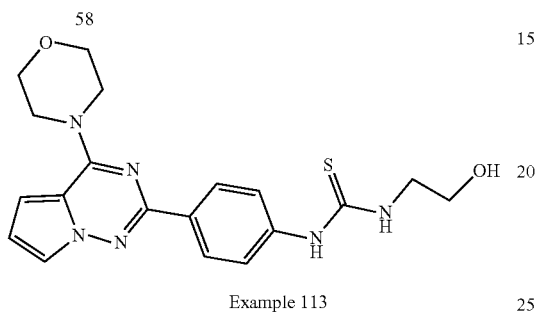

Example 113

The procedure of Example 113 (19 mg, 40.2%) was similar to that of Example 111. $^1$H NMR (400 MHz, DMSO) δ 9.78 (s, 1H), 8.17 (d, 2H, J=8.8 Hz), 7.84 (s, 1H), 7.81-7.79 (m, 1H), 7.60 (d, 2H, J=8.4 Hz), 7.00-6.99 (m, 1H), 6.73-6.71 (m, 1H), 4.81 (s, 1H), 4.08-4.05 (m, 4H), 3.79-3.77 (m, 4H), 3.58-3.55 (m, 4H).

Synthesis of Example 114

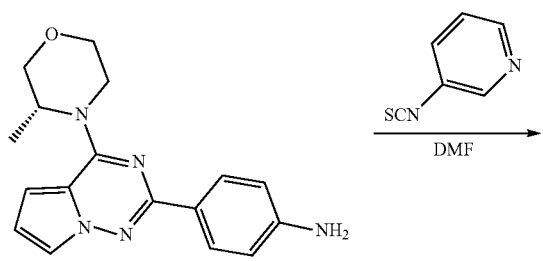

13

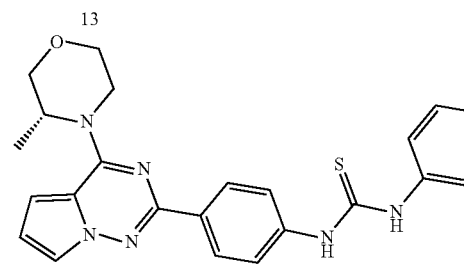

Example 114

The procedure of Example 114 (17 mg, 59%) was similar to that of Example 111. $^1$H NMR (400 MHz, MeOD) δ 9.78 (s, 1H), 8.17 (d, 2H, J=8.8 Hz), 7.84 (s, 1H), 7.81-7.79 (m, 2H), 7.60 (d, 2H, J=8.4 Hz), 7.00-6.99 (m, 2H), 6.73-6.71 (m, 1H), 4.81 (s, 1H), 4.08-4.05 (m, 2H), 3.79-3.77 (m, 2H), 3.58-3.55 (m, 2H), 1.48 (d, 3H, J=6.8 Hz).

Synthesis of Example 115

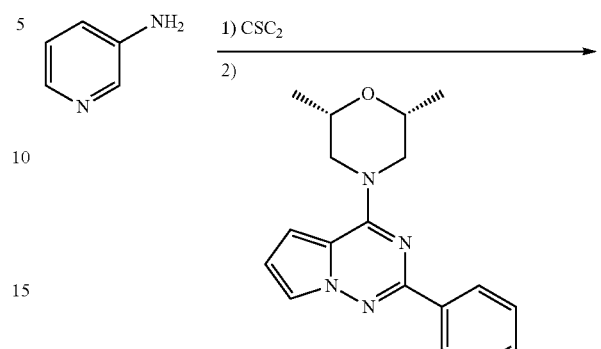

59

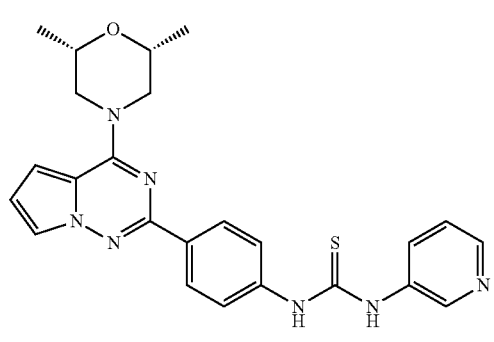

Example 115

The procedure of Example 115 (120 mg, 36%) was similar to that of Example 106. $^1$H NMR (DMSO-d$_6$, 400 MHz): δ 10.20 (s, 1H), 9.96 (s, 1H), 8.64 (d, 1H, J=2.4 Hz), 8.34 (dd, 1H, J=4.8, 1.2 Hz), 8.22 (d, 2H, J=8.8 Hz), 7.99-7.96 (m, 1H), 7.82 (dd, 1H, J=2.8, 1.6 Hz), 7.63 (d, 2H, J=8.8 Hz), 7.39 (dd, 1H, J=8.4, 4.8 Hz), 7.05 (dd, 1H, J=4.4, 1.2 Hz), 6.74 (dd, 1H, J=4.4, 2.4 Hz), 4.78 (d, 2H, J=12.4 Hz), 3.74-3.70 (m, 2H), 2.92 (d, 2H, J=12.4 Hz), 1.24 (d, 6H, J=6.4 Hz). ESI-MS (M+H)$^+$: 460.

Synthesis of Example 116

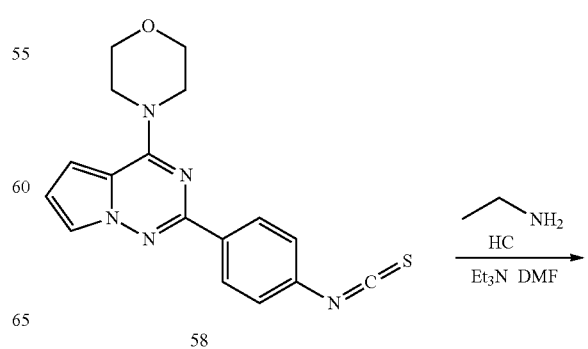

58

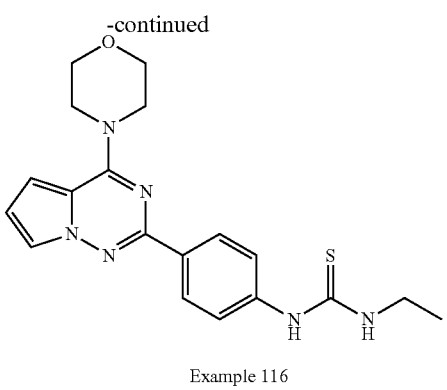

Example 116

The procedure of Example 116 (40 mg, 63%) was similar to that of Example 111. $^1$H NMR (CDCl$_3$, 400 MHz): δ 8.30 (d, 2H, J=8.4 Hz), 7.80-7.79 (m, 1H), 7.71-7.70 (m, 1H), 7.31-8.30 (d, 2H, J=8.4 Hz), 6.81-6.80 (m, 1H), 6.72 (dd, 1H, J=4.4, 2.8 Hz), 6.28-6.20 (m, 1H), 4.15 (t, 4H, J=4.8 Hz), 3.91 (t, 4H, J=5.2 Hz), 3.72-3.67 (m, 2H), 1.21 (t, 3H, J=7.2 Hz). ESI-MS (M+H)$^+$: 383.

Synthesis of Example 117

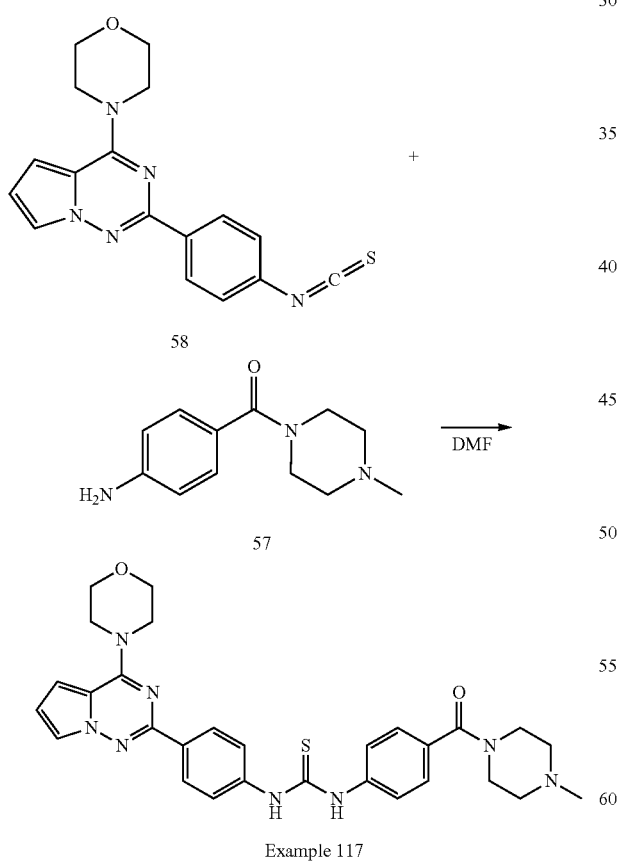

Example 117

The procedure of Example 117 (25 mg, 33.2%) was similar to that of Example 111. $^1$H NMR (DMSO-d$_6$, 400 MHz): δ 10.10 (s, 1H), 10.06 (s, 1H), 8.19 (d, 2H, J=8.8 Hz), 7.82 (dd, 1H, J=2.4, 1.2 Hz), 7.61-7.56 (m, 4H), 7.35 (d, 2H, J=8.8 Hz), 7.01 (dd, 1H, J=4.8, 1.6 Hz), 6.74 (dd, 1H, J=4.4, 2.8 Hz), 4.08 (t, 4H, J=4.8 Hz), 3.79 (t, 4H, J=4.8 Hz), 3.46 (s, 4H), 2.30 (s, 4H), 2.18 (s, 3H). ESI-MS (M+H)$^+$: 557.

Synthesis of Example 118

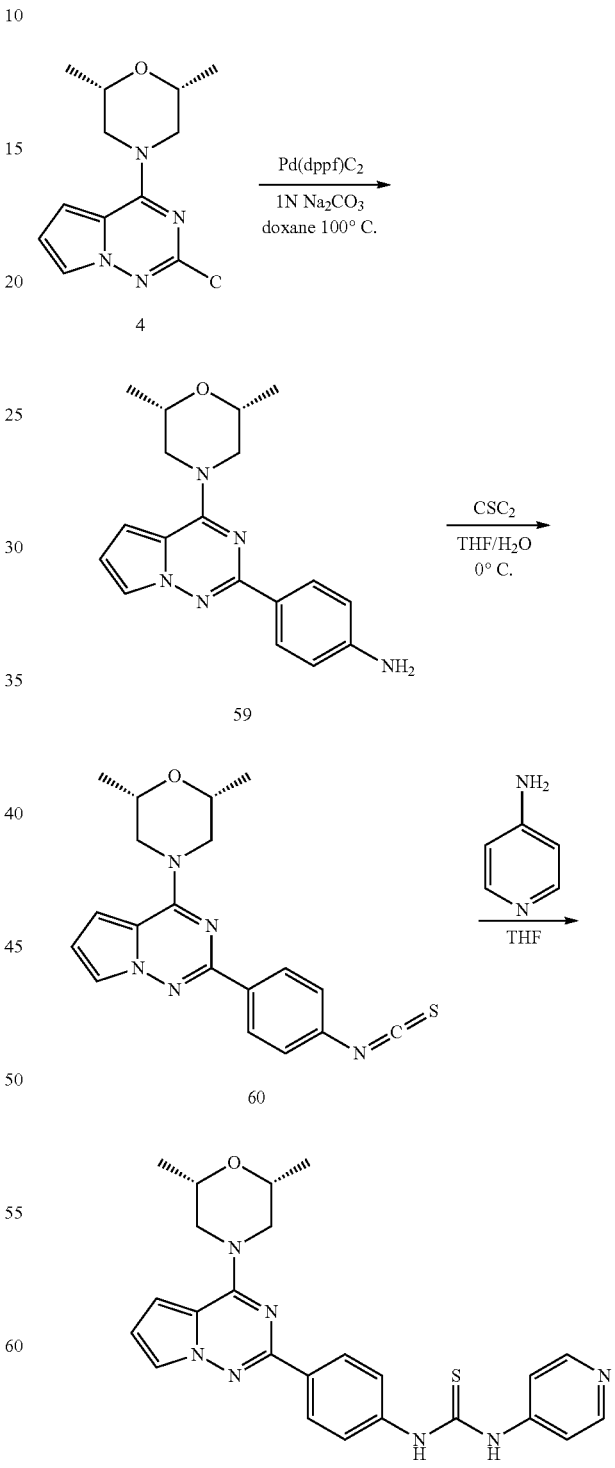

Example 118

Synthesis of Compound 59

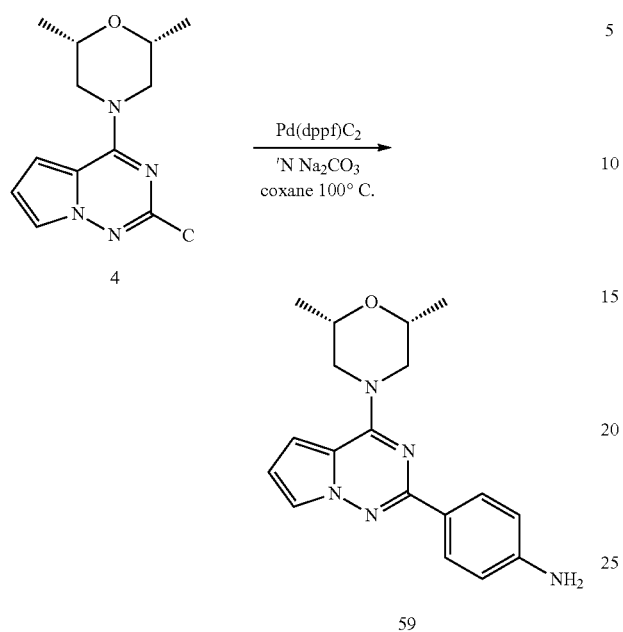

Method B: used 1.0 g of compound 4 to obtained 1.1 g of compound 59, yield in 90.2%. $^1$H NMR (CDCl$_3$, 400 MHz): δ 8.10 (d, 2H, J=8.8 Hz), 7.63 (dd, 1H, J=2.4, 1.6 Hz), 6.74 (d, 2H, J=8.4 Hz), 6.67-6.62 (m, 2H), 4.78 (d, 2H, J=12.8 Hz), 3.79-3.73 (m, 2H), 2.93-2.91 (m, 2H), 1.31 (d, 6H, J=6.0 Hz).

Synthesis of Compound 60

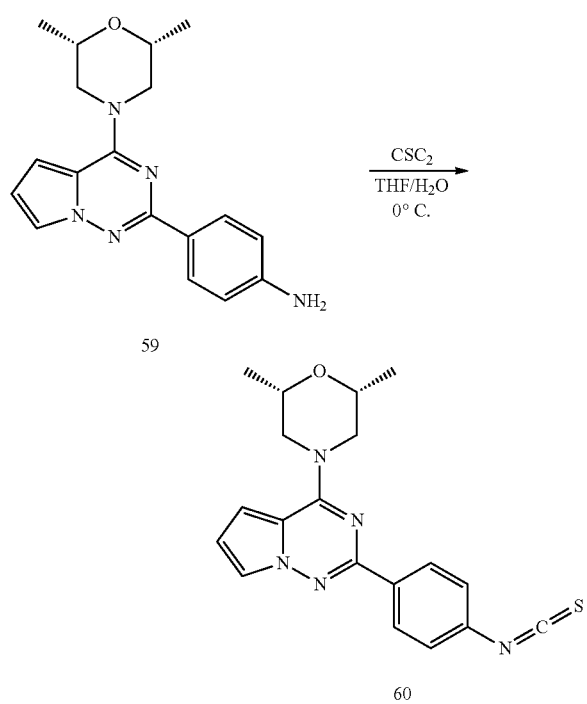

To a stirred solution of compound 59 (100 mg, 0.309 mmol) in 10 ml of dry THF was added a solution of CSCl$_2$ (71 mg, 0.618 mmol) in 1 mL of THF dropwise at 0° C., then 1 mL H$_2$O was added. The reaction mixture was stirred 0° C. for 1.5 h. Then the reaction mixture was quenched by 10 mL of saturated sodium hydrogen carbonate solution, the aqueous layer was separated and extracted with EA. The organic layer was combined and dried over anhydrous Na$_2$SO$_4$ and filtered. The filtrate was concentrated to the residue, which was purified by column chromatography (SiO$_2$, EtOAc/PE=½) to afford 90 mg compound 60 (79.4%). $^1$H NMR (CDCl$_3$, 400 MHz): δ 8.30-8.26 (m, 2H), 7.66 (dd, 1H, J=2.4, 1.2 Hz), 7.31-7.28 (m, 2H), 6.73-6.68 (m, 2H), 4.78 (d, 2H, J=12.8 Hz), 3.82-3.74 (m, 2H), 2.96-2.94 (m, 2H), 1.33 (d, 6H, J=6.0 Hz).

Synthesis of Example 118

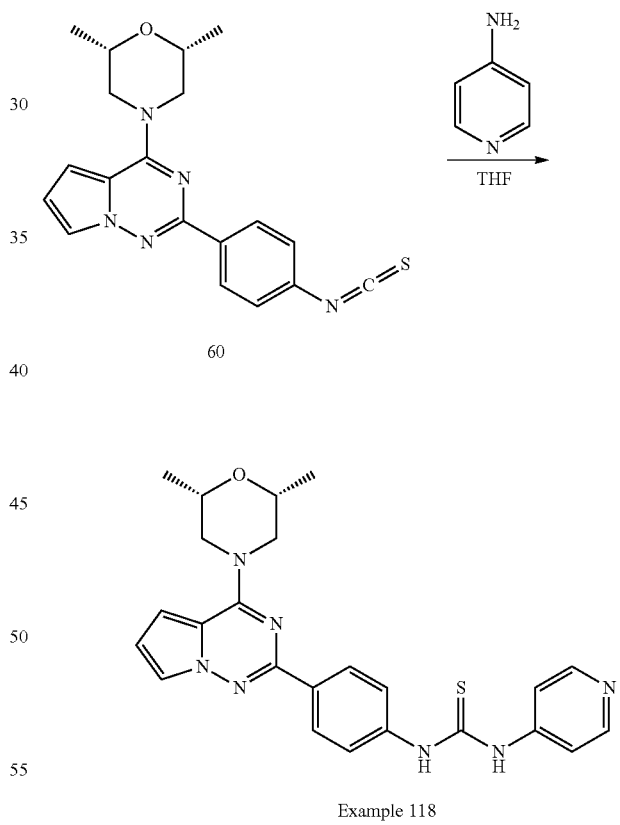

The procedure of Example 118 (21 mg, 32%) was similar to that of Example 111. $^1$H NMR (DMSO-d$_6$, 400 MHz): δ 10.38 (s, 1H), 10.25 (s, 1H), 8.44 (d, 2H, J=5.6 Hz), 8.22 (d, 2H, J=8.8 Hz), 7.82 (t, 1H, J=1.4 Hz), 7.66-7.64 (m, 4H), 7.05 (d, 1H, J=4.4 Hz), 6.74 (dd, 1H, J=4.4, 2.8 Hz), 4.79 (d, 2H, J=13.0 Hz), 3.75-3.70 (m, 2H), 2.93-2.91 (m, 2H), 1.24 (d, 6H, J=6.0 Hz). ESI-MS (M+H)$^+$: 460.

Synthesis of Example 119
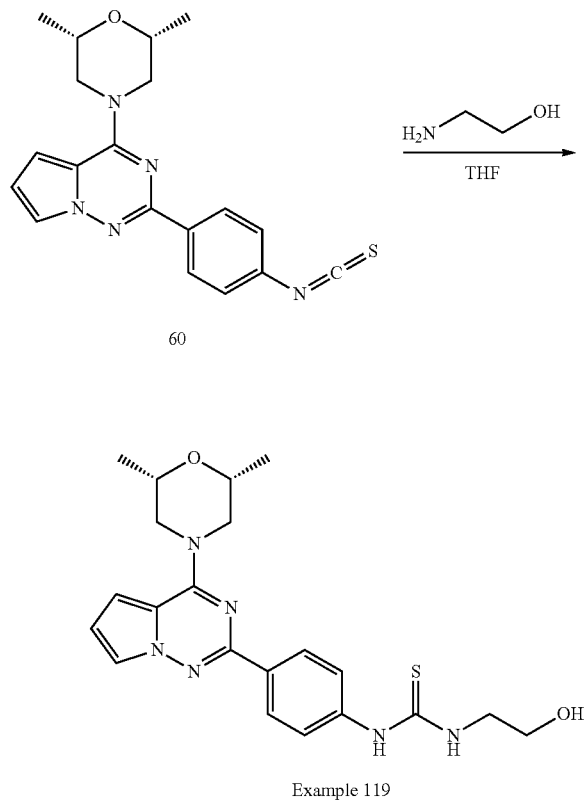
Synthesis of Example 119
The procedure of Example 119 (56 mg, 44%) was similar to that of Example 111. $^1$H NMR (DMSO-$d_6$, 400 MHz): δ 9.80 (s, 1H), 8.17 (d, 2H, J=8.8 Hz), 7.86 (s, 1H), 7.81 (dd, 1H, J=2.8, 1.6 Hz), 7.62 (d, 2H, J=8.8 Hz), 7.04 (dd, 1H, J=4.8, 1.6 Hz), 6.73 (dd, 1H, J=4.8, 2.4 Hz), 4.83-4.76 (m, 3H), 3.74-3.70 (m, 2H), 3.58 (s, 4H), 2.92-2.91 (m, 2H), 1.24 (d, 6H, J=6.0 Hz). ESI-MS (M+H)$^+$: 427.
Synthesis of Example 120
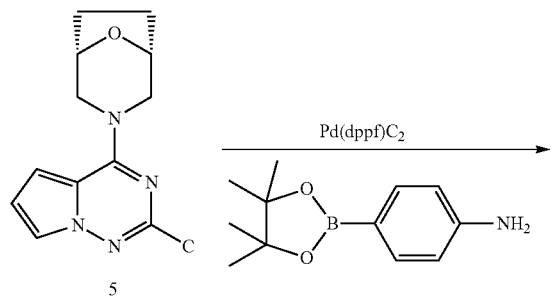
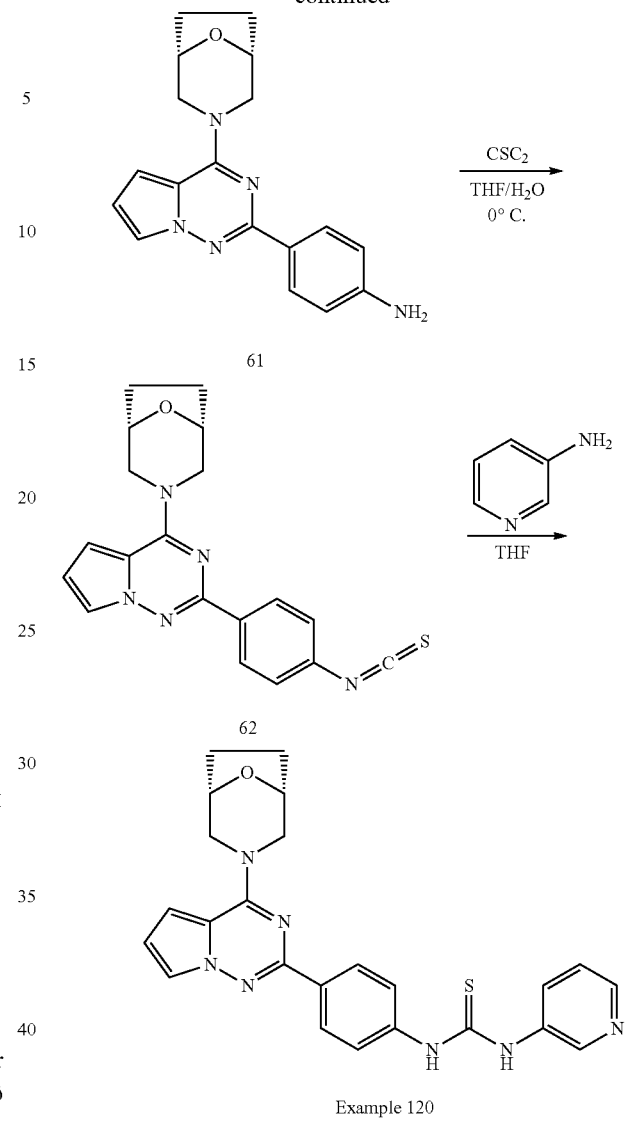
Synthesis of Compound 61

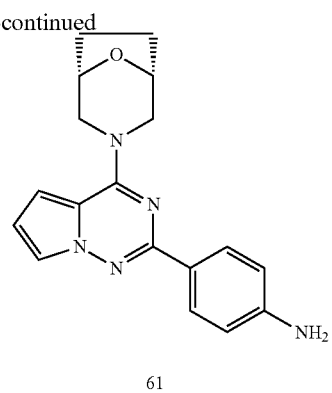

61

Method B: used 814 mg of compound 5 to obtained 938 mg of compound 61, yield in 95%. $^1$H NMR (CDCl$_3$, 400 MHz): δ 8.11-8.08 (m, 2H), 7.63 (dd, 1H, J=2.8, 1.6 Hz), 6.75-6.70 (m, 2H), 6.66-6.60 (m, 2H), 4.61-4.53 (m, 4H), 3.83 (s, 2H), 3.57-3.53 (m, 2H), 2.01-1.89 (m, 4H).

Synthesis of Compound 62

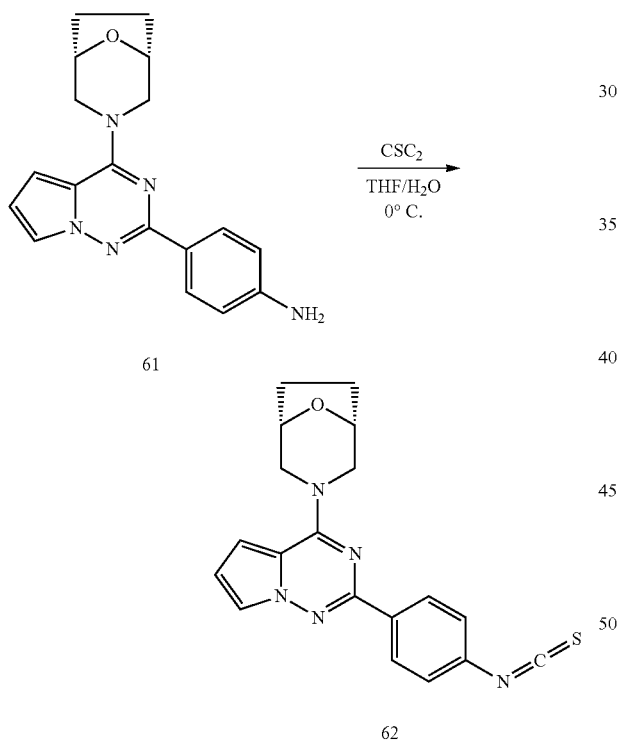

To a stirred solution of compound 61 (110 mg, 0.343 mmol) in 10 mL of dry THF was added a solution of CSCl$_2$ (78 mg, 0.686 mmol) in 1 mL of THF dropwise at 0° C., then 1 mL H$_2$O was added. The reaction mixture was stirred 0° C. for 1.5 h. Then the reaction mixture was quenched by 10 mL of saturated sodium hydrogen carbonate solution, the aqueous layer was separated and extracted by EA. The organic layer was combined and dried over anhydrous Na$_2$SO$_4$ and filtered. The filtrate was concentrated to the residue, which was purified by column chromatography (SiO$_2$, EtOAc/PE=¼) to afford 104 mg compound 62 (85%). $^1$H NMR (DMSO-d$_6$, 400 MHz): δ 8.30-8.27 (m, 2H), 7.66 (dd, 1H, J=2.8, 1.6 Hz), 7.30-7.28 (m, 2H), 6.72-6.66 (m, 2H), 4.61-4.56 (m, 4H), 3.61-3.56 (m, 2H), 2.05-1.87 (m, 4H).

Synthesis of Example 120

Example 120

The procedure of Example 120 (31 mg, 67%) was similar to that of Example 111. $^1$H NMR (DMSO-d$_6$, 400 MHz): δ 10.18 (s, 1H), 9.94 (s, 1H), 8.64 (d, 1H, J=2.4 Hz), 8.34 (dd, 1H, J=4.8, 1.2 Hz), 8.20 (d, 2H, J=8.4 Hz), 7.99-7.96 (m, 1H), 7.81 (dd, 1H, J=2.8, 1.6 Hz), 7.62 (d, 2H, J=8.4 Hz), 7.39 (dd, 1H, J=8.4, 4.8 Hz), 6.97 (dd, 1H, J=4.4, 1.2 Hz), 6.72 (dd, 1H, J=4.4, 2.8 Hz), 4.58-4.52 (m, 4H), 3.49-3.46 (m, 2H), 1.90-1.77 (m, 4H). ESI-MS (M+H)$^+$: 458.

Synthesis of Example 121

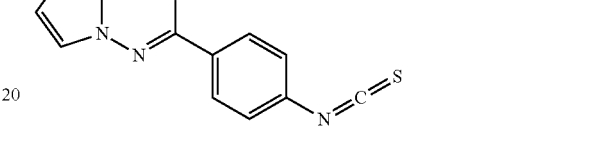

-continued

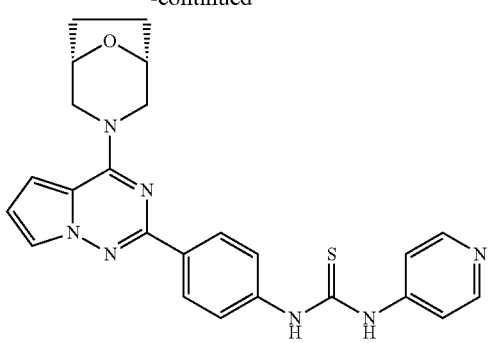

Example 121

The procedure of Example 121 (34 mg, 73%) was similar to that of Example 111. $^1$H NMR (DMSO-$d_6$, 400 MHz): δ 10.36 (s, 1H), 10.22 (s, 1H), 8.44 (d, 2H, J=6.0 Hz), 8.20 (d, 2H, J=8.8 Hz), 7.81 (dd, 1H, J=2.8, 1.6 Hz), 7.65 (dd, 4H, J=14.4, 8.8 Hz), 6.97 (dd, 1H, J=4.4, 1.2 Hz), 6.72 (dd, 1H, J=4.4, 2.8 Hz), 4.58-4.52 (m, 4H), 3.49-3.46 (m, 2H), 1.90-1.76 (m, 4H). ESI-MS (M+H)$^+$: 458.

Synthesis of Example 122

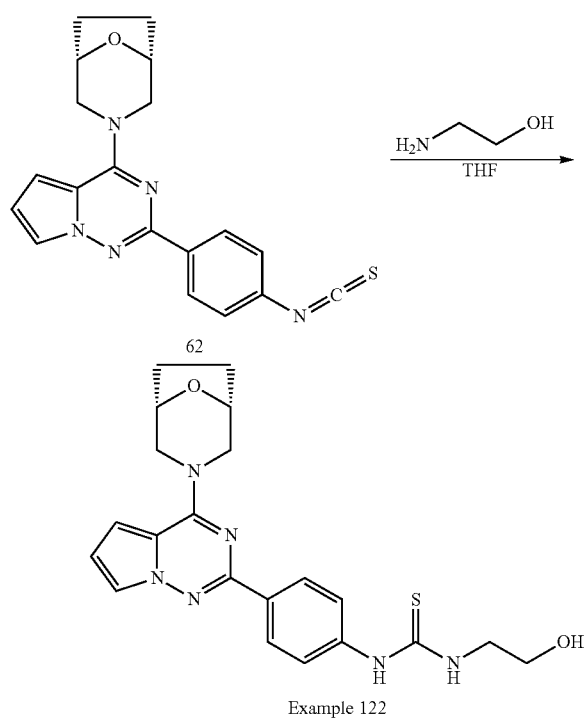

Example 122

The procedure of Example 122 (60 mg, 62%) was similar to that of Example 111.

$^1$H NMR (DMSO-$d_6$, 400 MHz): δ 9.81 (s, 1H), 8.16 (d, 2H, J=8.8 Hz), 7.86 (s, 1H), 7.80 (dd, 1H, J=2.4, 1.2 Hz), 7.60 (d, 2H, J=8.8 Hz), 6.97 (dd, 1H, J=4.8, 1.6 Hz), 6.72 (dd, 1H, J=4.4, 2.4 Hz), 4.84 (s, 1H), 4.58-4.51 (m, 4H), 3.57 (t, 4H, J=2.0 Hz), 3.48-3.45 (m, 2H), 1.89-1.77 (m, 4H). ESI-MS (M+H)$^+$: 425.

Synthesis of Example 123

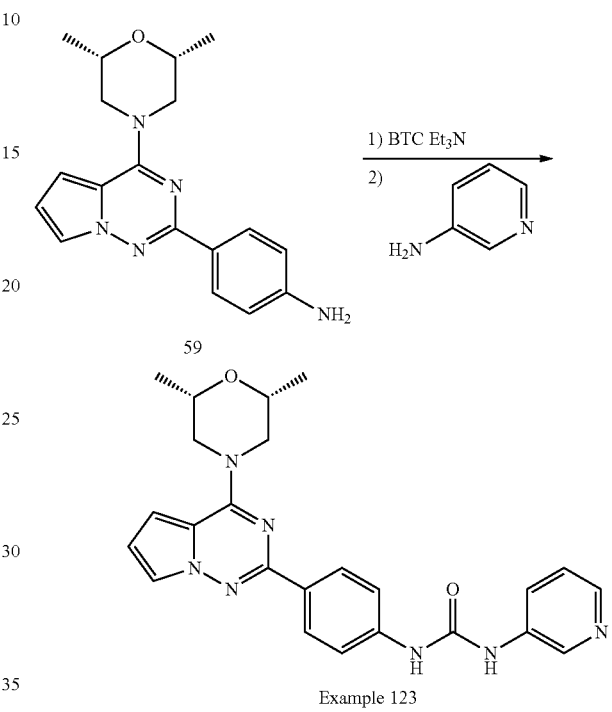

Example 123

The procedure of Example 123 (32 mg, 36%) was similar to that of Example 15. $^1$H NMR (DMSO-$d_6$, 400 MHz): δ 9.03 (s, 1H), 8.90 (s, 1H), 8.63 (d, 1H, J=2.4 Hz), 8.22-8.17 (m, 3H), 7.98-7.95 (m, 1H), 7.80 (dd, 1H, J=2.4, 1.6 Hz), 7.58 (d, 2H, J=8.8 Hz), 7.33 (dd, 1H, J=8.4, 4.8 Hz), 7.03 (dd, 1H, J=4.8, 1.2 Hz), 6.72 (dd, 1H, J=4.8, 2.8 Hz), 4.78 (d, 2H, J=12.4 Hz), 3.75-3.70 (m, 2H), 2.94-2.89 (m, 2H), 1.25 (d, 6H, J=6.4 Hz). ESI-MS (M+H)$^+$: 444.

Synthesis of Example 124

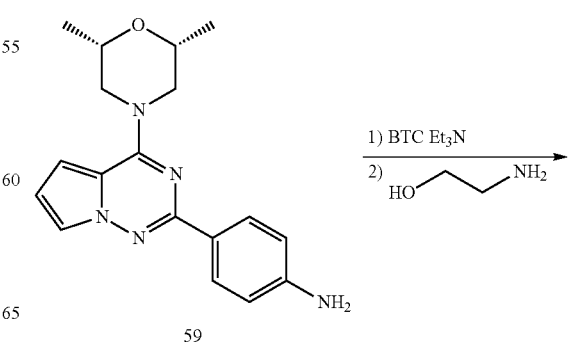

-continued

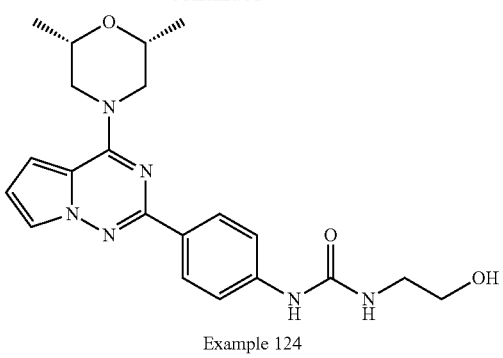

Example 124

The procedure of Example 124 (38 mg, 50%) was similar to that of Example 15. ¹H NMR (DMSO-$d_6$, 400 MHz): δ 8.76 (s, 1H), 8.10 (d, 2H, J=8.8 Hz), 7.78 (dd, 1H, J=2.4, 1.2 Hz), 7.49 (d, 2H, J=8.8 Hz), 7.01 (dd, 1H, J=4.4, 1.2 Hz), 6.71 (dd, 1H, J=4.4, 2.8 Hz), 6.25 (t, 1H, J=5.6 Hz), 4.75 (dd, 3H, J=10.0, 5.2 Hz), 3.75-3.68 (m, 2H), 3.47 (q, 2H, J=5.6 Hz), 3.18 (q, 2H, J=5.6 Hz), 2.93-2.87 (m, 2H), 1.24 (d, 6H, J=6.0 Hz). ESI-MS (M+H)⁺: 411.

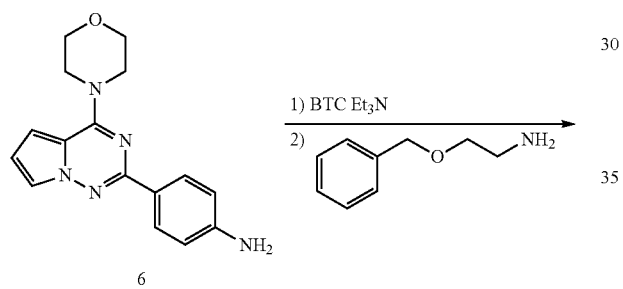

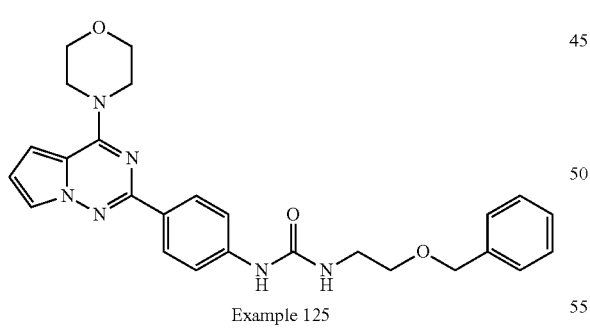

Example 125

The procedure of Example 125 (71 mg, 74%) was similar to that of Example 15. ¹H NMR (DMSO-$d_6$, 400 MHz): δ 8.78 (s, 1H), 8.11 (d, 2H, J=8.8 Hz), 7.79-7.78 (m, 1H), 7.49 (d, 2H, J=8.8 Hz), 7.38-7.34 (m, 4H), 7.32-7.28 (m, 1H), 6.98 (t, 1H, J=2.2 Hz), 6.71 (dd, 1H, J=4.4, 2.8 Hz), 6.29 (t, 1H, J=5.6 Hz), 4.53 (s, 2H), 4.06 (t, 4H, J=4.6 Hz), 3.79 (t, 4H, J=4.8 Hz), 3.52 (t, 2H, J=5.4 Hz), 3.34 (t, 2H, J=5.6 Hz). ESI-MS (M+H)⁺: 473.

Synthesis of Example 126

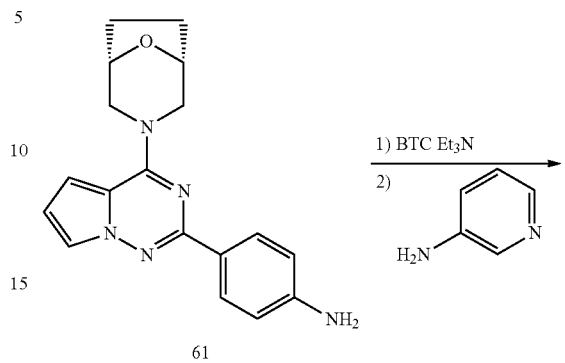

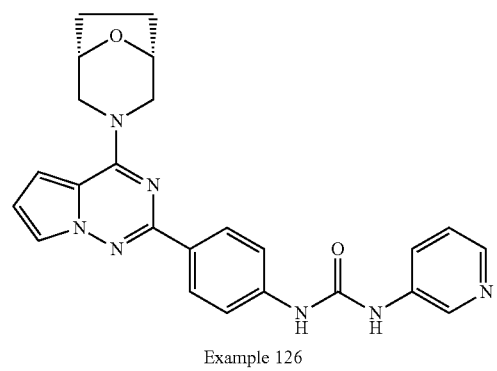

Example 126

The procedure of Example 126 (36 mg, 37.4%) was similar to that of Example 15. ¹H NMR (DMSO-$d_6$, 400 MHz): δ 9.09 (s, 1H), 8.97 (s, 1H), 8.63 (d, 1H, J=2.8 Hz), 8.22-8.21 (m, 1H), 8.17 (d, 2H, J=8.8 Hz), 7.99-7.96 (m, 1H), 7.79 (t, 1H, J=2.4 Hz), 7.57 (d, 2H, J=8.8 Hz), 7.34 (dd, 1H, J=8.4, 4.8 Hz), 6.95 (d, 1H, J=4.4 Hz), 6.71 (dd, 1H, J=4.4, 2.8 Hz), 4.56-4.54 (m, 4H), 3.47 (d, 2H, J=12.4 Hz), 1.90-1.76 (m, 4H). ESI-MS (M+H)⁺: 442.

Synthesis of Example 127

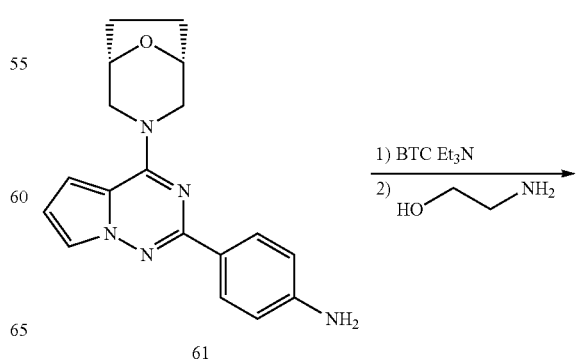

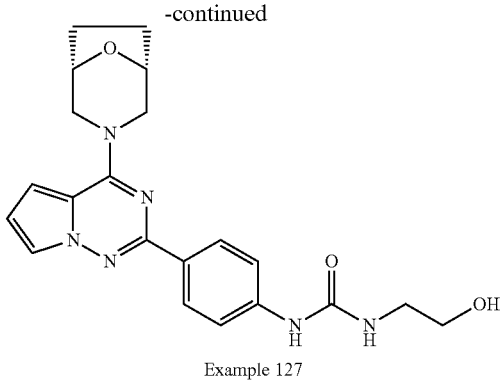

Example 127

The procedure of Example 127 (47 mg, 52%) was similar to that of Example 15. ¹H NMR (DMSO-d₆, 400 MHz): δ 8.77 (s, 1H), 8.09 (d, 2H, J=8.8 Hz), 7.77 (s, 1H), 7.48 (d, 2H, J=8.8 Hz), 6.94 (d, 1H, J=4.8 Hz), 6.69 (dd, 1H, J=4.4, 2.8 Hz), 6.24 (t, 1H, J=2.8 Hz), 4.74 (s, 1H), 4.56-4.51 (m, 4H), 3.46 (t, 4H, J=5.6 Hz), 3.18 (q, 2H, J=5.6 Hz), 1.89-1.77 (m, 4H). ESI-MS (M+H)⁺: 409.

Synthesis of Example 128

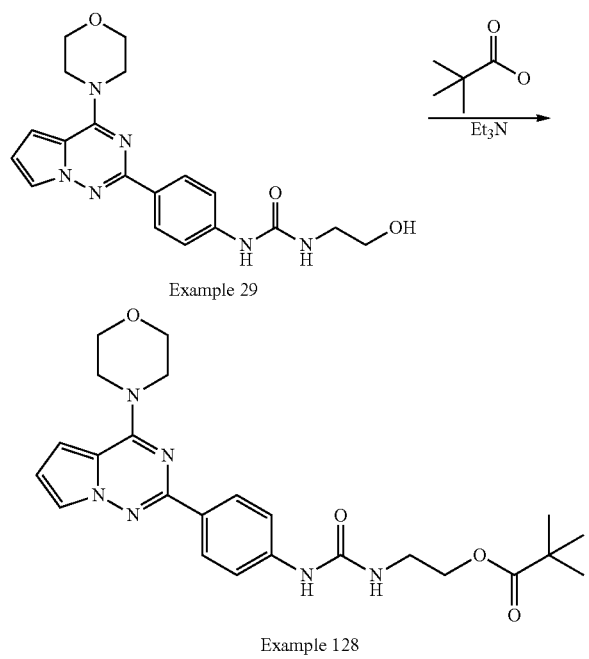

To a stirred solution of Example 29 (100 mg, 0.26 mmol) in dry THF (10 mL) was added a solution of pivaloyl chloride (94 mg, 0.78 mmol) and triethylamine (106 mg, 1.05 mmol) in THF (2 mL). The resulting mixture was stirred at 65° C. for 1.5 h. After adding 20 mL of EA, the reaction mixture was quenched by 5 mL of brine, the aqueous layer was extracted with EA, dried over anhydrous Na₂SO₄ and filtered. The filtrate was concentrated to the residue, which was purified by column chromatography (SiO₂, EA/PE=1/1) to afford 54 mg of Example 128 (44%). ¹H NMR (DMSO-d₆, 400 MHz): δ 8.83 (s, 1H), 8.10 (d, 2H, J=8.8 Hz), 7.79 (dd, 1H, J=2.4, 1.6 Hz), 7.50 (d, 2H, J=8.8 Hz), 6.99 (dd, 1H, J=4.4, 1.2 Hz), 6.71 (dd, 1H, J=4.8, 2.8 Hz), 6.26 (t, 1H, J=5.8 Hz), 4.08-4.05 (m, 6H), 3.79 (t, 4H, J=2.4 Hz), 3.39-3.34 (m, 2H), 1.16 (s, 9H). ESI-MS (M+H)⁺: 467.

Synthesis of Example 129

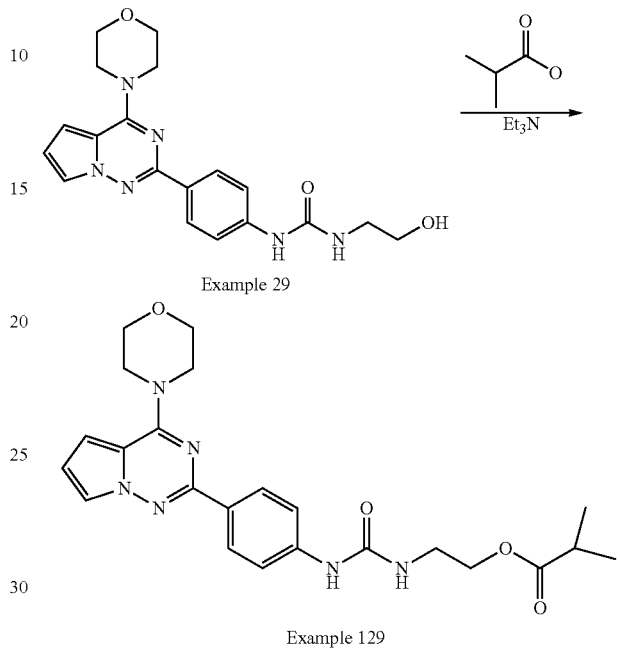

To a stirred solution of Example 29 (150 mg, 0.39 mmol) in dry THF (10 mL) was added a solution of isopropyl chloride (126 mg, 1.18 mmol) and triethylamine (159 mg, 1.57 mmol) in THF (2 mL). The resulting mixture was stirred at 65° C. for 1.5 h. After adding 20 mL of EA, the reaction mixture was quenched by 5 mL of brine, the aqueous layer was extracted with EA, dried over anhydrous Na₂SO₄ and filtered. The filtrate was concentrated to the residue, which was purified by column chromatography (SiO₂, EA/PE=2/1) to afford 46 mg of Example 129 (26%). ¹H NMR (DMSO-d₆, 400 MHz): δ 8.81 (s, 1H), 8.11 (d, 2H, J=8.8 Hz), 7.79 (dd, 1H, J=2.4, 1.6 Hz), 7.50 (d, 2H, J=8.8 Hz), 6.99 (dd, 1H, J=4.8, 1.6 Hz), 6.71 (dd, 1H, J=4.8, 2.8 Hz), 6.30 (t, 1H, J=5.6 Hz), 4.07 (dd, 6H, J=10.4, 5.2 Hz), 3.79 (t, 4H, J=2.4 Hz), 3.38-3.37 (m, 2H), 2.56 (dd, 1H, J=14.0, 6.4 Hz), 1.11 (d, 6H, J=6.8 Hz). ESI-MS (M+H)⁺: 453.

Synthesis of Example 130

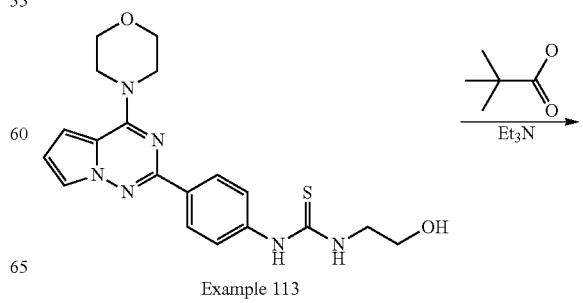

Example 113

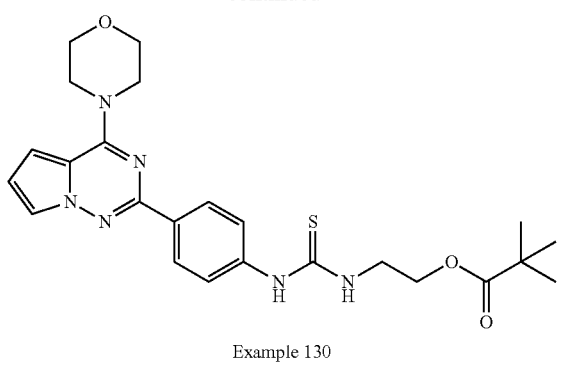

Example 130

The procedure of Example 130 (50 mg, 41.5%) was similar to that of Example 128. ¹H NMR (400 MHz, DMSO) δ 9.87 (s, 1H), 8.18 (d, 2H, J=8.4 Hz), 7.98 (s, 1H), 7.82 (m, 1H), 7.53 (d, 2H, J=8.8 Hz), 7.02-7.01 (m, 1H), 6.74-6.73 (m, 1H), 4.19 (t, 2H, J=5.6 Hz), 4.07 (t, 4H, J=4.4 Hz), 3.80-3.78 (m, 6H), 1.18 (s, 9H).

Synthesis of Example 131

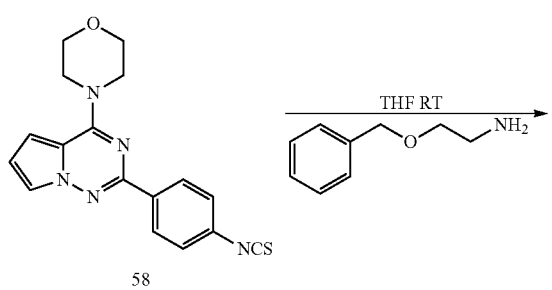

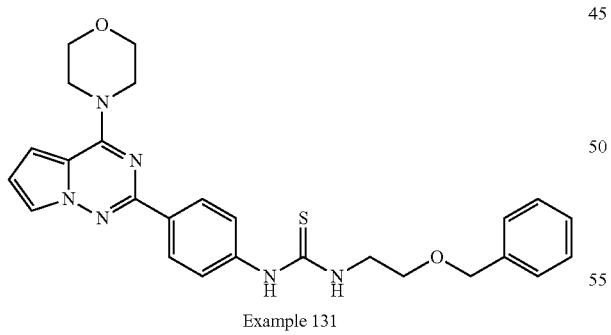

Example 131

The procedure of Example 131 (60 mg, 62%) was similar to that of Example 111. ¹H NMR (400 MHz, DMSO) δ 9.84 (s, 1H), 8.18 (d, 2H, J=8.4 Hz), 7.93 (s, 1H), 7.83-7.81 (m, 1H), 7.58 (d, 2H, J=8.8 Hz), 7.39-7.36 (m, 4H), 7.35-7.25 (m, 1H), 7.02 (d, 1H, J=4.4 Hz), 6.74 (d, 1H, J=4.4 Hz), 4.54 (s, 2H), 4.14-4.03 (m, 4H), 3.83-3.77 (m, 4H), 3.74 (d, 2H, J=4.4 Hz), 3.63 (t, 2H, J=5.4 Hz).

Synthesis of Example 132

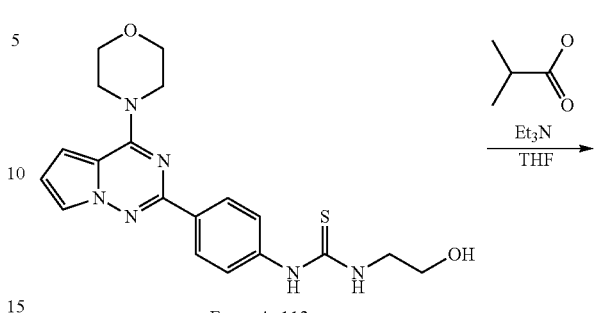

Example 113

Example 132

The procedure of Example 132 (30 mg, 17%) was similar to that of Example 128. ¹H NMR (400 MHz, DMSO), δ 9.84 (s, 1H), 8.19 (d, 2H, J=8.8 Hz), 7.97 (s, 1H), 7.87-7.74 (m, 1H), 7.54 (d, 2H, J=8.8 Hz), 7.03-7.00 (m, 1H), 6.74 (d, 1H, J=4.4 Hz), 4.20 (t, J=5.6 Hz, 2H), 4.07 (t, J=4.4 Hz, 4H), 3.80-3.77 (m, 6H), 2.61-2.55 (m, 1H), 1.13 (d, J=6.8 Hz, 6H).

Synthesis of Example 133

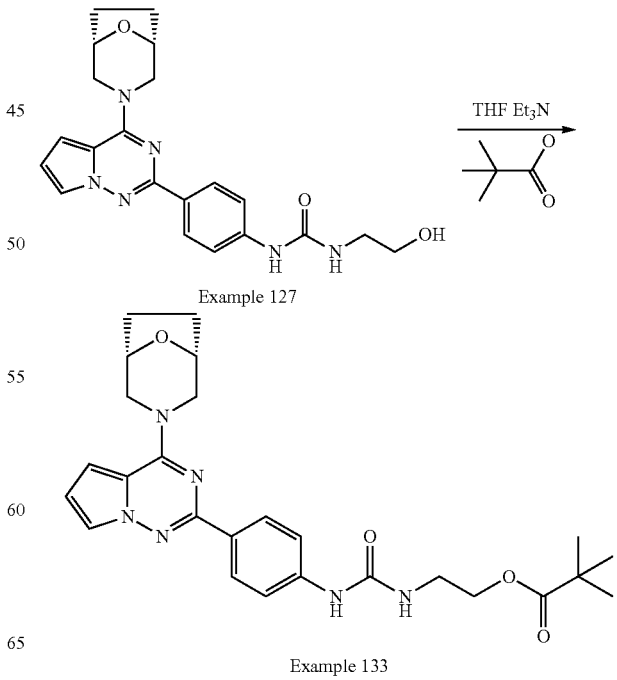

Example 127

Example 133

The procedure of Example 133 (15 mg, 41%) was similar to that of Example 128. ¹H NMR (400 MHz, CDCl₃) δ 8.36 (d, 2H, J=8.4 Hz), 7.69-7.67 (m, 1H), 7.34 (d, 2H, J=8.4 Hz), 6.71 (d, 1H, J=4.4 Hz), 6.67 (d, 1H, J=4.4 Hz), 4.60-4.57 (m, 4H), 3.79 (t, 2H, J=4.8 Hz), 3.58 (d, 2H, J=12.8 Hz), 3.49 (t, 2H, J=2.4 Hz), 2.03-1.99 (m, 2H), 1.94-1.86 (m, 2H), 1.07 (s, 9H).

Synthesis of Example 134

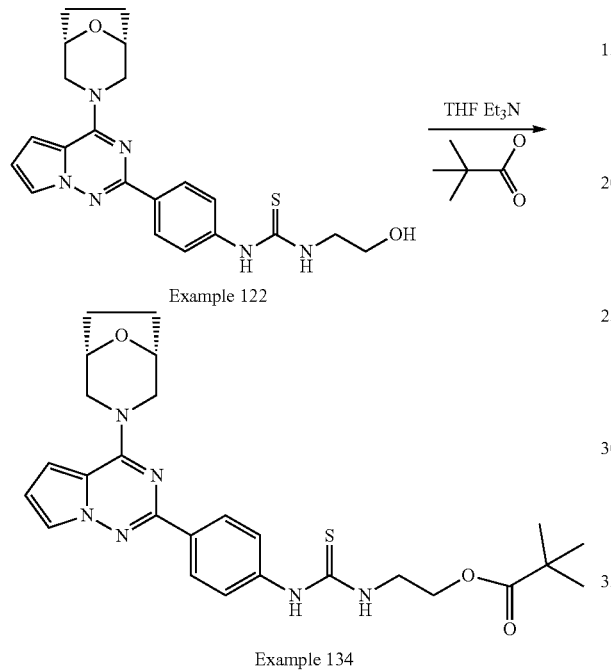

Example 134

The procedure of Example 134 (90 mg, 75%) was similar to that of Example 128. ¹H NMR (400 MHz, CDCl₃) δ 9.91 (s, 1H), 8.18 (d, 2H, J=8.8 Hz), 7.98 (s, 1H), 7.82-7.80 (m, 1H), 7.53 (d, 2H, J=8.8 Hz), 6.97 (d, 1H, J=4.4 Hz), 6.72 (d, 1H, J=4.4 Hz), 4.61-4.49 (m, 4H), 4.19 (t, 2H, J=5.6 Hz), 3.78 (d, 2H, J=5.2 Hz), 3.53-3.41 (m, 2H), 1.90-1.88 (m, 2H), 1.81-1.73 (m, 2H), 1.18 (s, 9H).

Synthesis of Compound 63

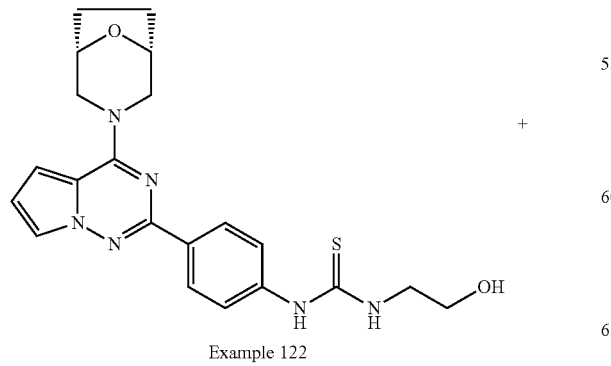

Example 122

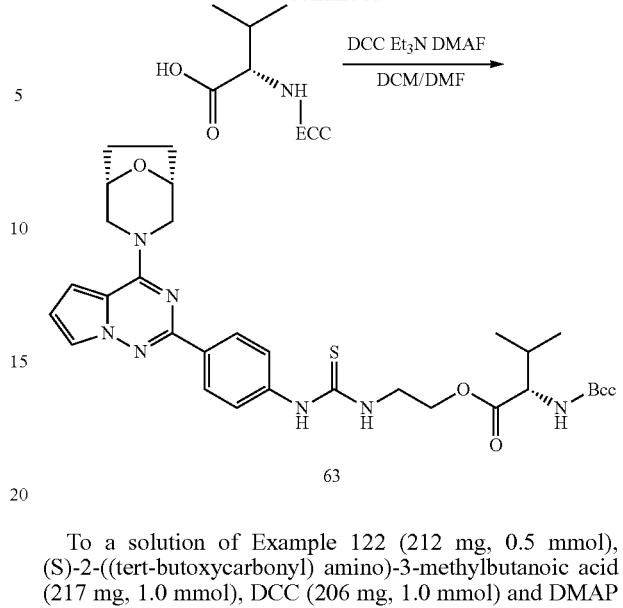

63

To a solution of Example 122 (212 mg, 0.5 mmol), (S)-2-((tert-butoxycarbonyl) amino)-3-methylbutanoic acid (217 mg, 1.0 mmol), DCC (206 mg, 1.0 mmol) and DMAP (30 mg, 0.25 mmol) in DCM (5 mL)/DMF (2 mL) was added Et₃N (0.21 mL, 1.5 mmol), the mixture was stirred at 20° C. for 12 h. TLC showed the reaction was completed. The mixture was poured into water and extracted by DCM, combined the organic layer and washed with brine, dried by Na₂SO₄, filtered and concentrated in vacuo, the crude was purified by TLC (PE:EA=1:1) to obtained colorless oil (180 mg, 57.8%).

Synthesis of Example 135

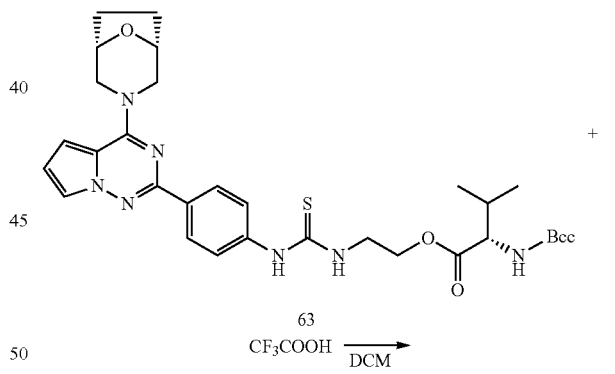

63

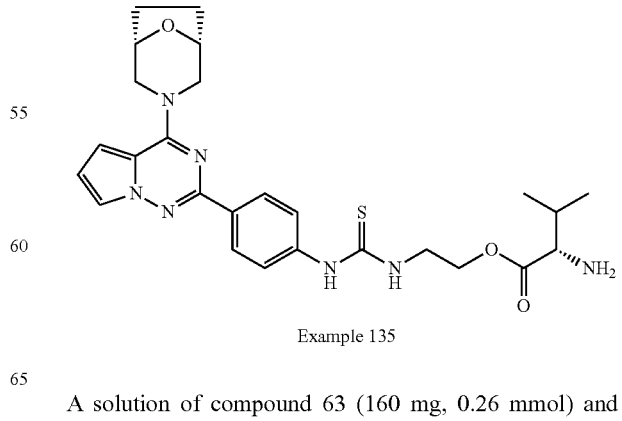

Example 135

A solution of compound 63 (160 mg, 0.26 mmol) and CF₃COOH (2 mL) was added into DCM (4 mL), the mixture was stirred at 20° C. for 2 hrs. TLC showed the reaction was completed. The reaction was poured into saturate $NH_4Cl$, extracted by DCM, combined the organic layer and washed with NaCl (aq.) (100 mL), dried by $Na_2SO_4$, filtered and concentrated. The crude was purified by TLC (DCM: MeOH=10:1) to obtained Example 135 (30 mg, 22.1%). $^1H$ NMR (400 MHz, MeOD) δ 8.30 (d, 2H, J=8.6 Hz), 7.70 (s, 1H), 7.45 (d, 2H, J=8.6 Hz), 6.92 (d, 1H, J=4.5 Hz), 6.72 (d, 1H, J=4.5 Hz), 4.69 (d, 2H, J=12.9 Hz), 4.56 (d, 2H, J=2.0 Hz), 4.43 (t, 2H, J=5.4 Hz), 3.98 (m, 2H), 3.68 (d, 1H, J=4.8 Hz), 3.55 (d, 2H, J=12.5 Hz), 2.22 (m, 1H), 2.00 (m, 2H), 1.92 (m, 2H), 1.05 (d, 3H, J=6.9 Hz), 1.02 (d, 3H, J=6.9 Hz).

Biological Activities

The compounds of present invention are selective inhibitors of mTOR kinase and/or one or more Class I PI3K isoforms. The preferred compounds are selective mTOR kinase inhibitor with minimum activities against PI3K and other kinases such as VEGF2, FGFR1, HER1 (EGFR) and HER2. As discussed in background of invention, the selective mTOR inhibitors are useful for treatment of PI3K/mTOR-associated diseases and disorders, especially for cancer, immune disorders, cardiovascular disease, viral infection, inflammation, metabolism/endocrine function disorders and neurological disorders. The compounds of the present invention can be used alone or in combination with one or more other therapeutic agent(s).

The K-LISA™ mTOR (Recombinant) Activity Kit (EMD:Calbiochem), an ELISA-based activity assay that utilizes a p70S6K-GST fusion protein as a specific mTOR substrate, was used to determine the ability of test compounds to inhibit phosphorylation by recombinant mTOR. The principle of the assay is that the mTOR Substrate is bound to the wells of a Glutathione-Coated 96-Well Plate then incubated with mTOR-containing sample. Active mTOR phosphorylates p70S6K at $Thr^{389}$ in the presence of ATP. The phosphorylated substrate is detected with Anti-p70S6K-pT389 antibody, followed by detection with HRP-Antibody Conjugate and TMB Substrate. Relative activity is determined by reading the absorbance at dual wavelengths of 450/540 nm or 450/595 nm. Inhibition profiles can be generated based on mTOR activity in the presence and absence of test inhibitors. Most of the compounds tested exhibited $IC_{50}$ values less than 1 µM. Many compounds described herein exhibited an $IC_{50}$ less than 0.1 µM.

Some of the example compounds were submitted to Life Technologies Corporation SelectScreen® Profiling Service to test their potency in inhibiting the kinase catalytic activities of mTOR, PI3Kα, VEGF2, FGFR1, HER1 (EGFR) and HER2. A concentration of ATP at the Km of the corresponding kinase was used for all assays. The mTOR (FRAP1), VEGF2, FGFR1, HER1 (EGFR) and HER2 assays used Z'-LYTE® technology. The PI3Kα assay used Adapta® technology. The results are shown in Table 1. The symbol "inh %" as used herein generally refers to inhibition percentage. Unlike GDC0941, which is a PI3Kα inhibitor without significant mTOR activity, the compounds of formula I-III are potent mTOR inhibitors with at least >10× weaker PI3Kα activity (based on estimated Ki values) and minimum VEGF2, FGFR1, HER1 (EGFR) and HER2 activities.

TABLE 1

Inhibitory Activity of the Selected Example Compounds Against mTOR and Selected Kinases

| Compounds | mTOR inh% @0.1 µM | PI3Kα inh % @0.1 µM | VEGF 2 inh % @1 µM | FGFR 1 inh % @1 µM | HER1 inh % @1 µM | HER2 inh % @1 µM |
|---|---|---|---|---|---|---|
| GDC0941 | 6 | 91 | | | | |
| Example 4 | 72 | 10 | | | | |
| Example 14 | 87 | 11 | 8 | 1 | −1 | −8 |
| Example 15 | 98 | 54 | 8 | 4 | −2 | −7 |
| Example 17 | | 25 | | | | |
| Example 18 | | −13 | | | | |
| Example 29 | 94 | 9 | 11 | −1 | −1 | −7 |
| Example 38 | 69 | −8 | | | | |
| Example 45 | 98 | 0 | 10 | 4 | −2 | −9 |
| Example 46 | 86 | | 11 | −3 | 0 | −6 |
| Example 47 | 89 | | 10 | 6 | 1 | −5 |
| Example 48 | 69 | −15 | | | | |
| Example 49 | 88 | | | | | |
| Example 52 | 74 | 6 | | | | |
| Example 54 | 95 | | 7 | −4 | −1 | 4 |
| Example 55 | 90 | | 11 | −1 | 0 | 5 |
| Example 56 | 88 | | | | | |
| Example 58 | 97 | | 10 | 4 | 1 | −5 |
| Example 59 | 93 | | 10 | 7 | 2 | −2 |
| Example 61 | 71 | | | | | |
| Example 62 | 53 | 10 | | | | |
| Example 63 | 71 | | | | | |
| Example 64 | 62 | | | | | |
| Example 65 | 63 | 19 | | | | |
| Example 66 | 77 | 20 | | | | |
| Example 67 | 87 | | | | | |
| Example 68 | 86 | | | | | |
| Example 86 | 82 | | | | | |
| Example 122 | 94 | 8 | −10 | 0 | 1 | −1 |
| Example 133 | 90 | | 9 | 4 | 1 | 5 |

The cytotoxic or cytostatic activity of Formula I-III exemplary compounds was measured by establishing proliferating mammalian tumor cell lines such as PC-3, LNCAP, U87, Huh-7, HepG2 and MDA-MB-468 in a cell culture medium, adding a test compound, culturing the cells for a period of 5 days by measuring cell viability via MTT assays. Dose response data were obtained for each test compound and the degree of inhibition of tumor cell growth was expressed as an $IC_{50}$ value. Majority of the compounds tested exhibited $IC_{50}$ values less than 5 µM. Many compounds described herein exhibited an $IC_{50}$ less than 0.5 µM. For example. For example, compounds of example 14, 15, 46, 29, 45, 49, 122, 88, 54, 55, 58, 59, 63, 64, 66, 67, 68, 113, 86, 90.

Cell Proliferation/Survival Assay Conditions

PC-3 (or U87) cells were seeded in 96-well plates at low density (at 2,000 cells per well) in media supplemented with 10% FBS (growth media) and transferred to serum-free media (1% FBS) after 24 h. Designated concentrations of drug were added to each well. The cells were incubated for 120 h. At the end of drug exposure, 20 µL/well of MTT solution was added. After 4 h at 37° C. in a humidified 5% $CO_2$ atmosphere, the absorbance at 490 nm was recorded by using a microplate reader. $IC_{50}$ was calculated using Graph-Pad Prism version 5 for Windows. The curves were fit using a nonlinear regression model with a log (inhibitor) versus response formula.

Cell growth inhibitory activities against cancer cells of the present compounds were also evaluated by submitting selected the example compounds to US NCI-Chemotherapeutic Agents Repository for screening against NCI60 panel. The United States NCI-60 platform is a cancer cell platform established with 60 different human cancer cell lines from 9 different kinds of organs. This platform represents the biological characteristics of the corresponding tumor type. The drugs were screened by measuring the ability of each test compound at a range of concentrations to inhibit the growth of various tumor cells. The results are summarized in following Table 2. The tested example compounds demonstrated potent anti-proliferative activities against NCI 60 human cell lines with averaged $GI_{50}$'s of 59-120 nM.

TABLE 2

Growth Inhibition ($GI_{50}$) of Selected Example Compounds against NCI 60 Cell Lines

| Cell Lines | Example 14 (nM) | Example 15 (nM) | Example 46 (nM) | Example 122 (nM) |
|---|---|---|---|---|
| PC-3 | 51 | 25 | 23 | 41 |
| MCF-7 | 48.3 | <10 | 14.4 | 26.8 |
| HCT-116 | 41 | 65.7 | 60.2 | 364 |
| NCI-H23 | 269 | 123 | 96.2 | 70.3 |
| NCI-H460 | 142 | 67 | 59.7 | 35.9 |
| SKOV-3 | 98.7 | 46.3 | 26.8 | 18.9 |
| A549 | 244 | 54.5 | 66.5 | 110 |
| NCI60 cell lines (avg. $GI_{50}$) | 120 | 76 | 59 | 62 |

Pharmacokinetic Studies

Active mTOR inhibitors in enzymatic and/or cell-based assays herein were evaluated for pharmacokinetic properties. Preferable compounds are with pharmacokinetic properties of low clearance, long half-life and/or good oral bioavailability (Fpo). In vitro, selected example compounds were evaluated for metabolic stability by incubating with human liver microsome (HLM) for 60 min. Compounds that were metabolized slower (i.e. higher % remaining) are preferred. Many example compounds were found to be metabolically stable, for example, Example 14, 15, 46, 29, 55, 56, 64, 67, 89, 96, 122, 106 and 127. The more metabolic stable example compounds in the HLM assay were further evaluated for pharmacokinetic properties in vivo. In a representative experiment, selected example compounds were dosed to rats intravenously (IV, 5 mg/kg, 30% PEG400+30% PG+1% DMSO in saline) and orally (PO, 10 mg/kg, 2.4% DMSO+0.1% Tween80 in 0.5% CMC-Na), rat blood samples were taken at designed time points after dosing and analyzed for tested drug concentrations using LC-MS/MS. Pharmacokinetic parameters were derived from the time curve of drug concentrations. Results of selected example compounds are summarized in following Table 3.

TABLE 3

Results of Rat Pharmacokinetic Studies of Selected Example compounds

| Example Compound | Dosing method | Cmax (μg/ml) | Tmax (h) | $AUC_{0-t}$ (ug · h/ml) | $T_{1/2}$ (h) | MRT (h) | CL (L/h/kg) | Fpo (%) |
|---|---|---|---|---|---|---|---|---|
| Example 14 | IV(5 mg/kg) | 6.555 | — | 10.088 | 1.304 | 1.703 | 0.616 | |
|  | PO(10 mg/kg) | 0.784 | 1 | 4.896 | 3.284 | 5.709 | 1.808 | 22 |
| Example 15 | IV(5 mg/kg) | 4.71 | — | 3.43 | 4.98 | 5.57 | 1.07 | |
|  | PO(10 mg/kg) | N.D. | — | — | — | — | — | N.D. |
| Example 29 | IV(5 mg/kg) | 11.87 | — | 16.56 | 1.49 | 1.84 | 0.29 | |
|  | PO(10 mg/kg) | 0.38 | 2 | 1.65 | 1.12 | 2.9 | 5.94 | 5 |
| Example 128 (prodrug of 29) | PO(10 mg/kg) | 1.517 | 1.667 | 7.286 | 1.899 | 3.45 | 1.503 | 22 |
| Example 46 | IV(5 mg/kg) | 8.46 | — | 8.76 | 3.25 | 3.658 | 0.497 | |
|  | PO(10 mg/kg) | N.D. | — | — | — | — | — | N.D. |
| Example 106 | IV(5 mg/kg) | 21.2 | — | 41.455 | 1.416 | 1.672 | 0.122 | |
|  | PO(10 mg/kg) | 9.987 | 2.5 | 73.44 | 3.258 | 5.68 | 0.247 | 89 |
| Example 127 | IV(5 mg/kg) | 3.375 | — | 3.418 | 1.467 | 1.301 | 1.461 | |
|  | PO(10 mg/kg) | 0.296 | 0.417 | 1.4 | 3.295 | 5.107 | 6.772 | 22 |
| Example 122 | IV(5 mg/kg) | 4.7 | — | 11.371 | 2.132 | 3.032 | 0.441 | |
|  | PO(10 mg/kg) | 1.907 | 0.833 | 11.94 | 4.721 | 7.331 | 0.796 | 48 |

N.D.: tested drug was not detected in rat plasma

Tumor Xenograft Models

More potent mTOR inhibitors in both enzymatic and cell-based assays mentioned above with appropriate pharmacokinetic properties can be further evaluated in mouse tumor xenograft models (e.g. U87, PC-3 and Huh-7) for in vivo efficacy. In these studies, tumor cells are implanted into immunodeficient animals, and the effect of the compound on tumor cell survival, growth, metastasis and volume, among other properties, is evaluated by administration (via either IP, PO or IV) of the test compound to the animal, general starting a different times after implantation. Using this assay compounds can be shown to demonstrate ability to tumor growth when the mice are treated with the compounds. More preferably, compounds can prevent the regrowth of the tumors even after the drug treatment (4-6 weeks) has been stopped.

The invention claimed is:

1. A compound of formula (I):

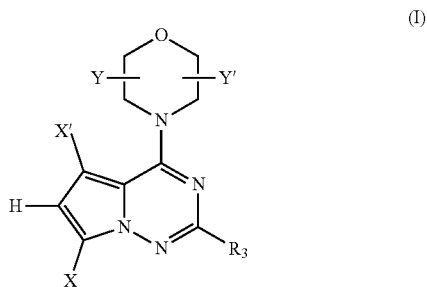

or a pharmaceutically acceptable salt, solvate, stereoisomer or tautomer thereof, wherein X' is H;

X is H, $C_{1-8}$ alkyl, $CF_3$, —C(O)$NR_{11}R_{12}$, halogen, cyano, —S(O)$R_{13}$, —S(O)$_2R_{13}$, —S(O)$_2NR_{11}R_{12}$, —$NR_{13}$S(O)$_2NR_{11}R_{12}$, —$OR_{13}$, —$NR_{13}$C(O)$NR_{11}R_{12}$ or $C_{1-6}$ alkyl substituted with —OH, or —$OR_{13}$; wherein when X is $C_{1-8}$ alkyl, $CF_3$, —C(O)NR$_{11}$R$_{12}$, halogen, cyano, —S(O)R$_{13}$, —S(O)$_2$R$_{13}$, —S(O)$_2$NR$_{11}$R$_{12}$, —NR$_{13}$S(o)$_2$NR$_{11}$R$_{12}$, —OR$_{13}$, —NR$_{13}$C(O)NR$_{11}$R$_{12}$ or $C_{1-6}$ alkyl substituted with —OH, or —OR$_{13}$, R$_3$ is phenyl unsubstituted or substituted with at least one R$_{14}$, pyridine unsubstituted or substituted with one or more R$_{14}$, indole unsubstituted or substituted with one or more R$_{15}$, azaindole unsubstituted or substituted with one or more R$_{15}$, indazole unsubstituted or substituted with one or more R$_{15}$, azaindazole unsubstituted or substituted with one or more R$_{15}$;

when X is H, R$_3$ is phenyl with a 4-substitution of —NHC(W)NHR$_{18}$, wherein W is O, S, N—CN, NH or N—NO$_2$;

R$_{18}$ is $C_{1-6}$ alkyl unsubstituted or substituted with one or more R$_{18a}$, $C_{1-6}$ cyclic alkyl unsubstituted or substituted with one or more R$_{18a}$, 5- or 6-membered heteroaryl, or phenyl unsubstituted or substituted with a 4-substitution of —C(O)NR$_{19}$R$_{20}$;

R$_{18a}$ is —OH, cyano, —NR$_{11}$R$_{12}$, —OR$_{13}$, morpholine, piperazine, or heterocycle;

R$_{19}$ and R$_{20}$ are each independently H, $C_{1-6}$ alkyl unsubstituted or substituted with one or more R$_{19a}$, or R$_{19}$ and R$_{20}$, together with the nitrogen atom to which they are attached, form a 3- to 8-membered monocyclic ring or a 5- to 10-membered bicyclic ring, wherein any atom in the monocyclic ring or bicyclic ring may be NR$_{21}$ or CR$_{22}$;

R$_{19a}$ is —OH, —OR$_{13}$, —NR$_{11}$R$_{12}$, cyano, or morpholine;

R$_{21}$ is H, methyl, $C_{1-3}$ alkyl or cyclic alkyl;

R$_{22}$ is H, —OH or —NR$_{23}$R$_{24}$; and

R$_{23}$ and R$_{24}$ are each independently H, methyl, $C_{1-3}$ alkyl or cyclic alkyl;

Y and Y' are each independently H, $C_{1-3}$ alkyl, oxo or cyano, or Y and Y', together with the atom to which they are attached, form a 4- to 7-membered ring including 1-4 atoms of the morpholine;

Ru$_{11}$ and R$_{12}$ are each independently H, alkyl, hydroxyalkyl, aryl, heteroaryl, arylalkyl or heteroarylalkyl, or Ru$_{11}$ and R$_{12}$, together with the nitrogen atom to which they are attached, form a 4- to 7-membered ring;

R$_{13}$ is H, alkyl, aryl, heteroaryl, alkylaryl, arylalkyl, alkylheteroaryl or heteroarylalkyl;

R$_{14}$ is H, alkyl, halogen, $C_{1-3}$ alkoxy, $CF_3$, amino, cyano, —NR$_{13}$C(O)NR$_{11}$R$_{12}$, —C(O)NR$_{11}$R$_{12}$, —S(O)$_2$NR$_{11}$R$_{12}$, —NR$_{13}$S(O)$_2$NR$_{11}$R$_{12}$, —NR$_{13}$C(S)NR$_{11}$R$_{12}$, —NR$_{13}$C(=N—CN)NR$_{11}$R$_{12}$, —NR$_{13}$C(=NH)NR$_{11}$R$_{12}$, or —NR$_{13}$C(=N—NO$_2$)NR$_{11}$R$_{12}$; and R$_{15}$ is H, halogen, alkyl, cyano, alkoxy, —C(O)NR$_{11}$R$_{12}$, —S(O)$_2$NR$_{11}$R$_{12}$, —NR$_{13}$S(O)$_2$NR$_{11}$R$_{12}$ or —NR$_{13}$C(O)NR$_{11}$R$_{12}$.

2. The compound of claim 1, wherein

R$_3$ is phenyl with a 4-substitution of —NHC(S)NHR$_{18}$;

R$_{18}$ is $C_{1-6}$ alkyl unsubstituted or substituted with one or more R$_{18a}$, $C_{1-6}$ cyclic alkyl unsubstituted or substituted with one or more R$_{18a}$, 5- or 6-membered heteroaryl, or phenyl unsubstituted or substituted with a 4-substitution of —C(O)NR$_{19}$R$_{20}$;

R$_{18a}$ is —OH, cyano, —NR$_{11}$R$_{12}$, —OR$_{13}$, morpholine, piperazine, or heterocycle;

R$_{19}$ and R$_{20}$ are each independently H, $C_{1-6}$ alkyl unsubstituted or substituted with one or more R$_{19a}$, or R$_{19}$ and R$_{20}$, together with the nitrogen atom to which they are attached, form a 3-to 8-membered monocyclic ring or a 5- to 10-membered bicyclic ring, wherein any atom in the monocyclic ring or bicyclic ring may be NR$_{21}$ or CR$_{22}$;

R$_{19a}$ is —OH, —OR$_{13}$, —NR$_{11}$R$_{12}$, cyano, or morpholine;

R$_{21}$ is H, methyl, $C_{1-3}$ alkyl or cyclic alkyl;

R$_{22}$ is H, —OH or —NR$_{23}$R$_{24}$; and

R$_{23}$ and R$_{24}$ are each independently H, methyl, $C_{1-3}$ alkyl or cyclic alkyl.

3. The compound of claim 1, wherein the compound is according to formula (II):

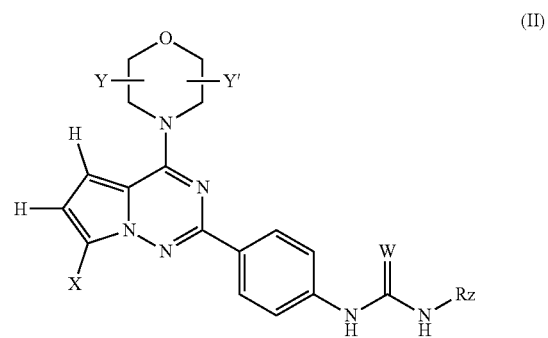

(II)

or a pharmaceutically acceptable salt, solvate, stereoisomer or tautomer thereof, wherein X is H, $C_{1-8}$ alkyl, CF3, —C(O)NR$_{11}$R$_{12}$, halogen, cyano, —S(O)R$_{13}$, —S(O)$_2$R$_{13}$, —S(O)$_2$NR$_{11}$R$_{12}$, —NR$_{13}$S(O)$_2$NR$_{11}$R$_{12}$, —OR$_{13}$, —NR$_{13}$C(O)NR$_{11}$R$_{12}$ or $C_{1-6}$ alkyl substituted with —OH, or —OR$_{13}$;

Y and Y' are each independently H, methyl, ethyl, oxo or cyano, or Y and Y', together with the atom to which they are attached, form a 4- to 7-membered ring including 1-4 atoms of the morpholine;

W is S, N—CN, NH or N—NO$_2$;

Rz is $C_{1-6}$ alkyl unsubstituted or substituted with one or more R$_{18a}$, $C_{1-6}$ cyclic alkyl unsubstituted or substituted with one or more R$_{18a}$, 5- or 6-membered heteroaryl, or phenyl unsubstituted or substituted with a 4-substitution of —C(O)NR$_{19}$R$_{20}$;

R$_{18a}$ is —OH, cyano, —NR$_{11}$R$_{12}$, —OR$_{13}$, morpholine, piperazine, or heterocycle;

R$_{19}$ and R$_{20}$ are each independently H, $C_{1-6}$ alkyl unsubstituted or substituted with one or more R$_{19a}$, or R$_{19}$ and R$_{20}$, together with the nitrogen atom to which they are attached, form a 3-to 8-membered monocyclic ring or a 5- to 10-membered bicyclic ring, wherein any atom in the monocyclic ring or bicyclic ring may be NR$_{21}$ or CR$_{22}$;

R$_{19a}$ is —OH, —OR$_{13}$, —NR$_{11}$R$_{12}$, cyano, or morpholine;

R$_{21}$ is H, methyl, $C_{1-3}$ alkyl or cyclic alkyl;

R$_{22}$ is H, —OH or —NR$_{23}$R$_{24}$; and

R$_{23}$ and R$_{24}$ are each independently H, methyl, $C_{1-3}$ alkyl or cyclic alkyl.

4. The compound of claim 3, wherein X is hydrogen.

5. The compound of claim 3, wherein R$_z$ is $C_{1-4}$ alkyl, $C_{1-4}$ cyclic alkyl, or $C_{1-6}$ alkyl substituted with one or more R$_{18a}$.

6. The compound of claim 3, wherein R$_z$ is 5- or 6-membered heteroaryl selected from the group consisting of pyridine, pyrimidine, pyrazine, pyridazine, imidazole, triazine, oxazole and thiazole.

7. The compound of claim 3, wherein $R_z$ is phenyl unsubstituted or substituted with a 4-substitution of —C(O)NR$_{19}$R$_{20}$.

8. The compound of claim 3, wherein W is S.

9. A compound for formula (II):

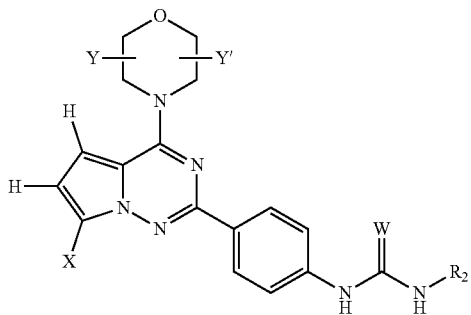

(II)

or a pharmaceutically acceptable salt, solvate, stereoisomer or tautomer thereof, wherein X is H, $C_{1-8}$ alkyl, CF3, —C(O)NR$_{11}$R$_{12}$, halogen, cyano, —S(O)R$_{13}$, —S(O)$_2$R$_{13}$, —S(O)$_2$NR$_{11}$R$_{12}$, —NR$_{13}$S(O)$_2$NR$_{11}$R$_{12}$, —OR$_{13}$, —NR$_{13}$C(O)NR$_{11}$R$_{12}$ or $C_{1-6}$ alkyl substituted with —OH, or —OR$_{13}$;

Y and Y' are each independently H, methyl, ethyl, oxo or cyano, or Y and Y', together with the atom to which they are attached, form a 4- to 7-membered ring including 1-4 atoms of the morpholine;

W is S, N—CN, NH or N—NO$_2$;

Rz is $C_{1-6}$ alkyl unsubstituted or substituted with one or more R$_{18a}$, $C_{1-6}$ cyclic alkyl unsubstituted or substituted with one or more R$_{18a}$, 5- or 6-membered heteroaryl, or phenyl unsubstituted or substituted with a 4-substitution of —C(O)NR$_{19}$R$_{20}$;

R$_{18a}$ is —OH, cyano, —NR$_{11}$R$_{12}$, —OR$_{13}$, morpholine, piperazine, or heterocycle;

R$_{19}$ and R$_{20}$ are each independently H, $C_{1-6}$ alkyl unsubstituted or substituted with one or more R$_{19a}$, or R$_{19}$ and R$_{20}$, together with the nitrogen atom to which they are attached, form a 3- to 8-membered monocyclic ring or a 5- to 10-membered bicyclic ring, wherein any atom in the monocyclic ring or bicyclic ring may be NR$_{21}$ or CR$_{22}$;

R$_{19a}$ is —OH, —OR$_{13}$, —NR$_{11}$R$_{12}$, cyano, or morpholine;

R$_{21}$ is H, methyl, $C_{1-3}$ alkyl or cyclic alkyl;

R$_{22}$ is H, —OH or —NR$_{23}$R$_{24}$; and

R$_{23}$ and R$_{24}$ are each independently H, methyl, $C_{1-3}$ alkyl or cyclic alkyl;

at least one —OH group in Rz is independently converted to a corresponding phosphate ester —OP(O)(OH)$_2$ or —OR$_{25}$, and wherein R$_{25}$ is independently an ester, ether or substituted ether;

or at least one NH group of the —NHC(=W)NHR$_{18}$ group in R$_3$ is independently substituted with alkyl, alkylaryl, arylalkyl, alkylheteroaryl, heteroarylalkyl, or —CH$_2$OR$_{26}$, and wherein R$_{26}$ is independently phosphate, ester, alkyl or alkylaryl.

10. The compound of claim 1, wherein the compound is according to formula (III)

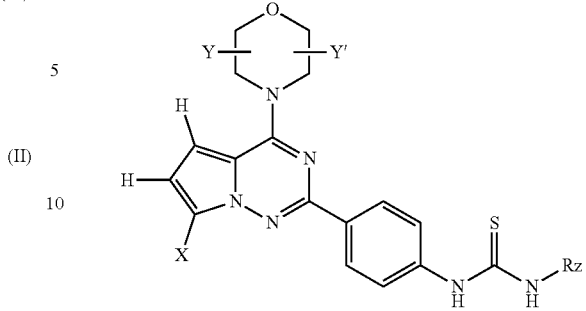

(III)

or a pharmaceutically acceptable salt, solvate, stereoisomer or tautomer thereof, wherein X is H, $C_{1-8}$ alkyl, CF3, —C(O)NR$_{11}$R$_{12}$, halogen, cyano, —S(O)R$_{13}$, —S(O)$_2$R$_{13}$, —S(O)$_2$NR$_{11}$R$_{12}$, —NR$_{13}$S(O)$_2$NR$_{11}$R$_{12}$, —OR$_{13}$, —NR$_{13}$C(O)NR$_{11}$R$_{12}$ or $C_{1-6}$ alkyl substituted with —OH, or —OR$_{13}$;

Y and Y' are each independently H, methyl, ethyl, oxo or cyano, or Y and Y', together with the atom to which they are attached, form a 4- to 7-membered ring including 1-4 atoms of the morpholine;

Rz is $C_{1-6}$ alkyl unsubstituted or substituted with one or more R$_{18a}$, $C_{1-6}$ cyclic alkyl unsubstituted or substituted with one or more R$_{18a}$, 5- or 6-membered heteroaryl, or phenyl unsubstituted or substituted with a 4-substitution of —C(O)NR$_{19}$R$_{20}$;

R$_{18a}$ is —OH, cyano, —NR$_{11}$R$_{12}$, —OR$_{13}$, morpholine, piperazine, or heterocycle;

R$_{19a}$ and R$_{20}$ are each independently H, $C_{1-6}$ alkyl unsubstituted or substituted with one or more R$_{19a}$, or R$_{19}$ and R$_{20}$, together with the nitrogen atom to which they are attached, form a 3- to 8-membered monocyclic ring or a 5- to 10-membered bicyclic ring, wherein any atom in the monocyclic ring or bicyclic ring may be NR$_{21}$ or CR$_{22}$;

R$_{19a}$ is —OH, —OR$_{13}$, —NR$_{11}$R$_{12}$, cyano, or morpholine;

R$_{21}$ is H, methyl, $C_{1-3}$ alkyl or cyclic alkyl;

R$_{22}$ is H, —OH or —NR$_{23}$R$_{24}$; and

R$_{23}$ and R$_{24}$ are each independently H, methyl, $C_{1-3}$ alkyl or cyclic alkyl.

11. The compound of claim 10, wherein $R_z$ is selected from $C_{1-4}$ alkyl, $C_{1-4}$ cyclic alkyl or $C_{1-6}$ alkyl substituted with one or more R$_{18a}$.

12. The compound of claim 10, wherein $R_z$ is a 5- or 6-membered heteroaryl selected from the group consisting of pyridine, pyrimidine, pyrazine, pyridazine, imidazole, triazine, oxazole and thiazole.

13. The compound of claim 10, wherein $R_z$ is a phenyl unsubstituted or substituted with a 4-substitution of —C(O)NR$_{19}$R$_{20}$.

14. A pharmaceutical composition comprising a compound of formula (I) in claim 1 or a pharmaceutically acceptable salt thereof and a pharmaceutically acceptable carrier.

15. A method for inhibiting mammalian target of rapamycin (mTOR) in a patient diagnosed with a disease or disorder related to inhibiting ATP-binding proteins comprising administering to the patient a pharmaceutical composition according to claim 14 in an effective amount to inhibit mTOR in a cell of the patient.

16. The method of claim 15, wherein the ATP-binding proteins are PI3K kinases or protein kinases.

17. The method of claim 15, wherein the disease or disorder is related hyperplasia related to PI3K pathway dysregulation or related hyperplasia related to mTOR pathway dysregulation.

18. A compound selected from the group consisting of:

Example 2
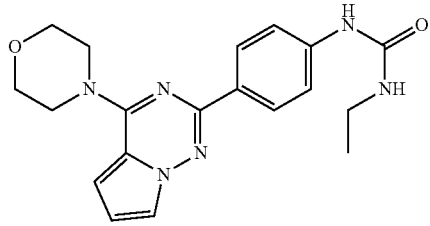

Example 4
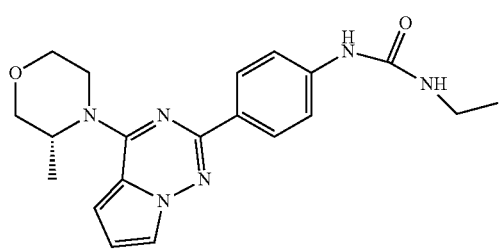

Example 5
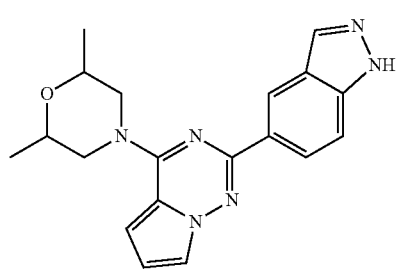

Example 6
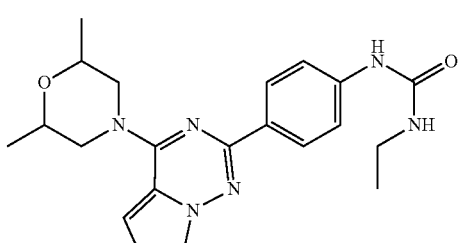

Example 7
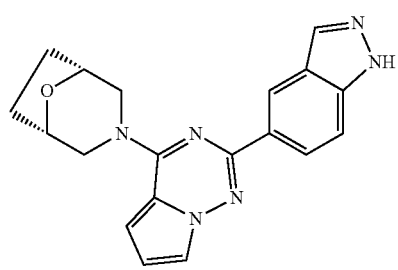

Example 8
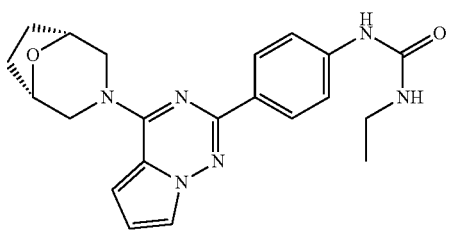

Example 13
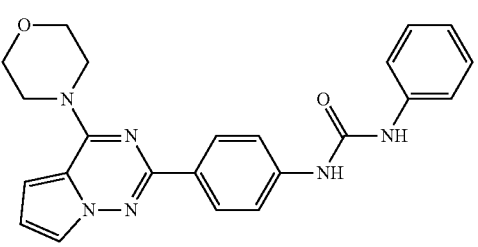

Example 14
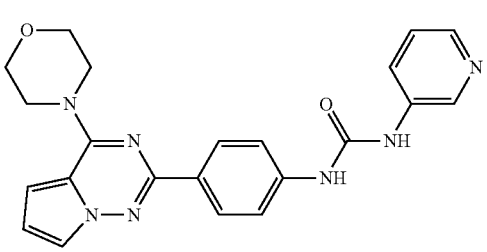

Example 15
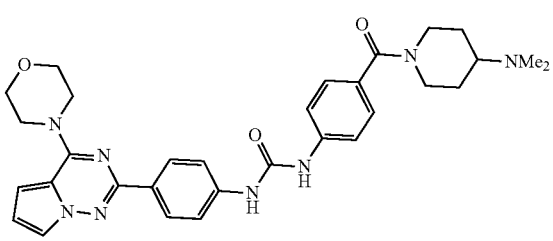

Example 16
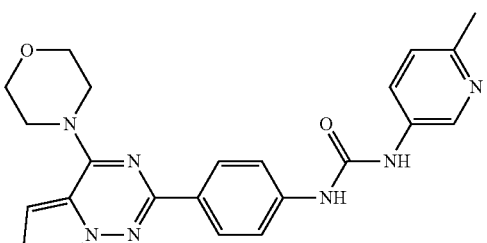

Example 17
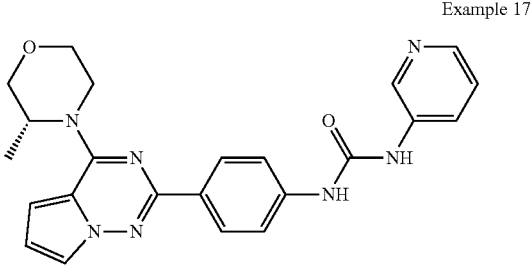

Example 18
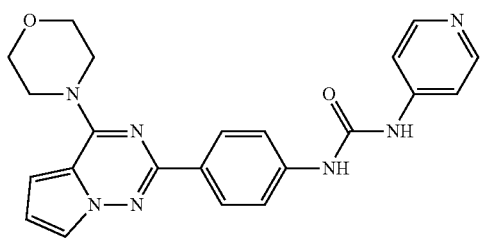
Example 29
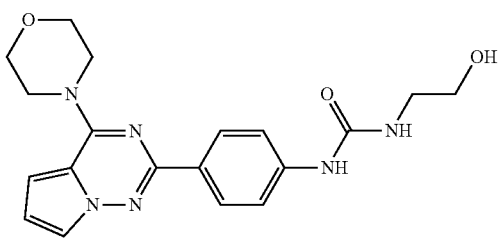
Example 19
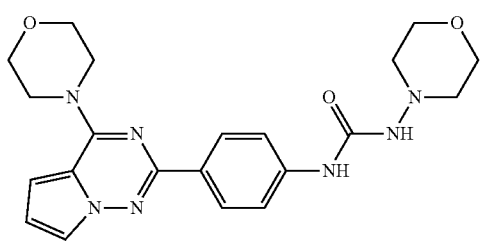
Example 30
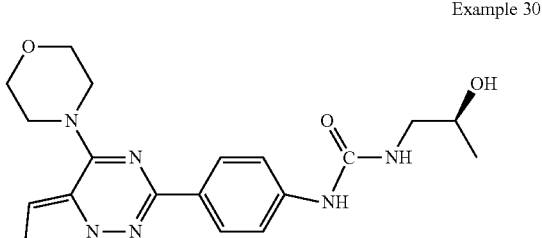
Example 20
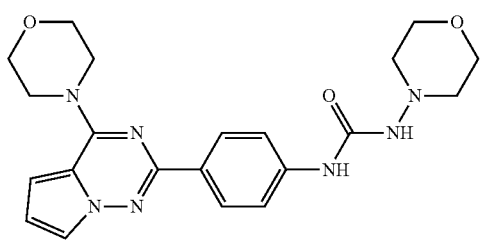
Example 34
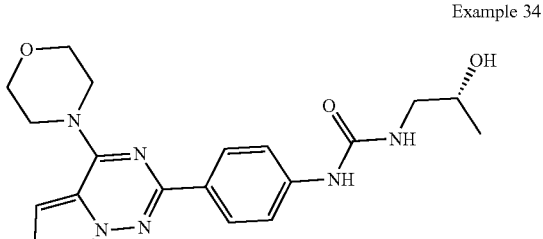
Example 21
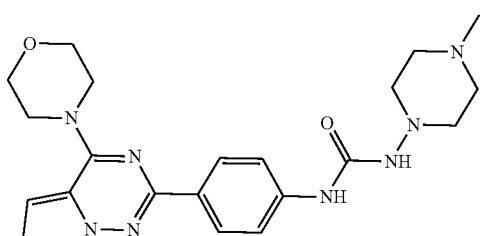
Example 35
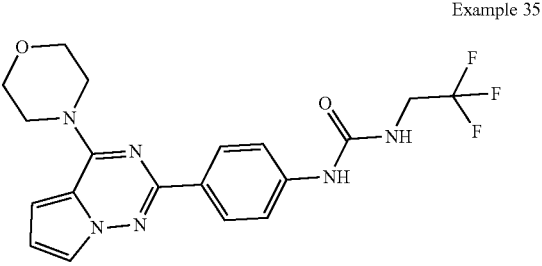
Example 22
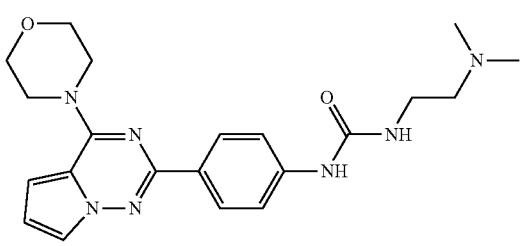
Example 36
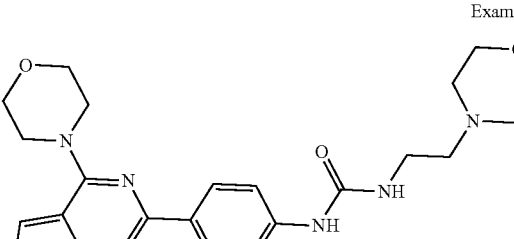
Example 23
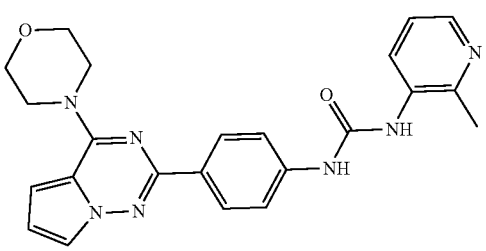
Example 37
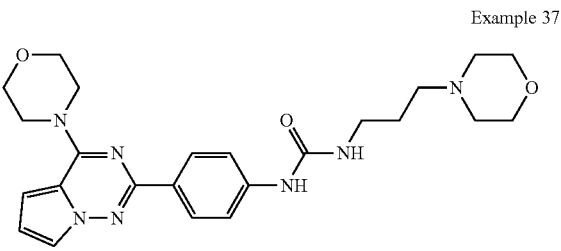

Example 38
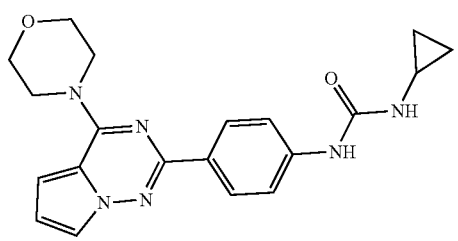
Example 39
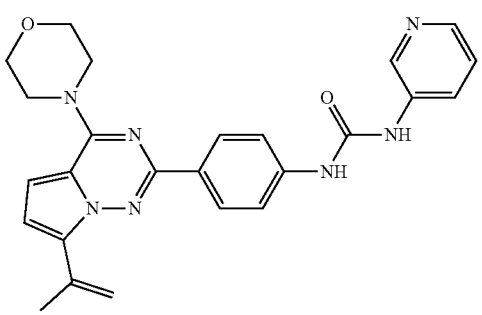
Example 40
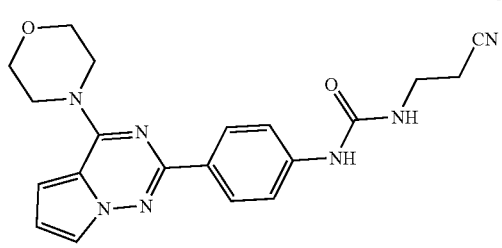
Example 41
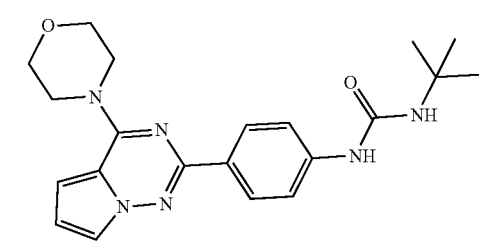
Example 42
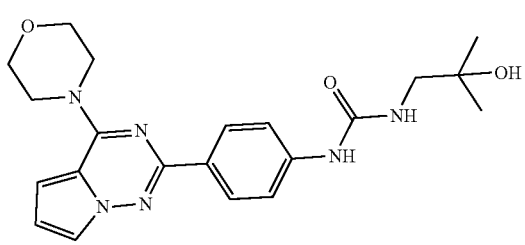
Example 43
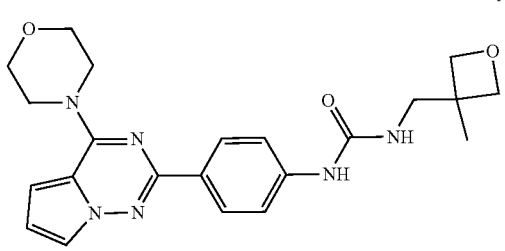
Example 44
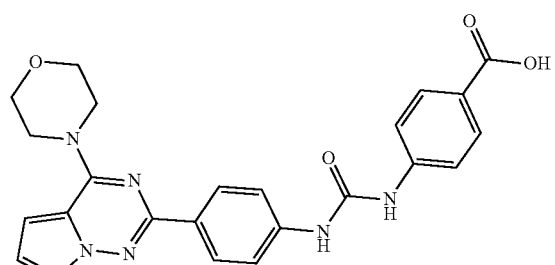
Example 45
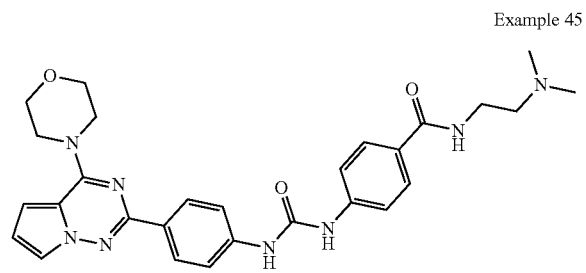
Example 46
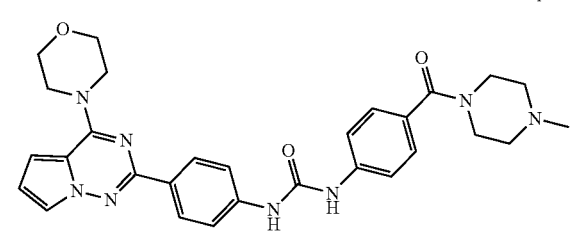
Example 47
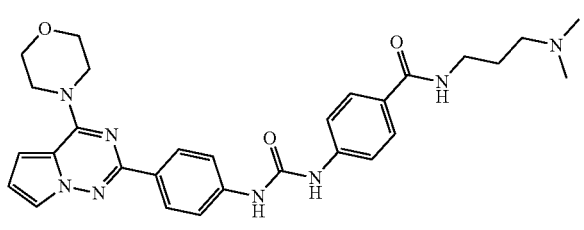
Example 48
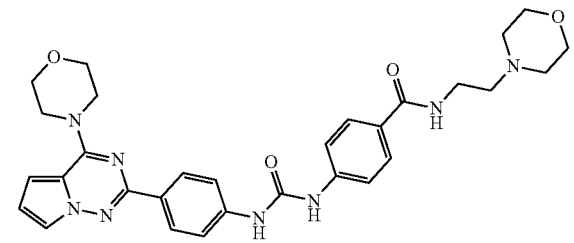
Example 49
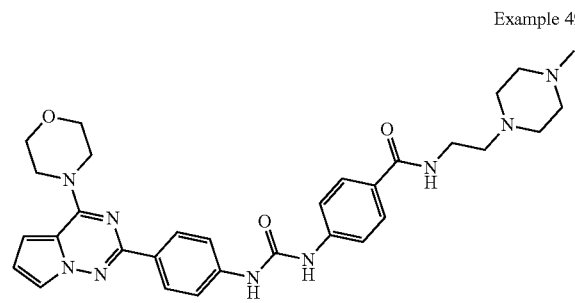

Example 50
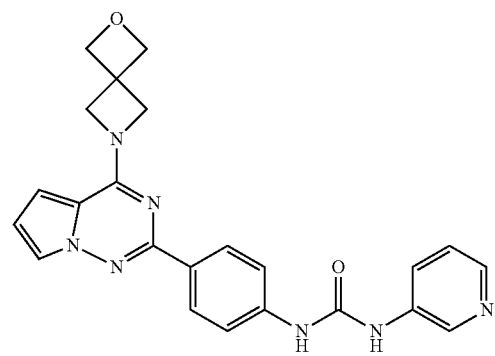
Example 51
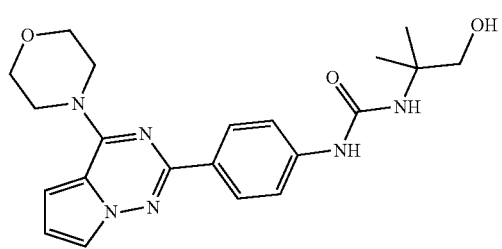
Example 52
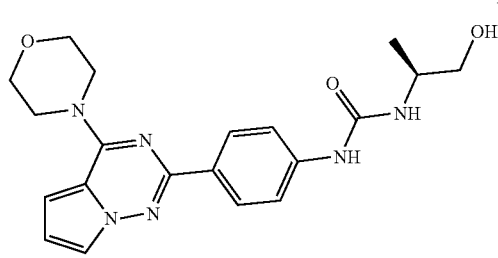
Example 53
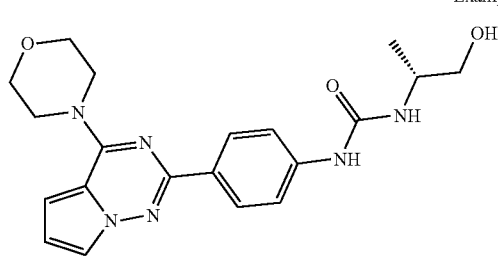
Example 54
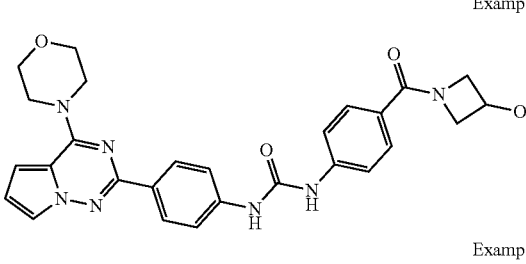
Example 55
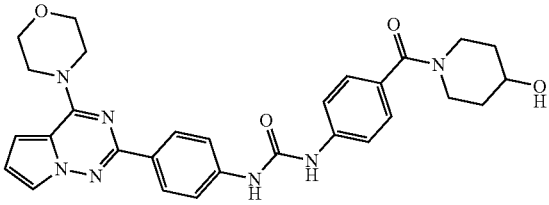
Example 56
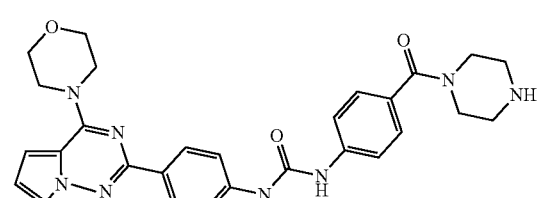
Example 57
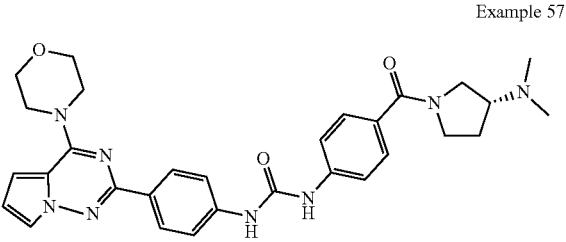
Example 58
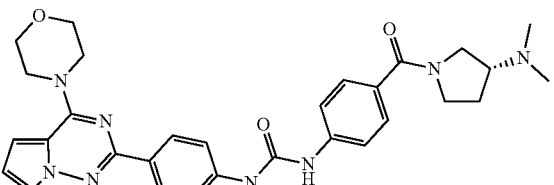
Example 59
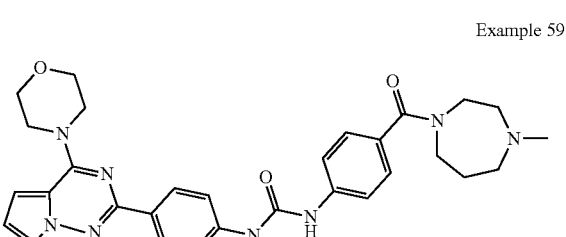
Example 60
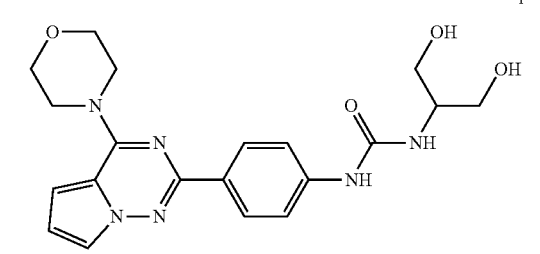
Example 62
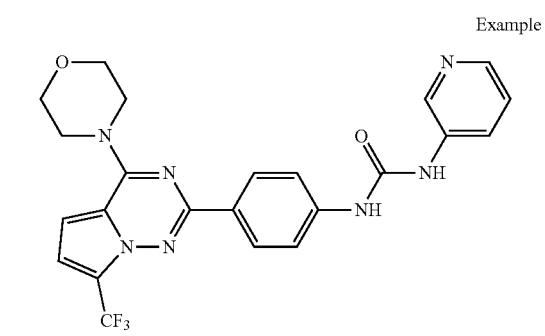

Example 63
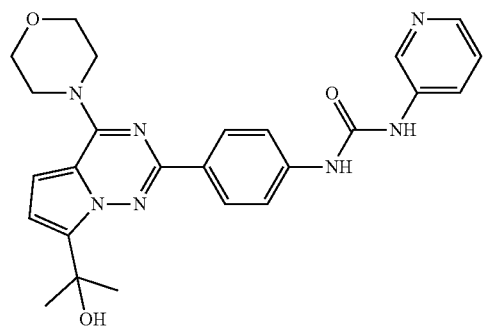
Example 68
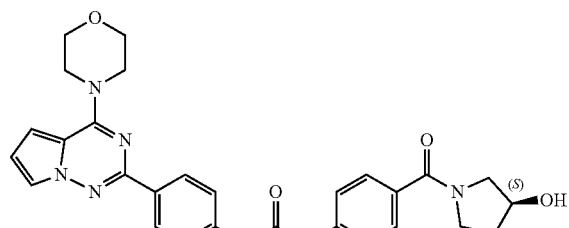
Example 64
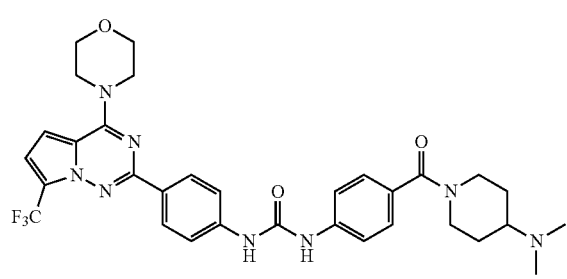
Example 69
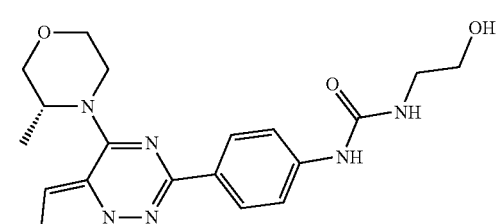
Example 65
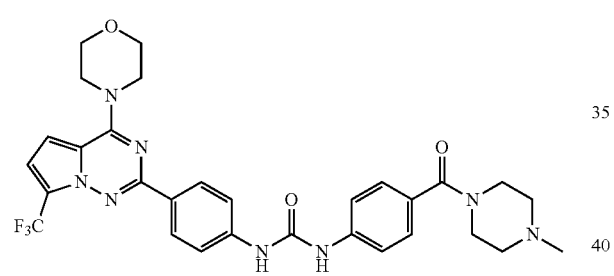
Example 70
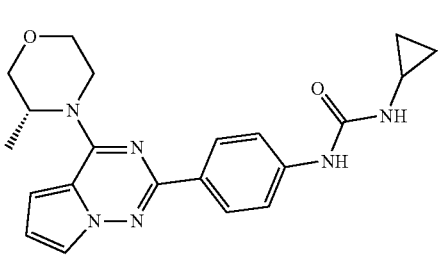
Example 73
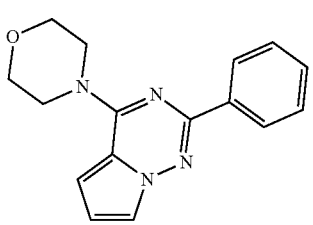
Example 66
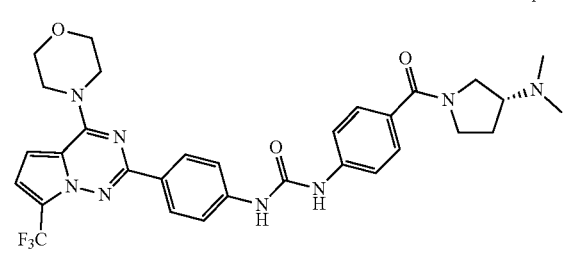
Example 76
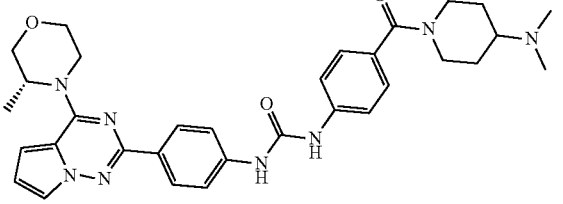
Example 67
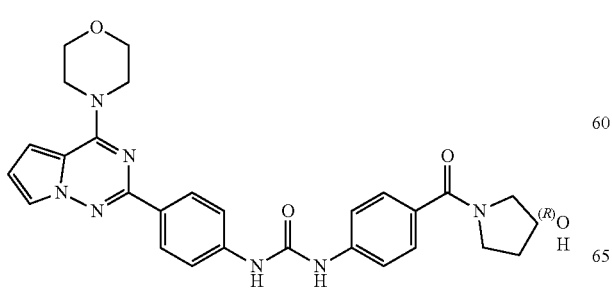
Example 77
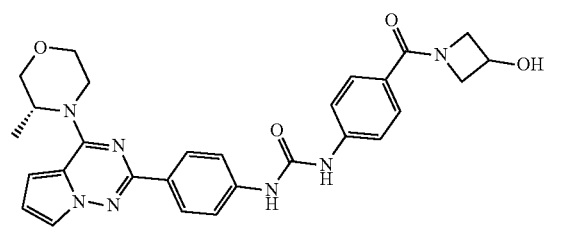

Example 78
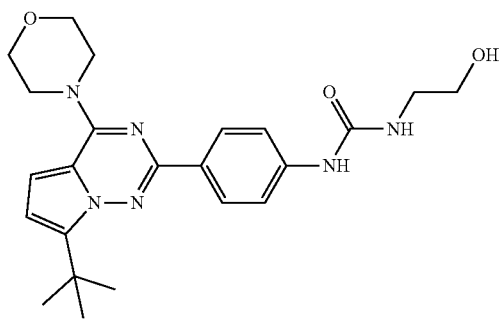
Example 79
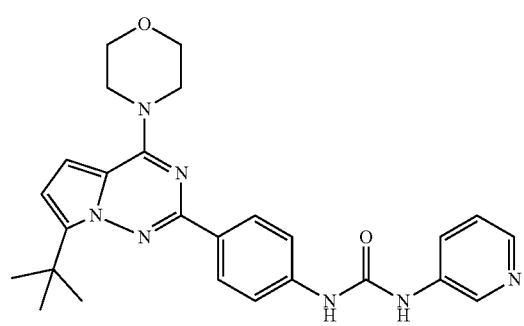
Example 80
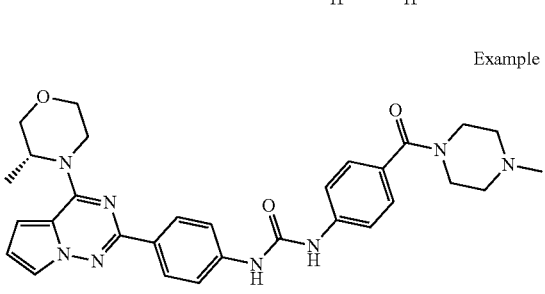
Example 81
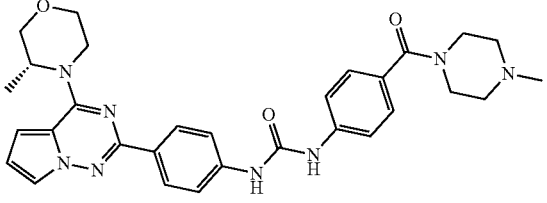
Example 82
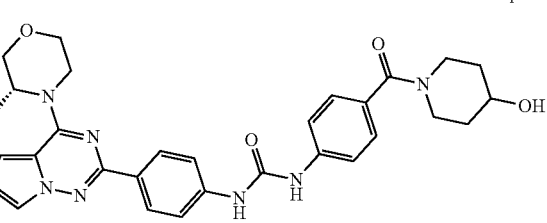
Example 83
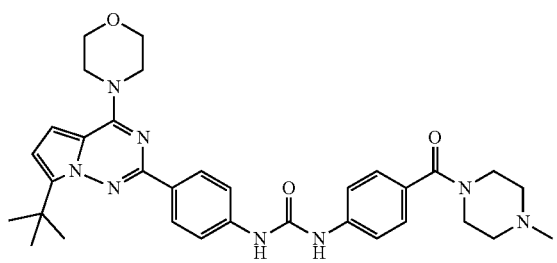
Example 84
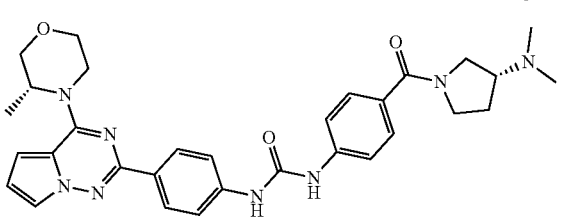
Example 85
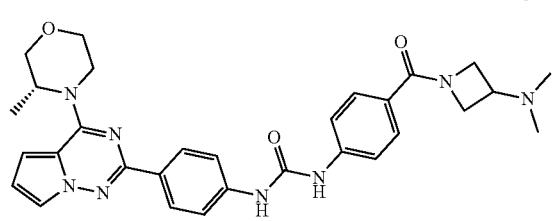
Example 86
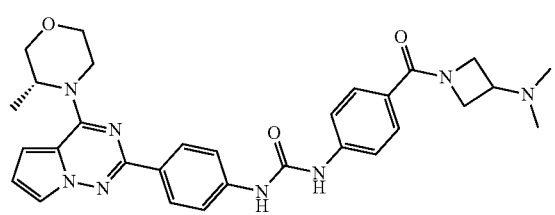
Example 87
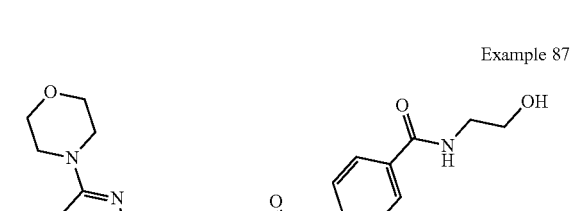
Example 88
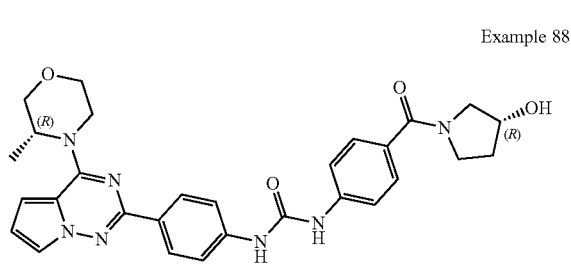

Example 89
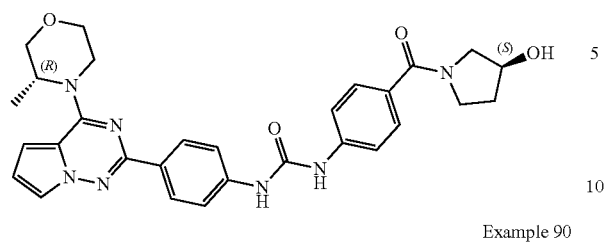
Example 90
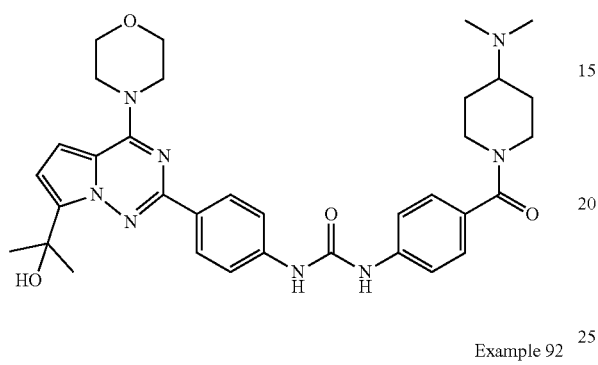
Example 92
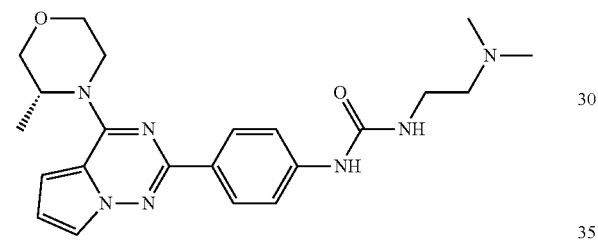
Example 93
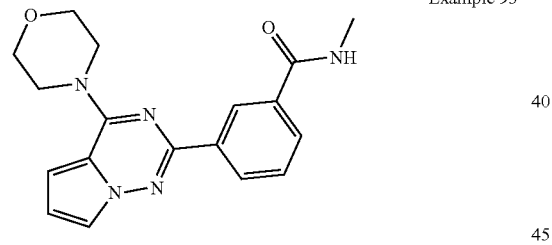
Example 95
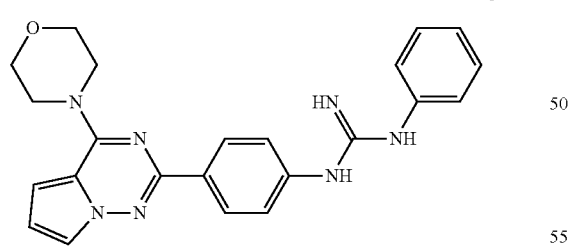
Example 96
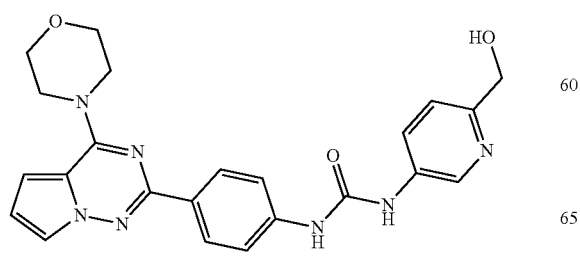
Example 97
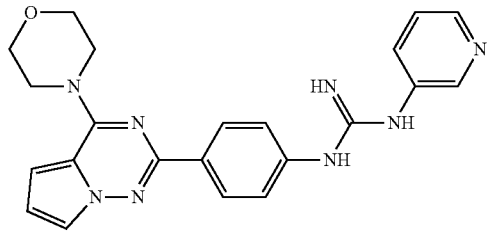
Example 98
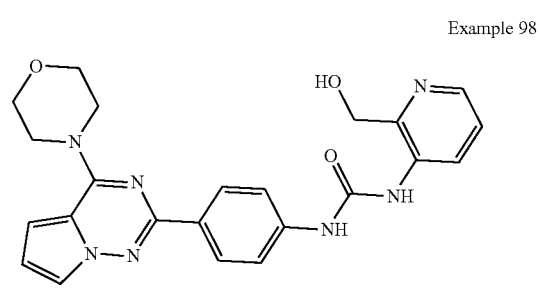
Example 99
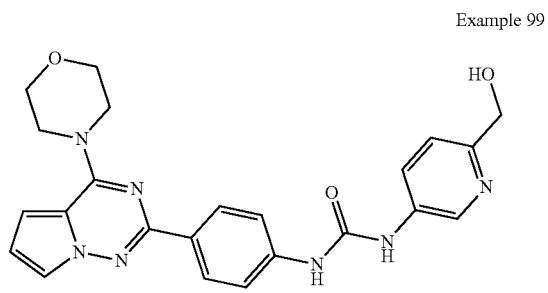
Example 100
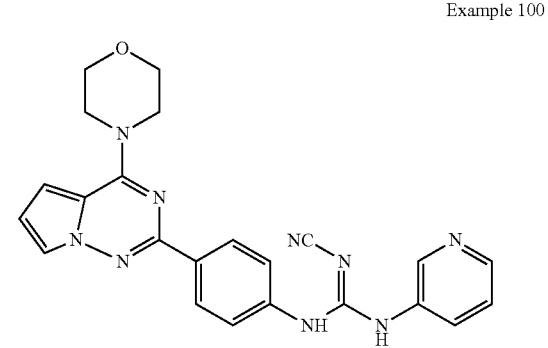
Example 103
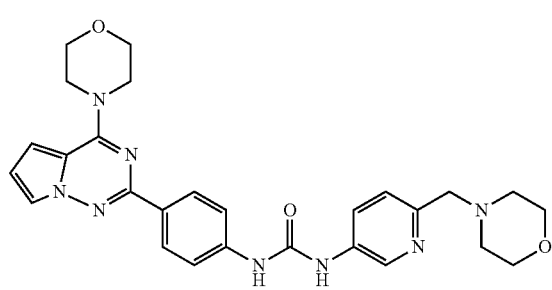

Example 104
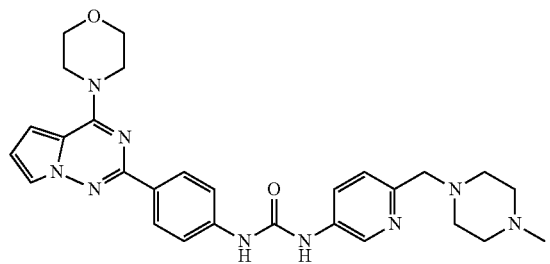
Example 106
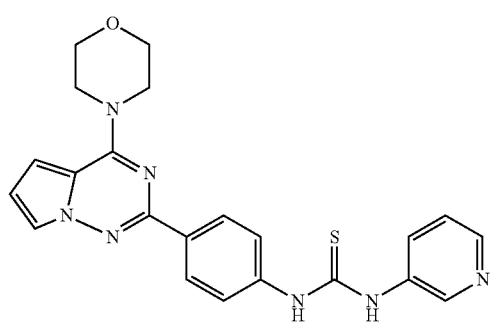
Example 107
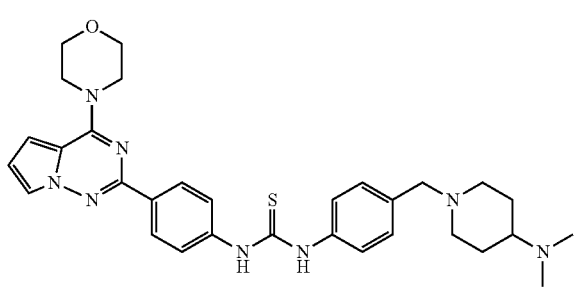
Example 108
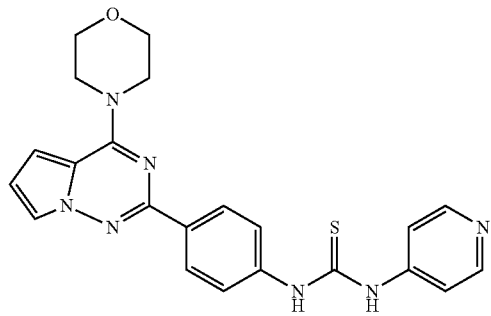
Example 109
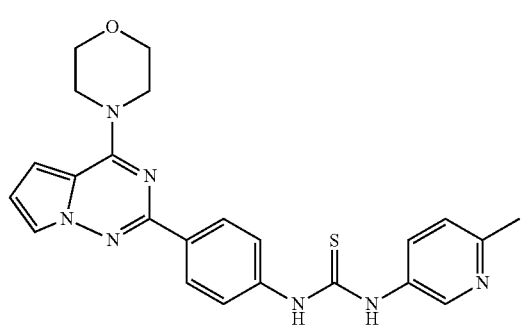
Example 110
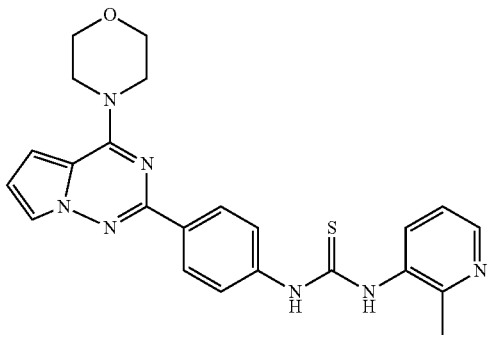
Example 111
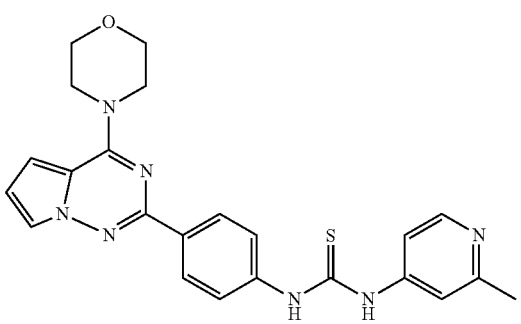
Example 112
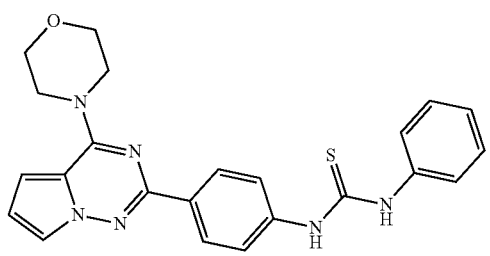
Example 113
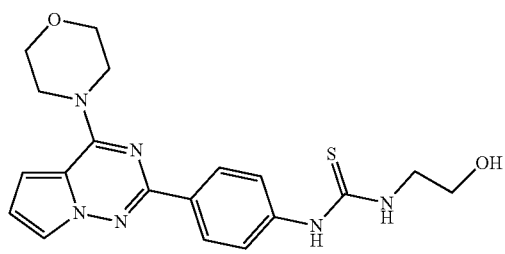
Example 114
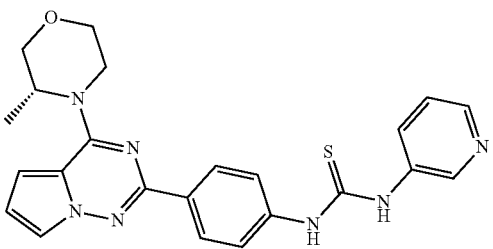

Example 115
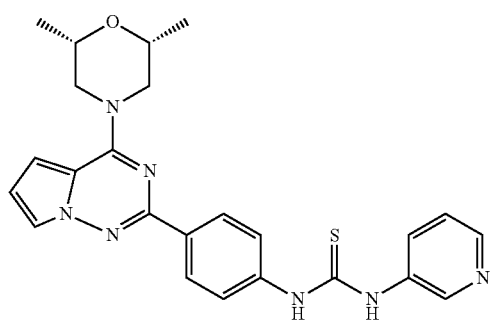
Example 116
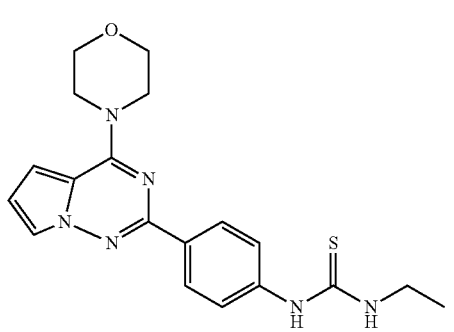
Example 117
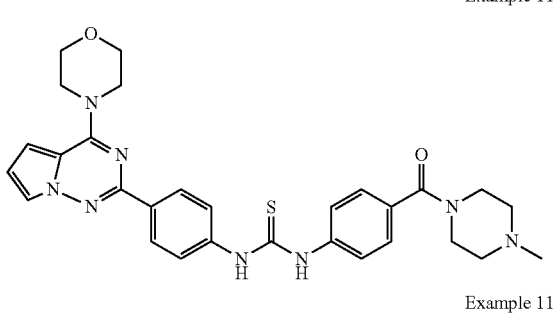
Example 118
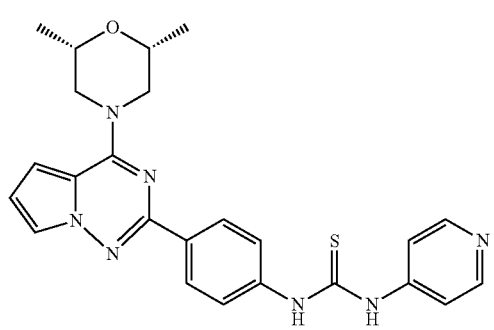
Example 119
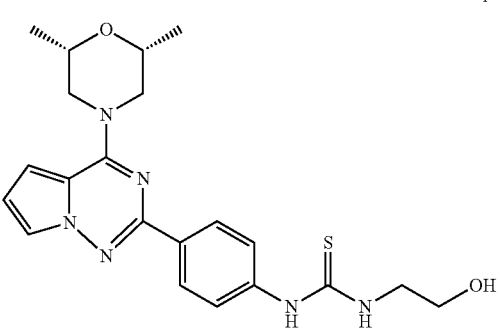
Example 120
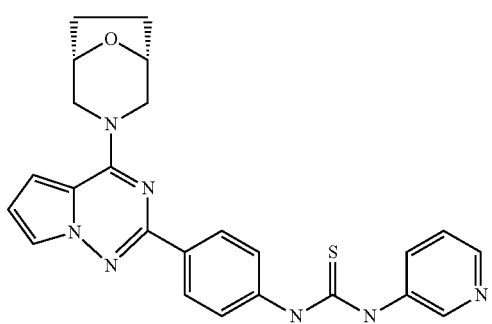
Example 121
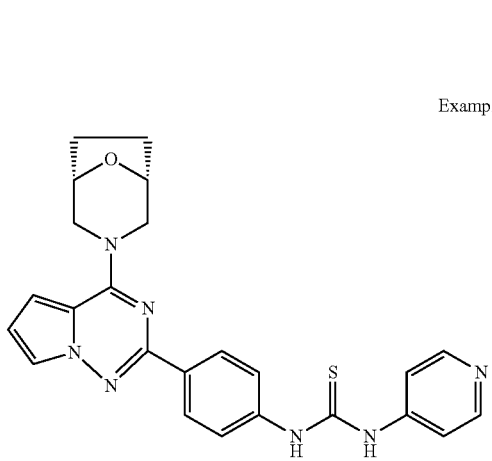
Example 122
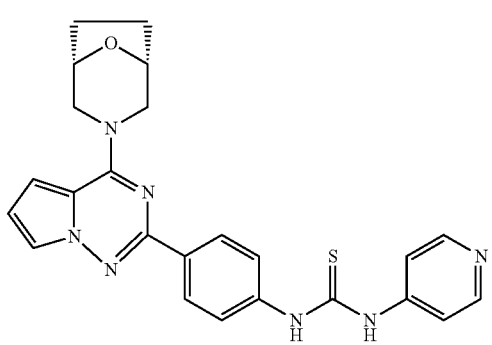
Example 123
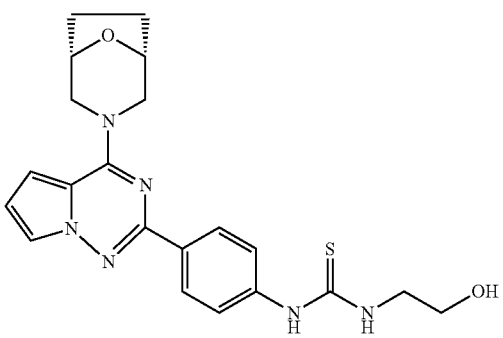

Example 124
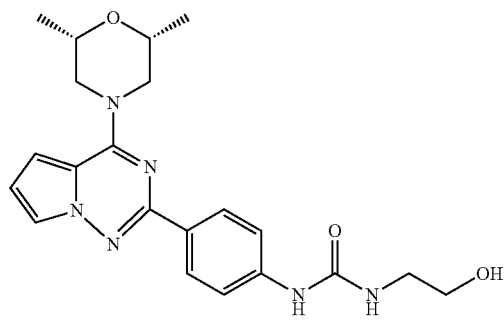
Example 125
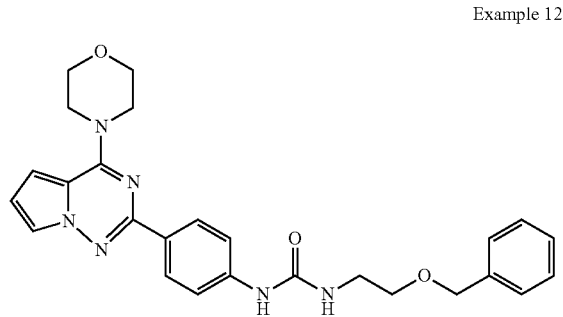
Example 126
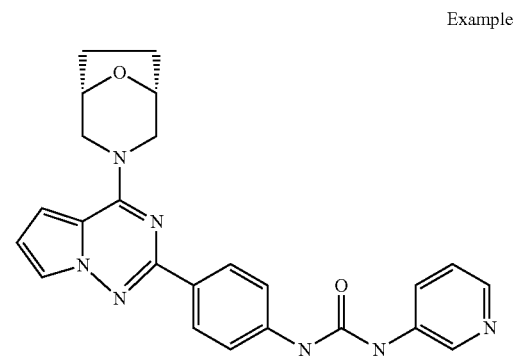
Example 127
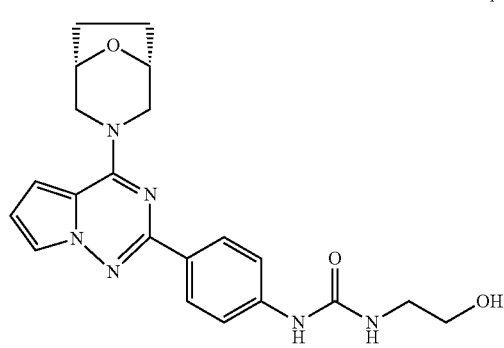
Example 128
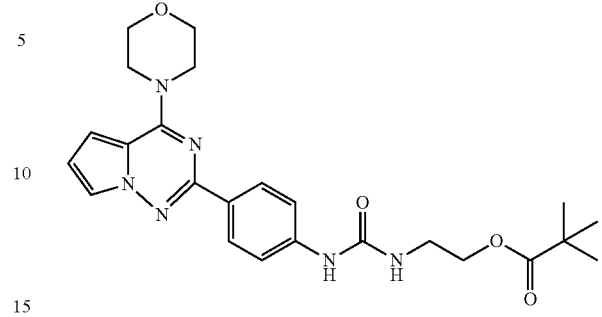
Example 129
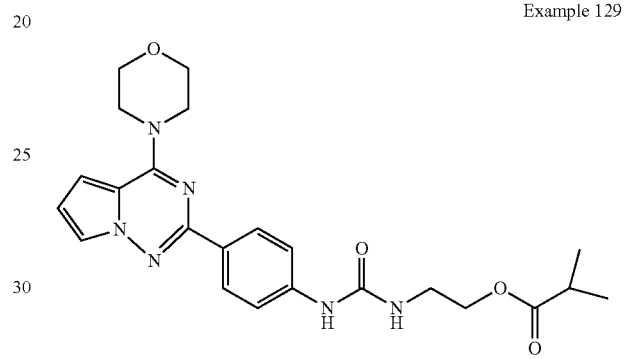
Example 130
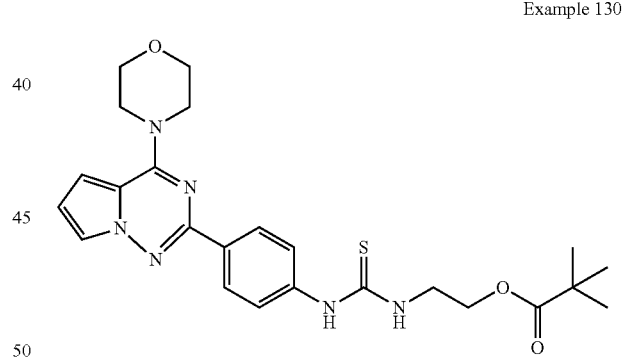
Example 131
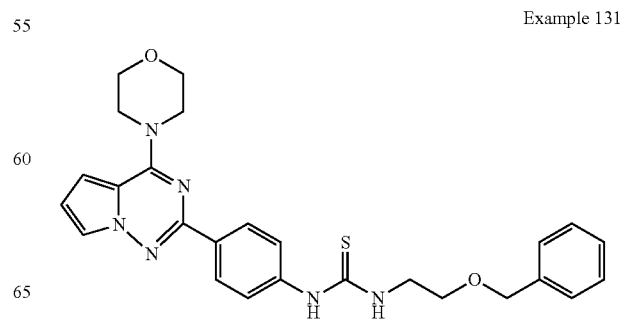

Example 132
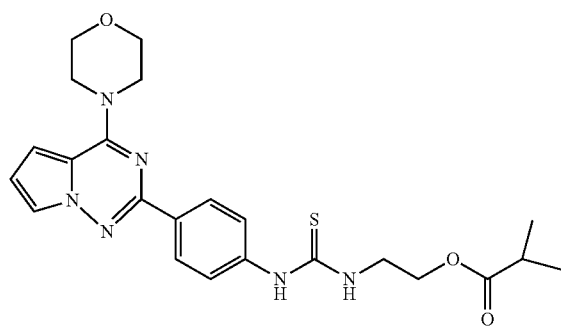
Example 133
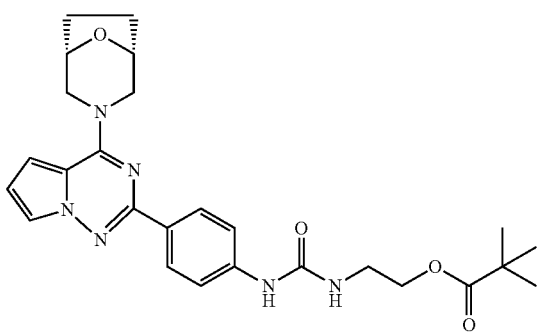
Example 134
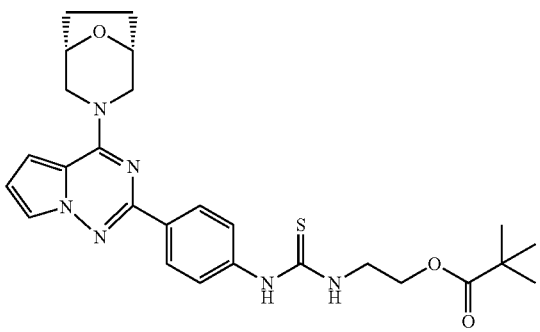
Example 135
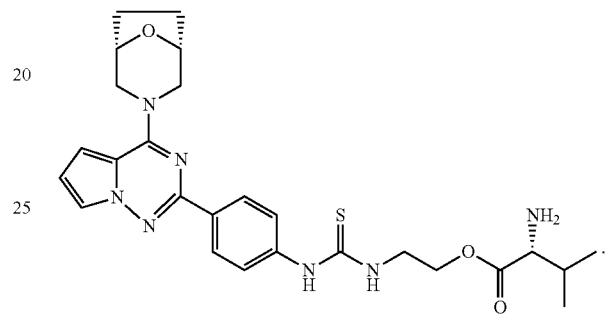
* * * * *